US012758635B2

(12) United States Patent
Hou et al.

(10) Patent No.: US 12,758,635 B2
(45) Date of Patent: Oct. 13, 2026

(54) ANTIBODIES AND METHODS FOR TREATING CLAUDIN-ASSOCIATED DISEASES

(71) Applicant: ANTENGENE BIOLOGICS LIMITED, Shanghai (CN)

(72) Inventors: Bin Hou, Shanghai (CN); Peng Chen, Shanghai (CN); Hui Yuwen, Shanghai (CN); Bo Shan, Shanghai (CN); Jay Mei, Shanghai (CN)

(73) Assignee: ANTENGENE BIOLOGICS LIMITED, Shanghai (CN)

( * ) Notice: Subject to any disclaimer, the term of this patent is extended or adjusted under 35 U.S.C. 154(b) by 1012 days.

(21) Appl. No.: 17/794,265

(22) PCT Filed: Jun. 23, 2021

(86) PCT No.: PCT/CN2021/101713
§ 371 (c)(1),
(2) Date: Jul. 21, 2022

(87) PCT Pub. No.: WO2021/259304
PCT Pub. Date: Dec. 30, 2021

(65) Prior Publication Data

US 2023/0095569 A1 Mar. 30, 2023

(30) Foreign Application Priority Data

Jun. 23, 2020 (WO) ................ PCT/CN2020/097635
Jun. 4, 2021 (WO) ................ PCT/CN2021/098416

(51) Int. Cl.

| | |
|---|---|
| ***A61K 45/06*** | (2006.01) |
| ***A61K 47/68*** | (2017.01) |
| ***A61P 35/00*** | (2006.01) |
| ***C07K 16/28*** | (2006.01) |
| ***C12N 15/86*** | (2006.01) |

(52) U.S. Cl.
CPC ........ *A61K 45/06* (2013.01); *A61K 47/68031* (2023.08); *A61P 35/00* (2018.01); *C07K 16/28* (2013.01); *C12N 15/86* (2013.01); *C07K 2317/24* (2013.01); *C07K 2317/31* (2013.01); *C07K 2317/565* (2013.01)

(58) Field of Classification Search
CPC .............. A61K 45/06; A61K 47/68031; A61K 2039/505; A61K 47/6849; A61K 47/6851; A61K 39/395; A61K 47/6803; A61P 35/00; C07K 16/28; C07K 2317/24; C07K 2317/31; C07K 2317/565; C07K 2317/30; C07K 2317/732; C07K 2317/734; C07K 2317/76; C07K 2317/92; C07K 16/30; C07K 2317/56; C07K 14/70503; C12N 15/86; G01N 33/57484
See application file for complete search history.

(56) References Cited

U.S. PATENT DOCUMENTS 10,421,817 B1 9/2019 Hu et al.

FOREIGN PATENT DOCUMENTS

| | | | |
|---|---|---|---|
| CN | 109762067 | A | 5/2019 |
| CN | 109762067 | B | 2/2020 |
| EP | 2976360 | B1 | 11/2019 |
| WO | 2014146672 | A1 | 9/2014 |
| WO | 2014146778 | A1 | 9/2014 |
| WO | 2016165762 | A1 | 10/2016 |
| WO | 2018123949 | A1 | 7/2018 |
| WO | 2019174617 | A1 | 9/2019 |
| WO | 2019219089 | A1 | 11/2019 |
| WO | 2020043044 | A1 | 3/2020 |

OTHER PUBLICATIONS

Baek et al. "Claudin 18.2 Is Not a Promising Biomarker for Targeted Immunotherapy in Prostatic Cancers." In Vivo. Mar. 3, 2025;39(2):819-823. (Year: 2025).*
Pan et al. "Research progress of Claudin-low breast cancer." Front Oncol. Oct. 11, 2023;13:1226118. (Year: 2023).*
Kyuno et al. "Claudin-18.2 as a therapeutic target in cancers: cumulative findings from basic research and clinical trials." Tissue Barriers. Sep. 5, 2021;10(1):1967080 (Year: 2021).*
Singh, P. et al., "Anti-Claudin 18.2 Antibody as New Targeted Therapy for Advanced Gastric Cancer", Journal of Hematology & Oncology, vol. 10, Dec. 31, 2017 (Dec. 31, 2017), Article No. 105, pp. 1-5.
Holland, J., "Development of a Highly Potent Bispecific Antibody Format Targeting the Novel Tumor-Specific Antigen CLDN18.2", J.G.U., Nov. 30, 2014 (Nov. 30, 2014), the whole document.
Kuraoka, M. et al., "Immunoglobulin Heavy Chain Variable Region, Partial [Mus Musculus]", Genbank: AML31651.1, Mar. 10, 2016 (Mar. 10, 2016), orgin.
The International Search Report for PCT/CN2021/101713 mailed on Sep. 27, 2021.
The Extended European Search Report of the corresponding European Application No. 21827898.4, mailed on Aug. 30, 2024.
The Office Action for the counterpart Colombia patent application NC2023/0000557, mailed on Mar. 26, 2026.

* cited by examiner

*Primary Examiner* — Titilayo Moloye
(74) *Attorney, Agent, or Firm* — Junhe Law Office P.C.; James J. Zhu

(57) ABSTRACT

Provided are anti-CLDN18 antibodies or antigen-binding fragments thereof, isolated polynucleotides encoding the same, pharmaceutical compositions comprising the same, and the uses thereof.

19 Claims, 40 Drawing Sheets

Specification includes a Sequence Listing.

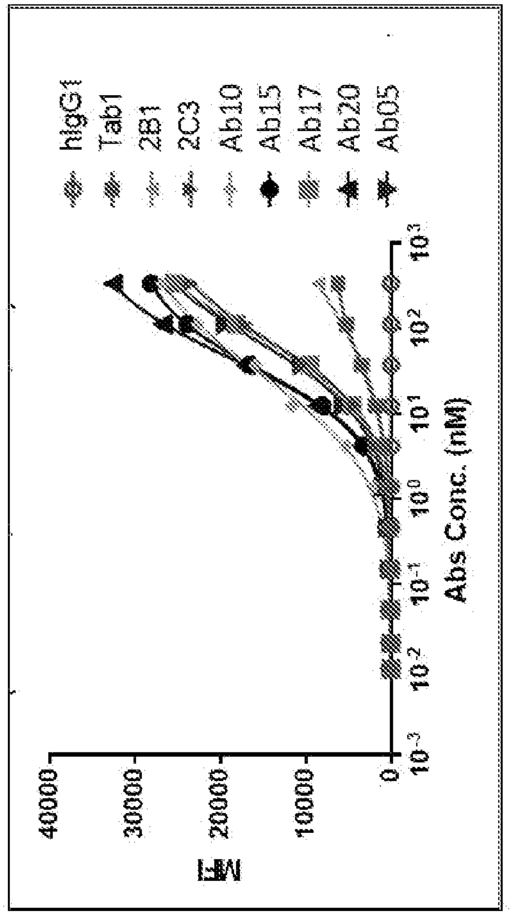
Figure 3B
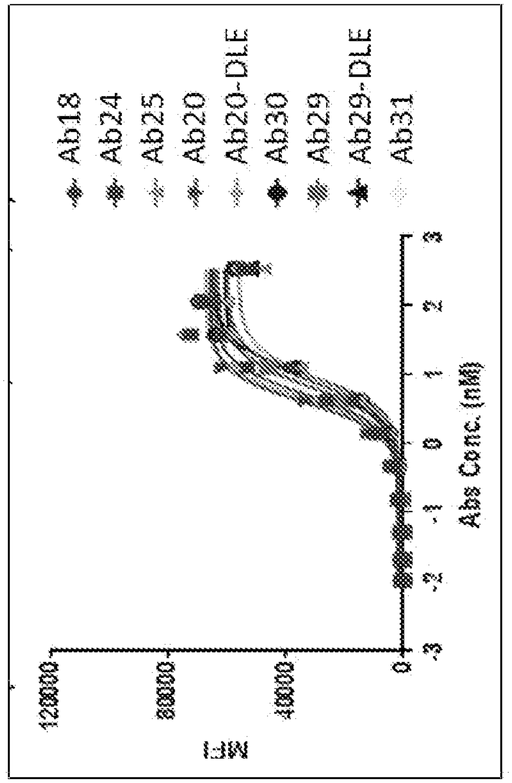

| | TOP (%cytotoxicity) | EC50 (nM) |
|---|---|---|
| hIgG1 | | |
| Tab1 | 52.522 | 809.427 |
| 2C3 | 69.870 | 30.904 |

| | TOP (%cytotoxicity) | EC50 (nM) |
|---|---|---|
| chAb08 | 68.370 | 13.599 |
| chAb11 | 71.147 | 19.413 |
| chAb18 | 75.297 | 35.019 |

| | TOP (%cytotoxicity) | EC50 (nM) |
|---|---|---|
| chAb24 | 70.731 | 12.815 |
| chAb25 | 72.882 | 25.386 |
| chAb30 | 78.080 | 23.170 |

| No. | antibody | Max MFI | EC50(nM) |
|---|---|---|---|
| 1 | hIgG1 | - | - |
| 2 | IMAB362 | 2487.1 | 452.2 |
| 3 | Ab15-chimeric | 36915.5 | 25.11 |
| 4 | Ab15-VH3xVLN1 | 36812.3 | 28.63 |
| 5 | Ab15-VHN1xVL2 | 36752.3 | 32.25 |
| 6 | Ab10-chimeric | 35931.4 | 49.23 |
| 7 | Ab10-VHN1xVLN1 | 34828.8 | 43.84 |
| 8 | Ab10-VH3xVLN1 | 35183 | 60.89 |
| 9 | Ab17-chimeric | 29885 | 47.02 |
| 10 | Ab17-VH5xVLN1 | 30874.1 | 48.89 |
| 11 | Ab17-VH1xVLN1 | 27492.7 | 43.68 |

Figure 7B

| | Ab15 | Ab10 | Ab17 |
|---|---|---|---|
| EC50 | 27.19 | 20.89 | 39.31 |

| | Ab15 | Ab10 | Ab17 | IMB362 |
|---|---|---|---|---|
| EC50 | 5.317 | 5.538 | 10.79 | ~ 7537 |

| Entry | Kinetics model | Immobilized ligand | Analyte 1 Solution | Kinetics Chi² (RU²) | ka (1/Ms) | kd (1/s) | KD (M) |
|---|---|---|---|---|---|---|---|
| 1 | 1:1 binding | 200ug/ml CLDN18.2-biotin | Ab15-VH3xVLN1 | 5.03E-01 | 5.26E+05 | 3.72E-07 | 7.07E-13 |
| 2 | 1:1 binding | 200ug/ml CLDN18.2-biotin | Ab15-VHN1xVL2 | 6.19E-01 | 5.69E+05 | 5.35E-06 | 9.40E-12 |
| 3 | 1:1 binding | 200ug/ml CLDN18.2-biotin | Ab10-VHN1xVLN1 | 6.03E-01 | 5.47E+05 | 7.57E-05 | 1.39E-10 |
| 4 | 1:1 binding | 200ug/ml CLDN18.2-biotin | Ab10-VH3xVLN1 | 3.48E-01 | 4.89E+05 | 2.16E-04 | 4.41E-10 |
| 5 | 1:1 binding | 200ug/ml CLDN18.2-biotin | Ab17-VH5xVLN1 | 1.47E-01 | 5.26E+05 | 2.42E-04 | 4.60E-10 |
| 6 | 1:1 binding | 200ug/ml CLDN18.2-biotin | Ab17-VH1xVLN1 | 1.03E-01 | 4.23E+05 | 2.09E-04 | 4.95E-10 |

Figure 9G

| | Ab15-chimeric-vc-MMAE | Ab15-VH3xVLN1-vc-MMAE | Ab15-VHN1xVL2-vc-MMAE |
|---|---|---|---|
| IC50 | 7.750 | 6.930 | 5.065 |

| | Ab17-chimeric-vc-MMAE | Ab17-VH5xVLN1-vc-MMAE | Ab17-VH1xVLN1-vc-MMAE |
|---|---|---|---|
| IC50 | 7.535 | 6.686 | 8.258 |

ADC cytotoxicity assay on CHOK1-CLDN18.2 cells

| | Ab10-chimeric-vc-MMAE | Ab10-VHN1xVLN1-vc-MMAE | Ab10-VH3xVLN1-vc-MMAE |
|---|---|---|---|
| IC50 | 2.711 | 2.865 | 1.988 |

ADC cytotoxicity assay on CHOK1-CLDN18.2 cells

| | Ab15-VHN1xVL2-vc-MMAE | Ab10-VH3xVLN1-vc-MMAE | Ab17-VH1xVLN1-vc-MMAE | IgG-vc-MMAE |
|---|---|---|---|---|
| IC50 | 4.033 | 6.418 | 8.614 | 266.8 |

| | GAXC031, 2000/well, 120h | |
|---|---|---|
| Samples ID. | **Max inhibition%** | **IC50 (nM)** |
| hIgG1-vc-MMAE | 63.94 | - |
| Ab15-chimeric-vc-MMAE | 96.89 | 0.20 |
| Ab15-VH3xVLN1-vc-MMAE | 97.28 | 0.25 |
| Ab15-VHN1xVL2-vc-MMAE | 97.11 | 0.25 |
| Ab10-chimeric-vc-MMAE | 97.49 | 0.36 |
| Ab10-VHN1xVLN1-vc-MMAE | 97.28 | 0.41 |
| Ab10-VH3xVLN1-vc-MMAE | 97.05 | 0.46 |
| Ab17-chimeric-vc-MMAE | 96.69 | 0.58 |
| Ab17-VH5xVLN1-vc-MMAE | 96.39 | 0.51 |
| Ab17-VH1xVLN1-vc-MMAE | 96.47 | 0.53 |

Figure 10F

SEQUENCE LISTING

```
<160> NUMBER OF SEQ ID NOS: 728

<210> SEQ ID NO 1
<211> LENGTH: 30
<212> TYPE: PRT
<213> ORGANISM: Mus musculus

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr
            20                  25                  30


<210> SEQ ID NO 2
<211> LENGTH: 5
<212> TYPE: PRT
<213> ORGANISM: Mus musculus

<400> SEQUENCE: 2

Ser Tyr Trp Ile Asn
1               5


<210> SEQ ID NO 3
<211> LENGTH: 14
<212> TYPE: PRT
<213> ORGANISM: Mus musculus

<400> SEQUENCE: 3

Trp Val Lys Gln Arg Pro Gly Gln Gly Leu Glu Trp Ile Gly
1               5                   10


<210> SEQ ID NO 4
<211> LENGTH: 17
<212> TYPE: PRT
<213> ORGANISM: Mus musculus

<400> SEQUENCE: 4

Asn Ile Tyr Pro Ser Asp Ser Tyr Thr Asn Tyr Asn Gln Lys Phe Lys
1               5                   10                  15

Asp


<210> SEQ ID NO 5
<211> LENGTH: 32
<212> TYPE: PRT
<213> ORGANISM: Mus musculus

<400> SEQUENCE: 5

Lys Ala Thr Leu Thr Val Asp Lys Ser Ser Ser Thr Ala Tyr Met Gln
1               5                   10                  15

Leu Ser Ser Pro Thr Ser Glu Asp Ser Ala Val Tyr Tyr Cys Thr Arg
            20                  25                  30


<210> SEQ ID NO 6
```

<211> LENGTH: 9
<212> TYPE: PRT
<213> ORGANISM: Mus musculus

<400> SEQUENCE: 6

Ser Trp Arg Gly Asn Ser Phe Asp Tyr
1 5

<210> SEQ ID NO 7
<211> LENGTH: 12
<212> TYPE: PRT
<213> ORGANISM: Mus musculus

<400> SEQUENCE: 7

Trp Gly Gln Gly Thr Thr Leu Thr Val Ser Ser Ala
1 5 10

<210> SEQ ID NO 8
<211> LENGTH: 119
<212> TYPE: PRT
<213> ORGANISM: Mus musculus

<400> SEQUENCE: 8

Gln Val Gln Leu Gln Gln Pro Gly Ala Glu Leu Val Arg Pro Gly Ala
1 5 10 15

Ser Val Lys Leu Ser Cys Lys Ala Ser Gly Tyr Thr Phe Thr Ser Tyr
20 25 30

Trp Ile Asn Trp Val Lys Gln Arg Pro Gly Gln Gly Leu Glu Trp Ile
35 40 45

Gly Asn Ile Tyr Pro Ser Asp Ser Tyr Thr Asn Tyr Asn Gln Lys Phe
50 55 60

Lys Asp Lys Ala Thr Leu Thr Val Asp Lys Ser Ser Ser Thr Ala Tyr
65 70 75 80

Met Gln Leu Ser Ser Pro Thr Ser Glu Asp Ser Ala Val Tyr Tyr Cys
85 90 95

Thr Arg Ser Trp Arg Gly Asn Ser Phe Asp Tyr Trp Gly Gln Gly Thr
100 105 110

Thr Leu Thr Val Ser Ser Ala
115

<210> SEQ ID NO 9
<211> LENGTH: 23
<212> TYPE: PRT
<213> ORGANISM: Mus musculus

<400> SEQUENCE: 9

Asp Ile Val Met Thr Gln Ser Pro Ser Ser Leu Thr Val Thr Ala Gly
1 5 10 15

Glu Lys Val Thr Met Ser Cys
20

<210> SEQ ID NO 10
<211> LENGTH: 17
<212> TYPE: PRT
<213> ORGANISM: Mus musculus

<400> SEQUENCE: 10

Lys Ser Ser Gln Ser Leu Leu Asn Ser Gly Asn Gln Lys Asn Tyr Leu
1 5 10 15

Thr

<210> SEQ ID NO 11
<211> LENGTH: 15
<212> TYPE: PRT
<213> ORGANISM: Mus musculus

<400> SEQUENCE: 11

Trp Tyr Gln Gln Lys Pro Gly Gln Pro Pro Lys Leu Leu Ile Tyr
1 5 10 15

<210> SEQ ID NO 12
<211> LENGTH: 7
<212> TYPE: PRT
<213> ORGANISM: Mus musculus

<400> SEQUENCE: 12

Trp Ala Ser Thr Arg Glu Ser
1 5

<210> SEQ ID NO 13
<211> LENGTH: 32
<212> TYPE: PRT
<213> ORGANISM: Mus musculus

<400> SEQUENCE: 13

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 14
<211> LENGTH: 9
<212> TYPE: PRT
<213> ORGANISM: Mus musculus

<400> SEQUENCE: 14

Gln Asn Asp Tyr Ser Tyr Pro Phe Thr
1 5

<210> SEQ ID NO 15
<211> LENGTH: 9
<212> TYPE: PRT
<213> ORGANISM: Mus musculus

<400> SEQUENCE: 15

Phe Gly Ser Gly Thr Lys Leu Glu Ile
1 5

<210> SEQ ID NO 16
<211> LENGTH: 114
<212> TYPE: PRT
<213> ORGANISM: Mus musculus

<400> SEQUENCE: 16

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr

```
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg


<210> SEQ ID NO 17
<211> LENGTH: 30
<212> TYPE: PRT
<213> ORGANISM: Mus musculus

<400> SEQUENCE: 17

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr
            20                  25                  30


<210> SEQ ID NO 18
<211> LENGTH: 6
<212> TYPE: PRT
<213> ORGANISM: Mus musculus

<400> SEQUENCE: 18

Ser Gly Tyr Tyr Trp Asn
1               5


<210> SEQ ID NO 19
<211> LENGTH: 14
<212> TYPE: PRT
<213> ORGANISM: Mus musculus

<400> SEQUENCE: 19

Trp Ile Arg Gln Phe Pro Gly Asn Lys Leu Glu Trp Met Gly
1               5                   10


<210> SEQ ID NO 20
<211> LENGTH: 16
<212> TYPE: PRT
<213> ORGANISM: Mus musculus

<400> SEQUENCE: 20

Tyr Ile Thr Tyr Asp Gly Ser Asn Asn Tyr Asn Pro Ser Leu Lys Asn
1               5                   10                  15


<210> SEQ ID NO 21
<211> LENGTH: 32
<212> TYPE: PRT
<213> ORGANISM: Mus musculus

<400> SEQUENCE: 21

Arg Ile Ser Ile Thr Arg Asp Thr Ser Lys Asn Gln Phe Phe Leu Lys
1               5                   10                  15

Leu Asn Ser Val Thr Thr Glu Asp Ala Ala Thr Tyr Phe Cys Ala Arg
            20                  25                  30


<210> SEQ ID NO 22
<211> LENGTH: 15
<212> TYPE: PRT
<213> ORGANISM: Mus musculus

<400> SEQUENCE: 22
```

Asp Pro Asn Tyr Tyr Gly Thr Thr Leu Pro Ala Trp Phe Val Tyr
1 5 10 15

<210> SEQ ID NO 23
<211> LENGTH: 11
<212> TYPE: PRT
<213> ORGANISM: Mus musculus

<400> SEQUENCE: 23

Trp Gly Gln Gly Thr Leu Val Thr Val Ser Ala
1 5 10

<210> SEQ ID NO 24
<211> LENGTH: 372
<212> TYPE: DNA
<213> ORGANISM: Mus musculus

<400> SEQUENCE: 24
gatgtacagc ttcaggagtc aggacctggc ctcgtgaaac cttctcagtc tctgtctctc 60
acctgctctg tcactggcta ctccatcacc agtggttatt actggaactg gatccggcag 120
tttccaggaa acaaattgga atggatgggc tacataacct acgatggtag caataactac 180
aacccatctc tcaaaaatcg aatctccatc actcgtgaca catctaagaa ccagtttttc 240
ctgaagttga attctgtgac tactgaggac gcagccacat atttctgtgc aagagatcca 300
aattactacg gtactaccct accggcctgg tttgtttact ggggccaagg gactctggtc 360
actgtctctg ca 372

<210> SEQ ID NO 25
<211> LENGTH: 124
<212> TYPE: PRT
<213> ORGANISM: Mus musculus

<400> SEQUENCE: 25

Asp Val Gln Leu Gln Glu Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Thr Tyr Asp Gly Ser Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Ala Ala Thr Tyr Phe Cys
85 90 95

Ala Arg Asp Pro Asn Tyr Tyr Gly Thr Thr Leu Pro Ala Trp Phe Val
100 105 110

Tyr Trp Gly Gln Gly Thr Leu Val Thr Val Ser Ala
115 120

<210> SEQ ID NO 26
<211> LENGTH: 23
<212> TYPE: PRT
<213> ORGANISM: Mus musculus

<400> SEQUENCE: 26

Asp Ile Val Val Thr Gln Ser His Lys Phe Met Ser Thr Ser Val Gly
1 5 10 15

Asp Arg Val Ser Ile Thr Cys
20

<210> SEQ ID NO 27
<211> LENGTH: 11
<212> TYPE: PRT
<213> ORGANISM: Mus musculus

<400> SEQUENCE: 27

Lys Ala Ser Gln Asp Val Gly Thr Ala Val Ala
1 5 10

<210> SEQ ID NO 28
<211> LENGTH: 15
<212> TYPE: PRT
<213> ORGANISM: Mus musculus

<400> SEQUENCE: 28

Trp Tyr Gln Gln Lys Pro Gly Gln Ser Pro Lys Leu Leu Ile Tyr
1 5 10 15

<210> SEQ ID NO 29
<211> LENGTH: 7
<212> TYPE: PRT
<213> ORGANISM: Mus musculus

<400> SEQUENCE: 29

Trp Ala Ser Thr Arg His Thr
1 5

<210> SEQ ID NO 30
<211> LENGTH: 32
<212> TYPE: PRT
<213> ORGANISM: Mus musculus

<400> SEQUENCE: 30

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Thr Asp Tyr Phe Cys
20 25 30

<210> SEQ ID NO 31
<211> LENGTH: 8
<212> TYPE: PRT
<213> ORGANISM: Mus musculus

<400> SEQUENCE: 31

Gln Gln Tyr Ser Ser Tyr Val Thr
1 5

<210> SEQ ID NO 32
<211> LENGTH: 10
<212> TYPE: PRT
<213> ORGANISM: Mus musculus

<400> SEQUENCE: 32

Phe Gly Ala Gly Thr Lys Leu Glu Leu Lys
1 5 10

<210> SEQ ID NO 33
<211> LENGTH: 318
<212> TYPE: DNA
<213> ORGANISM: Mus musculus

<400> SEQUENCE: 33

```
gacattgtgg tgacccagtc tcacaaattc atgtccacat cagtaggaga cagggtcagc     60

atcacctgca aggccagtca ggatgtgggt actgctgtag cctggtatca acagaaacca    120

gggcaatctc ctaaattact gatttactgg gcatccaccc ggcacactgg agtccctgat    180

cgcttcacag gcagtggatc tgggacagat ttcactctca ccattagcaa tgtgcagtct    240

gaagacttga cagattattt ctgtcagcaa tatagcagct atgtcacgtt cggtgctggg    300

accaagctgg agctgaaa                                                  318


<210> SEQ ID NO 34
<211> LENGTH: 106
<212> TYPE: PRT
<213> ORGANISM: Mus musculus

<400> SEQUENCE: 34

Asp Ile Val Val Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Tyr Val Thr
                85                  90                  95

Phe Gly Ala Gly Thr Lys Leu Glu Leu Lys
            100                 105


<210> SEQ ID NO 35
<211> LENGTH: 30
<212> TYPE: PRT
<213> ORGANISM: Mus musculus

<400> SEQUENCE: 35

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30


<210> SEQ ID NO 36
<211> LENGTH: 5
<212> TYPE: PRT
<213> ORGANISM: Mus musculus

<400> SEQUENCE: 36

Ser Tyr Ala Ile Asn
1               5


<210> SEQ ID NO 37
<211> LENGTH: 14
<212> TYPE: PRT
<213> ORGANISM: Mus musculus

<400> SEQUENCE: 37

Trp Val Arg Gln Pro Pro Gly Lys Gly Leu Glu Trp Leu Gly
1               5                   10
```

<210> SEQ ID NO 38
<211> LENGTH: 16
<212> TYPE: PRT
<213> ORGANISM: Mus musculus

<400> SEQUENCE: 38

Val Ile Trp Thr Gly Gly Gly Thr Asn Tyr Asn Ser Ala Leu Lys Ser
1 5 10 15

<210> SEQ ID NO 39
<211> LENGTH: 32
<212> TYPE: PRT
<213> ORGANISM: Mus musculus

<400> SEQUENCE: 39

Arg Leu Ser Ile Asn Lys Asp Asn Ser Lys Ser Gln Val Phe Leu Lys
1 5 10 15

Met Asn Ser Leu Gln Thr Asp Asp Thr Ala Arg Tyr Tyr Cys Ala Arg
20 25 30

<210> SEQ ID NO 40
<211> LENGTH: 11
<212> TYPE: PRT
<213> ORGANISM: Mus musculus

<400> SEQUENCE: 40

Phe Tyr Asp Gly Tyr Tyr Ser Trp Phe Ala Tyr
1 5 10

<210> SEQ ID NO 41
<211> LENGTH: 11
<212> TYPE: PRT
<213> ORGANISM: Mus musculus

<400> SEQUENCE: 41

Trp Gly Gln Gly Thr Leu Val Thr Val Ser Ala
1 5 10

<210> SEQ ID NO 42
<211> LENGTH: 357
<212> TYPE: DNA
<213> ORGANISM: Mus musculus

<400> SEQUENCE: 42
caggtgcagc tgaaggagtc aggacctggc ctggtggcgc cctcacagag cctgtccatc 60
acatgcactg tctctgggtt ctcattaacc agctatgcta taaactgggt tcgccagcca 120
ccaggaaagg gtctggagtg gcttggagta atttggactg gtggaggcac aaattataat 180
tcagctctca aatccagact gagcatcaac aaagacaact ccaagagtca agttttctta 240
aaaatgaaca gtctgcaaac tgatgacaca gccaggtact actgtgcccg attctatgat 300
ggttactact cctggtttgc ttactggggc caagggactc tggtcactgt ctctgca 357

<210> SEQ ID NO 43
<211> LENGTH: 119
<212> TYPE: PRT
<213> ORGANISM: Mus musculus

<400> SEQUENCE: 43

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr Ser Tyr
20 25 30

```
Ala Ile Asn Trp Val Arg Gln Pro Pro Gly Lys Gly Leu Glu Trp Leu
        35                  40                  45

Gly Val Ile Trp Thr Gly Gly Gly Thr Asn Tyr Asn Ser Ala Leu Lys
    50                  55                  60

Ser Arg Leu Ser Ile Asn Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Phe Tyr Asp Gly Tyr Tyr Ser Trp Phe Ala Tyr Trp Gly Gln Gly
            100                 105                 110

Thr Leu Val Thr Val Ser Ala
        115


<210> SEQ ID NO 44
<211> LENGTH: 23
<212> TYPE: PRT
<213> ORGANISM: Mus musculus

<400> SEQUENCE: 44

Asp Ile Val Met Thr Gln Ser His Lys Phe Met Ser Thr Ser Val Gly
1               5                   10                  15

Asp Arg Val Ser Ile Thr Cys
            20


<210> SEQ ID NO 45
<211> LENGTH: 11
<212> TYPE: PRT
<213> ORGANISM: Mus musculus

<400> SEQUENCE: 45

Lys Ala Ser Gln Asp Val Gly Thr Ala Val Thr
1               5                   10


<210> SEQ ID NO 46
<211> LENGTH: 15
<212> TYPE: PRT
<213> ORGANISM: Mus musculus

<400> SEQUENCE: 46

Trp Tyr Gln Gln Lys Pro Gly Gln Ser Pro Lys Leu Leu Ile Tyr
1               5                   10                  15


<210> SEQ ID NO 47
<211> LENGTH: 7
<212> TYPE: PRT
<213> ORGANISM: Mus musculus

<400> SEQUENCE: 47

Trp Ala Ser Thr Arg His Thr
1               5


<210> SEQ ID NO 48
<211> LENGTH: 32
<212> TYPE: PRT
<213> ORGANISM: Mus musculus

<400> SEQUENCE: 48

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Asp Tyr Phe Cys
            20                  25                  30
```

<210> SEQ ID NO 49
<211> LENGTH: 9
<212> TYPE: PRT
<213> ORGANISM: Mus musculus

<400> SEQUENCE: 49

```
Gln Gln Tyr Ser Ser Tyr Pro Phe Thr
1               5
```

<210> SEQ ID NO 50
<211> LENGTH: 10
<212> TYPE: PRT
<213> ORGANISM: Mus musculus

<400> SEQUENCE: 50

```
Phe Gly Ser Gly Thr Lys Leu Glu Ile Lys
1               5                   10
```

<210> SEQ ID NO 51
<211> LENGTH: 321
<212> TYPE: DNA
<213> ORGANISM: Mus musculus

<400> SEQUENCE: 51

```
gacattgtga tgacccagtc tcacaaattc atgtccacat cagtaggaga cagggtcagc      60

atcacctgca aggccagtca ggatgtgggt actgctgtaa cctggtatca acagaaacca     120

gggcaatctc ctaaactact gatttactgg gcatccaccc ggcacactgg agtccctgat     180

cgcttcacag gcagtggatc tgggacagat ttcactctca ccattagcaa tgtgcagtct     240

gaagacttgg cagattattt ctgtcaacaa tatagtagct atccattcac gttcggctcg     300

gggacaaagt tggaaataaa a                                               321
```

<210> SEQ ID NO 52
<211> LENGTH: 107
<212> TYPE: PRT
<213> ORGANISM: Mus musculus

<400> SEQUENCE: 52

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Thr Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Phe
                85                  90                  95

Thr Phe Gly Ser Gly Thr Lys Leu Glu Ile Lys
            100                 105
```

<210> SEQ ID NO 53
<211> LENGTH: 30
<212> TYPE: PRT
<213> ORGANISM: Mus musculus

<400> SEQUENCE: 53

Glu Val Gln Leu Gln Gln Ser Gly Pro Glu Leu Val Lys Pro Gly Ala
1 5 10 15

Ser Val Lys Ile Ala Cys Lys Ala Ser Gly Tyr Thr Phe Thr
20 25 30

<210> SEQ ID NO 54
<211> LENGTH: 5
<212> TYPE: PRT
<213> ORGANISM: Mus musculus

<400> SEQUENCE: 54

Asp Tyr Asn Met Asp
1 5

<210> SEQ ID NO 55
<211> LENGTH: 14
<212> TYPE: PRT
<213> ORGANISM: Mus musculus

<400> SEQUENCE: 55

Trp Val Lys Gln Ser His Gly Lys Ser Leu Glu Trp Ile Gly
1 5 10

<210> SEQ ID NO 56
<211> LENGTH: 17
<212> TYPE: PRT
<213> ORGANISM: Mus musculus

<400> SEQUENCE: 56

Asn Ile Asn Ser Tyr Tyr Gly Gly Thr Ile Tyr Asn Gln Lys Phe Lys
1 5 10 15

Gly

<210> SEQ ID NO 57
<211> LENGTH: 32
<212> TYPE: PRT
<213> ORGANISM: Mus musculus

<400> SEQUENCE: 57

Lys Ala Thr Leu Thr Val Asp Lys Ser Ser Ser Thr Ala Tyr Met Val
1 5 10 15

Leu Arg Ser Leu Thr Ser Glu Asp Asn Ala Val Tyr Tyr Cys Ala Arg
20 25 30

<210> SEQ ID NO 58
<211> LENGTH: 9
<212> TYPE: PRT
<213> ORGANISM: Mus musculus

<400> SEQUENCE: 58

Pro His Leu Gly Asn Ala Leu Asp Tyr
1 5

<210> SEQ ID NO 59
<211> LENGTH: 11
<212> TYPE: PRT
<213> ORGANISM: Mus musculus

<400> SEQUENCE: 59

Trp Gly Gln Gly Thr Ser Ile Thr Val Ser Ser
1 5 10

<210> SEQ ID NO 60
<211> LENGTH: 354
<212> TYPE: DNA
<213> ORGANISM: Mus musculus

<400> SEQUENCE: 60
gaggtccagc tgcaacagtc tggacctgag ctggtgaagc ctggggcttc agtgaagata 60
gcctgcaagg cttctggata cacattcact gactacaaca tggactgggt gaagcagagc 120
catggaaaga gccttgagtg gattggaaat attaattctt attatggtgg tactatctat 180
aatcagaaat tcaaaggcaa ggccacattg actgtagaca agtcttccag cacagcctac 240
atggtcctcc gcagcctgac atctgaggac aatgcagtct attactgtgc aagaccccac 300
ttggggaatg ctctggacta ctggggtcaa ggaacctcaa tcaccgtctc ctca 354

<210> SEQ ID NO 61
<211> LENGTH: 118
<212> TYPE: PRT
<213> ORGANISM: Mus musculus

<400> SEQUENCE: 61

Glu Val Gln Leu Gln Gln Ser Gly Pro Glu Leu Val Lys Pro Gly Ala
1 5 10 15

Ser Val Lys Ile Ala Cys Lys Ala Ser Gly Tyr Thr Phe Thr Asp Tyr
20 25 30

Asn Met Asp Trp Val Lys Gln Ser His Gly Lys Ser Leu Glu Trp Ile
35 40 45

Gly Asn Ile Asn Ser Tyr Tyr Gly Gly Thr Ile Tyr Asn Gln Lys Phe
50 55 60

Lys Gly Lys Ala Thr Leu Thr Val Asp Lys Ser Ser Ser Thr Ala Tyr
65 70 75 80

Met Val Leu Arg Ser Leu Thr Ser Glu Asp Asn Ala Val Tyr Tyr Cys
85 90 95

Ala Arg Pro His Leu Gly Asn Ala Leu Asp Tyr Trp Gly Gln Gly Thr
100 105 110

Ser Ile Thr Val Ser Ser
115

<210> SEQ ID NO 62
<211> LENGTH: 23
<212> TYPE: PRT
<213> ORGANISM: Mus musculus

<400> SEQUENCE: 62

Asp Ile Val Val Thr Gln Ser Pro Ser Ser Leu Thr Val Thr Pro Gly
1 5 10 15

Glu Lys Val Thr Met Ser Cys
20

<210> SEQ ID NO 63
<211> LENGTH: 17
<212> TYPE: PRT
<213> ORGANISM: Mus musculus

<400> SEQUENCE: 63

Lys Ser Ser Gln Ser Leu Phe Asn Ser Gly Asn Gln Lys Asn Tyr Leu
1 5 10 15

Ser

<210> SEQ ID NO 64
<211> LENGTH: 15
<212> TYPE: PRT
<213> ORGANISM: Mus musculus

<400> SEQUENCE: 64

Trp Tyr Gln Gln Asn Pro Gly Gln Pro Pro Lys Leu Leu Ile Tyr
1 5 10 15

<210> SEQ ID NO 65
<211> LENGTH: 7
<212> TYPE: PRT
<213> ORGANISM: Mus musculus

<400> SEQUENCE: 65

Trp Ala Ser Thr Arg Gln Ser
1 5

<210> SEQ ID NO 66
<211> LENGTH: 32
<212> TYPE: PRT
<213> ORGANISM: Mus musculus

<400> SEQUENCE: 66

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Gly Tyr Tyr Cys
20 25 30

<210> SEQ ID NO 67
<211> LENGTH: 9
<212> TYPE: PRT
<213> ORGANISM: Mus musculus

<400> SEQUENCE: 67

Gln Asn Asp Tyr Ile Phe Pro Leu Thr
1 5

<210> SEQ ID NO 68
<211> LENGTH: 10
<212> TYPE: PRT
<213> ORGANISM: Mus musculus

<400> SEQUENCE: 68

Phe Gly Ala Gly Thr Lys Leu Glu Leu Lys
1 5 10

<210> SEQ ID NO 69
<211> LENGTH: 339
<212> TYPE: DNA
<213> ORGANISM: Mus musculus

<400> SEQUENCE: 69
gacattgtgg tgacacagtc tccatcctcc ctgactgtga caccaggaga aaaggtcact 60
atgagctgca agtccagtca gagtctgttt aacagtggaa atcaaaagaa ctacttgtcc 120
tggtaccagc agaacccagg gcagcctcct aaactgttga tctactgggc atccactagg 180
caatctgggg tccctgatcg cttcactggc agtggatctg gaacagattt cactctcacc 240
atcagcagtg tgcaggctga agacctggca ggttattact gtcagaatga ttatattttt 300
ccgctcacgt tcggtgctgg gaccaagctg gagctgaaa 339

<210> SEQ ID NO 70

<211> LENGTH: 113
<212> TYPE: PRT
<213> ORGANISM: Mus musculus

<400> SEQUENCE: 70

Asp Ile Val Val Thr Gln Ser Pro Ser Ser Leu Thr Val Thr Pro Gly
1 5 10 15

Glu Lys Val Thr Met Ser Cys Lys Ser Ser Gln Ser Leu Phe Asn Ser
20 25 30

Gly Asn Gln Lys Asn Tyr Leu Ser Trp Tyr Gln Gln Asn Pro Gly Gln
35 40 45

Pro Pro Lys Leu Leu Ile Tyr Trp Ala Ser Thr Arg Gln Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Gly Tyr Tyr Cys Gln Asn
85 90 95

Asp Tyr Ile Phe Pro Leu Thr Phe Gly Ala Gly Thr Lys Leu Glu Leu
100 105 110

Lys

<210> SEQ ID NO 71
<211> LENGTH: 30
<212> TYPE: PRT
<213> ORGANISM: Mus musculus

<400> SEQUENCE: 71

Glu Val Gln Leu Gln Gln Ser Gly Pro Glu Leu Val Lys Pro Gly Ala
1 5 10 15

Ser Val Lys Met Ser Cys Met Ala Ser Gly Tyr Thr Phe Thr
20 25 30

<210> SEQ ID NO 72
<211> LENGTH: 5
<212> TYPE: PRT
<213> ORGANISM: Mus musculus

<400> SEQUENCE: 72

Asp Tyr Asn Ile His
1 5

<210> SEQ ID NO 73
<211> LENGTH: 14
<212> TYPE: PRT
<213> ORGANISM: Mus musculus

<400> SEQUENCE: 73

Trp Val Lys Arg Ser His Gly Ser Arg Leu Glu Trp Ile Gly
1 5 10

<210> SEQ ID NO 74
<211> LENGTH: 17
<212> TYPE: PRT
<213> ORGANISM: Mus musculus

<400> SEQUENCE: 74

Tyr Ile Ser Pro Ile Ser Gly Gly Ala Gly Tyr Asn Gln Lys Phe Met
1 5 10 15

Asp

<210> SEQ ID NO 75
<211> LENGTH: 32
<212> TYPE: PRT
<213> ORGANISM: Mus musculus

<400> SEQUENCE: 75

```
Lys Ala Thr Leu Thr Val Asp Lys Ser Ser Asn Thr Ala Tyr Met Glu
1               5                   10                  15

Leu Arg Ser Leu Thr Ser Glu Asp Ser Ala Val Tyr Tyr Cys Thr Arg
            20                  25                  30
```

<210> SEQ ID NO 76
<211> LENGTH: 106
<212> TYPE: PRT
<213> ORGANISM: Mus musculus

<400> SEQUENCE: 76

```
Gln Ile Val Leu Thr Gln Ser Pro Ala Ile Met Ser Ala Ser Pro Gly
1               5                   10                  15

Glu Lys Val Thr Met Thr Cys Thr Ala Ser Leu Ser Leu Asn Tyr Ile
            20                  25                  30

His Trp Tyr Arg Gln Arg Ser Gly Thr Ser Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105
```

<210> SEQ ID NO 77
<211> LENGTH: 11
<212> TYPE: PRT
<213> ORGANISM: Mus musculus

<400> SEQUENCE: 77

```
Trp Gly Gln Gly Thr Thr Leu Thr Val Ser Ser
1               5                   10
```

<210> SEQ ID NO 78
<211> LENGTH: 336
<212> TYPE: DNA
<213> ORGANISM: Mus musculus

<400> SEQUENCE: 78

```
gaggtccagc tgcaacagtc tggacctgag ctggtgaagc ctggggcttc agtgaagatg      60

tcctgcatgg cttctggata cacattcact gactacaaca tacactgggt gaagcggagc     120

catggatccc gtcttgagtg gattggatat attagtccta tcagtggtgg tgctggctac     180

aaccagaagt tcatggacaa ggccacattg actgtagaca agtcctccaa cacagcctac     240

atggagctcc gcagcctgac atcggaagat tctgcagtct attactgtac aagaggggac     300

tactggggcc agggcaccac tctcacagtc tcctca                               336
```

<210> SEQ ID NO 79
<211> LENGTH: 112
<212> TYPE: PRT
<213> ORGANISM: Mus musculus

<400> SEQUENCE: 79

```
Glu Val Gln Leu Gln Gln Ser Gly Pro Glu Leu Val Lys Pro Gly Ala
1               5                   10                  15

Ser Val Lys Met Ser Cys Met Ala Ser Gly Tyr Thr Phe Thr Asp Tyr
            20                  25                  30

Asn Ile His Trp Val Lys Arg Ser His Gly Ser Arg Leu Glu Trp Ile
        35                  40                  45

Gly Tyr Ile Ser Pro Ile Ser Gly Gly Ala Gly Tyr Asn Gln Lys Phe
    50                  55                  60

Met Asp Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Asp Tyr Trp Gly Gln Gly Thr Thr Leu Thr Val Ser Ser
            100                 105                 110
```

<210> SEQ ID NO 80
<211> LENGTH: 23
<212> TYPE: PRT
<213> ORGANISM: Mus musculus

<400> SEQUENCE: 80

```
Asp Ile Val Met Thr Gln Ser Pro Ser Ser Leu Ala Val Thr Val Gly
1               5                   10                  15

Glu Lys Val Thr Met Ser Cys
            20
```

<210> SEQ ID NO 81
<211> LENGTH: 17
<212> TYPE: PRT
<213> ORGANISM: Mus musculus

<400> SEQUENCE: 81

```
Lys Ser Ser Gln Ser Leu Leu Asn Ser Gly Asn Gln Lys Asn Tyr Leu
1               5                   10                  15

Thr
```

<210> SEQ ID NO 82
<211> LENGTH: 15
<212> TYPE: PRT
<213> ORGANISM: Mus musculus

<400> SEQUENCE: 82

```
Trp Tyr Gln Gln Lys Pro Gly Gln Pro Pro Lys Leu Leu Ile Tyr
1               5                   10                  15
```

<210> SEQ ID NO 83
<211> LENGTH: 7
<212> TYPE: PRT
<213> ORGANISM: Mus musculus

<400> SEQUENCE: 83

```
Trp Ala Ser Thr Arg Lys Ser
1               5
```

<210> SEQ ID NO 84
<211> LENGTH: 32
<212> TYPE: PRT
<213> ORGANISM: Mus musculus

<400> SEQUENCE: 84

```
Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Gly Ile Tyr Tyr Cys
            20                  25                  30


<210> SEQ ID NO 85
<211> LENGTH: 9
<212> TYPE: PRT
<213> ORGANISM: Mus musculus

<400> SEQUENCE: 85

Leu Asn Asp Tyr Gly Phe Pro Leu Thr
1               5


<210> SEQ ID NO 86
<211> LENGTH: 10
<212> TYPE: PRT
<213> ORGANISM: Mus musculus

<400> SEQUENCE: 86

Phe Gly Ala Gly Ser Lys Leu Glu Leu Lys
1               5                   10


<210> SEQ ID NO 87
<211> LENGTH: 339
<212> TYPE: DNA
<213> ORGANISM: Mus musculus

<400> SEQUENCE: 87

gacattgtga tgacacagtc tccatcctcc ctggctgtga cagtaggaga gaaggtcact      60

atgagctgca agtccagtca gagtctgtta aacagtggaa atcaaaagaa ctacttgacc     120

tggtatcagc agaaaccagg gcagcctcct aaattgttga tctactgggc atccactagg     180

aaatctgggg tccctgatcg cttcacaggc agtggatctg gaacagattt cactctcacc     240

atcagcagtg tgcaggctga agacctggga atttattact gtctgaatga ttatggtttt     300

ccgctcacgt tcggtgctgg gtccaagctg gagctgaaa                            339


<210> SEQ ID NO 88
<211> LENGTH: 113
<212> TYPE: PRT
<213> ORGANISM: Mus musculus

<400> SEQUENCE: 88

Asp Ile Val Met Thr Gln Ser Pro Ser Ser Leu Ala Val Thr Val Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Gly Ile Tyr Tyr Cys Leu Asn
                85                  90                  95

Asp Tyr Gly Phe Pro Leu Thr Phe Gly Ala Gly Ser Lys Leu Glu Leu
            100                 105                 110

Lys
```

<210> SEQ ID NO 89
<211> LENGTH: 30
<212> TYPE: PRT
<213> ORGANISM: Mus musculus

<400> SEQUENCE: 89

Asp Val Lys Leu Val Glu Ser Gly Glu Asp Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 90
<211> LENGTH: 5
<212> TYPE: PRT
<213> ORGANISM: Mus musculus

<400> SEQUENCE: 90

Asn Tyr Ala Met Ser
1               5

<210> SEQ ID NO 91
<211> LENGTH: 14
<212> TYPE: PRT
<213> ORGANISM: Mus musculus

<400> SEQUENCE: 91

Trp Val Arg Gln Thr Pro Glu Lys Arg Leu Glu Trp Val Ala
1               5                   10

<210> SEQ ID NO 92
<211> LENGTH: 17
<212> TYPE: PRT
<213> ORGANISM: Mus musculus

<400> SEQUENCE: 92

Tyr Val Ser Ser Gly Gly Asp Tyr Ile Tyr Tyr Ala Asp Thr Val Lys
1               5                   10                  15

Gly

<210> SEQ ID NO 93
<211> LENGTH: 32
<212> TYPE: PRT
<213> ORGANISM: Mus musculus

<400> SEQUENCE: 93

Arg Phe Ile Ile Ser Arg Asp Asn Ala Arg Asn Thr Leu Tyr Leu Gln
1               5                   10                  15

Met Asn Ser Leu Arg Ser Glu Asp Thr Ala Met Tyr Tyr Cys Ala Arg
            20                  25                  30

<210> SEQ ID NO 94
<211> LENGTH: 9
<212> TYPE: PRT
<213> ORGANISM: Mus musculus

<400> SEQUENCE: 94

Val Tyr Phe Gly Asn Ser Leu Asp Tyr
1               5

<210> SEQ ID NO 95
<211> LENGTH: 11
<212> TYPE: PRT

```
<213> ORGANISM: Mus musculus

<400> SEQUENCE: 95

Trp Gly Gln Gly Thr Thr Leu Thr Val Ser Ser
1               5                   10


<210> SEQ ID NO 96
<211> LENGTH: 354
<212> TYPE: DNA
<213> ORGANISM: Mus musculus

<400> SEQUENCE: 96

gacgtgaagt tggtggagtc tggggaagac ttagtgaagc ctggagggtc cctgaaactc      60

tcctgtgctg cctctgggtt cactttcagt aactatgcca tgtcttgggt tcgccagact     120

ccagagaaga ggctggagtg ggtcgcatat gttagtagtg gtggtgatta catctactat     180

gcagacactg tgaagggccg attcatcatc tccagagaca atgccaggaa caccctgtac     240

ctgcaaatga acagtctgag gtctgaggac acagccatgt attactgtgc aagagtctac     300

tttggtaact cccttgacta ctggggccaa ggcaccactc tcacagtctc ctca           354


<210> SEQ ID NO 97
<211> LENGTH: 118
<212> TYPE: PRT
<213> ORGANISM: Mus musculus

<400> SEQUENCE: 97

Asp Val Lys Leu Val Glu Ser Gly Glu Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Tyr Val Ser Ser Gly Gly Asp Tyr Ile Tyr Tyr Ala Asp Thr Val
    50                  55                  60

Lys Gly Arg Phe Ile Ile Ser Arg Asp Asn Ala Arg Asn Thr Leu Tyr
65                  70                  75                  80

Leu Gln Met Asn Ser Leu Arg Ser Glu Asp Thr Ala Met Tyr Tyr Cys
                85                  90                  95

Ala Arg Val Tyr Phe Gly Asn Ser Leu Asp Tyr Trp Gly Gln Gly Thr
            100                 105                 110

Thr Leu Thr Val Ser Ser
        115


<210> SEQ ID NO 98
<211> LENGTH: 23
<212> TYPE: PRT
<213> ORGANISM: Mus musculus

<400> SEQUENCE: 98

Asp Ile Val Met Thr Gln Ser Pro Ser Ser Leu Thr Val Thr Ala Gly
1               5                   10                  15

Glu Lys Val Thr Leu Ser Cys
            20


<210> SEQ ID NO 99
<211> LENGTH: 17
<212> TYPE: PRT
<213> ORGANISM: Mus musculus
```

<400> SEQUENCE: 99

Lys Ser Ser Gln Ser Leu Leu Asn Gly Gly Asn Gln Lys Asn Tyr Leu
1               5                   10                  15

Thr

<210> SEQ ID NO 100
<211> LENGTH: 15
<212> TYPE: PRT
<213> ORGANISM: Mus musculus

<400> SEQUENCE: 100

Trp Tyr Gln Gln Arg Pro Gly Gln Pro Pro Lys Leu Leu Ile Tyr
1               5                   10                  15

<210> SEQ ID NO 101
<211> LENGTH: 7
<212> TYPE: PRT
<213> ORGANISM: Mus musculus

<400> SEQUENCE: 101

Trp Ala Ser Thr Arg Glu Ser
1               5

<210> SEQ ID NO 102
<211> LENGTH: 32
<212> TYPE: PRT
<213> ORGANISM: Mus musculus

<400> SEQUENCE: 102

Gly Val Pro Asp Arg Phe Thr Gly Ser Gly Ser Gly Thr Asp Phe Thr
1               5                   10                  15

Leu Ile Ile Ser Ser Val Gln Ala Glu Asp Leu Ala Val Tyr Tyr Cys
            20                  25                  30

<210> SEQ ID NO 103
<211> LENGTH: 9
<212> TYPE: PRT
<213> ORGANISM: Mus musculus

<400> SEQUENCE: 103

Gln Asn Asp Tyr Tyr Tyr Pro Trp Thr
1               5

<210> SEQ ID NO 104
<211> LENGTH: 10
<212> TYPE: PRT
<213> ORGANISM: Mus musculus

<400> SEQUENCE: 104

Phe Gly Gly Gly Thr Lys Leu Glu Ile Lys
1               5                   10

<210> SEQ ID NO 105
<211> LENGTH: 339
<212> TYPE: DNA
<213> ORGANISM: Mus musculus

<400> SEQUENCE: 105
gacattgtga tgacacagtc tccatcctcc ctgactgtga cagcaggaga gaaggtcact     60
ctgagctgca agtccagtca gagtctctta aatggtggaa atcaaaagaa ctacttgacc    120
tggtaccagc agagaccagg acagcctcct aaactgttga tctactgggc atccactagg    180

```
gaatctgggg tccctgatcg cttcacaggc agtggatctg gaacagattt cactctcatc    240

atcagcagtg tgcaggctga agacctggca gtttattact gtcagaatga ttattattat    300

ccgtggacgt tcggtggagg caccaagctg gaaatcaaa                           339


<210> SEQ ID NO 106
<211> LENGTH: 113
<212> TYPE: PRT
<213> ORGANISM: Mus musculus

<400> SEQUENCE: 106

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Leu Asn Gly
            20                  25                  30

Gly Asn Gln Lys Asn Tyr Leu Thr Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ile
65                  70                  75                  80

Ile Ser Ser Val Gln Ala Glu Asp Leu Ala Val Tyr Tyr Cys Gln Asn
                85                  90                  95

Asp Tyr Tyr Tyr Pro Trp Thr Phe Gly Gly Gly Thr Lys Leu Glu Ile
            100                 105                 110

Lys


<210> SEQ ID NO 107
<211> LENGTH: 30
<212> TYPE: PRT
<213> ORGANISM: Mus musculus

<400> SEQUENCE: 107

Glu Val Gln Leu Val Ala Ser Gly Gly Gly Leu Val Lys Pro Gly Gly
1               5                   10                  15

Ser Leu Lys Leu Ser Cys Ala Ala Ser Gly Ile Thr Phe Arg
            20                  25                  30


<210> SEQ ID NO 108
<211> LENGTH: 5
<212> TYPE: PRT
<213> ORGANISM: Mus musculus

<400> SEQUENCE: 108

Ser Tyr Ala Met Ser
1               5


<210> SEQ ID NO 109
<211> LENGTH: 14
<212> TYPE: PRT
<213> ORGANISM: Mus musculus

<400> SEQUENCE: 109

Trp Val Arg Gln Thr Pro Glu Lys Arg Leu Glu Trp Val Ala
1               5                   10


<210> SEQ ID NO 110
<211> LENGTH: 17
<212> TYPE: PRT
<213> ORGANISM: Mus musculus
```

<400> SEQUENCE: 110

Thr Ile Thr Asp Gly Gly Ser Tyr Ile Phe Tyr Pro Asp Asn Val Lys
1 5 10 15

Gly

<210> SEQ ID NO 111
<211> LENGTH: 32
<212> TYPE: PRT
<213> ORGANISM: Mus musculus

<400> SEQUENCE: 111

Arg Phe Thr Ile Ser Gly Asp His Ala Lys Asn Asn Leu Tyr Leu Gln
1 5 10 15

Met Ser His Leu Lys Ser Glu Asp Thr Ala Leu Tyr Phe Cys Val Arg
20 25 30

<210> SEQ ID NO 112
<211> LENGTH: 9
<212> TYPE: PRT
<213> ORGANISM: Mus musculus

<400> SEQUENCE: 112

Leu Tyr Tyr Gly Asn Ser Phe Ala Tyr
1 5

<210> SEQ ID NO 113
<211> LENGTH: 11
<212> TYPE: PRT
<213> ORGANISM: Mus musculus

<400> SEQUENCE: 113

Trp Gly Gln Gly Thr Leu Val Thr Val Ser Ala
1 5 10

<210> SEQ ID NO 114
<211> LENGTH: 354
<212> TYPE: DNA
<213> ORGANISM: Mus musculus

<400> SEQUENCE: 114
gaagtgcagc tggtggcgtc tgggggaggc ttagtgaagc ctggagggtc cctgaaactc 60
tcctgtgcag cctctggaat cactttcaga agttatgcca tgtcttgggt tcgccagact 120
ccggaaaaga ggctggagtg ggtcgcaacc attactgatg gtggtagtta catcttctat 180
ccagacaatg taaagggccg attcaccatc tccggagacc atgccaagaa caacctgtac 240
ctgcaaatga gccatctgaa gtctgaggac acagccttgt atttctgtgt aagactctac 300
tatggaaact cgtttgctta ctggggccaa gggactctgg tcactgtctc tgca 354

<210> SEQ ID NO 115
<211> LENGTH: 118
<212> TYPE: PRT
<213> ORGANISM: Mus musculus

<400> SEQUENCE: 115

Glu Val Gln Leu Val Ala Ser Gly Gly Gly Leu Val Lys Pro Gly Gly
1 5 10 15

Ser Leu Lys Leu Ser Cys Ala Ala Ser Gly Ile Thr Phe Arg Ser Tyr
20 25 30

Ala Met Ser Trp Val Arg Gln Thr Pro Glu Lys Arg Leu Glu Trp Val
35 40 45

```
Ala Thr Ile Thr Asp Gly Gly Ser Tyr Ile Phe Tyr Pro Asp Asn Val
    50                  55                  60

Lys Gly Arg Phe Thr Ile Ser Gly Asp His Ala Lys Asn Asn Leu Tyr
65                  70                  75                  80

Leu Gln Met Ser His Leu Lys Ser Glu Asp Thr Ala Leu Tyr Phe Cys
                85                  90                  95

Val Arg Leu Tyr Tyr Gly Asn Ser Phe Ala Tyr Trp Gly Gln Gly Thr
            100                 105                 110

Leu Val Thr Val Ser Ala
        115


<210> SEQ ID NO 116
<211> LENGTH: 23
<212> TYPE: PRT
<213> ORGANISM: Mus musculus

<400> SEQUENCE: 116

Asp Ile Val Met Thr Gln Ser Pro Ser Ser Leu Thr Val Thr Ala Gly
1               5                   10                  15

Glu Lys Val Thr Leu Asn Cys
            20


<210> SEQ ID NO 117
<211> LENGTH: 17
<212> TYPE: PRT
<213> ORGANISM: Mus musculus

<400> SEQUENCE: 117

Lys Ser Ser Gln Ser Leu Phe Asn Ser Gly Asn Gln Lys Asn Tyr Leu
1               5                   10                  15

Thr


<210> SEQ ID NO 118
<211> LENGTH: 15
<212> TYPE: PRT
<213> ORGANISM: Mus musculus

<400> SEQUENCE: 118

Trp Tyr Gln Gln Lys Pro Gly Gln Pro Pro Lys Leu Leu Ile Tyr
1               5                   10                  15


<210> SEQ ID NO 119
<211> LENGTH: 7
<212> TYPE: PRT
<213> ORGANISM: Mus musculus

<400> SEQUENCE: 119

Trp Ala Ser Thr Arg Glu Ser
1               5


<210> SEQ ID NO 120
<211> LENGTH: 32
<212> TYPE: PRT
<213> ORGANISM: Mus musculus

<400> SEQUENCE: 120

Gly Val Pro Asp Arg Phe Thr Gly Ser Gly Ser Gly Thr Asp Phe Thr
1               5                   10                  15

Leu Thr Phe Ser Ser Val Gln Ala Glu Asp Leu Ala Val Tyr Tyr Cys
            20                  25                  30
```

```
<210> SEQ ID NO 121
<211> LENGTH: 9
<212> TYPE: PRT
<213> ORGANISM: Mus musculus

<400> SEQUENCE: 121

Gln Asn Ala Tyr Ile Tyr Pro Phe Thr
1               5


<210> SEQ ID NO 122
<211> LENGTH: 10
<212> TYPE: PRT
<213> ORGANISM: Mus musculus

<400> SEQUENCE: 122

Phe Gly Ser Gly Thr Lys Leu Glu Ile Lys
1               5                   10


<210> SEQ ID NO 123
<211> LENGTH: 339
<212> TYPE: DNA
<213> ORGANISM: Mus musculus

<400> SEQUENCE: 123

gacattgtga tgacacagtc tccatcctcc ctgactgtga cagcaggaga gaaggtcact      60

ttgaactgca agtccagtca gagtctgttc aacagtggaa atcaaaagaa ctacttgacc     120

tggtaccagc agaaaccagg gcagcctcct aaactgttga tctactgggc atccactagg     180

gaatctgggg tccctgatcg cttcacaggc agtggatctg gaacagattt cactctcacc     240

ttcagcagtg tgcaggctga agacctggca gtttattact gtcagaatgc ttatatttat     300

ccattcacgt tcggctcggg gacaaaattg gaaataaaa                            339


<210> SEQ ID NO 124
<211> LENGTH: 113
<212> TYPE: PRT
<213> ORGANISM: Mus musculus

<400> SEQUENCE: 124

Asp Ile Val Met Thr Gln Ser Pro Ser Ser Leu Thr Val Thr Ala Gly
1               5                   10                  15

Glu Lys Val Thr Leu Asn Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Phe Ser Ser Val Gln Ala Glu Asp Leu Ala Val Tyr Tyr Cys Gln Asn
                85                  90                  95

Ala Tyr Ile Tyr Pro Phe Thr Phe Gly Ser Gly Thr Lys Leu Glu Ile
            100                 105                 110

Lys


<210> SEQ ID NO 125
<211> LENGTH: 30
<212> TYPE: PRT
<213> ORGANISM: Mus musculus
```

<400> SEQUENCE: 125

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr
            20                  25                  30

<210> SEQ ID NO 126
<211> LENGTH: 5
<212> TYPE: PRT
<213> ORGANISM: Mus musculus

<400> SEQUENCE: 126

Asp Tyr Phe Met Asn
1               5

<210> SEQ ID NO 127
<211> LENGTH: 14
<212> TYPE: PRT
<213> ORGANISM: Mus musculus

<400> SEQUENCE: 127

Trp Val Lys Gln Ser His Gly Lys Gly Leu Glu Trp Ile Gly
1               5                   10

<210> SEQ ID NO 128
<211> LENGTH: 17
<212> TYPE: PRT
<213> ORGANISM: Mus musculus

<400> SEQUENCE: 128

Arg Ile Asn Pro Tyr Asn Gly Asp Thr Phe Tyr Asn Gln Lys Phe Lys
1               5                   10                  15

Gly

<210> SEQ ID NO 129
<211> LENGTH: 31
<212> TYPE: PRT
<213> ORGANISM: Mus musculus

<400> SEQUENCE: 129

Lys Ala Thr Leu Thr Val Asp Lys Ser Ser Ser Thr Ala His Met Glu
1               5                   10                  15

Leu Leu Ser Leu Thr Ser Glu Asp Phe Ala Val Tyr Tyr Cys Ala
            20                  25                  30

<210> SEQ ID NO 130
<211> LENGTH: 11
<212> TYPE: PRT
<213> ORGANISM: Mus musculus

<400> SEQUENCE: 130

Leu Tyr Asp Gly Tyr Trp Gly Ala Phe Val Tyr
1               5                   10

<210> SEQ ID NO 131
<211> LENGTH: 11
<212> TYPE: PRT
<213> ORGANISM: Mus musculus

<400> SEQUENCE: 131

Trp Gly Gln Gly Thr Leu Val Thr Val Ser Ala
1               5                   10

<210> SEQ ID NO 132
<211> LENGTH: 357
<212> TYPE: DNA
<213> ORGANISM: Mus musculus

<400> SEQUENCE: 132
gaggttcagc tgcagcagtc tggacctgag ctggtgaagc ctggggcttc agtgaagata 60
tcctgcaagg cttctggtta ctcatttact gactacttta tgaactgggt gaagcagagc 120
catggaaagg gccttgagtg gattggacgt attaatcctt acaatggtga tactttctac 180
aaccagaagt tcaagggcaa ggccacattg actgtagaca aatcctctag cacagcccac 240
atggagctcc tgagcctgac atctgaggac tttgcagtct attattgtgc cctctatgat 300
ggttactggg gggcttttgt ttactggggc caagggactc tggtcactgt ctctgca 357

<210> SEQ ID NO 133
<211> LENGTH: 119
<212> TYPE: PRT
<213> ORGANISM: Mus musculus

<400> SEQUENCE: 133

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Ser Phe Thr Asp Tyr
20 25 30

Phe Met Asn Trp Val Lys Gln Ser His Gly Lys Gly Leu Glu Trp Ile
35 40 45

Gly Arg Ile Asn Pro Tyr Asn Gly Asp Thr Phe Tyr Asn Gln Lys Phe
50 55 60

Lys Gly Lys Ala Thr Leu Thr Val Asp Lys Ser Ser Ser Thr Ala His
65 70 75 80

Met Glu Leu Leu Ser Leu Thr Ser Glu Asp Phe Ala Val Tyr Tyr Cys
85 90 95

Ala Leu Tyr Asp Gly Tyr Trp Gly Ala Phe Val Tyr Trp Gly Gln Gly
100 105 110

Thr Leu Val Thr Val Ser Ala
115

<210> SEQ ID NO 134
<211> LENGTH: 23
<212> TYPE: PRT
<213> ORGANISM: Mus musculus

<400> SEQUENCE: 134

Asp Ile Gln Met Thr Gln Ser Pro Ala Ser Leu Ser Val Phe Val Gly
1 5 10 15

Glu Thr Val Thr Ile Thr Cys
20

<210> SEQ ID NO 135
<211> LENGTH: 11
<212> TYPE: PRT
<213> ORGANISM: Mus musculus

<400> SEQUENCE: 135

Arg Ala Ser Glu Asn Ile Tyr Ser Asn Leu Ala
1 5 10

<210> SEQ ID NO 136

<211> LENGTH: 15
<212> TYPE: PRT
<213> ORGANISM: Mus musculus

<400> SEQUENCE: 136

Trp Tyr Gln Gln Lys Gln Gly Lys Ser Pro Gln Leu Leu Val Tyr
1 5 10 15

<210> SEQ ID NO 137
<211> LENGTH: 7
<212> TYPE: PRT
<213> ORGANISM: Mus musculus

<400> SEQUENCE: 137

Ala Ala Thr Asn Leu Ala Asp
1 5

<210> SEQ ID NO 138
<211> LENGTH: 32
<212> TYPE: PRT
<213> ORGANISM: Mus musculus

<400> SEQUENCE: 138

Gly Val Pro Ser Arg Phe Ser Gly Ser Gly Ser Gly Thr Gln Tyr Ser
1 5 10 15

Leu Lys Ile Asn Ser Leu Gln Ser Glu Asp Phe Gly Ser Tyr Tyr Cys
20 25 30

<210> SEQ ID NO 139
<211> LENGTH: 9
<212> TYPE: PRT
<213> ORGANISM: Mus musculus

<400> SEQUENCE: 139

Gln His Phe Trp Gly Thr Pro Leu Thr
1 5

<210> SEQ ID NO 140
<211> LENGTH: 10
<212> TYPE: PRT
<213> ORGANISM: Mus musculus

<400> SEQUENCE: 140

Phe Gly Ala Gly Thr Lys Leu Glu Leu Lys
1 5 10

<210> SEQ ID NO 141
<211> LENGTH: 321
<212> TYPE: DNA
<213> ORGANISM: Mus musculus

<400> SEQUENCE: 141
gacatccaga tgactcagtc tccagcctcc ctctctgtat ttgtgggaga aactgtcacc 60
atcacatgtc gagcaagtga gaatatttac agtaatttag catggtatca gcagaaacag 120
ggaaaatctc ctcagctcct ggtctatgct gcaacaaact tagcagatgg tgtgccatca 180
aggttcagtg gcagtggatc aggcacacag tattccctca agatcaacag cctgcagtct 240
gaagattttg ggagttatta ctgtcaacat ttttggggta ctccgctcac gttcggtgct 300
gggaccaagc tggagctgaa a 321

<210> SEQ ID NO 142
<211> LENGTH: 107

<212> TYPE: PRT
<213> ORGANISM: Mus musculus

<400> SEQUENCE: 142

```
Asp Ile Gln Met Thr Gln Ser Pro Ala Ser Leu Ser Val Phe Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Leu
                85                  90                  95

Thr Phe Gly Ala Gly Thr Lys Leu Glu Leu Lys
            100                 105
```

<210> SEQ ID NO 143
<211> LENGTH: 30
<212> TYPE: PRT
<213> ORGANISM: Mus musculus

<400> SEQUENCE: 143

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr
            20                  25                  30
```

<210> SEQ ID NO 144
<211> LENGTH: 5
<212> TYPE: PRT
<213> ORGANISM: Mus musculus

<400> SEQUENCE: 144

```
Ser Tyr Leu Leu His
1               5
```

<210> SEQ ID NO 145
<211> LENGTH: 14
<212> TYPE: PRT
<213> ORGANISM: Mus musculus

<400> SEQUENCE: 145

```
Trp Val Lys Gln Arg Pro Gly Gln Gly Leu Glu Trp Ile Gly
1               5                   10
```

<210> SEQ ID NO 146
<211> LENGTH: 17
<212> TYPE: PRT
<213> ORGANISM: Mus musculus

<400> SEQUENCE: 146

```
Met Ile His Pro Asn Gly Gly Ser Thr Asn Tyr Asn Glu Lys Phe Lys
1               5                   10                  15

Thr
```

<210> SEQ ID NO 147
<211> LENGTH: 32
<212> TYPE: PRT

<213> ORGANISM: Mus musculus

<400> SEQUENCE: 147

Lys Ala Thr Leu Thr Val Asp Lys Ser Ser Ser Thr Ala Tyr Met Gln
1 5 10 15

Leu Ser Ser Leu Thr Ser Glu Asp Ser Ala Val Tyr Tyr Cys Ala Pro
20 25 30

<210> SEQ ID NO 148
<211> LENGTH: 9
<212> TYPE: PRT
<213> ORGANISM: Mus musculus

<400> SEQUENCE: 148

Val Tyr Phe Gly Asn Ser Phe Ala Tyr
1 5

<210> SEQ ID NO 149
<211> LENGTH: 11
<212> TYPE: PRT
<213> ORGANISM: Mus musculus

<400> SEQUENCE: 149

Trp Gly Gln Gly Thr Leu Val Thr Val Ser Ala
1 5 10

<210> SEQ ID NO 150
<211> LENGTH: 354
<212> TYPE: DNA
<213> ORGANISM: Mus musculus

<400> SEQUENCE: 150
caggtccaac tgcagcagcc tggggctgag ttggtaaagc ctggggcttc agtgaagttg 60
tcctgcaagg cttctggcta cactttcacc agctacttac tacactgggt gaaacagagg 120
cctggacaag gccttgagtg gattggaatg attcatccta atggtggtag tactaactac 180
aatgagaagt tcaagaccaa ggccacactg actgtagaca aatcctccag cacagcctac 240
atgcaactca gcagcctgac atctgaggac tctgcggtct attactgtgc ccctgtctac 300
tttggtaact cgtttgctta ctggggccaa gggactctgg tcactgtctc tgca 354

<210> SEQ ID NO 151
<211> LENGTH: 118
<212> TYPE: PRT
<213> ORGANISM: Mus musculus

<400> SEQUENCE: 151

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Leu Leu His Trp Val Lys Gln Arg Pro Gly Gln Gly Leu Glu Trp Ile
35 40 45

Gly Met Ile His Pro Asn Gly Gly Ser Thr Asn Tyr Asn Glu Lys Phe
50 55 60

Lys Thr Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Pro Val Tyr Phe Gly Asn Ser Phe Ala Tyr Trp Gly Gln Gly Thr

```
            100                 105                 110

Leu Val Thr Val Ser Ala
        115


<210> SEQ ID NO 152
<211> LENGTH: 23
<212> TYPE: PRT
<213> ORGANISM: Mus musculus

<400> SEQUENCE: 152

Asp Ile Val Met Thr Gln Ser Pro Ser Ser Leu Thr Val Thr Ala Gly
1               5                   10                  15

Glu Lys Val Thr Met Ser Cys
            20


<210> SEQ ID NO 153
<211> LENGTH: 17
<212> TYPE: PRT
<213> ORGANISM: Mus musculus

<400> SEQUENCE: 153

Lys Ser Ser Gln Ser Leu Leu Asn Ser Gly Asn Gln Lys Asn Tyr Leu
1               5                   10                  15

Thr


<210> SEQ ID NO 154
<211> LENGTH: 15
<212> TYPE: PRT
<213> ORGANISM: Mus musculus

<400> SEQUENCE: 154

Trp Tyr Gln Gln Lys Pro Gly Gln Pro Pro Lys Leu Leu Ile Tyr
1               5                   10                  15


<210> SEQ ID NO 155
<211> LENGTH: 7
<212> TYPE: PRT
<213> ORGANISM: Mus musculus

<400> SEQUENCE: 155

Trp Ala Ser Thr Arg Glu Ser
1               5


<210> SEQ ID NO 156
<211> LENGTH: 32
<212> TYPE: PRT
<213> ORGANISM: Mus musculus

<400> SEQUENCE: 156

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 157
<211> LENGTH: 9
<212> TYPE: PRT
<213> ORGANISM: Mus musculus

<400> SEQUENCE: 157

Gln Asn Asp Tyr Tyr Tyr Pro Phe Thr
1               5
```

<210> SEQ ID NO 158
<211> LENGTH: 10
<212> TYPE: PRT
<213> ORGANISM: Mus musculus

<400> SEQUENCE: 158

Phe Gly Ser Gly Thr Lys Leu Glu Lys Lys
1               5                   10

<210> SEQ ID NO 159
<211> LENGTH: 339
<212> TYPE: DNA
<213> ORGANISM: Mus musculus

<400> SEQUENCE: 159
gacattgtga tgacacagtc tccatcctcc ctgactgtga cagcaggaga gaaggtcact 60
atgagctgca agtccagtca gagtctgtta aacagtggaa atcaaaagaa ctacttgacc 120
tggtaccagc aaaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatga ttattattat 300
ccattcacgt tcggttcggg gacaaagttg gaaaaaaaa 339

<210> SEQ ID NO 160
<211> LENGTH: 113
<212> TYPE: PRT
<213> ORGANISM: Mus musculus

<400> SEQUENCE: 160

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Phe Thr Phe Gly Ser Gly Thr Lys Leu Glu Lys
            100                 105                 110

Lys

<210> SEQ ID NO 161
<211> LENGTH: 107
<212> TYPE: PRT
<213> ORGANISM: Mus musculus

<400> SEQUENCE: 161

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr His Gln Lys Pro Gly Gln Ser Pro Lys Leu Leu Ile
        35                  40                  45

```
Tyr Ser Ala Ser Asn Arg Tyr Thr Gly Val Pro Asp Arg Phe Ile Gly
    50                  55                  60

Ser Gly Ser Gly Thr Asp Phe Thr Leu Thr Ile Ser Asn Val Gln Ser
65                  70                  75                  80

Glu Asp Leu Gly Asn Tyr Phe Cys Gln Gln Tyr Ile Asn Tyr Leu Leu
                85                  90                  95

Thr Phe Gly Ser Gly Thr Lys Leu Glu Ile Lys
            100                 105


<210> SEQ ID NO 162
<211> LENGTH: 30
<212> TYPE: PRT
<213> ORGANISM: Mus musculus

<400> SEQUENCE: 162

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30


<210> SEQ ID NO 163
<211> LENGTH: 5
<212> TYPE: PRT
<213> ORGANISM: Mus musculus

<400> SEQUENCE: 163

Asn Tyr Trp Met Asn
1               5


<210> SEQ ID NO 164
<211> LENGTH: 14
<212> TYPE: PRT
<213> ORGANISM: Mus musculus

<400> SEQUENCE: 164

Trp Val Arg Gln Tyr Pro Glu Gln Gly Leu Glu Trp Val Ala
1               5                   10


<210> SEQ ID NO 165
<211> LENGTH: 19
<212> TYPE: PRT
<213> ORGANISM: Mus musculus

<400> SEQUENCE: 165

Gln Ile Arg Leu Asn Ser Asp Asn Tyr Ala Thr His Tyr Ala Glu Ser
1               5                   10                  15

Val Lys Gly


<210> SEQ ID NO 166
<211> LENGTH: 32
<212> TYPE: PRT
<213> ORGANISM: Mus musculus

<400> SEQUENCE: 166

Arg Phe Thr Ile Ser Arg Asp Asp Ser Arg Ser Thr Val Tyr Leu Gln
1               5                   10                  15

Met Asn Asn Leu Arg Ala Glu Asp Thr Gly Ile Tyr Tyr Cys Thr Gly
            20                  25                  30


<210> SEQ ID NO 167
<211> LENGTH: 4
<212> TYPE: PRT
```

<213> ORGANISM: Mus musculus

<400> SEQUENCE: 167

Gly Gly Glu Tyr
1

<210> SEQ ID NO 168
<211> LENGTH: 11
<212> TYPE: PRT
<213> ORGANISM: Mus musculus

<400> SEQUENCE: 168

Trp Gly Gln Gly Thr Thr Leu Thr Val Ser Ser
1 5 10

<210> SEQ ID NO 169
<211> LENGTH: 345
<212> TYPE: DNA
<213> ORGANISM: Mus musculus

<400> SEQUENCE: 169
gaagtgaagc ttgaggagtc tggaggaggc ttggtgcaac ctggaggatc catgaaactc 60
tcctgtgttg cctctggatt cactttcagt aactactgga tgaactgggt ccgccagtat 120
ccagagcagg ggcttgagtg ggttgctcaa attagattga attctgataa ttatgcaacg 180
cattatgcgg agtctgtgaa agggaggttc accatctcaa gagatgattc cagaagtact 240
gtctacctac aaatgaacaa cttaagggct gaagacactg gaatttatta ctgcacaggc 300
gggggggagt actggggcca aggcaccact ctcacagtct cctca 345

<210> SEQ ID NO 170
<211> LENGTH: 115
<212> TYPE: PRT
<213> ORGANISM: Mus musculus

<400> SEQUENCE: 170

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser Asn Tyr
20 25 30

Trp Met Asn Trp Val Arg Gln Tyr Pro Glu Gln Gly Leu Glu Trp Val
35 40 45

Ala Gln Ile Arg Leu Asn Ser Asp Asn Tyr Ala Thr His Tyr Ala Glu
50 55 60

Ser Val Lys Gly Arg Phe Thr Ile Ser Arg Asp Asp Ser Arg Ser Thr
65 70 75 80

Val Tyr Leu Gln Met Asn Asn Leu Arg Ala Glu Asp Thr Gly Ile Tyr
85 90 95

Tyr Cys Thr Gly Gly Gly Glu Tyr Trp Gly Gln Gly Thr Thr Leu Thr
100 105 110

Val Ser Ser
115

<210> SEQ ID NO 171
<211> LENGTH: 23
<212> TYPE: PRT
<213> ORGANISM: Mus musculus

<400> SEQUENCE: 171

Asp Ile Val Met Thr Gln Ser Gln Lys Phe Met Ser Thr Thr Ile Gly 1 5 10 15

Asp Arg Val Ser Ile Thr Cys
20

<210> SEQ ID NO 172
<211> LENGTH: 11
<212> TYPE: PRT
<213> ORGANISM: Mus musculus

<400> SEQUENCE: 172

Lys Ala Ser Gln Asn Val Asp Thr Ala Val Ala
1 5 10

<210> SEQ ID NO 173
<211> LENGTH: 15
<212> TYPE: PRT
<213> ORGANISM: Mus musculus

<400> SEQUENCE: 173

Trp Tyr Gln Gln Lys Pro Gly Gln Ser Pro Lys Leu Leu Ile Tyr
1 5 10 15

<210> SEQ ID NO 174
<211> LENGTH: 7
<212> TYPE: PRT
<213> ORGANISM: Mus musculus

<400> SEQUENCE: 174

Ser Ala Ser Thr Arg Tyr Thr
1 5

<210> SEQ ID NO 175
<211> LENGTH: 32
<212> TYPE: PRT
<213> ORGANISM: Mus musculus

<400> SEQUENCE: 175

Gly Val Pro Asp Arg Phe Thr Gly Ser Gly Ser Gly Thr Asp Phe Thr
1 5 10 15

Leu Thr Ile Ser Asn Met Gln Ser Glu Asp Leu Ala Asp Tyr Phe Cys
20 25 30

<210> SEQ ID NO 176
<211> LENGTH: 9
<212> TYPE: PRT
<213> ORGANISM: Mus musculus

<400> SEQUENCE: 176

Gln Gln Tyr Ile Ser Tyr Gln Leu Thr
1 5

<210> SEQ ID NO 177
<211> LENGTH: 10
<212> TYPE: PRT
<213> ORGANISM: Mus musculus

<400> SEQUENCE: 177

Phe Gly Ala Gly Thr Lys Leu Glu Leu Lys
1 5 10

<210> SEQ ID NO 178
<211> LENGTH: 321
<212> TYPE: DNA
<213> ORGANISM: Mus musculus

<400> SEQUENCE: 178

```
gacattgtga tgacccagtc tcaaaaattc atgtccacaa caataggaga cagggtcagc      60
atcacctgca aggccagtca gaatgtggat actgctgtag cctggtatca acagaaacca     120
ggacaatctc ctaaactact gatttactca gcatccactc ggtacactgg agtccctgat     180
cgcttcacag gcagtggatc tgggacagat ttcactctca ccattagtaa tatgcagtct     240
gaagacctgg cagattattt ctgtcagcaa tatatcagtt atcagctcac gttcggtgct     300
gggaccaagc tggagctgaa a                                               321
```

<210> SEQ ID NO 179
<211> LENGTH: 107
<212> TYPE: PRT
<213> ORGANISM: Mus musculus

<400> SEQUENCE: 179

```
Asp Ile Val Met Thr Gln Ser Gln Lys Phe Met Ser Thr Thr Ile Gly
1               5                   10                  15

Asp Arg Val Ser Ile Thr Cys Lys Ala Ser Gln Asn Val Asp Thr Ala
            20                  25                  30

Val Ala Trp Tyr Gln Gln Lys Pro Gly Gln Ser Pro Lys Leu Leu Ile
        35                  40                  45

Tyr Ser Ala Ser Thr Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ile Ser Tyr Gln Leu
                85                  90                  95

Thr Phe Gly Ala Gly Thr Lys Leu Glu Leu Lys
            100                 105
```

<210> SEQ ID NO 180
<211> LENGTH: 30
<212> TYPE: PRT
<213> ORGANISM: Mus musculus

<400> SEQUENCE: 180

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30
```

<210> SEQ ID NO 181
<211> LENGTH: 5
<212> TYPE: PRT
<213> ORGANISM: Mus musculus

<400> SEQUENCE: 181

```
Asn Tyr Gly Met Ser
1               5
```

<210> SEQ ID NO 182
<211> LENGTH: 14
<212> TYPE: PRT
<213> ORGANISM: Mus musculus

<400> SEQUENCE: 182

```
Trp Val Lys Gln Ala Pro Gly Lys Gly Leu Lys Trp Met Gly
1               5                   10
```

<210> SEQ ID NO 183
<211> LENGTH: 17
<212> TYPE: PRT
<213> ORGANISM: Mus musculus

<400> SEQUENCE: 183

Trp Ile Asn Thr Tyr Ser Gly Val Pro Thr Tyr Ala Asp Asp Phe Lys
1 5 10 15

Gly

<210> SEQ ID NO 184
<211> LENGTH: 32
<212> TYPE: PRT
<213> ORGANISM: Mus musculus

<400> SEQUENCE: 184

Arg Phe Val Phe Ser Leu Glu Ala Ser Ala Ser Thr Ala Tyr Leu Gln
1 5 10 15

Ile Asn Asn Leu Lys Asn Glu Asp Ala Ala Thr Tyr Phe Cys Ser Arg
20 25 30

<210> SEQ ID NO 185
<211> LENGTH: 10
<212> TYPE: PRT
<213> ORGANISM: Mus musculus

<400> SEQUENCE: 185

Trp Ser Gly Pro Asp Pro Leu Glu Asp His
1 5 10

<210> SEQ ID NO 186
<211> LENGTH: 11
<212> TYPE: PRT
<213> ORGANISM: Mus musculus

<400> SEQUENCE: 186

Trp Gly Gln Gly Thr Thr Leu Thr Val Ser Ser
1 5 10

<210> SEQ ID NO 187
<211> LENGTH: 357
<212> TYPE: DNA
<213> ORGANISM: Mus musculus

<400> SEQUENCE: 187
cagatccagt tggtacagtc tggacctgag ctgaagaagc ctggagagac agtcaagatc 60
tcctgcaagg cttctggata taccttcaca aactatggaa tgagttgggt gaaacaggct 120
ccaggaaagg gattaaagtg gatgggctgg ataaacacct attctggagt gccaacatat 180
gctgatgact tcaagggacg gtttgtcttc tctttggaag cctctgccag cactgcctat 240
ttgcagatca acaacctcaa aaatgaggac gcggctacat atttctgttc aaggtggtct 300
gggcccgatc cgcttgagga ccactggggc caaggcacca ctctcacagt ctcctca 357

<210> SEQ ID NO 188
<211> LENGTH: 119
<212> TYPE: PRT
<213> ORGANISM: Mus musculus

<400> SEQUENCE: 188

Gln Ile Gln Leu Val Gln Ser Gly Pro Glu Leu Lys Lys Pro Gly Glu

```
1               5                   10                  15

Thr Val Lys Ile Ser Cys Lys Ala Ser Gly Tyr Thr Phe Thr Asn Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Glu Ala Ser Ala Ser Thr Ala Tyr
65                  70                  75                  80

Leu Gln Ile Asn Asn Leu Lys Asn Glu Asp Ala Ala Thr Tyr Phe Cys
                85                  90                  95

Ser Arg Trp Ser Gly Pro Asp Pro Leu Glu Asp His Trp Gly Gln Gly
            100                 105                 110

Thr Thr Leu Thr Val Ser Ser
        115


<210> SEQ ID NO 189
<211> LENGTH: 23
<212> TYPE: PRT
<213> ORGANISM: Mus musculus

<400> SEQUENCE: 189

Gln Ile Val Leu Thr Gln Ser Pro Ala Ile Met Ser Ala Ser Pro Gly
1               5                   10                  15

Glu Lys Val Thr Met Thr Cys
            20


<210> SEQ ID NO 190
<211> LENGTH: 10
<212> TYPE: PRT
<213> ORGANISM: Mus musculus

<400> SEQUENCE: 190

Thr Ala Ser Leu Ser Leu Asn Tyr Ile His
1               5                   10


<210> SEQ ID NO 191
<211> LENGTH: 15
<212> TYPE: PRT
<213> ORGANISM: Mus musculus

<400> SEQUENCE: 191

Trp Tyr Arg Gln Arg Ser Gly Thr Ser Pro Lys Arg Trp Ile Tyr
1               5                   10                  15


<210> SEQ ID NO 192
<211> LENGTH: 7
<212> TYPE: PRT
<213> ORGANISM: Mus musculus

<400> SEQUENCE: 192

Asp Thr Ser Lys Leu Ala Ser
1               5


<210> SEQ ID NO 193
<211> LENGTH: 32
<212> TYPE: PRT
<213> ORGANISM: Mus musculus

<400> SEQUENCE: 193

Gly Val Pro Ser Arg Phe Ser Gly Ser Gly Ser Gly Thr Ser Tyr Ser
```

```
1               5                   10                  15

Leu Thr Ile Ser Ser Met Glu Ala Glu Asp Ala Ala Thr Tyr Tyr Cys
            20                  25                  30


<210> SEQ ID NO 194
<211> LENGTH: 9
<212> TYPE: PRT
<213> ORGANISM: Mus musculus

<400> SEQUENCE: 194

Gln Gln Trp Ser Ser Asn Pro Trp Thr
1               5


<210> SEQ ID NO 195
<211> LENGTH: 10
<212> TYPE: PRT
<213> ORGANISM: Mus musculus

<400> SEQUENCE: 195

Phe Gly Gly Gly Thr Lys Leu Glu Ile Lys
1               5                   10


<210> SEQ ID NO 196
<211> LENGTH: 318
<212> TYPE: DNA
<213> ORGANISM: Mus musculus

<400> SEQUENCE: 196

caaattgttc tcacccagtc tccagcaatc atgtctgcat ctccagggga gaaggtcacc     60

atgacctgca ctgccagttt aagtctaaat tacattcact ggtaccgaca gaggtcaggc    120

acctccccca aacgatggat ttatgacaca tccaagctgg cttctggagt cccttctcgt    180

ttcagtggca gtggatctgg gacctcttac tctctcacaa tcagcagcat ggaggctgaa    240

gatgctgcca cttattactg ccagcagtgg agtagtaacc cctggacgtt cggtggaggc    300

accaagctgg aaatcaaa                                                  318


<210> SEQ ID NO 197
<211> LENGTH: 30
<212> TYPE: PRT
<213> ORGANISM: Mus musculus

<400> SEQUENCE: 197

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr
            20                  25                  30


<210> SEQ ID NO 198
<211> LENGTH: 5
<212> TYPE: PRT
<213> ORGANISM: Mus musculus

<400> SEQUENCE: 198

Asp Tyr Asn Met His
1               5


<210> SEQ ID NO 199
<211> LENGTH: 14
<212> TYPE: PRT
<213> ORGANISM: Mus musculus

<400> SEQUENCE: 199
```

Trp Val Lys Leu Ser His Gly Lys Ser Leu Glu Trp Ile Gly
1               5                   10

<210> SEQ ID NO 200
<211> LENGTH: 17
<212> TYPE: PRT
<213> ORGANISM: Mus musculus

<400> SEQUENCE: 200

Tyr Ile Asn Pro Asn Asn Gly Gly Thr Ile Tyr Asn Gln Arg Phe Lys
1               5                   10                  15

Gly

<210> SEQ ID NO 201
<211> LENGTH: 32
<212> TYPE: PRT
<213> ORGANISM: Mus musculus

<400> SEQUENCE: 201

Lys Ala Thr Leu Thr Val Asn Lys Ser Ser Arg Thr Ala Tyr Met Asp
1               5                   10                  15

Leu Arg Ser Leu Thr Ser Glu Asp Ser Ala Val Tyr Tyr Cys Ala Arg
            20                  25                  30

<210> SEQ ID NO 202
<211> LENGTH: 10
<212> TYPE: PRT
<213> ORGANISM: Mus musculus

<400> SEQUENCE: 202

Gln Gly Tyr Tyr Gly Asn Ser Met Asp Tyr
1               5                   10

<210> SEQ ID NO 203
<211> LENGTH: 11
<212> TYPE: PRT
<213> ORGANISM: Mus musculus

<400> SEQUENCE: 203

Trp Gly Gln Gly Asn Ser Val Thr Val Ser Ser
1               5                   10

<210> SEQ ID NO 204
<211> LENGTH: 357
<212> TYPE: DNA
<213> ORGANISM: Mus musculus

<400> SEQUENCE: 204
gaggtccaac tgcaacagtc tggacctgag ctggtgaagc ctgggacttc agtgaagatg 60
tcctgcaagg cttctggata cacattcact gactacaaca tgcactgggt gaaactgagc 120
catggaaaga gccttgagtg gattggatat attaacccta ataatggggg tactatctac 180
aaccagcgat tcaagggcaa ggccacattg actgtaaaca agtcctccag aacagcctac 240
atggacctcc gcagcctgac atcggaggat tctgcagtct attactgtgc gcgacagggt 300
tactacggta actctatgga ctactggggt caaggaaatt cagtcaccgt ctcctca 357

<210> SEQ ID NO 205
<211> LENGTH: 119
<212> TYPE: PRT
<213> ORGANISM: Mus musculus

<400> SEQUENCE: 205

Glu Val Gln Leu Gln Gln Ser Gly Pro Glu Leu Val Lys Pro Gly Thr
1 5 10 15

Ser Val Lys Met Ser Cys Lys Ala Ser Gly Tyr Thr Phe Thr Asp Tyr
20 25 30

Asn Met His Trp Val Lys Leu Ser His Gly Lys Ser Leu Glu Trp Ile
35 40 45

Gly Tyr Ile Asn Pro Asn Asn Gly Gly Thr Ile Tyr Asn Gln Arg Phe
50 55 60

Lys Gly Lys Ala Thr Leu Thr Val Asn Lys Ser Ser Arg Thr Ala Tyr
65 70 75 80

Met Asp Leu Arg Ser Leu Thr Ser Glu Asp Ser Ala Val Tyr Tyr Cys
85 90 95

Ala Arg Gln Gly Tyr Tyr Gly Asn Ser Met Asp Tyr Trp Gly Gln Gly
100 105 110

Asn Ser Val Thr Val Ser Ser
115

<210> SEQ ID NO 206
<211> LENGTH: 23
<212> TYPE: PRT
<213> ORGANISM: Mus musculus

<400> SEQUENCE: 206

Asp Ile Val Met Thr Gln Ser Pro Ser Ser Leu Thr Val Thr Pro Gly
1 5 10 15

Glu Arg Val Thr Met Ser Cys
20

<210> SEQ ID NO 207
<211> LENGTH: 17
<212> TYPE: PRT
<213> ORGANISM: Mus musculus

<400> SEQUENCE: 207

Lys Ser Ser Gln Ser Leu Leu Asn Gly Gly Asn Gln Arg Asn Tyr Leu
1 5 10 15

Thr

<210> SEQ ID NO 208
<211> LENGTH: 15
<212> TYPE: PRT
<213> ORGANISM: Mus musculus

<400> SEQUENCE: 208

Trp Tyr Gln Gln Lys Pro Gly Gln Pro Pro Lys Leu Leu Ile Tyr
1 5 10 15

<210> SEQ ID NO 209
<211> LENGTH: 7
<212> TYPE: PRT
<213> ORGANISM: Mus musculus

<400> SEQUENCE: 209

Trp Ala Ser Thr Arg Glu Ser
1 5

<210> SEQ ID NO 210
<211> LENGTH: 32
<212> TYPE: PRT

<213> ORGANISM: Mus musculus

<400> SEQUENCE: 210

Gly Val Pro Asp Arg Phe Ala Gly Ser Gly Ser Gly Thr Asp Phe Thr
1 5 10 15

Leu Thr Ile Ser Arg Val Gln Ala Glu Asp Leu Ser Phe Tyr Tyr Cys
20 25 30

<210> SEQ ID NO 211
<211> LENGTH: 9
<212> TYPE: PRT
<213> ORGANISM: Mus musculus

<400> SEQUENCE: 211

Gln Asn Ser Tyr Phe Tyr Pro Phe Thr
1 5

<210> SEQ ID NO 212
<211> LENGTH: 10
<212> TYPE: PRT
<213> ORGANISM: Mus musculus

<400> SEQUENCE: 212

Phe Gly Ser Gly Thr Lys Leu Asp Leu Arg
1 5 10

<210> SEQ ID NO 213
<211> LENGTH: 339
<212> TYPE: DNA
<213> ORGANISM: Mus musculus

<400> SEQUENCE: 213
gacattgtga tgacacagtc tccatcctcc ctgactgtga caccaggaga gagggtcact 60
atgagctgca agtccagtca gagtctgtta aacggtggaa atcaaaggaa ctacttgacc 120
tggtaccagc aaaaaccagg gcagcctcct aaactgttga tctactgggc atccactagg 180
gaatctgggg tccctgatcg cttcgcaggc agtggatctg gaacagattt cactctcacc 240
atcagcagag tgcaggctga agacctgtca ttttattact gtcagaattc ttatttttat 300
ccgttcacgt tcggctcggg gacaaagttg gacctaaga 339

<210> SEQ ID NO 214
<211> LENGTH: 113
<212> TYPE: PRT
<213> ORGANISM: Mus musculus

<400> SEQUENCE: 214

Asp Ile Val Met Thr Gln Ser Pro Ser Ser Leu Thr Val Thr Pro Gly
1 5 10 15

Glu Arg Val Thr Met Ser Cys Lys Ser Ser Gln Ser Leu Leu Asn Gly
20 25 30

Gly Asn Gln Arg Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ala Gly Ser Gly Ser Gly Thr Asp Phe Thr Leu Thr
65 70 75 80

Ile Ser Arg Val Gln Ala Glu Asp Leu Ser Phe Tyr Tyr Cys Gln Asn
85 90 95

Ser Tyr Phe Tyr Pro Phe Thr Phe Gly Ser Gly Thr Lys Leu Asp Leu

```
            100                 105                 110

Arg


<210> SEQ ID NO 215
<211> LENGTH: 30
<212> TYPE: PRT
<213> ORGANISM: Mus musculus

<400> SEQUENCE: 215

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30


<210> SEQ ID NO 216
<211> LENGTH: 5
<212> TYPE: PRT
<213> ORGANISM: Mus musculus

<400> SEQUENCE: 216

Ser Tyr Thr Met Ser
1               5


<210> SEQ ID NO 217
<211> LENGTH: 14
<212> TYPE: PRT
<213> ORGANISM: Mus musculus

<400> SEQUENCE: 217

Trp Val Arg Gln Thr Pro Glu Lys Arg Leu Glu Trp Val Ala
1               5                   10


<210> SEQ ID NO 218
<211> LENGTH: 17
<212> TYPE: PRT
<213> ORGANISM: Mus musculus

<400> SEQUENCE: 218

Thr Ile Ser Val Ile Gly Gly Asn Thr Tyr Tyr Val Asp Ser Val Lys
1               5                   10                  15

Gly


<210> SEQ ID NO 219
<211> LENGTH: 32
<212> TYPE: PRT
<213> ORGANISM: Mus musculus

<400> SEQUENCE: 219

Arg Phe Thr Ile Ser Arg Asp Lys Ala Lys Asn Thr Leu Tyr Leu Gln
1               5                   10                  15

Met Ser Ser Leu Arg Ser Glu Asp Thr Ala Leu Tyr Tyr Cys Ala Arg
            20                  25                  30


<210> SEQ ID NO 220
<211> LENGTH: 11
<212> TYPE: PRT
<213> ORGANISM: Mus musculus

<400> SEQUENCE: 220

Leu Gly Gln Thr Gln Arg Asn Ala Met Asp Tyr
1               5                   10
```

<210> SEQ ID NO 221
<211> LENGTH: 11
<212> TYPE: PRT
<213> ORGANISM: Mus musculus

<400> SEQUENCE: 221

```
Trp Gly Gln Gly Thr Ser Val Thr Val Ser Ser
1               5                   10
```

<210> SEQ ID NO 222
<211> LENGTH: 360
<212> TYPE: DNA
<213> ORGANISM: Mus musculus

<400> SEQUENCE: 222

```
gaagtgatgc tggtggagtc tgggggaggc ttagtgaagc ctggagggtc cctgaaactc      60

tcctgtgcag cctctggatt cactttcagt agctatacca tgtcttgggt tcgccagact     120

ccggagaaga ggctggagtg ggtcgcaacc attagtgtta ttggtggtaa cacctactat     180

gtagacagtg tgaagggtcg attcaccatc tccagagaca aagccaagaa caccctgtac     240

ctgcaaatga gcagtctgag gtctgaggac acggccttat attactgtgc aagactggga     300

cagacacaga gaaatgctat ggactactgg ggtcaaggaa cctcagtcac cgtctcctca     360
```

<210> SEQ ID NO 223
<211> LENGTH: 120
<212> TYPE: PRT
<213> ORGANISM: Mus musculus

<400> SEQUENCE: 223

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Val Ile Gly Gly Asn Thr Tyr Tyr Val Asp Ser Val
    50                  55                  60

Lys Gly Arg Phe Thr Ile Ser Arg Asp Lys Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Leu Gly Gln Thr Gln Arg Asn Ala Met Asp Tyr Trp Gly Gln
            100                 105                 110

Gly Thr Ser Val Thr Val Ser Ser
        115                 120
```

<210> SEQ ID NO 224
<211> LENGTH: 23
<212> TYPE: PRT
<213> ORGANISM: Mus musculus

<400> SEQUENCE: 224

```
Asp Ile Val Met Thr Gln Ser Pro Ser Ser Leu Ser Val Ser Ala Gly
1               5                   10                  15

Glu Lys Val Thr Met Ser Cys
            20
```

<210> SEQ ID NO 225
<211> LENGTH: 17

<212> TYPE: PRT
<213> ORGANISM: Mus musculus

<400> SEQUENCE: 225

Lys Ser Ser Gln Ser Leu Leu Asn Ser Gly Asn Gln Lys Asn Tyr Leu
1 5 10 15

Ala

<210> SEQ ID NO 226
<211> LENGTH: 15
<212> TYPE: PRT
<213> ORGANISM: Mus musculus

<400> SEQUENCE: 226

Trp Tyr Gln Gln Lys Pro Gly Gln Pro Pro Lys Leu Leu Ile Tyr
1 5 10 15

<210> SEQ ID NO 227
<211> LENGTH: 7
<212> TYPE: PRT
<213> ORGANISM: Mus musculus

<400> SEQUENCE: 227

Gly Ala Ser Thr Arg Glu Ser
1 5

<210> SEQ ID NO 228
<211> LENGTH: 32
<212> TYPE: PRT
<213> ORGANISM: Mus musculus

<400> SEQUENCE: 228

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 229
<211> LENGTH: 9
<212> TYPE: PRT
<213> ORGANISM: Mus musculus

<400> SEQUENCE: 229

Gln Asn Asp Tyr Ser Tyr Pro Leu Thr
1 5

<210> SEQ ID NO 230
<211> LENGTH: 10
<212> TYPE: PRT
<213> ORGANISM: Mus musculus

<400> SEQUENCE: 230

Phe Gly Ala Gly Thr Lys Leu Glu Leu Lys
1 5 10

<210> SEQ ID NO 231
<211> LENGTH: 339
<212> TYPE: DNA
<213> ORGANISM: Mus musculus

<400> SEQUENCE: 231
gacattgtga tgacacagtc tccatcctct ctgagtgtgt cagcaggaga gaaggtcaca 60
atgagctgca agtccagtca gagtctgtta aacagtggaa atcaaaagaa ctacttggcc 120

```
tggtaccagc agaaaccagg gcagcctcct aaactgttga tctacggggc atctactagg    180

gaatctgggg tccctgatcg cttcacaggc agtggatctg gaaccgattt cactcttacc    240

atcagcagtg tgcaggctga agacctggca gtttattact gtcagaatga ttatagttat    300

ccgctcacgt tcggtgctgg gaccaagctg gagctgaaa                           339
```

```
<210> SEQ ID NO 232
<211> LENGTH: 113
<212> TYPE: PRT
<213> ORGANISM: Mus musculus

<400> SEQUENCE: 232

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys


<210> SEQ ID NO 233
<211> LENGTH: 30
<212> TYPE: PRT
<213> ORGANISM: Mus musculus

<400> SEQUENCE: 233

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30


<210> SEQ ID NO 234
<211> LENGTH: 5
<212> TYPE: PRT
<213> ORGANISM: Mus musculus

<400> SEQUENCE: 234

Arg Tyr Thr Met Ser
1               5


<210> SEQ ID NO 235
<211> LENGTH: 14
<212> TYPE: PRT
<213> ORGANISM: Mus musculus

<400> SEQUENCE: 235

Trp Val Arg Gln Thr Pro Glu Lys Arg Leu Glu Trp Val Ala
1               5                   10


<210> SEQ ID NO 236
<211> LENGTH: 17
```

<212> TYPE: PRT
<213> ORGANISM: Mus musculus

<400> SEQUENCE: 236

Thr Val Ser Val Gly Ser Gly Asn Thr Tyr Tyr Leu Asp Ser Val Lys
1 5 10 15

Gly

<210> SEQ ID NO 237
<211> LENGTH: 32
<212> TYPE: PRT
<213> ORGANISM: Mus musculus

<400> SEQUENCE: 237

Arg Phe Thr Ile Ser Arg Asp Asn Ala Lys Asn Thr Leu Phe Leu Gln
1 5 10 15

Met Asn Ser Leu Arg Ser Glu Asp Thr Ala Leu Tyr Tyr Cys Thr Arg
20 25 30

<210> SEQ ID NO 238
<211> LENGTH: 11
<212> TYPE: PRT
<213> ORGANISM: Mus musculus

<400> SEQUENCE: 238

Leu Gly Gln Thr Gln Arg Asn Ala Val Asp Tyr
1 5 10

<210> SEQ ID NO 239
<211> LENGTH: 11
<212> TYPE: PRT
<213> ORGANISM: Mus musculus

<400> SEQUENCE: 239

Trp Gly Gln Gly Thr Ser Val Thr Val Ser Ser
1 5 10

<210> SEQ ID NO 240
<211> LENGTH: 360
<212> TYPE: DNA
<213> ORGANISM: Mus musculus

<400> SEQUENCE: 240
gaagtgatgt tggtggaatc tgggggagac ttagtgaagc ctggagggtc cctgaaactc 60
tcctgtgcag cctctggatt cactttcagt cgttatacca tgtcttgggt tcgccagact 120
ccggagaaga ggctggagtg ggtcgcaacc gttagtgttg gttctggtaa cacctactat 180
ttagacagtg tgaagggtcg attcaccatc tccagagaca atgccaagaa caccctgttc 240
ctgcaaatga acagtctgag gtctgaggac acggccttat attactgtac aagactggga 300
cagacacaga gaaatgctgt ggactactgg ggtcaaggca cctcagtcac cgtctcctca 360

<210> SEQ ID NO 241
<211> LENGTH: 120
<212> TYPE: PRT
<213> ORGANISM: Mus musculus

<400> SEQUENCE: 241

Glu Val Met Leu Val Glu Ser Gly Gly Asp Leu Val Lys Pro Gly Gly
1 5 10 15

Ser Leu Lys Leu Ser Cys Ala Ala Ser Gly Phe Thr Phe Ser Arg Tyr
20 25 30

```
Thr Met Ser Trp Val Arg Gln Thr Pro Glu Lys Arg Leu Glu Trp Val
        35                  40                  45

Ala Thr Val Ser Val Gly Ser Gly Asn Thr Tyr Tyr Leu Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Ser Glu Asp Thr Ala Leu Tyr Tyr Cys
                85                  90                  95

Thr Arg Leu Gly Gln Thr Gln Arg Asn Ala Val Asp Tyr Trp Gly Gln
            100                 105                 110

Gly Thr Ser Val Thr Val Ser Ser
        115                 120


<210> SEQ ID NO 242
<211> LENGTH: 23
<212> TYPE: PRT
<213> ORGANISM: Mus musculus

<400> SEQUENCE: 242

Asp Ile Val Met Thr Gln Ser Pro Ser Phe Leu Ser Val Ser Ala Gly
1               5                   10                  15

Glu Lys Val Thr Met Ser Cys
            20


<210> SEQ ID NO 243
<211> LENGTH: 17
<212> TYPE: PRT
<213> ORGANISM: Mus musculus

<400> SEQUENCE: 243

Lys Ser Ser Gln Ser Leu Phe Asn Gly Gly Asn Gln Lys Asn Tyr Leu
1               5                   10                  15

Ala


<210> SEQ ID NO 244
<211> LENGTH: 15
<212> TYPE: PRT
<213> ORGANISM: Mus musculus

<400> SEQUENCE: 244

Trp Tyr Gln Gln Lys Pro Gly Gln Pro Pro Lys Leu Leu Ile Tyr
1               5                   10                  15


<210> SEQ ID NO 245
<211> LENGTH: 7
<212> TYPE: PRT
<213> ORGANISM: Mus musculus

<400> SEQUENCE: 245

Gly Ala Ser Thr Arg Asp Ser
1               5


<210> SEQ ID NO 246
<211> LENGTH: 32
<212> TYPE: PRT
<213> ORGANISM: Mus musculus

<400> SEQUENCE: 246

Gly Val Pro Asp Arg Phe Thr Gly Ser Gly Ser Gly Thr Asp Phe Thr
1               5                   10                  15
```

Leu Thr Ile Ser Asn Val Gln Ala Glu Asp Leu Ala Ile Tyr Phe Cys
20 25 30

<210> SEQ ID NO 247
<211> LENGTH: 9
<212> TYPE: PRT
<213> ORGANISM: Mus musculus

<400> SEQUENCE: 247

Gln Asn Asp His Ser Phe Pro Leu Thr
1 5

<210> SEQ ID NO 248
<211> LENGTH: 10
<212> TYPE: PRT
<213> ORGANISM: Mus musculus

<400> SEQUENCE: 248

Phe Gly Ala Gly Thr Lys Leu Glu Leu Lys
1 5 10

<210> SEQ ID NO 249
<211> LENGTH: 295
<212> TYPE: DNA
<213> ORGANISM: Mus musculus

<400> SEQUENCE: 249
gacattgtga tgacacagtc tccatccttc ctgagtgtgt cagcgggaga gaaggtcact 60
atgagctgca agtccagtca gagtctgttc aacggtggaa atcaaaagaa ctacttggcc 120
tggtaccagc agaaaccagg gcagcctcct aaactgttga tctacggggc atccactagg 180
gactctgggg tccctgatcg cttcacaggc agtggatctg gaaccgattt cactcttacc 240
atcagcaatg tgcaggctga agacctggca atttatttct gtcagaatga tcata 295

<210> SEQ ID NO 250
<211> LENGTH: 113
<212> TYPE: PRT
<213> ORGANISM: Mus musculus

<400> SEQUENCE: 250

Asp Ile Val Met Thr Gln Ser Pro Ser Phe Leu Ser Val Ser Ala Gly
1 5 10 15

Glu Lys Val Thr Met Ser Cys Lys Ser Ser Gln Ser Leu Phe Asn Gly
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Asp Ser Gly Val
50 55 60

Pro Asp Arg Phe Thr Gly Ser Gly Ser Gly Thr Asp Phe Thr Leu Thr
65 70 75 80

Ile Ser Asn Val Gln Ala Glu Asp Leu Ala Ile Tyr Phe Cys Gln Asn
85 90 95

Asp His Ser Phe Pro Leu Thr Phe Gly Ala Gly Thr Lys Leu Glu Leu
100 105 110

Lys

<210> SEQ ID NO 251
<211> LENGTH: 30
<212> TYPE: PRT
<213> ORGANISM: Mus musculus

<400> SEQUENCE: 251

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 252
<211> LENGTH: 5
<212> TYPE: PRT
<213> ORGANISM: Mus musculus

<400> SEQUENCE: 252

Ser Tyr Thr Met Ser
1 5

<210> SEQ ID NO 253
<211> LENGTH: 14
<212> TYPE: PRT
<213> ORGANISM: Mus musculus

<400> SEQUENCE: 253

Trp Val Arg Gln Thr Pro Glu Lys Arg Leu Glu Trp Val Ala
1 5 10

<210> SEQ ID NO 254
<211> LENGTH: 17
<212> TYPE: PRT
<213> ORGANISM: Mus musculus

<400> SEQUENCE: 254

Thr Ile Ile Gly Gly Tyr Gly Asn Thr Tyr Tyr Ala Asp Ser Val Lys
1 5 10 15

Gly

<210> SEQ ID NO 255
<211> LENGTH: 32
<212> TYPE: PRT
<213> ORGANISM: Mus musculus

<400> SEQUENCE: 255

Arg Phe Thr Ile Ser Arg Asp Ser Ala Lys Asn Thr Leu Tyr Leu Gln
1 5 10 15

Met Leu Ser Leu Arg Ser Glu Asp Thr Ala Leu Tyr Tyr Cys Thr Arg
20 25 30

<210> SEQ ID NO 256
<211> LENGTH: 11
<212> TYPE: PRT
<213> ORGANISM: Mus musculus

<400> SEQUENCE: 256

Leu Gly Gln Thr Gln Arg Asn Ala Met Asp Tyr
1 5 10

<210> SEQ ID NO 257
<211> LENGTH: 11
<212> TYPE: PRT
<213> ORGANISM: Mus musculus

<400> SEQUENCE: 257

Trp Gly Gln Gly Thr Ser Val Thr Val Ser Ser
1 5 10

<210> SEQ ID NO 258
<211> LENGTH: 360
<212> TYPE: DNA
<213> ORGANISM: Mus musculus

<400> SEQUENCE: 258
gaagtgatgc tggtggagtc tgggggaggc ttagtgaagc ctggagggtc cctgaaactc 60
tcctgtgcag cctctggatt cactttcagt agctatacca tgtcttgggt tcgccagact 120
ccggagaaga ggctggagtg ggtcgcaacc attattggtg gttatggtaa cacctactat 180
gcagacagtg tgaagggtcg attcaccatc tccagagaca gtgccaagaa caccctgtac 240
ctacaaatgc tcagtctgag gtctgaggac acggccttgt attactgtac aagactggga 300
cagacacaga gaaatgctat ggactactgg ggtcaaggaa cctcagtcac cgtctcctca 360

<210> SEQ ID NO 259
<211> LENGTH: 120
<212> TYPE: PRT
<213> ORGANISM: Mus musculus

<400> SEQUENCE: 259

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Ile Gly Gly Tyr Gly Asn Thr Tyr Tyr Ala Asp Ser Val
50 55 60

Lys Gly Arg Phe Thr Ile Ser Arg Asp Ser Ala Lys Asn Thr Leu Tyr
65 70 75 80

Leu Gln Met Leu Ser Leu Arg Ser Glu Asp Thr Ala Leu Tyr Tyr Cys
85 90 95

Thr Arg Leu Gly Gln Thr Gln Arg Asn Ala Met Asp Tyr Trp Gly Gln
100 105 110

Gly Thr Ser Val Thr Val Ser Ser
115 120

<210> SEQ ID NO 260
<211> LENGTH: 23
<212> TYPE: PRT
<213> ORGANISM: Mus musculus

<400> SEQUENCE: 260

Asp Ile Leu Met Thr Gln Ser Pro Ser Ser Leu Ser Val Ser Ala Gly
1 5 10 15

Glu Lys Val Thr Met Ser Cys
20

<210> SEQ ID NO 261
<211> LENGTH: 17
<212> TYPE: PRT
<213> ORGANISM: Mus musculus

<400> SEQUENCE: 261

Lys Ser Ser Gln Ser Leu Leu Asn Ser Gly Asn Gln Arg Asn Tyr Leu
1 5 10 15

Ala

<210> SEQ ID NO 262
<211> LENGTH: 15
<212> TYPE: PRT
<213> ORGANISM: Mus musculus

<400> SEQUENCE: 262

Trp Tyr Gln Gln Lys Pro Gly Gln Pro Pro Lys Leu Leu Ile Tyr
1 5 10 15

<210> SEQ ID NO 263
<211> LENGTH: 7
<212> TYPE: PRT
<213> ORGANISM: Mus musculus

<400> SEQUENCE: 263

Gly Ala Ser Thr Arg Glu Ser
1 5

<210> SEQ ID NO 264
<211> LENGTH: 32
<212> TYPE: PRT
<213> ORGANISM: Mus musculus

<400> SEQUENCE: 264

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 265
<211> LENGTH: 9
<212> TYPE: PRT
<213> ORGANISM: Mus musculus

<400> SEQUENCE: 265

Gln Asn Asp Tyr Tyr Tyr Pro Leu Thr
1 5

<210> SEQ ID NO 266
<211> LENGTH: 10
<212> TYPE: PRT
<213> ORGANISM: Mus musculus

<400> SEQUENCE: 266

Phe Gly Ala Gly Thr Lys Leu Glu Leu Lys
1 5 10

<210> SEQ ID NO 267
<211> LENGTH: 339
<212> TYPE: DNA
<213> ORGANISM: Mus musculus

<400> SEQUENCE: 267
gacattttga tgacacagtc tccatcctcc ctgagtgtgt cagcaggaga gaaggtcact 60
atgagctgca agtccagtca gagtctgtta aacagtggaa atcaaaggaa ctatttggcc 120
tggtaccaac agaaaccagg gcagcctcct aaattgttga tctatggggc atccactagg 180
gaatctgggg tccctgatcg cttcacaggc agtggatctg gaaccgattt cactcttacc 240
atcagcagtg tgcaggctga agacctggca gtttattatt gtcagaatga ttattattat 300
ccactcacgt tcggtgctgg gaccaagctg gagctgaaa 339

<210> SEQ ID NO 268
<211> LENGTH: 113
<212> TYPE: PRT
<213> ORGANISM: Mus musculus

<400> SEQUENCE: 268

```
Asp Ile Leu Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Leu Thr Phe Gly Ala Gly Thr Lys Leu Glu Leu
            100                 105                 110

Lys
```

<210> SEQ ID NO 269
<211> LENGTH: 30
<212> TYPE: PRT
<213> ORGANISM: Mus musculus

<400> SEQUENCE: 269

```
Glu Val Arg Leu Val Glu Ser Gly Gly Gly Leu Val Lys Pro Gly Gly
1               5                   10                  15

Ser Leu Lys Leu Ser Cys Ala Gly Ser Gly Phe Thr Phe Ser
            20                  25                  30
```

<210> SEQ ID NO 270
<211> LENGTH: 5
<212> TYPE: PRT
<213> ORGANISM: Mus musculus

<400> SEQUENCE: 270

```
Ser Tyr Thr Met Ser
1               5
```

<210> SEQ ID NO 271
<211> LENGTH: 14
<212> TYPE: PRT
<213> ORGANISM: Mus musculus

<400> SEQUENCE: 271

```
Trp Val Arg Gln Thr Pro Glu Lys Arg Leu Glu Trp Val Ala
1               5                   10
```

<210> SEQ ID NO 272
<211> LENGTH: 16
<212> TYPE: PRT
<213> ORGANISM: Mus musculus

<400> SEQUENCE: 272

```
Thr Ile Thr Ile Gly Val Asn Ile Tyr Tyr Leu Asp Ser Val Lys Gly
1               5                   10                  15
```

<210> SEQ ID NO 273
<211> LENGTH: 32
<212> TYPE: PRT
<213> ORGANISM: Mus musculus

<400> SEQUENCE: 273

Arg Phe Thr Ile Ser Arg Asp Asn Ala Lys Asn Thr Leu Tyr Leu Gln
1 5 10 15

Met Asn Ser Leu Arg Ser Glu Asp Thr Ala Leu Tyr Tyr Cys Thr Arg
20 25 30

<210> SEQ ID NO 274
<211> LENGTH: 11
<212> TYPE: PRT
<213> ORGANISM: Mus musculus

<400> SEQUENCE: 274

Leu Gly Gln Thr Gln Arg Asn Ala Met Asp Tyr
1 5 10

<210> SEQ ID NO 275
<211> LENGTH: 11
<212> TYPE: PRT
<213> ORGANISM: Mus musculus

<400> SEQUENCE: 275

Trp Gly Gln Gly Thr Ser Val Thr Val Ser Ser
1 5 10

<210> SEQ ID NO 276
<211> LENGTH: 357
<212> TYPE: DNA
<213> ORGANISM: Mus musculus

<400> SEQUENCE: 276
gaagtgaggc tggtggagtc tgggggaggc ttagtgaagc ctggagggtc cctgaaactc 60
tcctgtgcag gctctggatt cactttcagt agctatacca tgtcttgggt tcgccagact 120
ccggagaaga ggctggagtg ggtcgcaacc attactattg gtgttaacat ctactatcta 180
gacagtgtga agggtcgatt caccatctcc agagacaatg ccaagaacac cctgtacctg 240
caaatgaaca gtctgaggtc tgaggacacg gccttgtatt attgtacaag actgggacag 300
acacagcgaa atgctatgga ctactggggt caaggaacct cagtcaccgt ctcctca 357

<210> SEQ ID NO 277
<211> LENGTH: 119
<212> TYPE: PRT
<213> ORGANISM: Mus musculus

<400> SEQUENCE: 277

Glu Val Arg Leu Val Glu Ser Gly Gly Gly Leu Val Lys Pro Gly Gly
1 5 10 15

Ser Leu Lys Leu Ser Cys Ala Gly Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Thr Ile Gly Val Asn Ile Tyr Tyr Leu Asp Ser Val Lys
50 55 60

Gly Arg Phe Thr Ile Ser Arg Asp Asn Ala Lys Asn Thr Leu Tyr Leu
65 70 75 80

Gln Met Asn Ser Leu Arg Ser Glu Asp Thr Ala Leu Tyr Tyr Cys Thr

```
                85                  90                  95

Arg Leu Gly Gln Thr Gln Arg Asn Ala Met Asp Tyr Trp Gly Gln Gly
            100                 105                 110

Thr Ser Val Thr Val Ser Ser
        115


<210> SEQ ID NO 278
<211> LENGTH: 23
<212> TYPE: PRT
<213> ORGANISM: Mus musculus

<400> SEQUENCE: 278

Asp Ile Val Met Thr Gln Ser Pro Thr Ser Leu Ser Val Ser Ala Gly
1               5                   10                  15

Glu Lys Val Thr Met Thr Cys
            20


<210> SEQ ID NO 279
<211> LENGTH: 17
<212> TYPE: PRT
<213> ORGANISM: Mus musculus

<400> SEQUENCE: 279

Lys Ser Ser Gln Ser Leu Leu Asn Ser Gly Asn Gln Lys Asn Tyr Leu
1               5                   10                  15

Ala


<210> SEQ ID NO 280
<211> LENGTH: 15
<212> TYPE: PRT
<213> ORGANISM: Mus musculus

<400> SEQUENCE: 280

Trp Tyr Gln Glu Lys Pro Gly Gln Pro Pro Lys Leu Leu Ile Tyr
1               5                   10                  15


<210> SEQ ID NO 281
<211> LENGTH: 7
<212> TYPE: PRT
<213> ORGANISM: Mus musculus

<400> SEQUENCE: 281

Gly Ala Ser Thr Arg Glu Ser
1               5


<210> SEQ ID NO 282
<211> LENGTH: 32
<212> TYPE: PRT
<213> ORGANISM: Mus musculus

<400> SEQUENCE: 282

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 283
<211> LENGTH: 9
<212> TYPE: PRT
<213> ORGANISM: Mus musculus

<400> SEQUENCE: 283
```

Gln Asn Asn His Phe Tyr Pro Leu Thr
1 5

<210> SEQ ID NO 284
<211> LENGTH: 10
<212> TYPE: PRT
<213> ORGANISM: Mus musculus

<400> SEQUENCE: 284

Phe Gly Ala Gly Thr Lys Leu Glu Leu Lys
1 5 10

<210> SEQ ID NO 285
<211> LENGTH: 339
<212> TYPE: DNA
<213> ORGANISM: Mus musculus

<400> SEQUENCE: 285
gacattgtga tgacacagtc tccaacctcc ctgagtgtgt cagcaggaga gaaggtcact 60
atgacctgca agtccagtca gagtctatta aacagtggaa atcaaaagaa ctacttggcc 120
tggtaccagg agaaaccagg gcagcctcct aaactgttga tctacggggc atccactagg 180
gaatctgggg tccctgatcg cttcacaggc agtggatctg gaaccgattt cactcttacc 240
atcagcagtg tgcaggctga agacctggca gtttattact gtcagaataa tcatttttat 300
ccgctcactt tcggtgctgg gaccaagctg gaactgaaa 339

<210> SEQ ID NO 286
<211> LENGTH: 113
<212> TYPE: PRT
<213> ORGANISM: Mus musculus

<400> SEQUENCE: 286

Asp Ile Val Met Thr Gln Ser Pro Thr Ser Leu Ser Val Ser Ala Gly
1 5 10 15

Glu Lys Val Thr Met Thr Cys Lys Ser Ser Gln Ser Leu Leu Asn Ser
20 25 30

Gly Asn Gln Lys Asn Tyr Leu Ala Trp Tyr Gln Glu Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asn His Phe Tyr Pro Leu Thr Phe Gly Ala Gly Thr Lys Leu Glu Leu
100 105 110

Lys

<210> SEQ ID NO 287
<211> LENGTH: 30
<212> TYPE: PRT
<213> ORGANISM: Mus musculus

<400> SEQUENCE: 287

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr
20 25 30

<210> SEQ ID NO 288
<211> LENGTH: 5
<212> TYPE: PRT
<213> ORGANISM: Mus musculus

<400> SEQUENCE: 288

Ser Tyr Leu Leu His
1 5

<210> SEQ ID NO 289
<211> LENGTH: 14
<212> TYPE: PRT
<213> ORGANISM: Mus musculus

<400> SEQUENCE: 289

Trp Val Lys Gln Arg Pro Gly Gln Gly Leu Glu Trp Ile Gly
1 5 10

<210> SEQ ID NO 290
<211> LENGTH: 17
<212> TYPE: PRT
<213> ORGANISM: Mus musculus

<400> SEQUENCE: 290

Met Ile His Pro Asn Gly Gly Ser Thr Asn Tyr Asn Glu Lys Phe Lys
1 5 10 15

Thr

<210> SEQ ID NO 291
<211> LENGTH: 32
<212> TYPE: PRT
<213> ORGANISM: Mus musculus

<400> SEQUENCE: 291

Lys Ala Thr Leu Thr Val Asp Lys Ser Ser Ser Thr Ala Tyr Met Gln
1 5 10 15

Leu Ser Ser Leu Thr Ser Glu Asp Ser Ala Val Tyr Tyr Cys Ala Pro
20 25 30

<210> SEQ ID NO 292
<211> LENGTH: 9
<212> TYPE: PRT
<213> ORGANISM: Mus musculus

<400> SEQUENCE: 292

Val Tyr Phe Gly Asn Ser Phe Ala Tyr
1 5

<210> SEQ ID NO 293
<211> LENGTH: 11
<212> TYPE: PRT
<213> ORGANISM: Mus musculus

<400> SEQUENCE: 293

Trp Gly Gln Gly Thr Leu Val Thr Val Ser Ala
1 5 10

<210> SEQ ID NO 294
<211> LENGTH: 354
<212> TYPE: DNA
<213> ORGANISM: Mus musculus

<400> SEQUENCE: 294

```
caggtccaac tgcagcagcc tggggctgag ttggtaaagc ctggggcttc agtgaagttg      60

tcctgcaagg cttctggcta cactttcacc agctacttac tacactgggt gaaacagagg    120

cctggacaag gccttgagtg gattggaatg attcatccta atggtggtag tactaactac    180

aatgagaagt tcaagaccaa ggccacactg actgtagaca aatcctccag cacagcctac    240

atgcaactca gcagcctgac atctgaggac tctgcggtct attactgtgc ccctgtctac    300

tttggtaact cgtttgctta ctggggccaa gggactctgg tcactgtctc tgca          354


<210> SEQ ID NO 295
<211> LENGTH: 118
<212> TYPE: PRT
<213> ORGANISM: Mus musculus

<400> SEQUENCE: 295

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Leu Leu His Trp Val Lys Gln Arg Pro Gly Gln Gly Leu Glu Trp Ile
        35                  40                  45

Gly Met Ile His Pro Asn Gly Gly Ser Thr Asn Tyr Asn Glu Lys Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Pro Val Tyr Phe Gly Asn Ser Phe Ala Tyr Trp Gly Gln Gly Thr
            100                 105                 110

Leu Val Thr Val Ser Ala
        115


<210> SEQ ID NO 296
<211> LENGTH: 23
<212> TYPE: PRT
<213> ORGANISM: Mus musculus

<400> SEQUENCE: 296

Asp Ile Val Met Thr Gln Ser Pro Ser Ser Leu Thr Val Thr Ala Gly
1               5                   10                  15

Glu Lys Val Thr Met Ser Cys
            20


<210> SEQ ID NO 297
<211> LENGTH: 17
<212> TYPE: PRT
<213> ORGANISM: Mus musculus

<400> SEQUENCE: 297

Lys Ser Ser Gln Ser Leu Leu Asn Ser Gly Asn Gln Lys Asn Tyr Leu
1               5                   10                  15

Thr


<210> SEQ ID NO 298
<211> LENGTH: 15
<212> TYPE: PRT
<213> ORGANISM: Mus musculus

<400> SEQUENCE: 298
```

```
Trp Tyr Gln Gln Lys Pro Gly Gln Pro Pro Lys Leu Leu Ile Tyr
1               5                   10                  15


<210> SEQ ID NO 299
<211> LENGTH: 7
<212> TYPE: PRT
<213> ORGANISM: Mus musculus

<400> SEQUENCE: 299

Trp Ala Ser Thr Arg Glu Ser
1               5


<210> SEQ ID NO 300
<211> LENGTH: 32
<212> TYPE: PRT
<213> ORGANISM: Mus musculus

<400> SEQUENCE: 300

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 301
<211> LENGTH: 9
<212> TYPE: PRT
<213> ORGANISM: Mus musculus

<400> SEQUENCE: 301

Gln Asn Asp Tyr Tyr Tyr Pro Phe Thr
1               5


<210> SEQ ID NO 302
<211> LENGTH: 10
<212> TYPE: PRT
<213> ORGANISM: Mus musculus

<400> SEQUENCE: 302

Phe Gly Ser Gly Thr Lys Leu Glu Lys Lys
1               5                   10


<210> SEQ ID NO 303
<211> LENGTH: 339
<212> TYPE: DNA
<213> ORGANISM: Mus musculus

<400> SEQUENCE: 303

gacattgtga tgacacagtc tccatcctcc ctgactgtga cagcaggaga gaaggtcact     60

atgagctgca agtccagtca gagtctgtta aacagtggaa atcaaaagaa ctacttgacc    120

tggtaccagc aaaaaccagg gcagcctcct aaactgttga tctactgggc atccactagg    180

gaatctgggg tccctgatcg cttcacaggc agtggatctg gaacagattt cactctcacc    240

atcagcagtg tgcaggctga agacctggca gtttattact gtcagaatga ttattattat    300

ccattcacgt tcggttcggg gacaaagttg gaaaaaaaa                           339


<210> SEQ ID NO 304
<211> LENGTH: 113
<212> TYPE: PRT
<213> ORGANISM: Mus musculus

<400> SEQUENCE: 304

Asp Ile Val Met Thr Gln Ser Pro Ser Ser Leu Thr Val Thr Ala Gly
```

```
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Phe Thr Phe Gly Ser Gly Thr Lys Leu Glu Lys
            100                 105                 110

Lys


<210> SEQ ID NO 305
<211> LENGTH: 30
<212> TYPE: PRT
<213> ORGANISM: Mus musculus

<400> SEQUENCE: 305

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30


<210> SEQ ID NO 306
<211> LENGTH: 5
<212> TYPE: PRT
<213> ORGANISM: Mus musculus

<400> SEQUENCE: 306

Thr Tyr Thr Met Ser
1               5


<210> SEQ ID NO 307
<211> LENGTH: 14
<212> TYPE: PRT
<213> ORGANISM: Mus musculus

<400> SEQUENCE: 307

Trp Val Arg Gln Thr Pro Glu Lys Arg Leu Glu Trp Val Ala
1               5                   10


<210> SEQ ID NO 308
<211> LENGTH: 17
<212> TYPE: PRT
<213> ORGANISM: Mus musculus

<400> SEQUENCE: 308

Thr Ile Val Gly Gly Gly Gly Tyr Thr Tyr Tyr Leu Asp Ser Val Lys
1               5                   10                  15

Gly


<210> SEQ ID NO 309
<211> LENGTH: 32
<212> TYPE: PRT
<213> ORGANISM: Mus musculus

<400> SEQUENCE: 309
```

```
Arg Phe Thr Ile Ser Arg Asp Asn Ala Lys Asn Thr Leu Tyr Leu Gln
1               5                   10                  15

Met Ile Ser Leu Arg Ser Glu Asp Thr Ala Leu Tyr Tyr Cys Ala Arg
            20                  25                  30


<210> SEQ ID NO 310
<211> LENGTH: 11
<212> TYPE: PRT
<213> ORGANISM: Mus musculus

<400> SEQUENCE: 310

Met Gly Leu Thr Gln Arg Asn Ala Leu Asp Tyr
1               5                   10


<210> SEQ ID NO 311
<211> LENGTH: 11
<212> TYPE: PRT
<213> ORGANISM: Mus musculus

<400> SEQUENCE: 311

Trp Gly Gln Gly Thr Ser Ile Thr Val Ser Ser
1               5                   10


<210> SEQ ID NO 312
<211> LENGTH: 360
<212> TYPE: DNA
<213> ORGANISM: Mus musculus

<400> SEQUENCE: 312

gaagtgatgc tggtggagtc tgggggagac ttagtgaagc ctggagggtc cctgaaactc      60

tcctgtgcag cctctggatt cactttcagt acctatacca tgtcttgggt tcgccagact     120

ccggagaaga ggctggagtg ggtcgcaacc attgttggtg gtggtggtta cacctactat     180

ctagacagtg tgaagggtcg attcaccatc tccagagaca atgccaagaa caccctgtac     240

ctgcaaatga tcagtctgag gtctgaggac acggccttat attactgtgc aagaatggga     300

ctgacacaga gaaatgctct ggactactgg ggtcaaggaa cctcaatcac cgtctcctca     360


<210> SEQ ID NO 313
<211> LENGTH: 120
<212> TYPE: PRT
<213> ORGANISM: Mus musculus

<400> SEQUENCE: 313

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Val Gly Gly Gly Gly Tyr Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ile Ser Leu Arg Ser Glu Asp Thr Ala Leu Tyr Tyr Cys
                85                  90                  95

Ala Arg Met Gly Leu Thr Gln Arg Asn Ala Leu Asp Tyr Trp Gly Gln
            100                 105                 110

Gly Thr Ser Ile Thr Val Ser Ser
        115                 120
```

<210> SEQ ID NO 314
<211> LENGTH: 23
<212> TYPE: PRT
<213> ORGANISM: Mus musculus

<400> SEQUENCE: 314

Asp Ile Val Met Thr Gln Ser Pro Ser Ser Leu Ser Val Ser Glu Gly
1 5 10 15

Glu Lys Val Thr Leu Asn Cys
20

<210> SEQ ID NO 315
<211> LENGTH: 17
<212> TYPE: PRT
<213> ORGANISM: Mus musculus

<400> SEQUENCE: 315

Lys Ser Ser Gln Ser Leu Phe Asn Ser Gly Asn Gln Lys Asn Tyr Leu
1 5 10 15

Ala

<210> SEQ ID NO 316
<211> LENGTH: 15
<212> TYPE: PRT
<213> ORGANISM: Mus musculus

<400> SEQUENCE: 316

Trp Tyr Gln Gln Lys Pro Gly Gln Pro Pro Lys Leu Leu Ile Tyr
1 5 10 15

<210> SEQ ID NO 317
<211> LENGTH: 7
<212> TYPE: PRT
<213> ORGANISM: Mus musculus

<400> SEQUENCE: 317

Gly Ala Ser Thr Arg Glu Ser
1 5

<210> SEQ ID NO 318
<211> LENGTH: 32
<212> TYPE: PRT
<213> ORGANISM: Mus musculus

<400> SEQUENCE: 318

Gly Val Pro Asp Arg Phe Thr Gly Ser Gly Phe Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 319
<211> LENGTH: 9
<212> TYPE: PRT
<213> ORGANISM: Mus musculus

<400> SEQUENCE: 319

Gln Asn Asp His Thr Tyr Pro Leu Thr
1 5

<210> SEQ ID NO 320
<211> LENGTH: 10
<212> TYPE: PRT

<213> ORGANISM: Mus musculus

<400> SEQUENCE: 320

Phe Gly Ala Gly Ala Lys Leu Glu Leu Lys
1               5                   10

<210> SEQ ID NO 321
<211> LENGTH: 339
<212> TYPE: DNA
<213> ORGANISM: Mus musculus

<400> SEQUENCE: 321
gacattgtga tgacacagtc tccatcctcc ctgagtgtgt cagaaggaga gaaggtcact      60
ctgaactgca agtccagtca gagtctgttc aacagtggaa atcaaaagaa ctacttggcc     120
tggtaccagc agaaaccagg gcagcctcct aaactgttaa tctacggggc atccactaga     180
gaatctgggg tccctgatcg tttcacaggc agtggatttg gcaccgattt cactcttacc     240
atcagcagtg tgcaggctga agacctggca gtttattact gtcagaatga tcatacttat     300
ccgctcacgt tcggtgctgg ggccaagctg gagctgaaa                            339

<210> SEQ ID NO 322
<211> LENGTH: 113
<212> TYPE: PRT
<213> ORGANISM: Mus musculus

<400> SEQUENCE: 322

Asp Ile Val Met Thr Gln Ser Pro Ser Ser Leu Ser Val Ser Glu Gly
1               5                   10                  15

Glu Lys Val Thr Leu Asn Cys Lys Ser Ser Gln Ser Leu Phe Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Phe Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Thr Tyr Pro Leu Thr Phe Gly Ala Gly Ala Lys Leu Glu Leu
            100                 105                 110

Lys

<210> SEQ ID NO 323
<211> LENGTH: 30
<212> TYPE: PRT
<213> ORGANISM: Mus musculus

<400> SEQUENCE: 323

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn
            20                  25                  30

<210> SEQ ID NO 324
<211> LENGTH: 5
<212> TYPE: PRT
<213> ORGANISM: Mus musculus

<400> SEQUENCE: 324

```
Ser Tyr Thr Met Ser
1               5


<210> SEQ ID NO 325
<211> LENGTH: 14
<212> TYPE: PRT
<213> ORGANISM: Mus musculus

<400> SEQUENCE: 325

Trp Val Arg Gln Thr Pro Glu Lys Arg Leu Glu Trp Val Ala
1               5                   10


<210> SEQ ID NO 326
<211> LENGTH: 17
<212> TYPE: PRT
<213> ORGANISM: Mus musculus

<400> SEQUENCE: 326

Thr Ile Thr Val Ile Gly Gly Asn Thr Tyr Tyr Leu Asp Ser Val Lys
1               5                   10                  15

Gly


<210> SEQ ID NO 327
<211> LENGTH: 32
<212> TYPE: PRT
<213> ORGANISM: Mus musculus

<400> SEQUENCE: 327

Arg Phe Thr Ile Ser Ile Asp Asn Gly Lys Asn Thr Leu Tyr Leu Gln
1               5                   10                  15

Met Ser Ser Leu Arg Ser Glu Asp Thr Ala Leu Tyr Tyr Cys Ala Arg
            20                  25                  30


<210> SEQ ID NO 328
<211> LENGTH: 11
<212> TYPE: PRT
<213> ORGANISM: Mus musculus

<400> SEQUENCE: 328

Met Gly Gln Thr Gln Arg Asn Ala Met Asp Tyr
1               5                   10


<210> SEQ ID NO 329
<211> LENGTH: 11
<212> TYPE: PRT
<213> ORGANISM: Mus musculus

<400> SEQUENCE: 329

Trp Gly Gln Gly Thr Ser Val Thr Val Ser Ser
1               5                   10


<210> SEQ ID NO 330
<211> LENGTH: 360
<212> TYPE: DNA
<213> ORGANISM: Mus musculus

<400> SEQUENCE: 330

gaagtgatgc tggtggagtc tgggggaggc ttagtgaagc ctggagggtc cctgaaactc      60

tcctgtgcag cctctggatt cactttcaat agttatacca tgtcttgggt tcgccagact     120

ccggagaaga ggctggagtg ggtcgcaacc attactgtta ttggtggtaa cacctactat     180

ttagacagtg tgaagggtcg attcaccatt tccatagaca atggcaagaa caccctgtac     240
```

```
ctgcaaatga gcagtctgag gtctgaggac acggccttgt attactgtgc aagaatggga    300

cagacacaga gaaatgctat ggactactgg ggtcaaggaa cctcagtcac cgtctcctca    360
```

```
<210> SEQ ID NO 331
<211> LENGTH: 120
<212> TYPE: PRT
<213> ORGANISM: Mus musculus

<400> SEQUENCE: 331

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser Tyr
            20                  25                  30

Thr Met Ser Trp Val Arg Gln Thr Pro Glu Lys Arg Leu Glu Trp Val
        35                  40                  45

Ala Thr Ile Thr Val Ile Gly Gly Asn Thr Tyr Tyr Leu Asp Ser Val
    50                  55                  60

Lys Gly Arg Phe Thr Ile Ser Ile Asp Asn Gly Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Met Gly Gln Thr Gln Arg Asn Ala Met Asp Tyr Trp Gly Gln
            100                 105                 110

Gly Thr Ser Val Thr Val Ser Ser
        115                 120


<210> SEQ ID NO 332
<211> LENGTH: 23
<212> TYPE: PRT
<213> ORGANISM: Mus musculus

<400> SEQUENCE: 332

Asp Ile Val Met Thr Gln Ser Pro Ser Ser Leu Ser Val Ser Ala Gly
1               5                   10                  15

Gln Lys Val Thr Met Arg Cys
            20


<210> SEQ ID NO 333
<211> LENGTH: 17
<212> TYPE: PRT
<213> ORGANISM: Mus musculus

<400> SEQUENCE: 333

Lys Ser Ser Gln Ser Leu Leu Asn Ser Gly Asn Gln Lys Asn Tyr Leu
1               5                   10                  15

Ala


<210> SEQ ID NO 334
<211> LENGTH: 15
<212> TYPE: PRT
<213> ORGANISM: Mus musculus

<400> SEQUENCE: 334

Trp Tyr Gln Gln Lys Leu Gly Gln Pro Pro Lys Leu Leu Ile Tyr
1               5                   10                  15


<210> SEQ ID NO 335
<211> LENGTH: 7
<212> TYPE: PRT
```

<213> ORGANISM: Mus musculus

<400> SEQUENCE: 335

Gly Ala Ser Thr Arg Glu Ser
1 5

<210> SEQ ID NO 336
<211> LENGTH: 32
<212> TYPE: PRT
<213> ORGANISM: Mus musculus

<400> SEQUENCE: 336

Gly Val Pro Asp Arg Phe Ser Gly Ser Gly Ser Gly Thr Asp Phe Thr
1 5 10 15

Leu Thr Ile Thr Ser Val Gln Ala Glu Asp Leu Ala Val Tyr Tyr Cys
20 25 30

<210> SEQ ID NO 337
<211> LENGTH: 9
<212> TYPE: PRT
<213> ORGANISM: Mus musculus

<400> SEQUENCE: 337

Gln Asn Asp Tyr Ser Phe Pro Leu Thr
1 5

<210> SEQ ID NO 338
<211> LENGTH: 10
<212> TYPE: PRT
<213> ORGANISM: Mus musculus

<400> SEQUENCE: 338

Phe Gly Ala Gly Thr Lys Leu Glu Leu Lys
1 5 10

<210> SEQ ID NO 339
<211> LENGTH: 339
<212> TYPE: DNA
<213> ORGANISM: Mus musculus

<400> SEQUENCE: 339
gacattgtga tgacacagtc tccatcctcc ctgagtgtgt cagcaggaca gaaggtcact 60
atgaggtgca agtccagtca gagtctgtta aacagtggaa atcaaaagaa ctacttggcc 120
tggtatcagc agaaactagg gcagcctcct aaactactga tctacggggc atccactagg 180
gaatctgggg tccctgatcg cttctcaggc agtggatctg gaaccgattt cactcttacc 240
atcaccagtg tgcaggctga agacctggca gtttattact gtcagaatga ttatagtttt 300
ccgctcacgt tcggtgctgg gaccaagctg gagctgaaa 339

<210> SEQ ID NO 340
<211> LENGTH: 113
<212> TYPE: PRT
<213> ORGANISM: Mus musculus

<400> SEQUENCE: 340

Asp Ile Val Met Thr Gln Ser Pro Ser Ser Leu Ser Val Ser Ala Gly
1 5 10 15

Gln Lys Val Thr Met Arg Cys Lys Ser Ser Gln Ser Leu Leu Asn Ser
20 25 30

Gly Asn Gln Lys Asn Tyr Leu Ala Trp Tyr Gln Gln Lys Leu Gly Gln
35 40 45

```
Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Val Gln Ala Glu Asp Leu Ala Val Tyr Tyr Cys Gln Asn
                85                  90                  95

Asp Tyr Ser Phe Pro Leu Thr Phe Gly Ala Gly Thr Lys Leu Glu Leu
            100                 105                 110

Lys


<210> SEQ ID NO 341
<211> LENGTH: 30
<212> TYPE: PRT
<213> ORGANISM: Mus musculus

<400> SEQUENCE: 341

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30


<210> SEQ ID NO 342
<211> LENGTH: 5
<212> TYPE: PRT
<213> ORGANISM: Mus musculus

<400> SEQUENCE: 342

Ser Tyr Ala Ile Ser
1               5


<210> SEQ ID NO 343
<211> LENGTH: 14
<212> TYPE: PRT
<213> ORGANISM: Mus musculus

<400> SEQUENCE: 343

Trp Val Arg Gln Pro Pro Gly Lys Gly Leu Glu Trp Leu Gly
1               5                   10


<210> SEQ ID NO 344
<211> LENGTH: 16
<212> TYPE: PRT
<213> ORGANISM: Mus musculus

<400> SEQUENCE: 344

Glu Ile Trp Thr Gly Gly Gly Thr Asn Tyr Asn Ser Ala Leu Lys Ser
1               5                   10                  15


<210> SEQ ID NO 345
<211> LENGTH: 32
<212> TYPE: PRT
<213> ORGANISM: Mus musculus

<400> SEQUENCE: 345

Arg Leu Ser Ile Ser Lys Asp Asn Ser Lys Ser Gln Val Phe Leu Lys
1               5                   10                  15

Met Asn Ser Leu Gln Thr Asp Asp Thr Ala Arg Tyr Tyr Cys Gly Arg
            20                  25                  30


<210> SEQ ID NO 346
<211> LENGTH: 9
```

<212> TYPE: PRT
<213> ORGANISM: Mus musculus

<400> SEQUENCE: 346

Leu Ser Tyr Gly Asn Ser Leu Asp Tyr
1               5

<210> SEQ ID NO 347
<211> LENGTH: 11
<212> TYPE: PRT
<213> ORGANISM: Mus musculus

<400> SEQUENCE: 347

Trp Gly Gln Gly Thr Thr Leu Thr Val Ser Ser
1               5                   10

<210> SEQ ID NO 348
<211> LENGTH: 351
<212> TYPE: DNA
<213> ORGANISM: Mus musculus

<400> SEQUENCE: 348
caggtgcagc tgaaggagtc aggacctggc ctggtggcgc cctcacagag cctgtccatc     60
acatgcactg tctctgggtt ctcattaacc agctatgcta taagctgggt tcgccagcca    120
ccaggaaagg gtctggagtg gcttggagaa atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtggcag actttcctat    300
ggtaattccc ttgactactg gggccaaggc accactctca cagtctcctc a             351

<210> SEQ ID NO 349
<211> LENGTH: 117
<212> TYPE: PRT
<213> ORGANISM: Mus musculus

<400> SEQUENCE: 349

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Leu
        35                  40                  45

Gly Glu Ile Trp Thr Gly Gly Gly Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Gly
                85                  90                  95

Arg Leu Ser Tyr Gly Asn Ser Leu Asp Tyr Trp Gly Gln Gly Thr Thr
            100                 105                 110

Leu Thr Val Ser Ser
        115

<210> SEQ ID NO 350
<211> LENGTH: 23
<212> TYPE: PRT
<213> ORGANISM: Mus musculus

<400> SEQUENCE: 350

```
Asp Ile Val Met Thr Gln Ser Pro Ser Ser Leu Thr Val Thr Ala Gly
1               5                   10                  15

Glu Lys Val Thr Met Ser Cys
            20


<210> SEQ ID NO 351
<211> LENGTH: 17
<212> TYPE: PRT
<213> ORGANISM: Mus musculus

<400> SEQUENCE: 351

Lys Ser Ser Gln Ser Leu Leu Asn Ser Gly Asn Gln Lys Asn Tyr Leu
1               5                   10                  15

Thr


<210> SEQ ID NO 352
<211> LENGTH: 15
<212> TYPE: PRT
<213> ORGANISM: Mus musculus

<400> SEQUENCE: 352

Trp Tyr Gln Gln Lys Pro Gly Gln Pro Pro Lys Leu Leu Ile Tyr
1               5                   10                  15


<210> SEQ ID NO 353
<211> LENGTH: 7
<212> TYPE: PRT
<213> ORGANISM: Mus musculus

<400> SEQUENCE: 353

Trp Ala Ser Thr Arg Glu Ser
1               5


<210> SEQ ID NO 354
<211> LENGTH: 32
<212> TYPE: PRT
<213> ORGANISM: Mus musculus

<400> SEQUENCE: 354

Gly Val Pro Asp Arg Phe Thr Gly Ser Gly Ser Gly Thr Asp Phe Thr
1               5                   10                  15

Leu Thr Val Ser Ser Val Gln Ala Glu Asp Leu Ala Val Tyr Tyr Cys
            20                  25                  30


<210> SEQ ID NO 355
<211> LENGTH: 9
<212> TYPE: PRT
<213> ORGANISM: Mus musculus

<400> SEQUENCE: 355

Gln Asn Asn Phe Ile Tyr Pro Leu Thr
1               5


<210> SEQ ID NO 356
<211> LENGTH: 10
<212> TYPE: PRT
<213> ORGANISM: Mus musculus

<400> SEQUENCE: 356

Phe Gly Pro Gly Thr Lys Leu Glu Leu Lys
1               5                   10


<210> SEQ ID NO 357
```

<211> LENGTH: 339
<212> TYPE: DNA
<213> ORGANISM: Mus musculus

<400> SEQUENCE: 357
gacattgtga tgacacagtc tccatcctcc ctgactgtga cagcaggaga gaaggtcact 60
atgagttgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcactggc agtggatctg gaacagattt cactctcacc 240
gtcagcagtg tgcaggctga agacctggca gtttattact gtcagaataa ttttatttat 300
cctctcacgt tcggtcctgg gaccaagctg gagttgaaa 339

<210> SEQ ID NO 358
<211> LENGTH: 113
<212> TYPE: PRT
<213> ORGANISM: Mus musculus

<400> SEQUENCE: 358

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Val Ser Ser Val Gln Ala Glu Asp Leu Ala Val Tyr Tyr Cys Gln Asn
85 90 95

Asn Phe Ile Tyr Pro Leu Thr Phe Gly Pro Gly Thr Lys Leu Glu Leu
100 105 110

Lys

<210> SEQ ID NO 359
<211> LENGTH: 30
<212> TYPE: PRT
<213> ORGANISM: Mus musculus

<400> SEQUENCE: 359

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr
20 25 30

<210> SEQ ID NO 360
<211> LENGTH: 5
<212> TYPE: PRT
<213> ORGANISM: Mus musculus

<400> SEQUENCE: 360

Thr Tyr Gly Ile Asn
1 5

<210> SEQ ID NO 361
<211> LENGTH: 14
<212> TYPE: PRT
<213> ORGANISM: Mus musculus

<400> SEQUENCE: 361

Trp Val Arg Gln Pro Pro Gly Lys Gly Leu Glu Trp Leu Gly
1 5 10

<210> SEQ ID NO 362
<211> LENGTH: 16
<212> TYPE: PRT
<213> ORGANISM: Mus musculus

<400> SEQUENCE: 362

Val Ile Trp Gly Asp Gly Ser Thr Asn Tyr His Ser Ala Leu Ile Ser
1 5 10 15

<210> SEQ ID NO 363
<211> LENGTH: 32
<212> TYPE: PRT
<213> ORGANISM: Mus musculus

<400> SEQUENCE: 363

Arg Leu Ser Ile Ser Lys Asp Asn Ser Lys Ser Gln Val Phe Leu Lys
1 5 10 15

Leu Asn Ser Leu Gln Thr Asp Asp Thr Ala Thr Tyr Tyr Cys Val Lys
20 25 30

<210> SEQ ID NO 364
<211> LENGTH: 10
<212> TYPE: PRT
<213> ORGANISM: Mus musculus

<400> SEQUENCE: 364

Ser Ser Tyr Tyr Gly Asn Ala Met Asp Tyr
1 5 10

<210> SEQ ID NO 365
<211> LENGTH: 10
<212> TYPE: PRT
<213> ORGANISM: Mus musculus

<400> SEQUENCE: 365

Trp Gly Gln Gly Thr Ser Val Thr Val Ser
1 5 10

<210> SEQ ID NO 366
<211> LENGTH: 354
<212> TYPE: DNA
<213> ORGANISM: Mus musculus

<400> SEQUENCE: 366
caggtgcagc tgaaggagtc aggacctggc ctggtggcgc cctcacagag cctgtccatc 60
acatgcactg tctcagggtt ctcattaacc acctatggta taaactgggt tcgccagcct 120
ccaggaaagg gtctggagtg gctgggagtc atatggggtg acgggagcac aaattatcat 180
tcagctctca tatccagact gagcatcagc aaggataact ccaagagcca agttttctta 240
aaactgaaca gtctgcaaac tgatgacaca gccacgtact actgtgtcaa atcctcttac 300
tacggtaatg ctatggacta ctggggtcaa ggaacctcag tcaccgtctc ctca 354

<210> SEQ ID NO 367
<211> LENGTH: 118
<212> TYPE: PRT
<213> ORGANISM: Mus musculus

<400> SEQUENCE: 367

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr Thr Tyr
20 25 30

Gly Ile Asn Trp Val Arg Gln Pro Pro Gly Lys Gly Leu Glu Trp Leu
35 40 45

Gly Val Ile Trp Gly Asp Gly Ser Thr Asn Tyr His Ser Ala Leu Ile
50 55 60

Ser Arg Leu Ser Ile Ser Lys Asp Asn Ser Lys Ser Gln Val Phe Leu
65 70 75 80

Lys Leu Asn Ser Leu Gln Thr Asp Asp Thr Ala Thr Tyr Tyr Cys Val
85 90 95

Lys Ser Ser Tyr Tyr Gly Asn Ala Met Asp Tyr Trp Gly Gln Gly Thr
100 105 110

Ser Val Thr Val Ser Ser
115

<210> SEQ ID NO 368
<211> LENGTH: 23
<212> TYPE: PRT
<213> ORGANISM: Mus musculus

<400> SEQUENCE: 368

Asp Ile Val Met Thr Gln Ser Pro Ser Ser Leu Thr Val Thr Ala Gly
1 5 10 15

Glu Thr Val Thr Met Ser Cys
20

<210> SEQ ID NO 369
<211> LENGTH: 17
<212> TYPE: PRT
<213> ORGANISM: Mus musculus

<400> SEQUENCE: 369

Lys Ser Ser Gln Ser Leu Leu Asn Ser Gly Asn Gln Lys Asn Tyr Leu
1 5 10 15

Thr

<210> SEQ ID NO 370
<211> LENGTH: 15
<212> TYPE: PRT
<213> ORGANISM: Mus musculus

<400> SEQUENCE: 370

Trp Tyr Gln Gln Lys Pro Gly Gln Pro Pro Lys Leu Leu Ile Tyr
1 5 10 15

<210> SEQ ID NO 371
<211> LENGTH: 7
<212> TYPE: PRT
<213> ORGANISM: Mus musculus

<400> SEQUENCE: 371

Trp Ala Ser Thr Arg Glu Ser
1 5

<210> SEQ ID NO 372
<211> LENGTH: 32
<212> TYPE: PRT

<213> ORGANISM: Mus musculus

<400> SEQUENCE: 372

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 373
<211> LENGTH: 9
<212> TYPE: PRT
<213> ORGANISM: Mus musculus

<400> SEQUENCE: 373

Gln Asn Val Tyr Ser Tyr Pro Phe Thr
1 5

<210> SEQ ID NO 374
<211> LENGTH: 10
<212> TYPE: PRT
<213> ORGANISM: Mus musculus

<400> SEQUENCE: 374

Phe Gly Ser Gly Thr Lys Leu Glu Ile Lys
1 5 10

<210> SEQ ID NO 375
<211> LENGTH: 339
<212> TYPE: DNA
<213> ORGANISM: Mus musculus

<400> SEQUENCE: 375
gacattgtga tgactcagtc tccatcctcc ctgactgtga cagcaggaga gacggtcact 60
atgagctgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatgt ttatagttat 300
ccattcacgt tcggctcggg gacaaagttg gaaataaaa 339

<210> SEQ ID NO 376
<211> LENGTH: 112
<212> TYPE: PRT
<213> ORGANISM: Mus musculus

<400> SEQUENCE: 376

Asp Ile Val Met Thr Gln Ser Pro Ser Ser Leu Thr Val Thr Ala Gly
1 5 10 15

Glu Thr Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Val Tyr Ser Tyr Pro Phe Thr Phe Gly Ser Gly Thr Lys Leu Glu Ile 100 105 110

<210> SEQ ID NO 377
<211> LENGTH: 30
<212> TYPE: PRT
<213> ORGANISM: Mus musculus

<400> SEQUENCE: 377

Glu Val Met Leu Val Glu Ser Gly Gly Asp Leu Val Lys Pro Gly Gly
1 5 10 15

Ser Leu Lys Leu Ser Cys Ala Ala Ser Gly Phe Ser Phe Ser
20 25 30

<210> SEQ ID NO 378
<211> LENGTH: 5
<212> TYPE: PRT
<213> ORGANISM: Mus musculus

<400> SEQUENCE: 378

Arg Tyr Thr Met Ser
1 5

<210> SEQ ID NO 379
<211> LENGTH: 14
<212> TYPE: PRT
<213> ORGANISM: Mus musculus

<400> SEQUENCE: 379

Trp Val Arg Gln Thr Pro Glu Lys Arg Leu Glu Trp Val Ala
1 5 10

<210> SEQ ID NO 380
<211> LENGTH: 17
<212> TYPE: PRT
<213> ORGANISM: Mus musculus

<400> SEQUENCE: 380

Thr Val Ser Val Gly Ser Gly Asn Thr Tyr Tyr Leu Asp Ser Val Lys
1 5 10 15

Gly

<210> SEQ ID NO 381
<211> LENGTH: 32
<212> TYPE: PRT
<213> ORGANISM: Mus musculus

<400> SEQUENCE: 381

Arg Phe Thr Ile Ser Arg Asp Asn Ala Lys Asn Thr Leu Phe Leu Gln
1 5 10 15

Met Ser Ser Leu Arg Ser Glu Asp Thr Ala Leu Tyr Tyr Cys Ala Arg
20 25 30

<210> SEQ ID NO 382
<211> LENGTH: 11
<212> TYPE: PRT
<213> ORGANISM: Mus musculus

<400> SEQUENCE: 382

Met Gly Gln Thr Gln Arg Asn Ala Val Asp Tyr
1 5 10

<210> SEQ ID NO 383
<211> LENGTH: 11

<212> TYPE: PRT
<213> ORGANISM: Mus musculus

<400> SEQUENCE: 383

Trp Gly Gln Gly Thr Ser Val Thr Val Ser Ser
1 5 10

<210> SEQ ID NO 384
<211> LENGTH: 360
<212> TYPE: DNA
<213> ORGANISM: Mus musculus

<400> SEQUENCE: 384
gaagtgatgc tggtggagtc tgggggagac ttagtgaagc ctggagggtc cctgaaactc 60
tcctgtgcag cctctggatt cagtttcagt cgctatacca tgtcttgggt tcgccagact 120
ccggagaaga ggctggagtg ggtcgcaacc gttagtgttg gttctggtaa cacctactat 180
ttagacagtg tgaagggtcg attcaccatc tccagagaca atgccaagaa caccctgttc 240
ctgcaaatga gtagtctgag gtctgaggac acggccttat attactgtgc aagaatggga 300
cagacacaga gaaatgctgt ggactactgg ggtcaaggca cctcagtcac cgtctcctca 360

<210> SEQ ID NO 385
<211> LENGTH: 120
<212> TYPE: PRT
<213> ORGANISM: Mus musculus

<400> SEQUENCE: 385

Glu Val Met Leu Val Glu Ser Gly Gly Asp Leu Val Lys Pro Gly Gly
1 5 10 15

Ser Leu Lys Leu Ser Cys Ala Ala Ser Gly Phe Ser Phe Ser Arg Tyr
20 25 30

Thr Met Ser Trp Val Arg Gln Thr Pro Glu Lys Arg Leu Glu Trp Val
35 40 45

Ala Thr Val Ser Val Gly Ser Gly Asn Thr Tyr Tyr Leu Asp Ser Val
50 55 60

Lys Gly Arg Phe Thr Ile Ser Arg Asp Asn Ala Lys Asn Thr Leu Phe
65 70 75 80

Leu Gln Met Ser Ser Leu Arg Ser Glu Asp Thr Ala Leu Tyr Tyr Cys
85 90 95

Ala Arg Met Gly Gln Thr Gln Arg Asn Ala Val Asp Tyr Trp Gly Gln
100 105 110

Gly Thr Ser Val Thr Val Ser Ser
115 120

<210> SEQ ID NO 386
<211> LENGTH: 23
<212> TYPE: PRT
<213> ORGANISM: Mus musculus

<400> SEQUENCE: 386

Asp Ile Val Met Thr Gln Ser Pro Ser Ser Leu Ser Val Ser Ala Gly
1 5 10 15

Glu Lys Val Thr Met Ser Cys
20

<210> SEQ ID NO 387
<211> LENGTH: 17
<212> TYPE: PRT
<213> ORGANISM: Mus musculus

<400> SEQUENCE: 387

Lys Ser Ser Gln Ser Leu Phe Asn Ser Gly Asn Gln Lys Asn Tyr Leu
1 5 10 15

Ala

<210> SEQ ID NO 388
<211> LENGTH: 15
<212> TYPE: PRT
<213> ORGANISM: Mus musculus

<400> SEQUENCE: 388

Trp Tyr Gln Gln Lys Pro Gly Gln Pro Pro Lys Leu Leu Ile Tyr
1 5 10 15

<210> SEQ ID NO 389
<211> LENGTH: 7
<212> TYPE: PRT
<213> ORGANISM: Mus musculus

<400> SEQUENCE: 389

Gly Ala Ser Thr Arg Glu Ser
1 5

<210> SEQ ID NO 390
<211> LENGTH: 32
<212> TYPE: PRT
<213> ORGANISM: Mus musculus

<400> SEQUENCE: 390

Gly Val Pro Asp Arg Phe Thr Gly Ser Gly Ser Gly Thr Asp Phe Thr
1 5 10 15

Leu Thr Ile Ser Asn Val Gln Ala Glu Asp Leu Ala Val Tyr Leu Cys
20 25 30

<210> SEQ ID NO 391
<211> LENGTH: 9
<212> TYPE: PRT
<213> ORGANISM: Mus musculus

<400> SEQUENCE: 391

Gln Asn Asp His Ser Phe Pro Leu Thr
1 5

<210> SEQ ID NO 392
<211> LENGTH: 9
<212> TYPE: PRT
<213> ORGANISM: Mus musculus

<400> SEQUENCE: 392

Phe Gly Ala Gly Thr Lys Leu Glu Leu
1 5

<210> SEQ ID NO 393
<211> LENGTH: 339
<212> TYPE: DNA
<213> ORGANISM: Mus musculus

<400> SEQUENCE: 393
gacattgtga tgacacagtc tccatcctcc ttgagtgtgt cagcaggaga gaaggtcact 60
atgagctgca agtccagtca gagtctgttc aacagtggaa atcaaaagaa ctacttggcc 120
tggtaccagc agaaaccagg gcagcctcct aagctgttga tctacggggc atccactagg 180
gaatctgggg tccctgatcg cttcacaggc agtggatctg gaaccgattt cactcttacc 240
atcagcaatg tgcaggctga agacctggca gtttatctct gtcagaatga tcatagtttt 300
ccgctgacgt tcggtgctgg gaccaagctg gagctgaga 339

<210> SEQ ID NO 394
<211> LENGTH: 112
<212> TYPE: PRT
<213> ORGANISM: Mus musculus

<400> SEQUENCE: 394

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Phe Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Asn Val Gln Ala Glu Asp Leu Ala Val Tyr Leu Cys Gln Asn
85 90 95

Asp His Ser Phe Pro Leu Thr Phe Gly Ala Gly Thr Lys Leu Glu Leu
100 105 110

<210> SEQ ID NO 395
<211> LENGTH: 30
<212> TYPE: PRT
<213> ORGANISM: Mus musculus

<400> SEQUENCE: 395

Glu Val Met Leu Val Glu Ser Gly Gly Gly Leu Val Lys Pro Gly Gly
1 5 10 15

Ser Leu Lys Leu Ser Cys Val Ala Ser Gly Phe Thr Phe Ser
20 25 30

<210> SEQ ID NO 396
<211> LENGTH: 5
<212> TYPE: PRT
<213> ORGANISM: Mus musculus

<400> SEQUENCE: 396

Ser Tyr Thr Met Ser
1 5

<210> SEQ ID NO 397
<211> LENGTH: 14
<212> TYPE: PRT
<213> ORGANISM: Mus musculus

<400> SEQUENCE: 397

Trp Val Arg Gln Thr Pro Glu Lys Arg Leu Glu Trp Val Ala
1 5 10

<210> SEQ ID NO 398
<211> LENGTH: 17
<212> TYPE: PRT
<213> ORGANISM: Mus musculus

<400> SEQUENCE: 398

Thr Ile Ile Gly Gly Tyr Gly Asn Thr Tyr Tyr Ser Asp Ser Val Lys
1 5 10 15

Gly

<210> SEQ ID NO 399
<211> LENGTH: 32
<212> TYPE: PRT
<213> ORGANISM: Mus musculus

<400> SEQUENCE: 399

Arg Ile Thr Ile Ser Arg Asp Ser Ala Lys Asn Thr Leu Tyr Leu Gln
1 5 10 15

Met Ile Ser Leu Arg Ser Glu Asp Thr Ala Leu Tyr Tyr Cys Thr Arg
20 25 30

<210> SEQ ID NO 400
<211> LENGTH: 11
<212> TYPE: PRT
<213> ORGANISM: Mus musculus

<400> SEQUENCE: 400

Leu Gly Gln Thr Gln Arg Asn Ala Met Asp Tyr
1 5 10

<210> SEQ ID NO 401
<211> LENGTH: 11
<212> TYPE: PRT
<213> ORGANISM: Mus musculus

<400> SEQUENCE: 401

Trp Gly Gln Gly Thr Ser Val Thr Val Ser Ser
1 5 10

<210> SEQ ID NO 402
<211> LENGTH: 360
<212> TYPE: DNA
<213> ORGANISM: Mus musculus

<400> SEQUENCE: 402
gaagtgatgc tggtggagtc tgggggaggc ttagtgaagc ctggagggtc cctgaaactc 60
tcctgtgtag cctctggatt cactttcagt agttatacca tgtcttgggt tcgccagact 120
ccggagaaga ggctggagtg ggtcgcaacc attattggtg gttatggtaa cacctactat 180
tcagacagtg tgaagggtcg aatcaccatc tccagagaca gcgccaagaa caccctgtac 240
ctgcaaatga tcagtctgag gtctgaggac acggccttgt attactgtac aagactggga 300
cagacacaga gaaatgctat ggactactgg ggtcaaggaa cctcagtcac cgtctcctca 360

<210> SEQ ID NO 403
<211> LENGTH: 120
<212> TYPE: PRT
<213> ORGANISM: Mus musculus

<400> SEQUENCE: 403

Glu Val Met Leu Val Glu Ser Gly Gly Gly Leu Val Lys Pro Gly Gly
1 5 10 15

Ser Leu Lys Leu Ser Cys Val Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Ile Gly Gly Tyr Gly Asn Thr Tyr Tyr Ser Asp Ser Val
    50                  55                  60

Lys Gly Arg Ile Thr Ile Ser Arg Asp Ser Ala Lys Asn Thr Leu Tyr
65                  70                  75                  80

Leu Gln Met Ile Ser Leu Arg Ser Glu Asp Thr Ala Leu Tyr Tyr Cys
                85                  90                  95

Thr Arg Leu Gly Gln Thr Gln Arg Asn Ala Met Asp Tyr Trp Gly Gln
            100                 105                 110

Gly Thr Ser Val Thr Val Ser Ser
        115                 120

<210> SEQ ID NO 404
<211> LENGTH: 23
<212> TYPE: PRT
<213> ORGANISM: Mus musculus

<400> SEQUENCE: 404

Asp Ile Leu Met Thr Gln Ser Pro Ser Ser Leu Ser Val Ser Ala Gly
1               5                   10                  15

Glu Lys Val Thr Met Asn Cys
            20

<210> SEQ ID NO 405
<211> LENGTH: 17
<212> TYPE: PRT
<213> ORGANISM: Mus musculus

<400> SEQUENCE: 405

Lys Ser Ser Gln Ser Leu Leu Asn Ser Gly Asn Gln Lys Asn Tyr Leu
1               5                   10                  15

Ala

<210> SEQ ID NO 406
<211> LENGTH: 15
<212> TYPE: PRT
<213> ORGANISM: Mus musculus

<400> SEQUENCE: 406

Trp Tyr Gln Gln Lys Pro Gly Gln Pro Pro Lys Leu Leu Ile Tyr
1               5                   10                  15

<210> SEQ ID NO 407
<211> LENGTH: 7
<212> TYPE: PRT
<213> ORGANISM: Mus musculus

<400> SEQUENCE: 407

Gly Ala Ser Thr Arg Glu Ser
1               5

<210> SEQ ID NO 408
<211> LENGTH: 32
<212> TYPE: PRT
<213> ORGANISM: Mus musculus

<400> SEQUENCE: 408

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 409
<211> LENGTH: 9
<212> TYPE: PRT
<213> ORGANISM: Mus musculus

<400> SEQUENCE: 409

Gln Asn Asp Tyr Tyr Tyr Pro Phe Thr
1 5

<210> SEQ ID NO 410
<211> LENGTH: 9
<212> TYPE: PRT
<213> ORGANISM: Mus musculus

<400> SEQUENCE: 410

Phe Gly Ala Gly Thr Lys Leu Glu Leu
1 5

<210> SEQ ID NO 411
<211> LENGTH: 339
<212> TYPE: DNA
<213> ORGANISM: Mus musculus

<400> SEQUENCE: 411
gacattttga tgacacagtc tccatcctcc ctgagtgtgt cagcaggaga gaaggtcact 60
atgaactgca agtccagtca gagtctgtta aacagtggaa atcaaaagaa ctatttggcc 120
tggtaccagc agaaaccagg gcagcctcct aaattgttga tctatggggc atccactagg 180
gaatctgggg tccctgatcg cttcacaggc agtggatctg gaaccgattt cactcttacc 240
atcagcagtg tgcaggctga agacctggca gtttattact gtcagaatga ttattattat 300
ccattcacgt tcggtgctgg gaccaagctg gagctgaaa 339

<210> SEQ ID NO 412
<211> LENGTH: 112
<212> TYPE: PRT
<213> ORGANISM: Mus musculus

<400> SEQUENCE: 412

Asp Ile Leu Met Thr Gln Ser Pro Ser Ser Leu Ser Val Ser Ala Gly
1 5 10 15

Glu Lys Val Thr Met Asn Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Tyr Tyr Pro Phe Thr Phe Gly Ala Gly Thr Lys Leu Glu Leu
100 105 110

<210> SEQ ID NO 413
<211> LENGTH: 30
<212> TYPE: PRT
<213> ORGANISM: Mus musculus

<400> SEQUENCE: 413

Glu Val Met Leu Val Glu Ser Gly Gly Gly Leu Val Lys Pro Gly Gly

```
1               5                   10                  15

Ser Leu Lys Leu Ser Cys Ala Ala Ser Gly Phe Thr Phe Ser
            20                  25                  30


<210> SEQ ID NO 414
<211> LENGTH: 5
<212> TYPE: PRT
<213> ORGANISM: Mus musculus

<400> SEQUENCE: 414

Ser Tyr Thr Met Ser
1               5


<210> SEQ ID NO 415
<211> LENGTH: 14
<212> TYPE: PRT
<213> ORGANISM: Mus musculus

<400> SEQUENCE: 415

Trp Val Arg Gln Thr Pro Glu Lys Arg Leu Glu Trp Val Ala
1               5                   10


<210> SEQ ID NO 416
<211> LENGTH: 17
<212> TYPE: PRT
<213> ORGANISM: Mus musculus

<400> SEQUENCE: 416

Thr Ile Ile Gly Gly Tyr Gly Asn Thr Tyr Tyr Val Asp Ser Val Lys
1               5                   10                  15

Gly


<210> SEQ ID NO 417
<211> LENGTH: 32
<212> TYPE: PRT
<213> ORGANISM: Mus musculus

<400> SEQUENCE: 417

Arg Phe Thr Ile Ser Arg Asp Ser Ala Lys Asn Thr Leu Tyr Leu Gln
1               5                   10                  15

Met Ile Ser Leu Arg Ser Glu Asp Thr Ala Leu Tyr Tyr Cys Thr Arg
            20                  25                  30


<210> SEQ ID NO 418
<211> LENGTH: 11
<212> TYPE: PRT
<213> ORGANISM: Mus musculus

<400> SEQUENCE: 418

Leu Gly Gln Thr Gln Arg Asn Ala Met Asp Tyr
1               5                   10


<210> SEQ ID NO 419
<211> LENGTH: 11
<212> TYPE: PRT
<213> ORGANISM: Mus musculus

<400> SEQUENCE: 419

Trp Gly Gln Gly Thr Ser Val Thr Val Ser Ser
1               5                   10


<210> SEQ ID NO 420
<211> LENGTH: 360
```

<212> TYPE: DNA
<213> ORGANISM: Mus musculus

<400> SEQUENCE: 420
gaagtgatgc tggtggaatc tgggggaggc ttagtgaagc ctggagggtc cctgaaactc 60
tcctgtgcag cctctggatt cactttcagt agctatacca tgtcttgggt tcgccagact 120
ccggagaaga gactggagtg ggtcgcaacc attattggtg gttatggtaa cacctactat 180
gtagacagtg tgaagggtcg attcaccatc tccagagaca gtgccaagaa caccctctac 240
ctacaaatga tcagtctgag gtctgaggac acggccttgt attactgtac aagactggga 300
cagacacaga gaaatgctat ggactactgg ggtcaaggaa cctcagtcac cgtctcctca 360

<210> SEQ ID NO 421
<211> LENGTH: 120
<212> TYPE: PRT
<213> ORGANISM: Mus musculus

<400> SEQUENCE: 421

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Ile Gly Gly Tyr Gly Asn Thr Tyr Tyr Val Asp Ser Val
50 55 60

Lys Gly Arg Phe Thr Ile Ser Arg Asp Ser Ala Lys Asn Thr Leu Tyr
65 70 75 80

Leu Gln Met Ile Ser Leu Arg Ser Glu Asp Thr Ala Leu Tyr Tyr Cys
85 90 95

Thr Arg Leu Gly Gln Thr Gln Arg Asn Ala Met Asp Tyr Trp Gly Gln
100 105 110

Gly Thr Ser Val Thr Val Ser Ser
115 120

<210> SEQ ID NO 422
<211> LENGTH: 23
<212> TYPE: PRT
<213> ORGANISM: Mus musculus

<400> SEQUENCE: 422

Asp Ile Leu Met Thr Gln Ser Pro Ser Ser Leu Ser Val Ser Ala Gly
1 5 10 15

Glu Lys Val Thr Met Ser Cys
20

<210> SEQ ID NO 423
<211> LENGTH: 17
<212> TYPE: PRT
<213> ORGANISM: Mus musculus

<400> SEQUENCE: 423

Lys Ser Ser Gln Ser Leu Leu Asn Ser Gly Asn Gln Lys Asn Tyr Leu
1 5 10 15

Ala

<210> SEQ ID NO 424
<211> LENGTH: 15

<212> TYPE: PRT
<213> ORGANISM: Mus musculus

<400> SEQUENCE: 424

Trp Tyr Gln Gln Lys Pro Gly Gln Pro Pro Lys Leu Leu Ile Tyr
1 5 10 15

<210> SEQ ID NO 425
<211> LENGTH: 7
<212> TYPE: PRT
<213> ORGANISM: Mus musculus

<400> SEQUENCE: 425

Gly Ala Ser Thr Arg Glu Ser
1 5

<210> SEQ ID NO 426
<211> LENGTH: 32
<212> TYPE: PRT
<213> ORGANISM: Mus musculus

<400> SEQUENCE: 426

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 427
<211> LENGTH: 9
<212> TYPE: PRT
<213> ORGANISM: Mus musculus

<400> SEQUENCE: 427

Gln Asn Asp Tyr Tyr Tyr Pro Phe Thr
1 5

<210> SEQ ID NO 428
<211> LENGTH: 9
<212> TYPE: PRT
<213> ORGANISM: Mus musculus

<400> SEQUENCE: 428

Phe Gly Ala Gly Thr Lys Leu Glu Leu
1 5

<210> SEQ ID NO 429
<211> LENGTH: 339
<212> TYPE: DNA
<213> ORGANISM: Mus musculus

<400> SEQUENCE: 429
gacattttga tgacacagtc tccatcctcc ctgagtgtgt cagcaggaga gaaggtcact 60
atgagctgca agtccagtca gagtctgtta aacagtggaa atcaaaagaa ctatttggcc 120
tggtaccagc agaaaccagg gcagcctcct aaattattga tctatggggc atctactagg 180
gaatctgggg tccctgatcg cttcacaggc agtggatctg gaaccgattt cactcttacc 240
atcagcagtg tgcaggctga agacctggca gtttattatt gtcagaatga ttattattat 300
ccgttcacgt tcggtgctgg gaccaagctg gagctgaaa 339

<210> SEQ ID NO 430
<211> LENGTH: 112
<212> TYPE: PRT

<213> ORGANISM: Mus musculus

<400> SEQUENCE: 430

Asp Ile Leu Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Tyr Tyr Pro Phe Thr Phe Gly Ala Gly Thr Lys Leu Glu Leu
100 105 110

<210> SEQ ID NO 431
<211> LENGTH: 30
<212> TYPE: PRT
<213> ORGANISM: Mus musculus

<400> SEQUENCE: 431

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 432
<211> LENGTH: 5
<212> TYPE: PRT
<213> ORGANISM: Mus musculus

<400> SEQUENCE: 432

Ser Tyr Thr Met Ser
1 5

<210> SEQ ID NO 433
<211> LENGTH: 14
<212> TYPE: PRT
<213> ORGANISM: Mus musculus

<400> SEQUENCE: 433

Trp Val Arg Gln Thr Pro Glu Lys Arg Leu Glu Trp Val Ala
1 5 10

<210> SEQ ID NO 434
<211> LENGTH: 17
<212> TYPE: PRT
<213> ORGANISM: Mus musculus

<400> SEQUENCE: 434

Thr Ile Ile Gly Gly Tyr Gly Asn Thr Tyr Tyr Ala Asp Ser Val Lys
1 5 10 15

Gly

<210> SEQ ID NO 435
<211> LENGTH: 32
<212> TYPE: PRT
<213> ORGANISM: Mus musculus

<400> SEQUENCE: 435

Arg Phe Thr Ile Ser Arg Asp Ser Ala Lys Asn Thr Leu Tyr Leu Gln
1 5 10 15

Met Ile Ser Leu Arg Ser Glu Asp Thr Ala Leu Tyr Tyr Cys Thr Arg
20 25 30

<210> SEQ ID NO 436
<211> LENGTH: 11
<212> TYPE: PRT
<213> ORGANISM: Mus musculus

<400> SEQUENCE: 436

Leu Gly Gln Thr Gln Arg Asn Ala Met Asp Tyr
1 5 10

<210> SEQ ID NO 437
<211> LENGTH: 11
<212> TYPE: PRT
<213> ORGANISM: Mus musculus

<400> SEQUENCE: 437

Trp Gly Gln Gly Thr Ser Val Thr Val Ser Ser
1 5 10

<210> SEQ ID NO 438
<211> LENGTH: 360
<212> TYPE: DNA
<213> ORGANISM: Mus musculus

<400> SEQUENCE: 438
gaagtgatgc tggtggagtc tgggggaggc ttagtgaagc ctggagggtc cctgaaactc 60
tcctgtgcag cctctggatt cactttcagt agctatacca tgtcttgggt tcgccagact 120
ccggagaaga ggctggagtg ggtcgcaacc attattggtg gttatggtaa cacctactat 180
gcagacagtg tgaagggtcg attcaccatc tccagagaca gtgccaagaa caccctgtac 240
ctgcaaatga tcagtctgag gtctgaggac acggccttgt attactgtac aagactggga 300
cagacacaga gaaatgctat ggactactgg ggtcaaggaa cctcagtcac cgtctcctca 360

<210> SEQ ID NO 439
<211> LENGTH: 120
<212> TYPE: PRT
<213> ORGANISM: Mus musculus

<400> SEQUENCE: 439

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Ile Gly Gly Tyr Gly Asn Thr Tyr Tyr Ala Asp Ser Val
50 55 60

Lys Gly Arg Phe Thr Ile Ser Arg Asp Ser Ala Lys Asn Thr Leu Tyr
65 70 75 80

Leu Gln Met Ile Ser Leu Arg Ser Glu Asp Thr Ala Leu Tyr Tyr Cys
85 90 95

Thr Arg Leu Gly Gln Thr Gln Arg Asn Ala Met Asp Tyr Trp Gly Gln
100 105 110

```
Gly Thr Ser Val Thr Val Ser Ser
        115                 120


<210> SEQ ID NO 440
<211> LENGTH: 23
<212> TYPE: PRT
<213> ORGANISM: Mus musculus

<400> SEQUENCE: 440

Asp Ile Leu Met Thr Gln Ser Pro Ser Ser Leu Ser Val Ser Ala Gly
1               5                   10                  15

Glu Lys Val Thr Met Ser Cys
            20


<210> SEQ ID NO 441
<211> LENGTH: 17
<212> TYPE: PRT
<213> ORGANISM: Mus musculus

<400> SEQUENCE: 441

Lys Ser Ser Gln Ser Leu Leu Asn Ser Gly Asn Gln Lys Asn Tyr Leu
1               5                   10                  15

Ala


<210> SEQ ID NO 442
<211> LENGTH: 15
<212> TYPE: PRT
<213> ORGANISM: Mus musculus

<400> SEQUENCE: 442

Trp Tyr Gln Gln Lys Pro Gly Gln Pro Pro Lys Leu Leu Ile Tyr
1               5                   10                  15


<210> SEQ ID NO 443
<211> LENGTH: 7
<212> TYPE: PRT
<213> ORGANISM: Mus musculus

<400> SEQUENCE: 443

Gly Ala Ser Thr Arg Glu Ser
1               5


<210> SEQ ID NO 444
<211> LENGTH: 32
<212> TYPE: PRT
<213> ORGANISM: Mus musculus

<400> SEQUENCE: 444

Gly Val Pro Asp Thr Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 445
<211> LENGTH: 9
<212> TYPE: PRT
<213> ORGANISM: Mus musculus

<400> SEQUENCE: 445

Gln Asn Asp Tyr Tyr Tyr Pro Phe Thr
1               5
```

<210> SEQ ID NO 446
<211> LENGTH: 9
<212> TYPE: PRT
<213> ORGANISM: Mus musculus

<400> SEQUENCE: 446

Phe Gly Ala Gly Thr Lys Leu Glu Leu
1 5

<210> SEQ ID NO 447
<211> LENGTH: 339
<212> TYPE: DNA
<213> ORGANISM: Mus musculus

<400> SEQUENCE: 447
gacattttga tgacacagtc tccatcctcc ctgagtgtgt cagcaggaga gaaggtcact 60
atgagctgca agtccagtca gagtctgtta aacagtggaa atcaaaagaa ctatttggcc 120
tggtaccagc agaaaccagg gcagcctcct aaattgttga tctatggggc atccactagg 180
gaatctgggg tccctgatac cttcacaggc agtggatctg gaaccgattt cactcttacc 240
atcagcagtg tgcaggctga agacctggca gtttattact gtcagaatga ttattattat 300
ccgttcacgt tcggtgctgg gaccaagctg gagctgaag 339

<210> SEQ ID NO 448
<211> LENGTH: 112
<212> TYPE: PRT
<213> ORGANISM: Mus musculus

<400> SEQUENCE: 448

Asp Ile Leu Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Thr Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Tyr Tyr Pro Phe Thr Phe Gly Ala Gly Thr Lys Leu Glu Leu
100 105 110

<210> SEQ ID NO 449
<211> LENGTH: 30
<212> TYPE: PRT
<213> ORGANISM: Mus musculus

<400> SEQUENCE: 449

Glu Val Met Leu Val Glu Ser Gly Gly Gly Leu Val Lys Pro Gly Gly
1 5 10 15

Ser Leu Lys Leu Ser Cys Val Ala Ser Gly Phe Thr Phe Ser
20 25 30

<210> SEQ ID NO 450
<211> LENGTH: 5
<212> TYPE: PRT
<213> ORGANISM: Mus musculus

<400> SEQUENCE: 450

Ser Tyr Thr Met Ser
1 5

<210> SEQ ID NO 451
<211> LENGTH: 14
<212> TYPE: PRT
<213> ORGANISM: Mus musculus

<400> SEQUENCE: 451

Trp Val Arg Gln Thr Pro Glu Lys Arg Leu Glu Trp Val Ala
1 5 10

<210> SEQ ID NO 452
<211> LENGTH: 17
<212> TYPE: PRT
<213> ORGANISM: Mus musculus

<400> SEQUENCE: 452

Thr Leu Ser Val Val Gly Gly Asn Thr Tyr Tyr Val Asp Ser Val Lys
1 5 10 15

Gly

<210> SEQ ID NO 453
<211> LENGTH: 32
<212> TYPE: PRT
<213> ORGANISM: Mus musculus

<400> SEQUENCE: 453

Arg Phe Thr Ile Ser Arg Asp Lys Ala Lys Asn Thr Leu Tyr Leu Gln
1 5 10 15

Met Ser Ser Leu Arg Ser Glu Asp Thr Ala Leu Tyr Tyr Cys Ala Arg
20 25 30

<210> SEQ ID NO 454
<211> LENGTH: 11
<212> TYPE: PRT
<213> ORGANISM: Mus musculus

<400> SEQUENCE: 454

Leu Gly Gln Thr Gln Arg Asn Ala Met Asp Tyr
1 5 10

<210> SEQ ID NO 455
<211> LENGTH: 11
<212> TYPE: PRT
<213> ORGANISM: Mus musculus

<400> SEQUENCE: 455

Trp Gly Gln Gly Thr Ser Val Thr Val Ser Ser
1 5 10

<210> SEQ ID NO 456
<211> LENGTH: 360
<212> TYPE: DNA
<213> ORGANISM: Mus musculus

<400> SEQUENCE: 456
gaagtgatgc tggtggagtc tgggggaggc ttagtgaagc ctggagggtc cctgaaactc 60
tcctgtgtag cctctggatt cactttcagt agctatacca tgtcttgggt tcgccagact 120
ccggagaaga ggctggagtg ggtcgcaacc cttagtgttg ttggtggtaa cacctactat 180
gtagacagtg tgaagggtcg attcaccatc tccagagaca aagccaagaa caccctgtac 240
ctgcaaatga gcagtctgag gtctgaggac acggccttat attactgtgc aagactggga 300
cagacacaga gaaatgctat ggactactgg ggtcaaggaa cctcagtcac cgtctcctca 360

<210> SEQ ID NO 457
<211> LENGTH: 120
<212> TYPE: PRT
<213> ORGANISM: Mus musculus

<400> SEQUENCE: 457

Glu Val Met Leu Val Glu Ser Gly Gly Gly Leu Val Lys Pro Gly Gly
1 5 10 15

Ser Leu Lys Leu Ser Cys Val Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Leu Ser Val Val Gly Gly Asn Thr Tyr Tyr Val Asp Ser Val
50 55 60

Lys Gly Arg Phe Thr Ile Ser Arg Asp Lys Ala Lys Asn Thr Leu Tyr
65 70 75 80

Leu Gln Met Ser Ser Leu Arg Ser Glu Asp Thr Ala Leu Tyr Tyr Cys
85 90 95

Ala Arg Leu Gly Gln Thr Gln Arg Asn Ala Met Asp Tyr Trp Gly Gln
100 105 110

Gly Thr Ser Val Thr Val Ser Ser
115 120

<210> SEQ ID NO 458
<211> LENGTH: 23
<212> TYPE: PRT
<213> ORGANISM: Mus musculus

<400> SEQUENCE: 458

Asp Ile Val Met Thr Gln Ser Pro Ser Ser Leu Ser Val Ser Ala Gly
1 5 10 15

Glu Lys Val Thr Met Ser Cys
20

<210> SEQ ID NO 459
<211> LENGTH: 17
<212> TYPE: PRT
<213> ORGANISM: Mus musculus

<400> SEQUENCE: 459

Lys Ser Ser Gln Ser Leu Leu Asn Ser Gly Asn Gln Lys Asn Tyr Leu
1 5 10 15

Ala

<210> SEQ ID NO 460
<211> LENGTH: 15
<212> TYPE: PRT
<213> ORGANISM: Mus musculus

<400> SEQUENCE: 460

Trp Tyr Gln Gln Lys Pro Gly Gln Pro Pro Lys Leu Leu Ile Tyr
1 5 10 15

<210> SEQ ID NO 461
<211> LENGTH: 7

<212> TYPE: PRT
<213> ORGANISM: Mus musculus

<400> SEQUENCE: 461

Gly Ala Ser Thr Arg Glu Ser
1 5

<210> SEQ ID NO 462
<211> LENGTH: 32
<212> TYPE: PRT
<213> ORGANISM: Mus musculus

<400> SEQUENCE: 462

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 463
<211> LENGTH: 9
<212> TYPE: PRT
<213> ORGANISM: Mus musculus

<400> SEQUENCE: 463

Gln Asn Asp Tyr Ser Tyr Pro Leu Thr
1 5

<210> SEQ ID NO 464
<211> LENGTH: 9
<212> TYPE: PRT
<213> ORGANISM: Mus musculus

<400> SEQUENCE: 464

Phe Gly Ala Gly Thr Lys Leu Glu Leu
1 5

<210> SEQ ID NO 465
<211> LENGTH: 339
<212> TYPE: DNA
<213> ORGANISM: Mus musculus

<400> SEQUENCE: 465
gacattgtga tgacacagtc tccatcctct ctgagtgtgt cagcaggaga gaaggtcaca 60
atgagttgca agtccagtca gagtctgtta aacagtggaa atcaaaagaa ctacttggcc 120
tggtaccagc agaaaccagg gcagcctcct aaactgttga tctacggggc atctactagg 180
gaatctgggg tccctgatcg cttcacaggc agtggatctg gaaccgattt cactcttacc 240
atcagtagtg tgcaggctga agacctggca gtttattact gtcagaatga ttatagttat 300
ccgctcacgt tcggtgctgg gaccaagctg gagctgaaa 339

<210> SEQ ID NO 466
<211> LENGTH: 112
<212> TYPE: PRT
<213> ORGANISM: Mus musculus

<400> SEQUENCE: 466

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln

```
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110


<210> SEQ ID NO 467
<211> LENGTH: 30
<212> TYPE: PRT
<213> ORGANISM: Mus musculus

<400> SEQUENCE: 467

Glu Val Lys Leu Val Glu Ser Gly Gly Gly Leu Val Lys Pro Gly Gly
1               5                   10                  15

Ser Leu Lys Leu Ser Cys Ala Gly Ser Gly Phe Thr Phe Ser
            20                  25                  30


<210> SEQ ID NO 468
<211> LENGTH: 5
<212> TYPE: PRT
<213> ORGANISM: Mus musculus

<400> SEQUENCE: 468

Ser Tyr Thr Met Ser
1               5


<210> SEQ ID NO 469
<211> LENGTH: 14
<212> TYPE: PRT
<213> ORGANISM: Mus musculus

<400> SEQUENCE: 469

Trp Val Arg Gln Thr Pro Glu Lys Arg Leu Glu Trp Val Ala
1               5                   10


<210> SEQ ID NO 470
<211> LENGTH: 16
<212> TYPE: PRT
<213> ORGANISM: Mus musculus

<400> SEQUENCE: 470

Thr Ile Thr Ile Gly Val Asn Ile Tyr Tyr Leu Asp Ser Val Lys Gly
1               5                   10                  15


<210> SEQ ID NO 471
<211> LENGTH: 32
<212> TYPE: PRT
<213> ORGANISM: Mus musculus

<400> SEQUENCE: 471

Arg Phe Thr Ile Ser Arg Asp Asn Ala Lys Asn Thr Leu Tyr Leu Gln
1               5                   10                  15

Met Asn Ser Leu Arg Ser Glu Asp Thr Ala Leu Tyr Tyr Cys Thr Arg
            20                  25                  30


<210> SEQ ID NO 472
<211> LENGTH: 11
<212> TYPE: PRT
```

<213> ORGANISM: Mus musculus

<400> SEQUENCE: 472

Leu Gly Gln Thr Gln Arg Asn Ala Met Asp Tyr
1 5 10

<210> SEQ ID NO 473
<211> LENGTH: 11
<212> TYPE: PRT
<213> ORGANISM: Mus musculus

<400> SEQUENCE: 473

Trp Gly Gln Gly Thr Ser Val Thr Val Ser Ser
1 5 10

<210> SEQ ID NO 474
<211> LENGTH: 357
<212> TYPE: DNA
<213> ORGANISM: Mus musculus

<400> SEQUENCE: 474
gaagtgaagc tggtggagtc tgggggaggc ttagtgaagc ctggagggtc cctgaaactc 60
tcctgtgcag gctctggatt cactttcagt agctatacca tgtcttgggt tcgccagact 120
ccggagaaga ggctggagtg ggtcgcaacc attactattg gtgttaacat ctactatcta 180
gacagtgtga agggtcgatt caccatctcc agagacaatg ccaagaacac cttgtacctg 240
caaatgaaca gtctgaggtc tgaggacacg gccttgtatt attgtacaag actgggacag 300
acacagcgaa atgctatgga ctactggggt caaggaacct cagtcaccgt ctcctca 357

<210> SEQ ID NO 475
<211> LENGTH: 119
<212> TYPE: PRT
<213> ORGANISM: Mus musculus

<400> SEQUENCE: 475

Glu Val Lys Leu Val Glu Ser Gly Gly Gly Leu Val Lys Pro Gly Gly
1 5 10 15

Ser Leu Lys Leu Ser Cys Ala Gly Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Thr Ile Gly Val Asn Ile Tyr Tyr Leu Asp Ser Val Lys
50 55 60

Gly Arg Phe Thr Ile Ser Arg Asp Asn Ala Lys Asn Thr Leu Tyr Leu
65 70 75 80

Gln Met Asn Ser Leu Arg Ser Glu Asp Thr Ala Leu Tyr Tyr Cys Thr
85 90 95

Arg Leu Gly Gln Thr Gln Arg Asn Ala Met Asp Tyr Trp Gly Gln Gly
100 105 110

Thr Ser Val Thr Val Ser Ser
115

<210> SEQ ID NO 476
<211> LENGTH: 23
<212> TYPE: PRT
<213> ORGANISM: Mus musculus

<400> SEQUENCE: 476

Asp Ile Val Met Thr Gln Ser Pro Thr Ser Leu Ser Val Ser Ala Gly

```
1               5                   10                  15

Glu Lys Val Thr Met Thr Cys
            20


<210> SEQ ID NO 477
<211> LENGTH: 17
<212> TYPE: PRT
<213> ORGANISM: Mus musculus

<400> SEQUENCE: 477

Lys Ser Ser Gln Ser Leu Phe Asn Ser Gly Asn Gln Lys Asn Tyr Leu
1               5                   10                  15

Ala


<210> SEQ ID NO 478
<211> LENGTH: 15
<212> TYPE: PRT
<213> ORGANISM: Mus musculus

<400> SEQUENCE: 478

Trp Tyr Gln Glu Lys Pro Gly Gln Pro Pro Lys Leu Leu Ile Tyr
1               5                   10                  15


<210> SEQ ID NO 479
<211> LENGTH: 7
<212> TYPE: PRT
<213> ORGANISM: Mus musculus

<400> SEQUENCE: 479

Gly Ala Ser Thr Arg Glu Ser
1               5


<210> SEQ ID NO 480
<211> LENGTH: 32
<212> TYPE: PRT
<213> ORGANISM: Mus musculus

<400> SEQUENCE: 480

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30


<210> SEQ ID NO 481
<211> LENGTH: 9
<212> TYPE: PRT
<213> ORGANISM: Mus musculus

<400> SEQUENCE: 481

Gln Asn Val His Phe Tyr Pro Phe Thr
1               5


<210> SEQ ID NO 482
<211> LENGTH: 9
<212> TYPE: PRT
<213> ORGANISM: Mus musculus

<400> SEQUENCE: 482

Phe Gly Ala Gly Thr Lys Leu Glu Leu
1               5


<210> SEQ ID NO 483
<211> LENGTH: 339
```

```
<212> TYPE: DNA
<213> ORGANISM: Mus musculus

<400> SEQUENCE: 483

gacattgtga tgacacagtc tccaacctcc ctgagtgtgt cagcaggaga gaaggtcact     60

atgacctgca agtccagtca gagtctgttc aacagtggaa atcaaaagaa ctacttggcc    120

tggtatcagg agaaaccagg acagcctcct aaactgttga tctacggggc atccactagg    180

gagtctgggg tccctgatcg cttcacaggc agtggatctg gaaccgattt cactcttacc    240

atcagcagtg tgcaggctga agacctggcc gtttattact gtcagaatgt tcatttttat    300

ccgttcacgt tcggtgctgg gaccaagctg gagctgaaa                           339


<210> SEQ ID NO 484
<211> LENGTH: 112
<212> TYPE: PRT
<213> ORGANISM: Mus musculus

<400> SEQUENCE: 484

Asp Ile Val Met Thr Gln Ser Pro Thr Ser Leu Ser Val Ser Ala Gly
1               5                   10                  15

Glu Lys Val Thr Met Thr Cys Lys Ser Ser Gln Ser Leu Phe Asn Ser
            20                  25                  30

Gly Asn Gln Lys Asn Tyr Leu Ala Trp Tyr Gln Glu Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Val His Phe Tyr Pro Phe Thr Phe Gly Ala Gly Thr Lys Leu Glu Leu
            100                 105                 110


<210> SEQ ID NO 485
<211> LENGTH: 30
<212> TYPE: PRT
<213> ORGANISM: Mus musculus

<400> SEQUENCE: 485

Glu Ala Gln Leu Gln Gln Ser Gly Pro Glu Leu Val Lys Pro Gly Ala
1               5                   10                  15

Ser Val Lys Ile Phe Cys Lys Ala Ser Gly Tyr Thr Phe Thr
            20                  25                  30


<210> SEQ ID NO 486
<211> LENGTH: 5
<212> TYPE: PRT
<213> ORGANISM: Mus musculus

<400> SEQUENCE: 486

Asp Tyr Tyr Ile Asn
1               5


<210> SEQ ID NO 487
<211> LENGTH: 14
<212> TYPE: PRT
<213> ORGANISM: Mus musculus

<400> SEQUENCE: 487
```

Trp Val Lys Gln Ser His Gly Lys Ser Leu Glu Trp Ile Gly
1 5 10

<210> SEQ ID NO 488
<211> LENGTH: 17
<212> TYPE: PRT
<213> ORGANISM: Mus musculus

<400> SEQUENCE: 488

Asp Ile Asn Pro Asn Asn Gly Gly Thr Thr Tyr Asn Gln Lys Phe Lys
1 5 10 15

Gly

<210> SEQ ID NO 489
<211> LENGTH: 32
<212> TYPE: PRT
<213> ORGANISM: Mus musculus

<400> SEQUENCE: 489

Lys Ala Thr Leu Thr Val Asp Lys Ser Ser Ser Thr Ala Ser Met Glu
1 5 10 15

Leu Arg Arg Leu Thr Ser Glu Asp Ser Ser Val Tyr Tyr Cys Ala Arg
20 25 30

<210> SEQ ID NO 490
<211> LENGTH: 6
<212> TYPE: PRT
<213> ORGANISM: Mus musculus

<400> SEQUENCE: 490

Arg Asp Ala Met Asp Tyr
1 5

<210> SEQ ID NO 491
<211> LENGTH: 11
<212> TYPE: PRT
<213> ORGANISM: Mus musculus

<400> SEQUENCE: 491

Trp Gly Gln Gly Thr Ser Val Thr Val Ser Ser
1 5 10

<210> SEQ ID NO 492
<211> LENGTH: 345
<212> TYPE: DNA
<213> ORGANISM: Mus musculus

<400> SEQUENCE: 492
gaggcccagc tgcaacaatc tggacctgag ctggtgaagc ctggggcgtc agtgaagata 60
ttctgtaagg cttctggata cacgttcact gactactaca tcaactgggt gaaacagagc 120
catggaaaga gccttgagtg gattggagat attaatccta acaatggtgg tactacctac 180
aaccagaagt tcaagggcaa ggccacattg actgtagaca agtcctccag cacagcctcc 240
atggagctcc gcagactgac atctgaagac tcttcagtct attactgtgc aagacgcgat 300
gctatggact actggggtca aggaacctca gtcaccgtct cctca 345

<210> SEQ ID NO 493
<211> LENGTH: 115
<212> TYPE: PRT
<213> ORGANISM: Mus musculus

<400> SEQUENCE: 493

Glu Ala Gln Leu Gln Gln Ser Gly Pro Glu Leu Val Lys Pro Gly Ala
1 5 10 15

Ser Val Lys Ile Phe Cys Lys Ala Ser Gly Tyr Thr Phe Thr Asp Tyr
20 25 30

Tyr Ile Asn Trp Val Lys Gln Ser His Gly Lys Ser Leu Glu Trp Ile
35 40 45

Gly Asp Ile Asn Pro Asn Asn Gly Gly Thr Thr Tyr Asn Gln Lys Phe
50 55 60

Lys Gly Lys Ala Thr Leu Thr Val Asp Lys Ser Ser Ser Thr Ala Ser
65 70 75 80

Met Glu Leu Arg Arg Leu Thr Ser Glu Asp Ser Ser Val Tyr Tyr Cys
85 90 95

Ala Arg Arg Asp Ala Met Asp Tyr Trp Gly Gln Gly Thr Ser Val Thr
100 105 110

Val Ser Ser
115

<210> SEQ ID NO 494
<211> LENGTH: 23
<212> TYPE: PRT
<213> ORGANISM: Mus musculus

<400> SEQUENCE: 494

Asp Ile Val Met Thr Gln Ser Gln Lys Phe Met Ser Thr Thr Val Gly
1 5 10 15

Asp Arg Val Ser Ile Thr Cys
20

<210> SEQ ID NO 495
<211> LENGTH: 11
<212> TYPE: PRT
<213> ORGANISM: Mus musculus

<400> SEQUENCE: 495

Thr Ala Ser Gln Asn Val Gly Pro Ala Val Ala
1 5 10

<210> SEQ ID NO 496
<211> LENGTH: 15
<212> TYPE: PRT
<213> ORGANISM: Mus musculus

<400> SEQUENCE: 496

Trp Tyr Gln Gln Lys Pro Gly Gln Ser Pro Lys Leu Leu Ile Tyr
1 5 10 15

<210> SEQ ID NO 497
<211> LENGTH: 7
<212> TYPE: PRT
<213> ORGANISM: Mus musculus

<400> SEQUENCE: 497

Ser Ala Ser Arg Arg Phe Thr
1 5

<210> SEQ ID NO 498
<211> LENGTH: 32
<212> TYPE: PRT
<213> ORGANISM: Mus musculus

<400> SEQUENCE: 498

```
Gly Val Pro Asp Arg Phe Thr Gly Ser Gly Ser Gly Thr Val Phe Thr
1               5                   10                  15

Leu Thr Ile Asn Asn Val Gln Ser Glu Asp Leu Ala Asp Tyr Phe Cys
            20                  25                  30


<210> SEQ ID NO 499
<211> LENGTH: 9
<212> TYPE: PRT
<213> ORGANISM: Mus musculus

<400> SEQUENCE: 499

Gln Gln Tyr Ile Ser Tyr Pro Leu Thr
1               5


<210> SEQ ID NO 500
<211> LENGTH: 10
<212> TYPE: PRT
<213> ORGANISM: Mus musculus

<400> SEQUENCE: 500

Phe Gly Ala Gly Thr Lys Leu Glu Leu Lys
1               5                   10


<210> SEQ ID NO 501
<211> LENGTH: 321
<212> TYPE: DNA
<213> ORGANISM: Mus musculus

<400> SEQUENCE: 501

gacattgtga tgacccagtc tcaaaaattc atgtccacaa cagtaggaga cagggtcagc     60

atcacctgca cggccagtca gaatgtgggt cctgctgttg cctggtatca acagaaacca    120

ggacaatctc ctaaactact gatttactca gcatcccgtc ggttcactgg agtccctgat    180

cgcttcacag gcagtggatc tgggacagtt ttcactctca ccattaacaa tgtgcagtct    240

gaagacctgg cagattattt ctgtcagcaa tatatcagct atcctctcac gttcggtgct    300

gggaccaagc tggagctgaa a                                              321


<210> SEQ ID NO 502
<211> LENGTH: 107
<212> TYPE: PRT
<213> ORGANISM: Mus musculus

<400> SEQUENCE: 502

Asp Ile Val Met Thr Gln Ser Gln Lys Phe Met Ser Thr Thr Val Gly
1               5                   10                  15

Asp Arg Val Ser Ile Thr Cys Thr Ala Ser Gln Asn Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Arg Arg Phe Thr Gly Val Pro Asp Arg Phe Thr Gly
    50                  55                  60

Ser Gly Ser Gly Thr Val Phe Thr Leu Thr Ile Asn Asn Val Gln Ser
65                  70                  75                  80

Glu Asp Leu Ala Asp Tyr Phe Cys Gln Gln Tyr Ile Ser Tyr Pro Leu
                85                  90                  95

Thr Phe Gly Ala Gly Thr Lys Leu Glu Leu Lys
            100                 105
```

```
<210> SEQ ID NO 503
<211> LENGTH: 30
<212> TYPE: PRT
<213> ORGANISM: Mus musculus

<400> SEQUENCE: 503

Glu Val Met Leu Val Glu Ser Gly Gly Gly Leu Val Lys Pro Gly Gly
1               5                   10                  15

Ser Leu Lys Leu Ser Cys Thr Ala Ser Gly Phe Thr Phe Arg
            20                  25                  30


<210> SEQ ID NO 504
<211> LENGTH: 5
<212> TYPE: PRT
<213> ORGANISM: Mus musculus

<400> SEQUENCE: 504

Ser Tyr Thr Met Ser
1               5


<210> SEQ ID NO 505
<211> LENGTH: 14
<212> TYPE: PRT
<213> ORGANISM: Mus musculus

<400> SEQUENCE: 505

Trp Val Arg Gln Thr Pro Glu Lys Arg Leu Glu Trp Val Ala
1               5                   10


<210> SEQ ID NO 506
<211> LENGTH: 17
<212> TYPE: PRT
<213> ORGANISM: Mus musculus

<400> SEQUENCE: 506

Thr Ile Thr Gly Gly Gly Gly Asn Thr Tyr Phe Leu Asp Ser Val Lys
1               5                   10                  15

Gly


<210> SEQ ID NO 507
<211> LENGTH: 32
<212> TYPE: PRT
<213> ORGANISM: Mus musculus

<400> SEQUENCE: 507

Arg Phe Thr Phe Ser Arg Asp Asn Ala Lys Asn Ala Leu Tyr Leu Gln
1               5                   10                  15

Met Asn Ser Leu Arg Ser Glu Asp Thr Ala Leu Tyr Tyr Cys Ala Arg
            20                  25                  30


<210> SEQ ID NO 508
<211> LENGTH: 11
<212> TYPE: PRT
<213> ORGANISM: Mus musculus

<400> SEQUENCE: 508

Leu Gly Gln Thr Gln Arg Asn Ala Met Asp Tyr
1               5                   10


<210> SEQ ID NO 509
<211> LENGTH: 11
<212> TYPE: PRT
<213> ORGANISM: Mus musculus
```

<400> SEQUENCE: 509

```
Trp Gly Gln Gly Thr Ser Val Thr Val Ser Ser
1               5                   10
```

<210> SEQ ID NO 510
<211> LENGTH: 360
<212> TYPE: DNA
<213> ORGANISM: Mus musculus

<400> SEQUENCE: 510

```
gaagtgatgc tggtggagtc tgggggaggc ttagtgaagc ctggagggtc cctgaaactc      60

tcctgtacag cctctggatt cactttcaga agctatacca tgtcttgggt tcgccagact     120

ccggagaaga ggctggagtg ggtcgcaact attactggtg gtggtggaaa tacctacttt     180

ctagacagtg tgaagggtcg attcaccttc tccagagaca atgccaagaa cgccctgtac     240

ctgcaaatga acagtctgag gtctgaggac acggccttgt attactgtgc aagactggga     300

cagacacaga gaaatgctat ggactactgg ggtcaaggaa cctcagtcac cgtctcctca     360
```

<210> SEQ ID NO 511
<211> LENGTH: 120
<212> TYPE: PRT
<213> ORGANISM: Mus musculus

<400> SEQUENCE: 511

```
Glu Val Met Leu Val Glu Ser Gly Gly Gly Leu Val Lys Pro Gly Gly
1               5                   10                  15

Ser Leu Lys Leu Ser Cys Thr Ala Ser Gly Phe Thr Phe Arg Ser Tyr
            20                  25                  30

Thr Met Ser Trp Val Arg Gln Thr Pro Glu Lys Arg Leu Glu Trp Val
        35                  40                  45

Ala Thr Ile Thr Gly Gly Gly Gly Asn Thr Tyr Phe Leu Asp Ser Val
    50                  55                  60

Lys Gly Arg Phe Thr Phe Ser Arg Asp Asn Ala Lys Asn Ala Leu Tyr
65                  70                  75                  80

Leu Gln Met Asn Ser Leu Arg Ser Glu Asp Thr Ala Leu Tyr Tyr Cys
                85                  90                  95

Ala Arg Leu Gly Gln Thr Gln Arg Asn Ala Met Asp Tyr Trp Gly Gln
            100                 105                 110

Gly Thr Ser Val Thr Val Ser Ser
        115                 120
```

<210> SEQ ID NO 512
<211> LENGTH: 23
<212> TYPE: PRT
<213> ORGANISM: Mus musculus

<400> SEQUENCE: 512

```
Asp Ile Val Met Thr Gln Ser Pro Ser Ser Leu Ser Val Ser Ala Gly
1               5                   10                  15

Glu Lys Val Thr Met Ser Cys
            20
```

<210> SEQ ID NO 513
<211> LENGTH: 17
<212> TYPE: PRT
<213> ORGANISM: Mus musculus

<400> SEQUENCE: 513

Lys Ser Ser Gln Ser Leu Leu Asn Ser Gly Asn Gln Met Asn Tyr Leu
1 5 10 15

Ala

<210> SEQ ID NO 514
<211> LENGTH: 15
<212> TYPE: PRT
<213> ORGANISM: Mus musculus

<400> SEQUENCE: 514

Trp Tyr Gln Gln Lys Pro Gly Gln Pro Pro Lys Leu Leu Ile Tyr
1 5 10 15

<210> SEQ ID NO 515
<211> LENGTH: 8
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 515

Gly Ala Ser Thr Arg Glu Ser Xaa
1 5

<210> SEQ ID NO 516
<211> LENGTH: 32
<212> TYPE: PRT
<213> ORGANISM: Mus musculus

<400> SEQUENCE: 516

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Ile Tyr Tyr Cys
20 25 30

<210> SEQ ID NO 517
<211> LENGTH: 9
<212> TYPE: PRT
<213> ORGANISM: Mus musculus

<400> SEQUENCE: 517

Gln Asn Asp His Thr Tyr Pro Leu Thr
1 5

<210> SEQ ID NO 518
<211> LENGTH: 9
<212> TYPE: PRT
<213> ORGANISM: Mus musculus

<400> SEQUENCE: 518

Phe Gly Ala Gly Thr Lys Leu Glu Leu
1 5

<210> SEQ ID NO 519
<211> LENGTH: 339
<212> TYPE: DNA
<213> ORGANISM: Mus musculus

<400> SEQUENCE: 519
gacattgtga tgacacagtc tccatcctcc ctgagtgtgt cagccggaga gaaggtcact 60
atgagctgca agtccagtca gagtctatta aacagtggaa atcaaatgaa ctacttggcc 120

```
tggtaccagc agaaaccagg acagcctcct aaattgttga tctatggggc atccactagg    180

gaatctgggg tccctgatcg cttcacaggc agtggatctg gaaccgattt cactcttacc    240

atcagcagtg tgcaggctga agacctggca atttattact gtcagaatga tcatacttat    300

ccgctcacgt tcggtgctgg gaccaaactg gagctgaaa                           339


<210> SEQ ID NO 520
<211> LENGTH: 112
<212> TYPE: PRT
<213> ORGANISM: Mus musculus

<400> SEQUENCE: 520

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Met Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Asp His Thr Tyr Pro Leu Thr Phe Gly Ala Gly Thr Lys Leu Glu Leu
            100                 105                 110


<210> SEQ ID NO 521
<211> LENGTH: 30
<212> TYPE: PRT
<213> ORGANISM: Mus musculus

<400> SEQUENCE: 521

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser
            20                  25                  30


<210> SEQ ID NO 522
<211> LENGTH: 5
<212> TYPE: PRT
<213> ORGANISM: Mus musculus

<400> SEQUENCE: 522

Asn Tyr Trp Met Asn
1               5


<210> SEQ ID NO 523
<211> LENGTH: 14
<212> TYPE: PRT
<213> ORGANISM: Mus musculus

<400> SEQUENCE: 523

Trp Val Lys Gln Arg Pro Gly Gln Gly Leu Glu Trp Ile Gly
1               5                   10


<210> SEQ ID NO 524
<211> LENGTH: 17
<212> TYPE: PRT
<213> ORGANISM: Mus musculus
```

<400> SEQUENCE: 524

Gln Ile Tyr Pro Gly Asn Gly Asp Thr Asn Tyr Asn Gly Lys Phe Lys
1 5 10 15

Gly

<210> SEQ ID NO 525
<211> LENGTH: 32
<212> TYPE: PRT
<213> ORGANISM: Mus musculus

<400> SEQUENCE: 525

Lys Ala Thr Leu Thr Ala Asp Lys Ser Ser Thr Thr Ala Tyr Ile Gln
1 5 10 15

Leu Ser Ser Leu Thr Ser Glu Asp Ser Ala Val Tyr Phe Cys Thr Arg
20 25 30

<210> SEQ ID NO 526
<211> LENGTH: 9
<212> TYPE: PRT
<213> ORGANISM: Mus musculus

<400> SEQUENCE: 526

Ile Tyr Tyr Gly Asn Ser Phe Ala Tyr
1 5

<210> SEQ ID NO 527
<211> LENGTH: 10
<212> TYPE: PRT
<213> ORGANISM: Mus musculus

<400> SEQUENCE: 527

Trp Gly Gln Gly Thr Leu Val Thr Val Ser
1 5 10

<210> SEQ ID NO 528
<211> LENGTH: 354
<212> TYPE: DNA
<213> ORGANISM: Mus musculus

<400> SEQUENCE: 528
caggttcagc tgcagcagtc tggggctgaa ctggtgaggc ctgggtcctc agtgaagatt 60
tcctgcaagg cttctggcta tgcattcagt aactactgga tgaactgggt gaagcagagg 120
cctggacagg gtcttgagtg gattggacag atttatcctg gaaatggtga tactaactac 180
aatggaaagt tcaagggtaa agccacactg actgcagaca aatcctccac cacagcctac 240
attcagctca gcagcctaac ttctgaggac tctgcggtct atttctgtac aaggatctac 300
tatggtaact cttttgctta ctggggccaa ggcactctgg tcactgtctc tgca 354

<210> SEQ ID NO 529
<211> LENGTH: 117
<212> TYPE: PRT
<213> ORGANISM: Mus musculus

<400> SEQUENCE: 529

Gln Val Gln Leu Gln Gln Ser Gly Ala Glu Leu Val Arg Pro Gly Ser
1 5 10 15

Ser Val Lys Ile Ser Cys Lys Ala Ser Gly Tyr Ala Phe Ser Asn Tyr
20 25 30

Trp Met Asn Trp Val Lys Gln Arg Pro Gly Gln Gly Leu Glu Trp Ile
35 40 45

```
Gly Gln Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Thr Thr Ala Tyr
65                  70                  75                  80

Ile Gln Leu Ser Ser Leu Thr Ser Glu Asp Ser Ala Val Tyr Phe Cys
                85                  90                  95

Thr Arg Ile Tyr Tyr Gly Asn Ser Phe Ala Tyr Trp Gly Gln Gly Thr
            100                 105                 110

Leu Val Thr Val Ser
        115


<210> SEQ ID NO 530
<211> LENGTH: 23
<212> TYPE: PRT
<213> ORGANISM: Mus musculus

<400> SEQUENCE: 530

Asp Ile Val Met Thr Gln Ser Pro Ser Ser Leu Thr Val Thr Ala Gly
1               5                   10                  15

Glu Arg Val Thr Met Ser Cys
            20


<210> SEQ ID NO 531
<211> LENGTH: 17
<212> TYPE: PRT
<213> ORGANISM: Mus musculus

<400> SEQUENCE: 531

Lys Ser Ser Gln Ser Leu Leu Asn Ser Gly Asn Gln Lys Asn Tyr Leu
1               5                   10                  15

Thr


<210> SEQ ID NO 532
<211> LENGTH: 15
<212> TYPE: PRT
<213> ORGANISM: Mus musculus

<400> SEQUENCE: 532

Trp Tyr Gln Gln Lys Pro Gly Gln Pro Pro Lys Leu Leu Ile Tyr
1               5                   10                  15


<210> SEQ ID NO 533
<211> LENGTH: 7
<212> TYPE: PRT
<213> ORGANISM: Mus musculus

<400> SEQUENCE: 533

Trp Ala Ser Thr Arg Glu Ser
1               5


<210> SEQ ID NO 534
<211> LENGTH: 32
<212> TYPE: PRT
<213> ORGANISM: Mus musculus

<400> SEQUENCE: 534

Gly Val Pro Asp Arg Phe Thr Gly Ser Gly Ser Gly Thr Asp Phe Thr
1               5                   10                  15

Leu Thr Ile Ser Arg Val Gln Ala Gln Asp Leu Ala Val Tyr Tyr Cys
            20                  25                  30
```

<210> SEQ ID NO 535
<211> LENGTH: 9
<212> TYPE: PRT
<213> ORGANISM: Mus musculus

<400> SEQUENCE: 535

Gln Asn Asp Tyr Tyr Tyr Pro Leu Thr
1 5

<210> SEQ ID NO 536
<211> LENGTH: 10
<212> TYPE: PRT
<213> ORGANISM: Mus musculus

<400> SEQUENCE: 536

Phe Gly Ala Gly Thr Lys Leu Glu Leu Lys
1 5 10

<210> SEQ ID NO 537
<211> LENGTH: 339
<212> TYPE: DNA
<213> ORGANISM: Mus musculus

<400> SEQUENCE: 537
gacattgtga tgacacagtc tccatcctcc ctgactgtga cagcaggaga gagggtcact 60
atgagctgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt caccctcacc 240
atcagcaggg tgcaggctca agacctggca gtttattact gtcagaatga ttattattat 300
ccactcacgt tcggtgctgg gaccaagctg gagctgaaa 339

<210> SEQ ID NO 538
<211> LENGTH: 113
<212> TYPE: PRT
<213> ORGANISM: Mus musculus

<400> SEQUENCE: 538

Asp Ile Val Met Thr Gln Ser Pro Ser Ser Leu Thr Val Thr Ala Gly
1 5 10 15

Glu Arg Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Arg Val Gln Ala Gln Asp Leu Ala Val Tyr Tyr Cys Gln Asn
85 90 95

Asp Tyr Tyr Tyr Pro Leu Thr Phe Gly Ala Gly Thr Lys Leu Glu Leu
100 105 110

Lys

<210> SEQ ID NO 539
<211> LENGTH: 30
<212> TYPE: PRT
<213> ORGANISM: Mus musculus

<400> SEQUENCE: 539

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr
20 25 30

<210> SEQ ID NO 540
<211> LENGTH: 5
<212> TYPE: PRT
<213> ORGANISM: Mus musculus

<400> SEQUENCE: 540

Ser His Gly Val His
1 5

<210> SEQ ID NO 541
<211> LENGTH: 14
<212> TYPE: PRT
<213> ORGANISM: Mus musculus

<400> SEQUENCE: 541

Trp Val Arg Gln Pro Pro Gly Lys Gly Leu Glu Trp Leu Gly
1 5 10

<210> SEQ ID NO 542
<211> LENGTH: 16
<212> TYPE: PRT
<213> ORGANISM: Mus musculus

<400> SEQUENCE: 542

Val Ile Trp Ala Gly Gly Ser Ile Asn Phe Asn Ser Ala Leu Met Ser
1 5 10 15

<210> SEQ ID NO 543
<211> LENGTH: 32
<212> TYPE: PRT
<213> ORGANISM: Mus musculus

<400> SEQUENCE: 543

Arg Leu Ser Ile Ser Lys Asp Asn Ser Lys Asn Gln Val Phe Leu Lys
1 5 10 15

Met Asn Ser Leu Gln Ser Asp Asp Thr Ala Met Tyr Tyr Cys Ala Arg
20 25 30

<210> SEQ ID NO 544
<211> LENGTH: 10
<212> TYPE: PRT
<213> ORGANISM: Mus musculus

<400> SEQUENCE: 544

Asp Tyr Tyr Tyr Gly Ile Gly Leu Asp Tyr
1 5 10

<210> SEQ ID NO 545
<211> LENGTH: 10
<212> TYPE: PRT
<213> ORGANISM: Mus musculus

<400> SEQUENCE: 545

Trp Gly Gln Gly Thr Thr Leu Thr Val Ser
1 5 10

<210> SEQ ID NO 546

<211> LENGTH: 354
<212> TYPE: DNA
<213> ORGANISM: Mus musculus

<400> SEQUENCE: 546
caggtgcagt tgaaggagtc aggaccaggc ctggtggcgc cctcacagag cctgtccatc 60
acttgcactg tctccgggtt ttcattaacc agccatggtg tacactgggt tcgccagcct 120
ccaggaaagg gtctggagtg gctgggagta atatgggctg gaggaagcat aaactttaat 180
tcggctctca tgtccagact gagcatcagc aaagacaact ccaaaaacca ggttttctta 240
aaaatgaaca gtctgcaaag tgatgacaca gccatgtact actgtgccag agactattac 300
tacggtattg gtcttgacta ttggggccaa ggcaccactc tcacagtctc ctca 354

<210> SEQ ID NO 547
<211> LENGTH: 117
<212> TYPE: PRT
<213> ORGANISM: Mus musculus

<400> SEQUENCE: 547

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr Ser His
20 25 30

Gly Val His Trp Val Arg Gln Pro Pro Gly Lys Gly Leu Glu Trp Leu
35 40 45

Gly Val Ile Trp Ala Gly Gly Ser Ile Asn Phe Asn Ser Ala Leu Met
50 55 60

Ser Arg Leu Ser Ile Ser Lys Asp Asn Ser Lys Asn Gln Val Phe Leu
65 70 75 80

Lys Met Asn Ser Leu Gln Ser Asp Asp Thr Ala Met Tyr Tyr Cys Ala
85 90 95

Arg Asp Tyr Tyr Tyr Gly Ile Gly Leu Asp Tyr Trp Gly Gln Gly Thr
100 105 110

Thr Leu Thr Val Ser
115

<210> SEQ ID NO 548
<211> LENGTH: 23
<212> TYPE: PRT
<213> ORGANISM: Mus musculus

<400> SEQUENCE: 548

Asp Ile Val Met Thr Gln Ser Pro Ser Ser Leu Ser Val Ser Ala Gly
1 5 10 15

Glu Lys Val Thr Met Ser Cys
20

<210> SEQ ID NO 549
<211> LENGTH: 17
<212> TYPE: PRT
<213> ORGANISM: Mus musculus

<400> SEQUENCE: 549

Lys Ser Ser Gln Ser Leu Leu Asn Ser Gly Asn Gln Lys Asn Tyr Leu
1 5 10 15

Ala

<210> SEQ ID NO 550

<211> LENGTH: 15
<212> TYPE: PRT
<213> ORGANISM: Mus musculus

<400> SEQUENCE: 550

Trp Tyr Gln Gln Lys Pro Gly Gln Pro Pro Lys Leu Leu Ile Tyr
1 5 10 15

<210> SEQ ID NO 551
<211> LENGTH: 7
<212> TYPE: PRT
<213> ORGANISM: Mus musculus

<400> SEQUENCE: 551

Gly Ala Ser Thr Arg Glu Ser
1 5

<210> SEQ ID NO 552
<211> LENGTH: 32
<212> TYPE: PRT
<213> ORGANISM: Mus musculus

<400> SEQUENCE: 552

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 553
<211> LENGTH: 9
<212> TYPE: PRT
<213> ORGANISM: Mus musculus

<400> SEQUENCE: 553

Gln Asn Asp Tyr Tyr Tyr Pro Phe Thr
1 5

<210> SEQ ID NO 554
<211> LENGTH: 10
<212> TYPE: PRT
<213> ORGANISM: Mus musculus

<400> SEQUENCE: 554

Phe Gly Ser Gly Thr Lys Leu Glu Ile Lys
1 5 10

<210> SEQ ID NO 555
<211> LENGTH: 339
<212> TYPE: DNA
<213> ORGANISM: Mus musculus

<400> SEQUENCE: 555
gacattgtga tgacacagtc tccatcctcc ctgagtgtgt cagcaggaga gaaggtcact 60
atgagctgca agtccagtca gagtctgtta aacagtggaa atcaaaagaa ctacttggcc 120
tggtaccagc agaaaccagg acagcctcct aaactgttga tctacggggc atccactagg 180
gaatctgggg tccctgatcg cttcacaggc agtgggtctg gaaccgattt cactcttacc 240
atcagcagtg tgcaggctga agacctggca gtttattact gtcagaatga ttattattat 300
ccattcacgt tcggctcggg gacaaagttg gaaataaaa 339

<210> SEQ ID NO 556
<211> LENGTH: 113

<212> TYPE: PRT
<213> ORGANISM: Mus musculus

<400> SEQUENCE: 556

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Tyr Tyr Pro Phe Thr Phe Gly Ser Gly Thr Lys Leu Glu Ile
100 105 110

Lys

<210> SEQ ID NO 557
<211> LENGTH: 30
<212> TYPE: PRT
<213> ORGANISM: Mus musculus

<400> SEQUENCE: 557

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Leu Thr
20 25 30

<210> SEQ ID NO 558
<211> LENGTH: 5
<212> TYPE: PRT
<213> ORGANISM: Mus musculus

<400> SEQUENCE: 558

Asp His Ser Met Asp
1 5

<210> SEQ ID NO 559
<211> LENGTH: 14
<212> TYPE: PRT
<213> ORGANISM: Mus musculus

<400> SEQUENCE: 559

Trp Val Lys Gln Ser His Gly Lys Ser Leu Glu Trp Ile Gly
1 5 10

<210> SEQ ID NO 560
<211> LENGTH: 17
<212> TYPE: PRT
<213> ORGANISM: Mus musculus

<400> SEQUENCE: 560

Asn Ile Leu Pro Asn Asn Gly Gly Asn Ile Tyr Asn Gln Lys Phe Arg
1 5 10 15

Gly

<210> SEQ ID NO 561

<211> LENGTH: 32
<212> TYPE: PRT
<213> ORGANISM: Mus musculus

<400> SEQUENCE: 561

Lys Ala Thr Leu Thr Val Asp Lys Ser Ser Ser Thr Ala Tyr Met Glu
1 5 10 15

Leu Arg Ser Leu Thr Ser Glu Asp Thr Ala Val Tyr Asn Cys Ala Arg
20 25 30

<210> SEQ ID NO 562
<211> LENGTH: 9
<212> TYPE: PRT
<213> ORGANISM: Mus musculus

<400> SEQUENCE: 562

Gly His Tyr Gly Asn Ser Phe Ala Tyr
1 5

<210> SEQ ID NO 563
<211> LENGTH: 10
<212> TYPE: PRT
<213> ORGANISM: Mus musculus

<400> SEQUENCE: 563

Trp Gly Gln Gly Thr Leu Val Ile Val Ser
1 5 10

<210> SEQ ID NO 564
<211> LENGTH: 354
<212> TYPE: DNA
<213> ORGANISM: Mus musculus

<400> SEQUENCE: 564
gaggtcctgc tgcaacagtc tggacctgaa ctggtgaagc ctggggcttc agtgaagata 60
ccctgcaagg cttctggata cactttgact gaccacagca tggactgggt gaagcagagc 120
catggaaaga gccttgagtg gattggaaat attcttccta ataatggtgg taatatatac 180
aaccagaagt tcaggggcaa ggccacactg actgtcgaca agtcctccag cacagcctac 240
atggagctcc gcagcctgac atctgaagac actgcagtct ataactgtgc aaggggccac 300
tatggtaact catttgctta ctggggccaa gggactctgg tcatagtctc tgca 354

<210> SEQ ID NO 565
<211> LENGTH: 117
<212> TYPE: PRT
<213> ORGANISM: Mus musculus

<400> SEQUENCE: 565

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Leu Thr Asp His
20 25 30

Ser Met Asp Trp Val Lys Gln Ser His Gly Lys Ser Leu Glu Trp Ile
35 40 45

Gly Asn Ile Leu Pro Asn Asn Gly Gly Asn Ile Tyr Asn Gln Lys Phe
50 55 60

Arg Gly Lys Ala Thr Leu Thr Val Asp Lys Ser Ser Ser Thr Ala Tyr
65 70 75 80

Met Glu Leu Arg Ser Leu Thr Ser Glu Asp Thr Ala Val Tyr Asn Cys
85 90 95

```
Ala Arg Gly His Tyr Gly Asn Ser Phe Ala Tyr Trp Gly Gln Gly Thr
            100                 105                 110

Leu Val Ile Val Ser
        115


<210> SEQ ID NO 566
<211> LENGTH: 23
<212> TYPE: PRT
<213> ORGANISM: Mus musculus

<400> SEQUENCE: 566

Asp Ile Val Met Thr Gln Ser Pro Ser Ser Leu Thr Val Arg Ala Gly
1               5                   10                  15

Glu Lys Val Thr Ile Tyr Cys
            20


<210> SEQ ID NO 567
<211> LENGTH: 17
<212> TYPE: PRT
<213> ORGANISM: Mus musculus

<400> SEQUENCE: 567

Lys Ser Ser Gln Ser Leu Phe Asn Ser Gly Asn Gln Lys Asn Tyr Leu
1               5                   10                  15

Thr


<210> SEQ ID NO 568
<211> LENGTH: 15
<212> TYPE: PRT
<213> ORGANISM: Mus musculus

<400> SEQUENCE: 568

Trp Tyr Gln Gln Lys Pro Gly Gln Pro Pro Lys Leu Leu Ile Tyr
1               5                   10                  15


<210> SEQ ID NO 569
<211> LENGTH: 7
<212> TYPE: PRT
<213> ORGANISM: Mus musculus

<400> SEQUENCE: 569

Trp Ala Ser Thr Arg Glu Ser
1               5


<210> SEQ ID NO 570
<211> LENGTH: 32
<212> TYPE: PRT
<213> ORGANISM: Mus musculus

<400> SEQUENCE: 570

Gly Val Pro His Arg Phe Thr Gly Ser Gly Ser Gly Thr Asp Phe Thr
1               5                   10                  15

Leu Thr Ile Ser Ser Met Gln Ala Asp Asp Leu Ala Thr Tyr Tyr Cys
            20                  25                  30


<210> SEQ ID NO 571
<211> LENGTH: 9
<212> TYPE: PRT
<213> ORGANISM: Mus musculus

<400> SEQUENCE: 571

Gln Asn Gly Tyr Phe Phe Pro Tyr Thr
```

1 5

<210> SEQ ID NO 572
<211> LENGTH: 10
<212> TYPE: PRT
<213> ORGANISM: Mus musculus

<400> SEQUENCE: 572

Phe Gly Gly Gly Thr Lys Leu Glu Ile Lys
1 5 10

<210> SEQ ID NO 573
<211> LENGTH: 339
<212> TYPE: DNA
<213> ORGANISM: Mus musculus

<400> SEQUENCE: 573
gacattgtga tgacacagtc tccatcctcc ctgactgtga gagcaggaga gaaggtcact 60
atatactgca agtccagtca gagtctgttt aacagtggaa atcaaaaaaa ctacttgacc 120
tggtaccagc agaaaccggg ccagcctcct aaattgttga tctactgggc atccactagg 180
gaatctgggg tccctcatcg cttcacaggc agtggatctg ggacagattt cactctcacc 240
atcagcagta tgcaggctga tgacctggca acttattact gtcagaatgg ttattttttt 300
ccgtacacgt tcggaggggg gaccaagctg gagataaaa 339

<210> SEQ ID NO 574
<211> LENGTH: 113
<212> TYPE: PRT
<213> ORGANISM: Mus musculus

<400> SEQUENCE: 574

Asp Ile Val Met Thr Gln Ser Pro Ser Ser Leu Thr Val Arg Ala Gly
1 5 10 15

Glu Lys Val Thr Ile Tyr Cys Lys Ser Ser Gln Ser Leu Phe Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro His Arg Phe Thr Gly Ser Gly Ser Gly Thr Asp Phe Thr Leu Thr
65 70 75 80

Ile Ser Ser Met Gln Ala Asp Asp Leu Ala Thr Tyr Tyr Cys Gln Asn
85 90 95

Gly Tyr Phe Phe Pro Tyr Thr Phe Gly Gly Gly Thr Lys Leu Glu Ile
100 105 110

Lys

<210> SEQ ID NO 575
<211> LENGTH: 30
<212> TYPE: PRT
<213> ORGANISM: Mus musculus

<400> SEQUENCE: 575

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr
20 25 30

<210> SEQ ID NO 576
<211> LENGTH: 5
<212> TYPE: PRT
<213> ORGANISM: Mus musculus

<400> SEQUENCE: 576

Lys Phe Gly Val Asn
1 5

<210> SEQ ID NO 577
<211> LENGTH: 14
<212> TYPE: PRT
<213> ORGANISM: Mus musculus

<400> SEQUENCE: 577

Trp Val Arg Gln Pro Pro Gly Lys Gly Leu Glu Trp Leu Gly
1 5 10

<210> SEQ ID NO 578
<211> LENGTH: 16
<212> TYPE: PRT
<213> ORGANISM: Mus musculus

<400> SEQUENCE: 578

Ala Ile Trp Gly Asp Gly Ser Thr Asn Tyr His Ser Ala Leu Ile Ser
1 5 10 15

<210> SEQ ID NO 579
<211> LENGTH: 32
<212> TYPE: PRT
<213> ORGANISM: Mus musculus

<400> SEQUENCE: 579

Arg Leu Ser Ile Asn Lys Asp Asn Ser Lys Ser Gln Val Phe Leu Lys
1 5 10 15

Leu Ser Ser Leu Gln Asn Val Asp Thr Ala Thr Tyr Tyr Cys Ala Lys
20 25 30

<210> SEQ ID NO 580
<211> LENGTH: 9
<212> TYPE: PRT
<213> ORGANISM: Mus musculus

<400> SEQUENCE: 580

Ser Gly Tyr Gly Asn Ala Met Asp Tyr
1 5

<210> SEQ ID NO 581
<211> LENGTH: 11
<212> TYPE: PRT
<213> ORGANISM: Mus musculus

<400> SEQUENCE: 581

Trp Gly His Gly Thr Ser Val Thr Val Ser Ser
1 5 10

<210> SEQ ID NO 582
<211> LENGTH: 351
<212> TYPE: DNA
<213> ORGANISM: Mus musculus

<400> SEQUENCE: 582
caggtacaac tgaaggagtc aggacctggc ctggtggcgc cctcacagag cctgtccatc 60
acatgcactg tctcagggtt ctcattaacc aagtttggtg taaactgggt tcgccagcct 120
ccaggaaagg gtctggagtg gctgggagca atatggggtg acgggagcac aaattatcat 180
tcagctctca tatccagact gagcatcaac aaggataact ccaagagcca agttttctta 240
aaactgagca gtctgcaaaa tgttgacaca gccacttact actgtgccaa aagtgggtac 300
ggtaatgcta tggactactg gggtcacgga acctcagtca ccgtctcctc a 351

<210> SEQ ID NO 583
<211> LENGTH: 117
<212> TYPE: PRT
<213> ORGANISM: Mus musculus

<400> SEQUENCE: 583

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr Lys Phe
20 25 30

Gly Val Asn Trp Val Arg Gln Pro Pro Gly Lys Gly Leu Glu Trp Leu
35 40 45

Gly Ala Ile Trp Gly Asp Gly Ser Thr Asn Tyr His Ser Ala Leu Ile
50 55 60

Ser Arg Leu Ser Ile Asn Lys Asp Asn Ser Lys Ser Gln Val Phe Leu
65 70 75 80

Lys Leu Ser Ser Leu Gln Asn Val Asp Thr Ala Thr Tyr Tyr Cys Ala
85 90 95

Lys Ser Gly Tyr Gly Asn Ala Met Asp Tyr Trp Gly His Gly Thr Ser
100 105 110

Val Thr Val Ser Ser
115

<210> SEQ ID NO 584
<211> LENGTH: 23
<212> TYPE: PRT
<213> ORGANISM: Mus musculus

<400> SEQUENCE: 584

Asp Ile Val Met Thr Gln Ser Pro Ser Ser Leu Thr Val Thr Thr Gly
1 5 10 15

Glu Lys Val Thr Leu Asn Cys
20

<210> SEQ ID NO 585
<211> LENGTH: 17
<212> TYPE: PRT
<213> ORGANISM: Mus musculus

<400> SEQUENCE: 585

Lys Ser Ser Gln Ser Leu Leu Asn Ser Gly Asn Leu Lys Asn Tyr Leu
1 5 10 15

Thr

<210> SEQ ID NO 586
<211> LENGTH: 15
<212> TYPE: PRT
<213> ORGANISM: Mus musculus

<400> SEQUENCE: 586

Trp Tyr Gln Gln Arg Pro Gly Gln Pro Pro Lys Leu Leu Ile Tyr
1 5 10 15

<210> SEQ ID NO 587
<211> LENGTH: 7
<212> TYPE: PRT
<213> ORGANISM: Mus musculus

<400> SEQUENCE: 587

Trp Ala Ser Thr Arg Glu Ser
1               5

<210> SEQ ID NO 588
<211> LENGTH: 32
<212> TYPE: PRT
<213> ORGANISM: Mus musculus

<400> SEQUENCE: 588

Gly Val Pro Tyr Arg Phe Thr Gly Ser Gly Ser Gly Thr Asp Phe Thr
1               5                   10                  15

Leu Thr Ile Ser Asn Val Gln Ala Glu Asp Leu Ala Ile Tyr Tyr Cys
            20                  25                  30

<210> SEQ ID NO 589
<211> LENGTH: 9
<212> TYPE: PRT
<213> ORGANISM: Mus musculus

<400> SEQUENCE: 589

Gln Asn Asp Tyr Phe Phe Pro Phe Thr
1               5

<210> SEQ ID NO 590
<211> LENGTH: 10
<212> TYPE: PRT
<213> ORGANISM: Mus musculus

<400> SEQUENCE: 590

Phe Gly Ser Gly Thr Lys Leu Glu Ile Lys
1               5                   10

<210> SEQ ID NO 591
<211> LENGTH: 339
<212> TYPE: DNA
<213> ORGANISM: Mus musculus

<400> SEQUENCE: 591
gacattgtga tgacacagtc tccatcctcc ctgactgtga caacaggaga gaaggtcact     60
ctgaactgca agtccagtca gagtctgtta aacagtggaa atctaaagaa ctacttgacc    120
tggtaccagc agagaccggg gcagcctcct aaactgttga tctactgggc atccactagg    180
gaatctgggg tcccttatcg cttcacaggc agtggatctg gaacagattt cactctcacc    240
atcagcaatg tgcaggctga agacctggca atttattact gtcagaatga ttattttttt    300
ccattcacgt tcggctcggg gacaaagttg gaaattaaa                           339

<210> SEQ ID NO 592
<211> LENGTH: 113
<212> TYPE: PRT
<213> ORGANISM: Mus musculus

<400> SEQUENCE: 592

Asp Ile Val Met Thr Gln Ser Pro Ser Ser Leu Thr Val Thr Thr Gly
1               5                   10                  15

Glu Lys Val Thr Leu Asn Cys Lys Ser Ser Gln Ser Leu Leu Asn Ser

```
            20                  25                  30

Gly Asn Leu Lys Asn Tyr Leu Thr Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Tyr Arg Phe Thr Gly Ser Gly Ser Gly Thr Asp Phe Thr Leu Thr
65                  70                  75                  80

Ile Ser Asn Val Gln Ala Glu Asp Leu Ala Ile Tyr Tyr Cys Gln Asn
                85                  90                  95

Asp Tyr Phe Phe Pro Phe Thr Phe Gly Ser Gly Thr Lys Leu Glu Ile
            100                 105                 110

Lys


<210> SEQ ID NO 593
<211> LENGTH: 30
<212> TYPE: PRT
<213> ORGANISM: Mus musculus

<400> SEQUENCE: 593

Gln Ile Gln Leu Ala Gln Ser Gly Pro Glu Leu Lys Lys Pro Gly Glu
1               5                   10                  15

Thr Val Lys Ile Ser Cys Lys Ala Ser Gly Tyr Ser Phe Thr
            20                  25                  30


<210> SEQ ID NO 594
<211> LENGTH: 5
<212> TYPE: PRT
<213> ORGANISM: Mus musculus

<400> SEQUENCE: 594

Asn Tyr Gly Met Asn
1               5


<210> SEQ ID NO 595
<211> LENGTH: 14
<212> TYPE: PRT
<213> ORGANISM: Mus musculus

<400> SEQUENCE: 595

Trp Val Lys Gln Ala Pro Gly Lys Gly Leu Lys Trp Met Gly
1               5                   10


<210> SEQ ID NO 596
<211> LENGTH: 17
<212> TYPE: PRT
<213> ORGANISM: Mus musculus

<400> SEQUENCE: 596

Trp Ile Asn Thr Tyr Ser Gly Glu Thr Lys Tyr Ala Asp Asp Phe Lys
1               5                   10                  15

Gly


<210> SEQ ID NO 597
<211> LENGTH: 32
<212> TYPE: PRT
<213> ORGANISM: Mus musculus

<400> SEQUENCE: 597

Arg Phe Asp Phe Ser Leu Glu Thr Ser Ala Arg Thr Ala Tyr Leu Gln
1               5                   10                  15
```

```
Ile Lys Asn Leu Lys Ile Glu Asp Thr Ala Thr Tyr Phe Cys Ala Arg
            20                  25                  30


<210> SEQ ID NO 598
<211> LENGTH: 6
<212> TYPE: PRT
<213> ORGANISM: Mus musculus

<400> SEQUENCE: 598

Arg Asp Ala Met Asp Tyr
1               5


<210> SEQ ID NO 599
<211> LENGTH: 11
<212> TYPE: PRT
<213> ORGANISM: Mus musculus

<400> SEQUENCE: 599

Trp Gly Gln Gly Thr Ser Val Thr Val Ser Ser
1               5                   10


<210> SEQ ID NO 600
<211> LENGTH: 345
<212> TYPE: DNA
<213> ORGANISM: Mus musculus

<400> SEQUENCE: 600

cagatccagt tggcgcagtc tggacctgag ctgaagaagc ctggagagac agtcaagatc      60

tcctgcaagg cttctgggta tagtttcaca aactatggaa tgaactgggt gaagcaggct     120

ccaggaaagg gcttaaagtg gatgggctgg ataaacacct acagtggaga gacaaaatat     180

gctgatgact tcaagggacg gttcgacttt tcattggaaa cctctgccag gacagcctat     240

ttgcagatca aaaacctcaa aattgaggac acggctacat atttctgtgc aagacgggat     300

gctatggact actggggtca aggaacctca gtcaccgtct cctca                     345


<210> SEQ ID NO 601
<211> LENGTH: 115
<212> TYPE: PRT
<213> ORGANISM: Mus musculus

<400> SEQUENCE: 601

Gln Ile Gln Leu Ala Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Glu Thr Lys Tyr Ala Asp Asp Phe
    50                  55                  60

Lys Gly Arg Phe Asp Phe Ser Leu Glu Thr Ser Ala Arg Thr Ala Tyr
65                  70                  75                  80

Leu Gln Ile Lys Asn Leu Lys Ile Glu Asp Thr Ala Thr Tyr Phe Cys
                85                  90                  95

Ala Arg Arg Asp Ala Met Asp Tyr Trp Gly Gln Gly Thr Ser Val Thr
            100                 105                 110

Val Ser Ser
        115


<210> SEQ ID NO 602
```

<211> LENGTH: 23
<212> TYPE: PRT
<213> ORGANISM: Mus musculus

<400> SEQUENCE: 602

Asp Ile Val Met Thr Gln Ala Ala Pro Ser Val Pro Val Thr Pro Gly
1 5 10 15

Glu Ser Val Ser Ile Ser Cys
20

<210> SEQ ID NO 603
<211> LENGTH: 16
<212> TYPE: PRT
<213> ORGANISM: Mus musculus

<400> SEQUENCE: 603

Arg Ser Ser Lys Ser Leu Leu Asn Ser Asn Gly Asn Thr Tyr Leu Tyr
1 5 10 15

<210> SEQ ID NO 604
<211> LENGTH: 15
<212> TYPE: PRT
<213> ORGANISM: Mus musculus

<400> SEQUENCE: 604

Trp Phe Leu Gln Arg Pro Gly Gln Ser Pro Gln Leu Leu Ile Tyr
1 5 10 15

<210> SEQ ID NO 605
<211> LENGTH: 7
<212> TYPE: PRT
<213> ORGANISM: Mus musculus

<400> SEQUENCE: 605

Arg Met Ser Asn Leu Ala Ser
1 5

<210> SEQ ID NO 606
<211> LENGTH: 32
<212> TYPE: PRT
<213> ORGANISM: Mus musculus

<400> SEQUENCE: 606

Gly Val Pro Asp Arg Phe Ser Gly Ser Gly Ser Gly Thr Ala Phe Thr
1 5 10 15

Leu Arg Ile Ser Arg Val Glu Ala Glu Asp Val Gly Val Tyr Tyr Cys
20 25 30

<210> SEQ ID NO 607
<211> LENGTH: 9
<212> TYPE: PRT
<213> ORGANISM: Mus musculus

<400> SEQUENCE: 607

Met Gln His Leu Glu Phe Pro Phe Thr
1 5

<210> SEQ ID NO 608
<211> LENGTH: 10
<212> TYPE: PRT
<213> ORGANISM: Mus musculus

<400> SEQUENCE: 608

Phe Gly Ser Gly Thr Lys Leu Glu Ile Lys 1 5 10

<210> SEQ ID NO 609
<211> LENGTH: 336
<212> TYPE: DNA
<213> ORGANISM: Mus musculus

<400> SEQUENCE: 609
gatattgtga tgactcaggc tgcaccctct gtacctgtca ctcctggaga gtcagtgtcc 60
atttcttgca ggtctagtaa gagtctcctg aatagtaatg gtaacactta tttgtattgg 120
ttcctacaga ggccaggcca gtctcctcag ctcctgatat atcggatgtc taaccttgcc 180
tcaggagtcc cagacaggtt cagtggcagt gggtcaggga ctgctttcac actgagaatc 240
agtagagtgg aggctgagga tgtgggtgtt tattattgta tgcaacatct agaatttcca 300
ttcacgttcg gctcggggac aaagttggaa ataaaa 336

<210> SEQ ID NO 610
<211> LENGTH: 112
<212> TYPE: PRT
<213> ORGANISM: Mus musculus

<400> SEQUENCE: 610

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu Asn Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Phe Pro Phe Thr Phe Gly Ser Gly Thr Lys Leu Glu Ile Lys
100 105 110

<210> SEQ ID NO 611
<211> LENGTH: 30
<212> TYPE: PRT
<213> ORGANISM: Mus musculus

<400> SEQUENCE: 611

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr
20 25 30

<210> SEQ ID NO 612
<211> LENGTH: 5
<212> TYPE: PRT
<213> ORGANISM: Mus musculus

<400> SEQUENCE: 612

Ser His Gly Val His
1 5

<210> SEQ ID NO 613
<211> LENGTH: 14

<212> TYPE: PRT
<213> ORGANISM: Mus musculus

<400> SEQUENCE: 613

Trp Val Arg Gln Pro Pro Gly Lys Gly Leu Glu Trp Leu Gly
1 5 10

<210> SEQ ID NO 614
<211> LENGTH: 16
<212> TYPE: PRT
<213> ORGANISM: Mus musculus

<400> SEQUENCE: 614

Val Ile Trp Ala Gly Gly Ser Ile Asn Phe Asn Ser Ala Leu Met Ser
1 5 10 15

<210> SEQ ID NO 615
<211> LENGTH: 32
<212> TYPE: PRT
<213> ORGANISM: Mus musculus

<400> SEQUENCE: 615

Arg Leu Ser Ile Ser Lys Asp Asn Ser Lys Asn Gln Val Phe Leu Lys
1 5 10 15

Met Asn Ser Leu Gln Ser Asp Asp Thr Ala Met Tyr Tyr Cys Ala Arg
20 25 30

<210> SEQ ID NO 616
<211> LENGTH: 10
<212> TYPE: PRT
<213> ORGANISM: Mus musculus

<400> SEQUENCE: 616

Asp Tyr Tyr Tyr Gly Ile Gly Leu Asp Tyr
1 5 10

<210> SEQ ID NO 617
<211> LENGTH: 10
<212> TYPE: PRT
<213> ORGANISM: Mus musculus

<400> SEQUENCE: 617

Trp Gly Gln Gly Thr Thr Leu Thr Val Ser
1 5 10

<210> SEQ ID NO 618
<211> LENGTH: 354
<212> TYPE: DNA
<213> ORGANISM: Mus musculus

<400> SEQUENCE: 618
caggtgcagt tgaaggagtc aggaccaggc ctggtggcgc cctcacagag cctgtccatc 60
acttgcactg tctccgggtt ttcattaacc agccatggtg tacactgggt tcgccagcct 120
ccaggaaagg gtctggagtg gctgggagta atatgggctg gaggaagcat aaactttaat 180
tcggctctca tgtccagact gagcatcagc aaagacaact ccaaaaacca ggttttctta 240
aaaatgaaca gtctgcaaag tgatgacaca gccatgtact actgtgccag agactattac 300
tacggtattg gtcttgacta ttggggccaa ggcaccactc tcacagtctc ctca 354

<210> SEQ ID NO 619
<211> LENGTH: 117
<212> TYPE: PRT

<213> ORGANISM: Mus musculus

<400> SEQUENCE: 619

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser His
            20                  25                  30

Gly Val His Trp Val Arg Gln Pro Pro Gly Lys Gly Leu Glu Trp Leu
        35                  40                  45

Gly Val Ile Trp Ala Gly Gly Ser Ile Asn Phe Asn Ser Ala Leu Met
    50                  55                  60

Ser Arg Leu Ser Ile Ser Lys Asp Asn Ser Lys Asn Gln Val Phe Leu
65                  70                  75                  80

Lys Met Asn Ser Leu Gln Ser Asp Asp Thr Ala Met Tyr Tyr Cys Ala
                85                  90                  95

Arg Asp Tyr Tyr Tyr Gly Ile Gly Leu Asp Tyr Trp Gly Gln Gly Thr
            100                 105                 110

Thr Leu Thr Val Ser
        115

<210> SEQ ID NO 620
<211> LENGTH: 23
<212> TYPE: PRT
<213> ORGANISM: Mus musculus

<400> SEQUENCE: 620

Asp Ile Val Met Thr Gln Ser Pro Ser Ser Leu Ser Val Ser Ala Gly
1               5                   10                  15

Glu Lys Val Thr Met Ser Cys
            20

<210> SEQ ID NO 621
<211> LENGTH: 17
<212> TYPE: PRT
<213> ORGANISM: Mus musculus

<400> SEQUENCE: 621

Lys Ser Ser Gln Ser Leu Leu Asn Ser Gly Asn Gln Lys Asn Tyr Leu
1               5                   10                  15

Ala

<210> SEQ ID NO 622
<211> LENGTH: 15
<212> TYPE: PRT
<213> ORGANISM: Mus musculus

<400> SEQUENCE: 622

Trp Tyr Gln Gln Lys Pro Gly Gln Pro Pro Lys Leu Leu Ile Tyr
1               5                   10                  15

<210> SEQ ID NO 623
<211> LENGTH: 7
<212> TYPE: PRT
<213> ORGANISM: Mus musculus

<400> SEQUENCE: 623

Gly Ala Ser Thr Arg Glu Ser
1               5

<210> SEQ ID NO 624

<211> LENGTH: 32
<212> TYPE: PRT
<213> ORGANISM: Mus musculus

<400> SEQUENCE: 624

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 625
<211> LENGTH: 9
<212> TYPE: PRT
<213> ORGANISM: Mus musculus

<400> SEQUENCE: 625

Gln Asn Asp Tyr Tyr Tyr Pro Phe Thr
1 5

<210> SEQ ID NO 626
<211> LENGTH: 10
<212> TYPE: PRT
<213> ORGANISM: Mus musculus

<400> SEQUENCE: 626

Phe Gly Ser Gly Thr Lys Leu Glu Ile Lys
1 5 10

<210> SEQ ID NO 627
<211> LENGTH: 339
<212> TYPE: DNA
<213> ORGANISM: Mus musculus

<400> SEQUENCE: 627
gacattgtga tgacacagtc tccatcctcc ctgagtgtgt cagcaggaga gaaggtcact 60
atgagctgca agtccagtca gagtctgtta aacagtggaa atcaaaagaa ctacttggcc 120
tggtaccagc agaaaccagg acagcctcct aaactgttga tctacggggc atccactagg 180
gaatctgggg tccctgatcg cttcacaggc agtgggtctg gaaccgattt cactcttacc 240
atcagcagtg tgcaggctga agacctggca gtttattact gtcagaatga ttattattat 300
ccattcacgt tcggctcggg gacaaagttg gaaataaaa 339

<210> SEQ ID NO 628
<211> LENGTH: 113
<212> TYPE: PRT
<213> ORGANISM: Mus musculus

<400> SEQUENCE: 628

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Tyr Tyr Pro Phe Thr Phe Gly Ser Gly Thr Lys Leu Glu Ile
100 105 110

Lys

<210> SEQ ID NO 629
<211> LENGTH: 30
<212> TYPE: PRT
<213> ORGANISM: Mus musculus

<400> SEQUENCE: 629

Asp Val Asn Leu Val Glu Ser Gly Gly Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 630
<211> LENGTH: 5
<212> TYPE: PRT
<213> ORGANISM: Mus musculus

<400> SEQUENCE: 630

Ser Tyr Thr Met Ser
1 5

<210> SEQ ID NO 631
<211> LENGTH: 14
<212> TYPE: PRT
<213> ORGANISM: Mus musculus

<400> SEQUENCE: 631

Trp Val Arg Gln Thr Pro Glu Lys Arg Leu Glu Trp Val Ala
1 5 10

<210> SEQ ID NO 632
<211> LENGTH: 17
<212> TYPE: PRT
<213> ORGANISM: Mus musculus

<400> SEQUENCE: 632

Thr Ile Thr Tyr Gly Arg Ile Tyr Thr Tyr Tyr Leu Asp Ser Val Lys
1 5 10 15

Gly

<210> SEQ ID NO 633
<211> LENGTH: 32
<212> TYPE: PRT
<213> ORGANISM: Mus musculus

<400> SEQUENCE: 633

Arg Phe Thr Ile Ser Arg Asp Asn Ala Lys Asn Thr Leu Tyr Leu Gln
1 5 10 15

Met Ser Ser Leu Arg Ser Glu Asp Thr Ala Met Tyr Tyr Cys Thr Arg
20 25 30

<210> SEQ ID NO 634
<211> LENGTH: 9
<212> TYPE: PRT
<213> ORGANISM: Mus musculus

<400> SEQUENCE: 634

Met Ile Thr Gly Asn Ala Met Asp Ser
1 5

<210> SEQ ID NO 635
<211> LENGTH: 11
<212> TYPE: PRT
<213> ORGANISM: Mus musculus

<400> SEQUENCE: 635

Trp Gly Leu Gly Thr Ser Val Thr Val Ser Ser
1 5 10

<210> SEQ ID NO 636
<211> LENGTH: 354
<212> TYPE: DNA
<213> ORGANISM: Mus musculus

<400> SEQUENCE: 636
gacgtgaacc tggtggagtc tgggggaggc ttagtgaagc ctggagggtc cctgaaactc 60
tcctgtgcag cctctggatt cactttcagt agctatacca tgtcttgggt tcgccagact 120
ccggagaaga ggctggagtg ggtcgcaacc attacttatg gtcgtattta cacctactat 180
ctagacagtg taaagggccg attcaccatc tccagagaca atgccaaaaa caccctgtac 240
ctgcagatga gcagtctgag gtctgaggac acagccatgt attactgtac aaggatgatt 300
acggggaatg ctatggactc ctggggtcta ggaacctcag tcaccgtctc ctca 354

<210> SEQ ID NO 637
<211> LENGTH: 118
<212> TYPE: PRT
<213> ORGANISM: Mus musculus

<400> SEQUENCE: 637

Asp Val Asn Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Thr Ile Thr Tyr Gly Arg Ile Tyr Thr Tyr Tyr Leu Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Arg Ser Glu Asp Thr Ala Met Tyr Tyr Cys
85 90 95

Thr Arg Met Ile Thr Gly Asn Ala Met Asp Ser Trp Gly Leu Gly Thr
100 105 110

Ser Val Thr Val Ser Ser
115

<210> SEQ ID NO 638
<211> LENGTH: 23
<212> TYPE: PRT
<213> ORGANISM: Mus musculus

<400> SEQUENCE: 638

Asp Ile Val Met Thr Gln Ser Pro Ser Ser Leu Thr Val Thr Ala Gly
1 5 10 15

Glu Lys Val Thr Met Ser Cys
20

<210> SEQ ID NO 639
<211> LENGTH: 17
<212> TYPE: PRT
<213> ORGANISM: Mus musculus

<400> SEQUENCE: 639

Lys Ser Ser Gln Ser Leu Leu Asn Ser Gly Asn Gln Lys Asn Tyr Leu
1               5                   10                  15

Thr

<210> SEQ ID NO 640
<211> LENGTH: 15
<212> TYPE: PRT
<213> ORGANISM: Mus musculus

<400> SEQUENCE: 640

Trp Tyr Gln Gln Lys Pro Gly Gln Pro Pro Lys Leu Leu Ile Tyr
1               5                   10                  15

<210> SEQ ID NO 641
<211> LENGTH: 7
<212> TYPE: PRT
<213> ORGANISM: Mus musculus

<400> SEQUENCE: 641

Trp Ala Ser Thr Arg Glu Ser
1               5

<210> SEQ ID NO 642
<211> LENGTH: 32
<212> TYPE: PRT
<213> ORGANISM: Mus musculus

<400> SEQUENCE: 642

Gly Val Pro Asp Arg Phe Thr Gly Ser Gly Ser Gly Thr Asp Phe Thr
1               5                   10                  15

Leu Thr Ile Ser Gly Val Gln Gly Glu Asp Leu Ala Val Tyr Tyr Cys
            20                  25                  30

<210> SEQ ID NO 643
<211> LENGTH: 9
<212> TYPE: PRT
<213> ORGANISM: Mus musculus

<400> SEQUENCE: 643

Gln Asn Asp Tyr Ser Tyr Pro Leu Thr
1               5

<210> SEQ ID NO 644
<211> LENGTH: 10
<212> TYPE: PRT
<213> ORGANISM: Mus musculus

<400> SEQUENCE: 644

Phe Gly Gly Gly Thr Lys Leu Glu Leu Lys
1               5                   10

<210> SEQ ID NO 645
<211> LENGTH: 339
<212> TYPE: DNA
<213> ORGANISM: Mus musculus

<400> SEQUENCE: 645
gacattgtga tgacacagtc tccatcctcc ctgactgtga cagcaggaga gaaggtcact     60

```
atgagctgca agtccagtca gagtctgtta aacagtggaa atcaaaaaaa ctacttgacc    120

tggtaccagc agaaaccagg gcagcctcct aaactgttga tctactgggc atccactagg    180

gaatctgggg tccctgatcg cttcacaggc agtggatctg gaacagattt cactctcacc    240

atcagcggtg tgcagggtga agacctggca gtttattact gtcagaatga ttatagttat    300

ccgctcacgt tcggtggtgg gaccaagctg gagctgaaa                           339


<210> SEQ ID NO 646
<211> LENGTH: 113
<212> TYPE: PRT
<213> ORGANISM: Mus musculus

<400> SEQUENCE: 646

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Gly Val Gln Gly Glu Asp Leu Ala Val Tyr Tyr Cys Gln Asn
                85                  90                  95

Asp Tyr Ser Tyr Pro Leu Thr Phe Gly Gly Gly Thr Lys Leu Glu Leu
            100                 105                 110

Lys


<210> SEQ ID NO 647
<211> LENGTH: 29
<212> TYPE: PRT
<213> ORGANISM: Mus musculus

<400> SEQUENCE: 647

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe
            20                  25


<210> SEQ ID NO 648
<211> LENGTH: 6
<212> TYPE: PRT
<213> ORGANISM: Mus musculus

<400> SEQUENCE: 648

Ser Asp Tyr Asn Met Asp
1               5


<210> SEQ ID NO 649
<211> LENGTH: 14
<212> TYPE: PRT
<213> ORGANISM: Mus musculus

<400> SEQUENCE: 649

Trp Val Lys Gln Ser His Gly Lys Ser Leu Glu Trp Ile Gly
1               5                   10
```

<210> SEQ ID NO 650
<211> LENGTH: 17
<212> TYPE: PRT
<213> ORGANISM: Mus musculus

<400> SEQUENCE: 650

His Ile Asn Pro Asn Asn Asp Asn Thr Ile Tyr Asn Gln Lys Phe Lys
1 5 10 15

Gly

<210> SEQ ID NO 651
<211> LENGTH: 32
<212> TYPE: PRT
<213> ORGANISM: Mus musculus

<400> SEQUENCE: 651

Lys Ala Thr Leu Thr Val Asp Lys Ser Ser Asn Thr Ala Tyr Met Asp
1 5 10 15

Leu Arg Ser Leu Ser Ser Glu Asp Thr Ala Val Tyr Tyr Cys Ala Arg
20 25 30

<210> SEQ ID NO 652
<211> LENGTH: 10
<212> TYPE: PRT
<213> ORGANISM: Mus musculus

<400> SEQUENCE: 652

Gly Ala Tyr Tyr Gly Asn Ser Met Asp Tyr
1 5 10

<210> SEQ ID NO 653
<211> LENGTH: 11
<212> TYPE: PRT
<213> ORGANISM: Mus musculus

<400> SEQUENCE: 653

Trp Gly Gln Gly Thr Ser Val Thr Val Ser Ser
1 5 10

<210> SEQ ID NO 654
<211> LENGTH: 357
<212> TYPE: DNA
<213> ORGANISM: Mus musculus

<400> SEQUENCE: 654
gaggtcctgc tgcaacagtc tggacctgag ttggtgaagc ctggggcttc agtgaaaata 60
ccctgcaagg cttctggata cacattctct gactacaaca tggactgggt gaagcagagc 120
catggaaaga gccttgagtg gattggacat attaatccta acaatgataa tactatctac 180
aaccagaagt tcaagggcaa ggccacattg actgtagaca agtcctccaa tacagcctac 240
atggacctcc gcagcctgtc atctgaggac actgcagtct attactgtgc aagaggggcc 300
tactatggta actctatgga ctactggggt caaggaacct cagtcaccgt ctcctca 357

<210> SEQ ID NO 655
<211> LENGTH: 119
<212> TYPE: PRT
<213> ORGANISM: Mus musculus

<400> SEQUENCE: 655

Glu Val Leu Leu Gln Gln Ser Gly Pro Glu Leu Val Lys Pro Gly Ala
1 5 10 15

```
Ser Val Lys Ile Pro Cys Lys Ala Ser Gly Tyr Thr Phe Ser Asp Tyr
            20                  25                  30

Asn Met Asp Trp Val Lys Gln Ser His Gly Lys Ser Leu Glu Trp Ile
        35                  40                  45

Gly His Ile Asn Pro Asn Asn Asp Asn Thr Ile Tyr Asn Gln Lys Phe
    50                  55                  60

Lys Gly Lys Ala Thr Leu Thr Val Asp Lys Ser Ser Asn Thr Ala Tyr
65                  70                  75                  80

Met Asp Leu Arg Ser Leu Ser Ser Glu Asp Thr Ala Val Tyr Tyr Cys
                85                  90                  95

Ala Arg Gly Ala Tyr Tyr Gly Asn Ser Met Asp Tyr Trp Gly Gln Gly
            100                 105                 110

Thr Ser Val Thr Val Ser Ser
        115
```

<210> SEQ ID NO 656
<211> LENGTH: 23
<212> TYPE: PRT
<213> ORGANISM: Mus musculus

<400> SEQUENCE: 656

```
Asp Ile Val Met Thr Gln Ser Pro Ser Ser Leu Thr Val Thr Ala Gly
1               5                   10                  15

Glu Arg Val Thr Met Ser Cys
            20
```

<210> SEQ ID NO 657
<211> LENGTH: 17
<212> TYPE: PRT
<213> ORGANISM: Mus musculus

<400> SEQUENCE: 657

```
Lys Ser Ser Gln Ser Leu Leu Asn Gly Gly Asn Gln Arg Asn Tyr Leu
1               5                   10                  15

Thr
```

<210> SEQ ID NO 658
<211> LENGTH: 15
<212> TYPE: PRT
<213> ORGANISM: Mus musculus

<400> SEQUENCE: 658

```
Trp Tyr Gln Gln Lys Pro Gly Gln Ser Pro Lys Leu Leu Ile Tyr
1               5                   10                  15
```

<210> SEQ ID NO 659
<211> LENGTH: 7
<212> TYPE: PRT
<213> ORGANISM: Mus musculus

<400> SEQUENCE: 659

```
Trp Ala Ser Thr Trp Glu Ser
1               5
```

<210> SEQ ID NO 660
<211> LENGTH: 32
<212> TYPE: PRT
<213> ORGANISM: Mus musculus

<400> SEQUENCE: 660

```
Gly Val Pro Asp Arg Phe Thr Gly Ser Gly Ser Gly Thr Asp Phe Thr
```

```
1               5                   10                  15

Leu Thr Ile Ser Ser Val Gln Ala Glu Asp Leu Ala Val Tyr Tyr Cys
            20                  25                  30


<210> SEQ ID NO 661
<211> LENGTH: 9
<212> TYPE: PRT
<213> ORGANISM: Mus musculus

<400> SEQUENCE: 661

Gln Asn Ala Tyr Phe Tyr Pro Tyr Thr
1               5


<210> SEQ ID NO 662
<211> LENGTH: 10
<212> TYPE: PRT
<213> ORGANISM: Mus musculus

<400> SEQUENCE: 662

Phe Gly Gly Gly Thr Lys Leu Glu Ile Lys
1               5                   10


<210> SEQ ID NO 663
<211> LENGTH: 339
<212> TYPE: DNA
<213> ORGANISM: Mus musculus

<400> SEQUENCE: 663

gacattgtga tgacacagtc tccatcctcc ctgactgtga cagcaggaga gagggtcact      60

atgagctgca agtccagtca gagtctgtta aacggtggaa atcaaaggaa ctacttgacc     120

tggtaccagc agaaaccagg gcagtctcct aaactgttga tctactgggc atccacttgg     180

gaatctgggg tccctgatcg cttcacaggc agtgggtctg gaacagattt cactctcacc     240

atcagcagtg tgcaggctga ggacctggca gtttattact gtcaaaatgc ttatttttat     300

ccgtacacgt tcggaggggg gaccaagctg gaaataaaa                            339


<210> SEQ ID NO 664
<211> LENGTH: 113
<212> TYPE: PRT
<213> ORGANISM: Mus musculus

<400> SEQUENCE: 664

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Leu Asn Gly
            20                  25                  30

Gly Asn Gln Arg Asn Tyr Leu Thr Trp Tyr Gln Gln Lys Pro Gly Gln
        35                  40                  45

Ser Pro Lys Leu Leu Ile Tyr Trp Ala Ser Thr Trp Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Phe Tyr Pro Tyr Thr Phe Gly Gly Gly Thr Lys Leu Glu Ile
            100                 105                 110

Lys
```

<210> SEQ ID NO 665
<211> LENGTH: 30
<212> TYPE: PRT
<213> ORGANISM: Mus musculus

<400> SEQUENCE: 665

Asp Val Phe Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr
            20                  25                  30

<210> SEQ ID NO 666
<211> LENGTH: 6
<212> TYPE: PRT
<213> ORGANISM: Mus musculus

<400> SEQUENCE: 666

Ser Asp Tyr Ala Trp Asn
1               5

<210> SEQ ID NO 667
<211> LENGTH: 14
<212> TYPE: PRT
<213> ORGANISM: Mus musculus

<400> SEQUENCE: 667

Trp Ile Arg Gln Phe Pro Gly Asn Lys Leu Glu Trp Val Thr
1               5                   10

<210> SEQ ID NO 668
<211> LENGTH: 16
<212> TYPE: PRT
<213> ORGANISM: Mus musculus

<400> SEQUENCE: 668

Tyr Ile Gly Tyr Ser Gly Thr Thr Ser Tyr Asn Pro Ser Leu Lys Ser
1               5                   10                  15

<210> SEQ ID NO 669
<211> LENGTH: 32
<212> TYPE: PRT
<213> ORGANISM: Mus musculus

<400> SEQUENCE: 669

Arg Ile Ser Ile Thr Arg Asp Thr Ser Lys Asn Gln Phe Phe Leu Gln
1               5                   10                  15

Leu Asn Ser Val Ser Thr Glu Asp Thr Ala Thr Tyr Tyr Cys Val Arg
            20                  25                  30

<210> SEQ ID NO 670
<211> LENGTH: 13
<212> TYPE: PRT
<213> ORGANISM: Mus musculus

<400> SEQUENCE: 670

Arg Gly Ser Tyr Tyr Gly Ser Tyr Trp Phe Phe Asp Val
1               5                   10

<210> SEQ ID NO 671
<211> LENGTH: 11
<212> TYPE: PRT
<213> ORGANISM: Mus musculus

<400> SEQUENCE: 671

```
Trp Gly Ala Gly Thr Thr Val Thr Val Ser Ser
1               5                   10


<210> SEQ ID NO 672
<211> LENGTH: 366
<212> TYPE: DNA
<213> ORGANISM: Mus musculus

<400> SEQUENCE: 672

gatgtgtttc ttcaggagtc gggacctggc ctggtgaaac cttctcagtc tctgtccctc     60

acctgcaccg tcactggcta ctcaatcacc agtgattatg cctggaactg gatccggcag    120

tttccaggaa acaaactgga gtgggtgacc tacataggct acagtggtac cactagctac    180

aacccatctc tcaaaagtcg aatctctatc actcgagaca catccaagaa ccagttcttc    240

ctgcagttga attctgtgtc tactgaggac acagccacat attactgtgt aagaaggggg    300

agttactatg ggagttactg gttcttcgat gtctggggcg cagggaccac ggtcaccgtc    360

tcctca                                                                366


<210> SEQ ID NO 673
<211> LENGTH: 122
<212> TYPE: PRT
<213> ORGANISM: Mus musculus

<400> SEQUENCE: 673

Asp Val Phe Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Val Thr Tyr Ile Gly Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Ser Thr Glu Asp Thr Ala Thr Tyr Tyr Cys
                85                  90                  95

Val Arg Arg Gly Ser Tyr Tyr Gly Ser Tyr Trp Phe Phe Asp Val Trp
            100                 105                 110

Gly Ala Gly Thr Thr Val Thr Val Ser Ser
        115                 120


<210> SEQ ID NO 674
<211> LENGTH: 23
<212> TYPE: PRT
<213> ORGANISM: Mus musculus

<400> SEQUENCE: 674

Gln Val Val Leu Ser Gln Ser Pro Ala Ile Leu Ser Ala Ser Pro Gly
1               5                   10                  15

Glu Lys Val Thr Met Thr Cys
            20


<210> SEQ ID NO 675
<211> LENGTH: 10
<212> TYPE: PRT
<213> ORGANISM: Mus musculus

<400> SEQUENCE: 675
```

Arg Ala Ser Ser Ser Val Ser Tyr Met His
1 5 10

<210> SEQ ID NO 676
<211> LENGTH: 15
<212> TYPE: PRT
<213> ORGANISM: Mus musculus

<400> SEQUENCE: 676

Trp Tyr Gln Gln Lys Pro Gly Ser Ser Pro Lys Pro Trp Ile Tyr
1 5 10 15

<210> SEQ ID NO 677
<211> LENGTH: 7
<212> TYPE: PRT
<213> ORGANISM: Mus musculus

<400> SEQUENCE: 677

Ala Thr Ser Asn Leu Ala Ser
1 5

<210> SEQ ID NO 678
<211> LENGTH: 32
<212> TYPE: PRT
<213> ORGANISM: Mus musculus

<400> SEQUENCE: 678

Gly Val Pro Pro His Phe Ser Gly Ser Gly Ser Gly Thr Ser Tyr Ser
1 5 10 15

Leu Thr Ile Ser Arg Val Glu Ala Glu Asp Ala Ala Thr Tyr Tyr Cys
20 25 30

<210> SEQ ID NO 679
<211> LENGTH: 9
<212> TYPE: PRT
<213> ORGANISM: Mus musculus

<400> SEQUENCE: 679

Gln Gln Trp Thr Ser Asn Pro Pro Thr
1 5

<210> SEQ ID NO 680
<211> LENGTH: 10
<212> TYPE: PRT
<213> ORGANISM: Mus musculus

<400> SEQUENCE: 680

Phe Gly Gly Gly Thr Lys Leu Glu Ile Lys
1 5 10

<210> SEQ ID NO 681
<211> LENGTH: 318
<212> TYPE: DNA
<213> ORGANISM: Mus musculus

<400> SEQUENCE: 681
caagttgttc tctcccagtc tccagcaatc ctgtctgcat ctccagggga gaaggtcaca 60
atgacttgca gggccagttc aagtgtaagt tacatgcact ggtatcagca gaagccagga 120
tcctccccca aaccctggat ttatgccaca tccaacctgg cttctggagt ccctcctcac 180
ttcagtggca gtgggtctgg gacctcgtac tctctcacaa tcagcagagt ggaggctgaa 240
gatgctgcca cttattactg ccagcagtgg actagtaacc cacccacgtt cggagggggg 300
accaagttgg aaataaaa 318

<210> SEQ ID NO 682
<211> LENGTH: 106
<212> TYPE: PRT
<213> ORGANISM: Mus musculus

<400> SEQUENCE: 682

Gln Val Val Leu Ser Gln Ser Pro Ala Ile Leu Ser Ala Ser Pro Gly
1 5 10 15

Glu Lys Val Thr Met Thr Cys Arg Ala Ser Ser Ser Val Ser Tyr Met
20 25 30

His Trp Tyr Gln Gln Lys Pro Gly Ser Ser Pro Lys Pro Trp Ile Tyr
35 40 45

Ala Thr Ser Asn Leu Ala Ser Gly Val Pro Pro His Phe Ser Gly Ser
50 55 60

Gly Ser Gly Thr Ser Tyr Ser Leu Thr Ile Ser Arg Val Glu Ala Glu
65 70 75 80

Asp Ala Ala Thr Tyr Tyr Cys Gln Gln Trp Thr Ser Asn Pro Pro Thr
85 90 95

Phe Gly Gly Gly Thr Lys Leu Glu Ile Lys
100 105

<210> SEQ ID NO 683
<211> LENGTH: 30
<212> TYPE: PRT
<213> ORGANISM: Mus musculus

<400> SEQUENCE: 683

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser
20 25 30

<210> SEQ ID NO 684
<211> LENGTH: 5
<212> TYPE: PRT
<213> ORGANISM: Mus musculus

<400> SEQUENCE: 684

Asn Tyr Trp Met Asn
1 5

<210> SEQ ID NO 685
<211> LENGTH: 14
<212> TYPE: PRT
<213> ORGANISM: Mus musculus

<400> SEQUENCE: 685

Trp Val Arg Gln Ser Pro Glu Lys Gly Leu Glu Trp Val Ala
1 5 10

<210> SEQ ID NO 686
<211> LENGTH: 19
<212> TYPE: PRT
<213> ORGANISM: Mus musculus

<400> SEQUENCE: 686

Gln Ile Arg Leu Lys Ser Asp Asn Tyr Ala Thr His Tyr Ala Glu Ser
1 5 10 15

Val Lys Gly

<210> SEQ ID NO 687
<211> LENGTH: 32
<212> TYPE: PRT
<213> ORGANISM: Mus musculus

<400> SEQUENCE: 687

Met Phe Thr Ile Ser Arg Asp Asp Ser Lys Ser Ser Val Tyr Leu Gln
1 5 10 15

Met Asn Asn Leu Arg Ala Glu Asp Thr Gly Ile Tyr Tyr Cys Thr Ala
20 25 30

<210> SEQ ID NO 688
<211> LENGTH: 4
<212> TYPE: PRT
<213> ORGANISM: Mus musculus

<400> SEQUENCE: 688

Gly Gly Asp Tyr
1

<210> SEQ ID NO 689
<211> LENGTH: 11
<212> TYPE: PRT
<213> ORGANISM: Mus musculus

<400> SEQUENCE: 689

Trp Gly Gln Gly Thr Thr Leu Thr Val Ser Ser
1 5 10

<210> SEQ ID NO 690
<211> LENGTH: 345
<212> TYPE: DNA
<213> ORGANISM: Mus musculus

<400> SEQUENCE: 690
gaagtgaagc ttgaggagtc tggaggaggc ttggtgcagc ctggaggatc catgaaactc 60
tcctgtgttg cctctggatt cactttcagt aactactgga tgaactgggt ccgccagtct 120
ccagagaagg ggcttgagtg ggttgctcaa attagattga aatctgataa ttatgcaaca 180
cattatgcgg agtctgtgaa agggatgttc accatctcaa gagatgattc caaaagtagt 240
gtctacctgc aaatgaacaa cttaagggct gaagacactg gaatttatta ctgcacagca 300
ggcggggact actggggcca aggcaccact ctcacagtct cctca 345

<210> SEQ ID NO 691
<211> LENGTH: 115
<212> TYPE: PRT
<213> ORGANISM: Mus musculus

<400> SEQUENCE: 691

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser Asn Tyr
20 25 30

Trp Met Asn Trp Val Arg Gln Ser Pro Glu Lys Gly Leu Glu Trp Val
35 40 45

Ala Gln Ile Arg Leu Lys Ser Asp Asn Tyr Ala Thr His Tyr Ala Glu
50 55 60

Ser Val Lys Gly Met Phe Thr Ile Ser Arg Asp Asp Ser Lys Ser Ser
65 70 75 80

```
Val Tyr Leu Gln Met Asn Asn Leu Arg Ala Glu Asp Thr Gly Ile Tyr
                85                  90                  95

Tyr Cys Thr Ala Gly Gly Asp Tyr Trp Gly Gln Gly Thr Thr Leu Thr
            100                 105                 110

Val Ser Ser
        115


<210> SEQ ID NO 692
<211> LENGTH: 23
<212> TYPE: PRT
<213> ORGANISM: Mus musculus

<400> SEQUENCE: 692

Asp Ile Val Met Thr Gln Ser Gln Lys Phe Met Ser Thr Thr Val Gly
1               5                   10                  15

Asp Arg Val Ser Ile Thr Cys
            20


<210> SEQ ID NO 693
<211> LENGTH: 11
<212> TYPE: PRT
<213> ORGANISM: Mus musculus

<400> SEQUENCE: 693

Lys Ala Ser Gln Asn Val Gly Thr Ala Val Ala
1               5                   10


<210> SEQ ID NO 694
<211> LENGTH: 15
<212> TYPE: PRT
<213> ORGANISM: Mus musculus

<400> SEQUENCE: 694

Trp Tyr His Gln Lys Pro Gly Gln Ser Pro Lys Leu Leu Ile Tyr
1               5                   10                  15


<210> SEQ ID NO 695
<211> LENGTH: 7
<212> TYPE: PRT
<213> ORGANISM: Mus musculus

<400> SEQUENCE: 695

Ser Ala Ser Asn Arg Tyr Thr
1               5


<210> SEQ ID NO 696
<211> LENGTH: 32
<212> TYPE: PRT
<213> ORGANISM: Mus musculus

<400> SEQUENCE: 696

Gly Val Pro Asp Arg Phe Ile Gly Ser Gly Ser Gly Thr Asp Phe Thr
1               5                   10                  15

Leu Thr Ile Ser Asn Val Gln Ser Glu Asp Leu Gly Asn Tyr Phe Cys
            20                  25                  30


<210> SEQ ID NO 697
<211> LENGTH: 9
<212> TYPE: PRT
<213> ORGANISM: Mus musculus

<400> SEQUENCE: 697
```

Gln Gln Tyr Ile Asn Tyr Leu Leu Thr
1 5

<210> SEQ ID NO 698
<211> LENGTH: 10
<212> TYPE: PRT
<213> ORGANISM: Mus musculus

<400> SEQUENCE: 698

Phe Gly Ser Gly Thr Lys Leu Glu Ile Lys
1 5 10

<210> SEQ ID NO 699
<211> LENGTH: 321
<212> TYPE: DNA
<213> ORGANISM: Mus musculus

<400> SEQUENCE: 699
gacattgtga tgacccagtc tcaaaaattc atgtccacaa cagtaggaga cagggtcagc 60
atcacctgca aggccagtca gaatgtgggt actgctgtag cctggtatca ccagaaacca 120
ggacaatctc ctaaactcct gatttactca gcatccaatc ggtacactgg agtccctgat 180
cgcttcatag gcagtggatc tgggacagat ttcactctca ccattagcaa tgtgcagtct 240
gaagacctgg gaaattattt ctgtcagcaa tatatcaact atcttctcac gttcggctcg 300
gggacaaagt tggaaataaa a 321

<210> SEQ ID NO 700
<211> LENGTH: 330
<212> TYPE: PRT
<213> ORGANISM: Homo sapiens

<400> SEQUENCE: 700

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn

```
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 701
<211> LENGTH: 330
<212> TYPE: PRT
<213> ORGANISM: Homo sapiens

<400> SEQUENCE: 701

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 702
<211> LENGTH: 330
<212> TYPE: PRT
<213> ORGANISM: Homo sapiens

<400> SEQUENCE: 702

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 703
<211> LENGTH: 330
<212> TYPE: PRT
<213> ORGANISM: Mus musculus

<400> SEQUENCE: 703

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys 325 330

<210> SEQ ID NO 704
<211> LENGTH: 120
<212> TYPE: PRT
<213> ORGANISM: Artificial Sequence
<220> FEATURE:
<223> OTHER INFORMATION: Synthetic

<400> SEQUENCE: 704

Glu Val Met Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Thr Met Ser Trp Val Arg Gln Thr Pro Glu Lys Arg Leu Glu Trp Val
35 40 45

Ala Thr Ile Val Gly Gly Gly Gly Tyr Thr Tyr Tyr Leu Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Leu Tyr Tyr Cys
85 90 95

Ala Arg Met Gly Leu Thr Gln Arg Asn Ala Leu Asp Tyr Trp Gly Gln
100 105 110

Gly Thr Leu Ile Thr Val Ser Ser
115 120

<210> SEQ ID NO 705
<211> LENGTH: 120
<212> TYPE: PRT
<213> ORGANISM: Artificial Sequence
<220> FEATURE:
<223> OTHER INFORMATION: Synthetic

<400> SEQUENCE: 705

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Thr Met Ser Trp Val Arg Gln Thr Pro Glu Lys Arg Leu Glu Trp Val
35 40 45

Ala Thr Ile Val Gly Gly Gly Gly Tyr Thr Tyr Tyr Leu Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Leu Tyr Tyr Cys
85 90 95

Ala Arg Met Gly Leu Thr Gln Arg Asn Ala Leu Asp Tyr Trp Gly Gln
100 105 110

Gly Thr Leu Ile Thr Val Ser Ser
115 120

<210> SEQ ID NO 706
<211> LENGTH: 120
<212> TYPE: PRT
<213> ORGANISM: Artificial Sequence
<220> FEATURE:
<223> OTHER INFORMATION: Synthetic

<400> SEQUENCE: 706

```
Glu Val Met Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Val Gly Gly Gly Gly Tyr Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Arg Met Gly Leu Thr Gln Arg Asn Ala Leu Asp Tyr Trp Gly Gln
            100                 105                 110

Gly Thr Leu Ile Thr Val Ser Ser
        115                 120


<210> SEQ ID NO 707
<211> LENGTH: 120
<212> TYPE: PRT
<213> ORGANISM: Artificial Sequence
<220> FEATURE:
<223> OTHER INFORMATION: Synthetic

<400> SEQUENCE: 707

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Thr Pro Gly Lys Arg Leu Glu Trp Val
        35                  40                  45

Ala Thr Ile Val Gly Gly Gly Gly Tyr Thr Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Leu Thr Gln Arg Asn Ala Leu Asp Tyr Trp Gly Gln
            100                 105                 110

Gly Thr Ser Ile Thr Val Ser Ser
        115                 120


<210> SEQ ID NO 708
<211> LENGTH: 113
<212> TYPE: PRT
<213> ORGANISM: Artificial Sequence
<220> FEATURE:
<223> OTHER INFORMATION: Synthetic

<400> SEQUENCE: 708

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
```

50 55 60

Pro Asp Arg Phe Thr Gly Ser Gly Phe Gly Thr Asp Phe Thr Leu Thr
65 70 75 80

Ile Ser Ser Leu Gln Ala Glu Asp Val Ala Val Tyr Tyr Cys Gln Asn
85 90 95

Asp His Thr Tyr Pro Leu Thr Phe Gly Ala Gly Thr Lys Leu Glu Ile
100 105 110

Lys

<210> SEQ ID NO 709
<211> LENGTH: 113
<212> TYPE: PRT
<213> ORGANISM: Artificial Sequence
<220> FEATURE:
<223> OTHER INFORMATION: Synthetic

<400> SEQUENCE: 709

Asp Ile Val Met Thr Gln Ser Pro Leu Ser Leu Pro Val Thr Pro Gly
1 5 10 15

Glu Pro Ala Ser Ile Ser Cys Lys Ser Ser Gln Ser Leu Phe Asn Ser
20 25 30

Gly Asn Gln Lys Asn Tyr Leu Ala Trp Tyr Leu Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Phe Gly Thr Asp Phe Thr Leu Lys
65 70 75 80

Ile Ser Arg Val Glu Ala Glu Asp Val Gly Val Tyr Tyr Cys Gln Asn
85 90 95

Asp His Thr Tyr Pro Leu Thr Phe Gly Ala Gly Thr Lys Leu Glu Ile
100 105 110

Lys

<210> SEQ ID NO 710
<211> LENGTH: 113
<212> TYPE: PRT
<213> ORGANISM: Artificial Sequence
<220> FEATURE:
<223> OTHER INFORMATION: Synthetic

<400> SEQUENCE: 710

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Ser Gly Ser Gly Phe Gly Thr Asp Phe Thr Leu Thr
65 70 75 80

Ile Ser Ser Leu Gln Ala Glu Asp Val Ala Val Tyr Tyr Cys Gln Asn
85 90 95

Asp His Thr Tyr Pro Leu Thr Phe Gly Ala Gly Thr Lys Leu Glu Ile
100 105 110

Lys

<210> SEQ ID NO 711
<211> LENGTH: 120
<212> TYPE: PRT
<213> ORGANISM: Artificial Sequence
<220> FEATURE:
<223> OTHER INFORMATION: Synthetic

<400> SEQUENCE: 711

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Glu Lys Arg Leu Glu Trp Val
        35                  40                  45

Ala Thr Ile Ser Val Ile Gly Gly Asn Thr Tyr Tyr Val Asp Ser Val
    50                  55                  60

Lys Gly Arg Phe Thr Ile Ser Arg Asp Lys Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Gly Gln Thr Gln Arg Asn Ala Met Asp Tyr Trp Gly Gln
            100                 105                 110

Gly Thr Leu Val Thr Val Ser Ser
        115                 120

<210> SEQ ID NO 712
<211> LENGTH: 120
<212> TYPE: PRT
<213> ORGANISM: Artificial Sequence
<220> FEATURE:
<223> OTHER INFORMATION: Synthetic

<400> SEQUENCE: 712

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Glu Lys Arg Leu Glu Trp Val
        35                  40                  45

Ala Thr Ile Ser Val Ile Gly Gly Asn Thr Tyr Tyr Val Asp Ser Val
    50                  55                  60

Lys Gly Arg Phe Thr Ile Ser Arg Asp Lys Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Gly Gln Thr Gln Arg Asn Ala Met Asp Tyr Trp Gly Gln
            100                 105                 110

Gly Thr Leu Val Thr Val Ser Ser
        115                 120

<210> SEQ ID NO 713
<211> LENGTH: 120
<212> TYPE: PRT
<213> ORGANISM: Artificial Sequence
<220> FEATURE:
<223> OTHER INFORMATION: Synthetic

<400> SEQUENCE: 713

Glu Val Met Leu Val Glu Ser Gly Gly Gly Leu Val Gln Pro Gly Gly

```
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Val Ile Gly Gly Asn Thr Tyr Tyr Val Asp Ser Val
    50                  55                  60

Lys Gly Arg Phe Thr Ile Ser Arg Asp Lys Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Gly Gln Thr Gln Arg Asn Ala Met Asp Tyr Trp Gly Gln
            100                 105                 110

Gly Thr Leu Val Thr Val Ser Ser
        115                 120


<210> SEQ ID NO 714
<211> LENGTH: 120
<212> TYPE: PRT
<213> ORGANISM: Artificial Sequence
<220> FEATURE:
<223> OTHER INFORMATION: Synthetic

<400> SEQUENCE: 714

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Gly Lys Arg Leu Glu Trp Val
        35                  40                  45

Ala Thr Ile Ser Val Ile Gly Gly Asn Thr Tyr Tyr Val Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gln Thr Gln Arg Asn Ala Met Asp Tyr Trp Gly Gln
            100                 105                 110

Gly Thr Leu Val Thr Val Ser Ser
        115                 120


<210> SEQ ID NO 715
<211> LENGTH: 113
<212> TYPE: PRT
<213> ORGANISM: Artificial Sequence
<220> FEATURE:
<223> OTHER INFORMATION: Synthetic

<400> SEQUENCE: 715

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60
```

Pro Asp Arg Phe Thr Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Tyr Ser Tyr Pro Leu Thr Phe Gly Ala Gly Thr Lys Leu Glu Ile
100 105 110

Lys

<210> SEQ ID NO 716
<211> LENGTH: 113
<212> TYPE: PRT
<213> ORGANISM: Artificial Sequence
<220> FEATURE:
<223> OTHER INFORMATION: Synthetic

<400> SEQUENCE: 716

Glu Ile Val Met Thr Gln Ser Pro Ala Thr Leu Ser Leu Ser Pro Gly
1 5 10 15

Glu Arg Ala Thr Leu Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Arg Lys Leu Ile Tyr Gly Ala Ser Thr Arg Glu Ser Gly Ile
50 55 60

Pro Ala Arg Phe Thr Gly Ser Gly Ser Gly Thr Asp Phe Thr Leu Thr
65 70 75 80

Ile Ser Ser Leu Gln Pro Glu Asp Phe Ala Val Tyr Tyr Cys Gln Asn
85 90 95

Asp Tyr Ser Tyr Pro Leu Thr Phe Gly Ala Gly Thr Lys Leu Glu Ile
100 105 110

Lys

<210> SEQ ID NO 717
<211> LENGTH: 113
<212> TYPE: PRT
<213> ORGANISM: Artificial Sequence
<220> FEATURE:
<223> OTHER INFORMATION: Synthetic

<400> SEQUENCE: 717

Asp Ile Val Met Thr Gln Ser Pro Asp Ser Leu Ala Val Ser Ala Gly
1 5 10 15

Glu Arg Ala Thr Met Asn Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Tyr Ser Tyr Pro Leu Thr Phe Gly Ala Gly Thr Lys Leu Glu Ile
100 105 110

Lys

<210> SEQ ID NO 718

<211> LENGTH: 117
<212> TYPE: PRT
<213> ORGANISM: Artificial Sequence
<220> FEATURE:
<223> OTHER INFORMATION: Synthetic

<400> SEQUENCE: 718

Gln Val Gln Leu Lys Glu Ser Gly Pro Gly Leu Val Lys Pro Ser Glu
1 5 10 15

Thr Leu Ser Leu Thr Cys Thr Val Ser Gly Phe Ser Leu Thr Ser Tyr
20 25 30

Ala Ile Ser Trp Val Arg Gln Pro Pro Gly Lys Gly Leu Glu Trp Leu
35 40 45

Gly Glu Ile Trp Thr Gly Gly Gly Thr Asn Tyr Asn Ser Ala Leu Lys
50 55 60

Ser Arg Val Ser Ile Ser Lys Asp Asn Ser Lys Ser Gln Val Phe Leu
65 70 75 80

Lys Leu Ser Ser Val Gln Ala Ala Asp Thr Ala Arg Tyr Tyr Cys Gly
85 90 95

Arg Leu Ser Tyr Gly Asn Ser Leu Asp Tyr Trp Gly Gln Gly Thr Leu
100 105 110

Val Thr Val Ser Ser
115

<210> SEQ ID NO 719
<211> LENGTH: 117
<212> TYPE: PRT
<213> ORGANISM: Artificial Sequence
<220> FEATURE:
<223> OTHER INFORMATION: Synthetic

<400> SEQUENCE: 719

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Leu Thr Ser Tyr
20 25 30

Ala Ile Ser Trp Val Arg Gln Pro Ala Gly Lys Gly Leu Glu Trp Leu
35 40 45

Gly Glu Ile Trp Thr Gly Gly Gly Thr Asn Tyr Asn Ser Ala Leu Lys
50 55 60

Ser Arg Val Ser Ile Ser Lys Asp Asn Ser Lys Ser Gln Val Phe Leu
65 70 75 80

Lys Leu Ser Ser Val Gln Ala Ala Asp Thr Ala Arg Tyr Tyr Cys Gly
85 90 95

Arg Leu Ser Tyr Gly Asn Ser Leu Asp Tyr Trp Gly Gln Gly Thr Leu
100 105 110

Val Thr Val Ser Ser
115

<210> SEQ ID NO 720
<211> LENGTH: 117
<212> TYPE: PRT
<213> ORGANISM: Artificial Sequence
<220> FEATURE:
<223> OTHER INFORMATION: Synthetic

<400> SEQUENCE: 720

Gln Val Gln Leu Gln Glu Ser Gly Pro Gly Leu Val Lys Pro Ser Gln
1 5 10 15

```
Thr Leu Ser Leu Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Leu
        35                  40                  45

Gly Glu Ile Trp Thr Gly Gly Gly Thr Asn Tyr Asn Pro Ala Leu Lys
    50                  55                  60

Ser Arg Val Ser Ile Ser Lys Asp Asn Ser Lys Ser Gln Val Phe Leu
65                  70                  75                  80

Lys Leu Ser Ser Val Thr Ala Ala Asp Thr Ala Arg Tyr Tyr Cys Gly
                85                  90                  95

Arg Leu Ser Tyr Gly Asn Ser Leu Asp Tyr Trp Gly Gln Gly Thr Leu
            100                 105                 110

Val Thr Val Ser Ser
        115


<210> SEQ ID NO 721
<211> LENGTH: 117
<212> TYPE: PRT
<213> ORGANISM: Artificial Sequence
<220> FEATURE:
<223> OTHER INFORMATION: Synthetic

<400> SEQUENCE: 721

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ala Ile Ser Trp Val Arg Gln Pro Ala Gly Lys Gly Leu Glu Trp Leu
        35                  40                  45

Gly Glu Ile Trp Thr Gly Gly Gly Thr Asn Tyr Asn Ser Ala Leu Lys
    50                  55                  60

Ser Arg Val Ser Ile Ser Lys Asp Asn Ser Lys Ser Gln Val Phe Leu
65                  70                  75                  80

Lys Leu Ser Ser Val Thr Ala Ala Asp Thr Ala Arg Tyr Tyr Cys Gly
                85                  90                  95

Arg Leu Ser Tyr Gly Asn Ser Leu Asp Tyr Trp Gly Gln Gly Thr Leu
            100                 105                 110

Val Thr Val Ser Ser
        115


<210> SEQ ID NO 722
<211> LENGTH: 117
<212> TYPE: PRT
<213> ORGANISM: Artificial Sequence
<220> FEATURE:
<223> OTHER INFORMATION: Synthetic

<400> SEQUENCE: 722

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Ile
        35                  40                  45

Gly Glu Ile Trp Thr Gly Gly Gly Thr Asn Tyr Asn Ser Ser Leu Lys
    50                  55                  60

Ser Arg Val Thr Ile Ser Lys Asp Asn Ser Lys Ser Gln Val Ser Leu
65                  70                  75                  80
```

Lys Leu Ser Ser Val Gln Ala Ala Asp Thr Ala Arg Tyr Tyr Cys Gly
85 90 95

Arg Leu Ser Tyr Gly Asn Ser Leu Asp Tyr Trp Gly Gln Gly Thr Leu
100 105 110

Val Thr Val Ser Ser
115

<210> SEQ ID NO 723
<211> LENGTH: 113
<212> TYPE: PRT
<213> ORGANISM: Artificial Sequence
<220> FEATURE:
<223> OTHER INFORMATION: Synthetic

<400> SEQUENCE: 723

Asp Ile Val Met Thr Gln Ser Pro Asp Ser Leu Thr Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asn Phe Ile Tyr Pro Leu Thr Phe Gly Pro Gly Thr Lys Leu Glu Ile
100 105 110

Lys

<210> SEQ ID NO 724
<211> LENGTH: 113
<212> TYPE: PRT
<213> ORGANISM: Artificial Sequence
<220> FEATURE:
<223> OTHER INFORMATION: Synthetic

<400> SEQUENCE: 724

Asp Ile Val Met Thr Gln Ser Pro Leu Ser Leu Pro Val Thr Leu Gly
1 5 10 15

Glu Pro Ala Ser Ile Ser Cys Lys Ser Ser Gln Ser Leu Leu Asn Ser
20 25 30

Gly Asn Gln Lys Asn Tyr Leu Thr Trp Tyr Leu Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Lys
65 70 75 80

Ile Ser Arg Val Glu Ala Glu Asp Val Gly Val Tyr Tyr Cys Gln Asn
85 90 95

Asn Phe Ile Tyr Pro Leu Thr Phe Gly Pro Gly Thr Lys Leu Glu Ile
100 105 110

Lys

<210> SEQ ID NO 725
<211> LENGTH: 113

<212> TYPE: PRT
<213> ORGANISM: Artificial Sequence
<220> FEATURE:
<223> OTHER INFORMATION: Synthetic

<400> SEQUENCE: 725

```
Asp Ile Val Met Thr Gln Ser Pro Asp Ser Thr Thr Val Leu Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn Phe Ile Tyr Pro Leu Thr Phe Gly Pro Gly Thr Lys Leu Glu Ile
            100                 105                 110

Lys
```

<210> SEQ ID NO 726
<211> LENGTH: 16
<212> TYPE: PRT
<213> ORGANISM: Artificial Sequence
<220> FEATURE:
<223> OTHER INFORMATION: Synthetic

<400> SEQUENCE: 726

```
Glu Ile Trp Thr Gly Gly Gly Thr Asn Tyr Asn Pro Ala Leu Lys Ser
1               5                   10                  15
```

<210> SEQ ID NO 727
<211> LENGTH: 16
<212> TYPE: PRT
<213> ORGANISM: Artificial Sequence
<220> FEATURE:
<223> OTHER INFORMATION: Synthetic

<400> SEQUENCE: 727

```
Glu Ile Trp Thr Gly Gly Gly Thr Asn Tyr Asn Ser Ser Leu Lys Ser
1               5                   10                  15
```

<210> SEQ ID NO 728
<211> LENGTH: 17
<212> TYPE: PRT
<213> ORGANISM: Artificial Sequence
<220> FEATURE:
<223> OTHER INFORMATION: Synthetic

<400> SEQUENCE: 728

```
Lys Ser Ser Gln Ser Leu Leu Asn Ser Gly Asn Gln Lys Asn Tyr Leu
1               5                   10                  15

Ala
```

ANTIBODIES AND METHODS FOR TREATING CLAUDIN-ASSOCIATED DISEASES

FIELD OF THE INVENTION

The present invention relates to antibodies, pharmaceutical compositions and methods for preventing, treating and/or diagnosing CLDN-18-associated diseases.

BACKGROUND

Claudins (CLDN) are a family of integral membrane proteins, which comprise a major structural protein of tight junctions in polarized cell types such as epithelial or endothelial cell sheets, and have been found to be a biological marker of various tumors.

CLDNs undergo endocytosis and the turnover time of some CLDNs is short relative to other membrane proteins (Van Raffle et al., 2004, PMID: 15366421). The expression of CLDNs is disregulated in cancer cells and tight junction structures among tumor cells are disrupted in cancer cells. These properties allow antibodies to selectively bind claudin proteins in neoplastic but not in normal tissues. While antibodies specific to individual claudins are useful, it is also possible that polyreactive claudin antibodies or anti-pan claudin antibodies would be more likely to facilitate the delivery of payloads to a broader patient population due to higher aggregate antigen density that reduces the likelihood of escape of tumor cells with low levels of antigen expression of any individual claudin.

CLDN18.1, the isoform 1 of CLDN 18, is lung-specific and is markedly decreased in lung adenocarcinoma. CLDN18.2, the isoform 2 of CLDN 18, is physiologically confined to gastric mucosa tight junctions, the epitopes of which would be exposed on the cancer cell surface upon malignant transformation, and is highly expressed in a significant proportion of gastric and pancreatic adenocarcinomas, which makes it a potential drug target for the treatment of gastric and pancreatic adenocarcinoma. Monoantibodies, bispecific antibodies and antibody drug conjugates etc. that target CLDN18.2 have been researched and developed (Zhu et al., Targeting CLDN18.2 by CD3 Bispecific and ADC Modalities for the Treatments of Gastric and pancreatic Cancer; Tureci et al., Characterization of zolbetuximab in pancreatic cancer models, Oncoimmunology 2019, vol. 8, no. 1, e1523096)). In particular, a monoclonal antibody, zolbetuximab (formerly known as IMAB362), generated against CLDN18.2 obtained preliminary results from the phase II 'FAST' trial in June 2016, which suggests it helpful for advanced gastric cancer.

However, the amplitude of antibody-dependent cellular cytotoxicity (ADCC) and complement-dependent cytotoxicity (CDC) directly correlate with cell surface CLDN18.2 levels (Tureci et al., Characterization of zolbetuximab in pancreatic cancer models, Oncoimmunology 2019, vol. 8, no. 1, e1523096). Therefore, for cancer cells with low expression of CLDN18.2, such as breast cancer, the therapeutic effect of anti-CLDN18.2 antibodies are poor.

Therefore, there is a need for an anti-CLDN18.2 antibody that has enhanced ADCC and/or CDC for cancer cells, optional cancer cells with low surface expression of CLDN18.2.

BRIEF SUMMARY OF THE INVENTION

Provided herein are antibodies and antigen-binding fragments and the modification thereof, and pharmaceutical compositions and methods of use for treating/preventing/diagnosing conditions associated with CLDN 18, in particularly, associated with CLDN18.2.

In one aspect, the present disclosure provides an antibody or antigen-binding fragment which specifically binds to Claudin-18 (CLDN 18), wherein the antibody or antigen-binding fragment comprises at least one heavy or light chain complementarity determining region (CDR) having an amino acid sequence selected from the group consisting of GDY, SEQ ID NOs: 18, 20, 22, 27, 29, 31, 36, 38, 40, 45, 47, 49, 54, 56, 58, 63, 65, 67, 72, 74, 81, 83, 85, 90, 92, 94, 99, 101, 103, 108, 110, 112, 117, 119, 121, 126, 128, 130, 135, 137, 139, 144, 146, 148, 153, 155, 157, 163, 165, 167, 172, 174, 176, 181, 183, 185, 190, 192, 194, 198, 200, 202, 207, 209, 211, 216, 218, 220, 225, 227, 229, 234, 236, 238, 243, 245, 247, 252, 254, 256, 261, 263, 265, 270, 272, 274, 279, 281, 283, 288, 290, 292, 297, 299, 301, 306, 308, 310, 315, 317, 319, 324, 326, 328, 333, 335, 337, 342, 344, 346, 351, 353, 355, 360, 362, 364, 369, 371, 373, 378, 380, 382, 387, 389, 391, 396, 398, 400, 405, 407, 409, 414, 416, 418, 423, 425, 427, 432, 434, 436, 441, 443, 445, 450, 452, 454, 459, 461, 463, 468, 470, 472, 477, 479, 481, 486, 488, 490, 495, 497, 499, 504, 506, 508, 513, 515, 517, 522, 524, 526, 531, 533, 535, 540, 542, 544, 549, 551, 553, 558, 560, 562, 567, 569, 571, 576, 578, 580, 585, 587, 589, 594, 596, 598, 603, 605, 607, 612, 614, 616, 621, 623, 625, 630, 632, 634, 639, 641, 643, 648, 650, 652, 657, 659, 661, 666, 668, 670, 675, 677, 679, 684, 686, 688, 693, 695, 726, 727, 728 and 697.

In some embodiments, the antibody or antigen-binding fragment provided herein comprises: a heavy chain variable (VH) region comprising 1, 2 or 3 VH-CDR having an amino acid sequence selected from the group consisting of GDY, SEQ ID NOs: 18, 20, 22, 36, 38, 40, 54, 56, 58, 72, 74, 90, 92, 94, 108, 110, 112, 126, 128, 130, 144, 146, 148, 163, 165, 167, 181, 183, 185, 198, 200, 202, 216, 218, 220, 234, 236, 238, 252, 254, 256, 270, 272, 274, 288, 290, 292, 206, 308, 310, 324, 326, 328, 342, 344, 346, 360, 362, 364, 378, 380, 382, 396, 398, 400, 414, 416, 418, 432, 434, 436, 450, 452, 454, 468, 470, 472, 486, 488, 490, 504, 506, 508, 522, 524, 526, 540, 542, 544, 558, 560, 562, 576, 578, 580, 594, 596, 598, 612, 614, 616, 630, 632, 634, 648, 650, 652, 666, 668, 670, 684, 686, 726, 727 and 688.

In some embodiments, the antibody or antigen-binding fragment provided herein further comprises a light chain variable (VL) region comprising 1, 2 or 3 VL-CDR having an amino acid sequence selected from the group consisting of SEQ ID NOs: 27, 29, 31, 45, 47, 49, 63, 65, 67, 81, 83, 85, 99, 101, 103, 117, 119, 121, 135, 137, 139, 153, 155, 157, 172, 174, 176, 190, 192, 194, 207, 209, 211, 225, 227, 229, 243, 245, 247, 261, 263, 265, 279, 281, 283, 297, 299, 301, 315, 317, 319, 333, 335, 337, 351, 353, 355, 369, 371, 373, 387, 389, 391, 405, 407, 409, 423, 425, 427, 441, 443, 445, 459, 461, 463, 477, 479, 481, 495, 497, 499, 513, 515, 517, 531, 533, 535, 549, 551, 553, 567, 569, 571, 585, 587, 589, 603, 605, 607, 621, 623, 625, 639, 641, 643, 657, 659, 661, 675, 677, 679, 693, 695, 728 and 697.

In some embodiments, the antibody or antigen-binding fragment provided herein comprises:

i. a VH-CDR 1 having an amino acid sequence selected from the group consisting of GDY, SEQ ID NOs: 18, 36, 54, 72, 90, 108, 126, 144, 163, 181, 198, 216, 234, 252, 270, 288, 206, 324, 342, 360, 378, 396, 414, 432, 450, 468, 486, 504, 522, 540, 558, 576, 594, 612, 630, 648, 666 and 684;

ii. a VH-CDR2 having an amino acid sequence selected from the group consisting of SEQ ID NOs: 20, 38, 56, 74, 92, 110, 128, 146, 165, 183, 200, 218, 236, 254, 272, 290, 308, 326, 344, 362, 380, 398, 416, 434, 452, 470, 488, 506, 524, 542, 560, 578, 596, 614, 632, 650, 668, 726, 727 and 686; and iii. a VH-CDR3 having an amino acid sequence selected from the group consisting of GDY and SEQ ID NOs: 22, 40, 58, 94, 112, 130, 148, 167, 185, 202, 220, 238, 256, 274, 292, 310, 328, 346, 364, 382, 400, 418, 436, 454, 472, 490, 508, 526, 544, 562, 580, 598, 616, 634, 652, 670 and 688.

In some embodiments, the antibody or antigen-binding fragment provided herein comprises:

i. a VL-CDR 1 having an amino acid sequence selected from the group consisting of SEQ ID NOs: 27, 45, 63, 81, 99, 117, 135, 153, 172, 190, 207, 225, 243, 261, 279, 297, 315, 333, 351, 369, 387, 405, 423, 441, 459, 477, 495, 513, 531, 549, 567, 585, 603, 621, 639, 657, 675, 728 and 693;

ii. a VL-CDR2 having an amino acid sequence selected from the group consisting of SEQ ID NOs: 29, 47, 65, 83, 101, 119, 137, 155, 174, 192, 209, 227, 245, 263, 281, 299, 317, 335, 353, 371, 389, 407, 425, 443, 461, 479, 497, 515, 533, 551, 569, 587, 605, 623, 641, 659, 677 and 695; and iii. a VL-CDR3 having an amino acid sequence selected from the group consisting of SEQ ID NOs: 31, 49, 67, 85, 103, 121, 139, 157, 176, 194, 211, 229, 247, 265, 283, 301, 319, 337, 355, 373, 391, 409, 427, 445, 463, 481, 499, 517, 535, 553, 571, 589, 607, 625, 643, 661, 679 and 697.

In some embodiments, the antibody or antigen-binding fragment provided herein comprises:

i. a VH-CDR 1 having an amino acid sequence of SEQ ID NO: 18, a VH-CDR 2 having an amino acid sequence of SEQ ID NO: 20, and a VH-CDR 3 having an amino acid sequence of SEQ ID NO: 22;

ii. a VH-CDR 1 having an amino acid sequence of SEQ ID NO: 36, a VH-CDR 2 having an amino acid sequence of SEQ ID NO: 38, and a VH-CDR 3 having an amino acid sequence of SEQ ID NO: 40;

iii. a VH-CDR 1 having an amino acid sequence of SEQ ID NO: 54, a VH-CDR 2 having an amino acid sequence of SEQ ID NO: 56, and a VH-CDR 3 having an amino acid sequence of SEQ ID NO: 58;

iv. a VH-CDR 1 having an amino acid sequence of SEQ ID NO: 72, a VH-CDR 2 having an amino acid sequence of SEQ ID NO: 74, and a VH-CDR 3 having an amino acid sequence of GDY;

v. a VH-CDR 1 having an amino acid sequence of SEQ ID NO: 90, a VH-CDR 2 having an amino acid sequence of SEQ ID NO: 92, and a VH-CDR 3 having an amino acid sequence of SEQ ID NO: 94;

vi. a VH-CDR 1 having an amino acid sequence of SEQ ID NO: 108, a VH-CDR 2 having an amino acid sequence of SEQ ID NO: 110, and a VH-CDR 3 having an amino acid sequence of SEQ ID NO: 112;

vii. a VH-CDR 1 having an amino acid sequence of SEQ ID NO: 126, a VH-CDR 2 having an amino acid sequence of SEQ ID NO: 128, and a VH-CDR 3 having an amino acid sequence of SEQ ID NO: 130;

viii. a VH-CDR 1 having an amino acid sequence of SEQ ID NO: 144, a VH-CDR 2 having an amino acid sequence of SEQ ID NO: 146, and a VH-CDR 3 having an amino acid sequence of SEQ ID NO: 148;

ix. a VH-CDR 1 having an amino acid sequence of SEQ ID NO: 163, a VH-CDR 2 having an amino acid sequence of SEQ ID NO: 165, and a VH-CDR 3 having an amino acid sequence of SEQ ID NO: 167;

x. a VH-CDR 1 having an amino acid sequence of SEQ ID NO: 181, a VH-CDR 2 having an amino acid sequence of SEQ ID NO: 183, and a VH-CDR 3 having an amino acid sequence of SEQ ID NO: 185;

xi. a VH-CDR 1 having an amino acid sequence of SEQ ID NO: 198, a VH-CDR 2 having an amino acid sequence of SEQ ID NO: 200, and a VH-CDR 3 having an amino acid sequence of SEQ ID NO: 202;

xii. a VH-CDR 1 having an amino acid sequence of SEQ ID NO: 216, a VH-CDR 2 having an amino acid sequence of SEQ ID NO: 218, and a VH-CDR 3 having an amino acid sequence of SEQ ID NO: 220;

xiii. a VH-CDR 1 having an amino acid sequence of SEQ ID NO: 234, a VH-CDR 2 having an amino acid sequence of SEQ ID NO: 236, and a VH-CDR 3 having an amino acid sequence of SEQ ID NO: 238;

xiv. a VH-CDR 1 having an amino acid sequence of SEQ ID NO: 252, a VH-CDR 2 having an amino acid sequence of SEQ ID NO: 254, and a VH-CDR 3 having an amino acid sequence of SEQ ID NO: 256;

xv. a VH-CDR 1 having an amino acid sequence of SEQ ID NO: 270, a VH-CDR 2 having an amino acid sequence of SEQ ID NO: 272, and a VH-CDR 3 having an amino acid sequence of SEQ ID NO: 274;

xvi. a VH-CDR 1 having an amino acid sequence of SEQ ID NO: 288, a VH-CDR 2 having an amino acid sequence of SEQ ID NO: 290, and a VH-CDR 3 having an amino acid sequence of SEQ ID NO: 292;

xvii. a VH-CDR 1 having an amino acid sequence of SEQ ID NO: 306, a VH-CDR 2 having an amino acid sequence of SEQ ID NO: 308, and a VH-CDR 3 having an amino acid sequence of SEQ ID NO: 310;

xviii. a VH-CDR 1 having an amino acid sequence of SEQ ID NO: 324, a VH-CDR 2 having an amino acid sequence of SEQ ID NO: 326, and a VH-CDR 3 having an amino acid sequence of SEQ ID NO: 328;

xix. a VH-CDR 1 having an amino acid sequence of SEQ ID NO: 342, a VH-CDR 2 having an amino acid sequence selected from the group consisting of SEQ ID NOs: 344, 726 and 727, and a VH-CDR 3 having an amino acid sequence of SEQ ID NO: 346;

xx. a VH-CDR 1 having an amino acid sequence of SEQ ID NO: 360, a VH-CDR 2 having an amino acid sequence of SEQ ID NO: 362, and a VH-CDR 3 having an amino acid sequence of SEQ ID NO: 364;

xxi. a VH-CDR 1 having an amino acid sequence of SEQ ID NO: 378, a VH-CDR 2 having an amino acid sequence of SEQ ID NO: 380, and a VH-CDR 3 having an amino acid sequence of SEQ ID NO: 382;

xxii. a VH-CDR 1 having an amino acid sequence of SEQ ID NO: 396, a VH-CDR 2 having an amino acid sequence of SEQ ID NO: 398, and a VH-CDR 3 having an amino acid sequence of SEQ ID NO: 400;

xxiii. a VH-CDR 1 having an amino acid sequence of SEQ ID NO: 414, a VH-CDR 2 having an amino acid sequence of SEQ ID NO: 416, and a VH-CDR 3 having an amino acid sequence of SEQ ID NO: 418;

xxiv. a VH-CDR 1 having an amino acid sequence of SEQ ID NO: 432, a VH-CDR 2 having an amino acid sequence of SEQ ID NO: 434, and a VH-CDR 3 having an amino acid sequence of SEQ ID NO: 436;

xxv. a VH-CDR 1 having an amino acid sequence of SEQ ID NO: 450, a VH-CDR 2 having an amino acid sequence of SEQ ID NO: 452, and a VH-CDR 3 having an amino acid sequence of SEQ ID NO: 454;

xxvi. a VH-CDR 1 having an amino acid sequence of SEQ ID NO: 468, a VH-CDR 2 having an amino acid sequence of SEQ ID NO: 470, and a VH-CDR 3 having an amino acid sequence of SEQ ID NO: 472;

xxvii. a VH-CDR 1 having an amino acid sequence of SEQ ID NO: 486, a VH-CDR 2 having an amino acid sequence of SEQ ID NO: 488, and a VH-CDR 3 having an amino acid sequence of SEQ ID NO: 490;

xxviii. a VH-CDR 1 having an amino acid sequence of SEQ ID NO: 504, a VH-CDR 2 having an amino acid sequence of SEQ ID NO: 506, and a VH-CDR 3 having an amino acid sequence of SEQ ID NO: 508;

xxix. a VH-CDR 1 having an amino acid sequence of SEQ ID NO: 522, a VH-CDR 2 having an amino acid sequence of SEQ ID NO: 524, and a VH-CDR 3 having an amino acid sequence of SEQ ID NO: 526;

xxx. a VH-CDR 1 having an amino acid sequence of SEQ ID NO: 540, a VH-CDR 2 having an amino acid sequence of SEQ ID NO: 542, and a VH-CDR 3 having an amino acid sequence of SEQ ID NO: 544;

xxxi. a VH-CDR 1 having an amino acid sequence of SEQ ID NO: 558, a VH-CDR 2 having an amino acid sequence of SEQ ID NO: 560, and a VH-CDR 3 having an amino acid sequence of SEQ ID NO: 562;

xxxii. a VH-CDR 1 having an amino acid sequence of SEQ ID NO: 576, a VH-CDR 2 having an amino acid sequence of SEQ ID NO: 578, and a VH-CDR 3 having an amino acid sequence of SEQ ID NO: 580;

xxxiii. a VH-CDR 1 having an amino acid sequence of SEQ ID NO: 594, a VH-CDR 2 having an amino acid sequence of SEQ ID NO: 596, and a VH-CDR 3 having an amino acid sequence of SEQ ID NO: 598;

xxxiv. a VH-CDR 1 having an amino acid sequence of SEQ ID NO: 612, a VH-CDR 2 having an amino acid sequence of SEQ ID NO: 614, and a VH-CDR 3 having an amino acid sequence of SEQ ID NO: 616;

xxxv. a VH-CDR 1 having an amino acid sequence of SEQ ID NO: 630, a VH-CDR 2 having an amino acid sequence of SEQ ID NO: 632, and a VH-CDR 3 having an amino acid sequence of SEQ ID NO: 634;

xxxvi. a VH-CDR 1 having an amino acid sequence of SEQ ID NO: 648, a VH-CDR 2 having an amino acid sequence of SEQ ID NO: 650, and a VH-CDR 3 having an amino acid sequence of SEQ ID NO: 652;

xxxvii. a VH-CDR 1 having an amino acid sequence of SEQ ID NO: 666, a VH-CDR 2 having an amino acid sequence of SEQ ID NO: 668, and a VH-CDR 3 having an amino acid sequence of SEQ ID NO: 670; or xxxviii. a VH-CDR 1 having an amino acid sequence of SEQ ID NO: 684, a VH-CDR 2 having an amino acid sequence of SEQ ID NO: 686, and a VH-CDR 3 having an amino acid sequence of SEQ ID NO: 688.

In some embodiments, the antibody or antigen-binding fragment provided herein further comprises:

i. a VL-CDR 1 having an amino acid sequence of SEQ ID NO: 27, a VL-CDR 2 having an amino acid sequence of SEQ ID NO: 29, and a VL-CDR 3 having an amino acid sequence of SEQ ID NO: 31;

ii. a VL-CDR 1 having an amino acid sequence of SEQ ID NO: 45, a VL-CDR 2 having an amino acid sequence of SEQ ID NO: 47, and a VL-CDR 3 having an amino acid sequence of SEQ ID NO: 49;

iii. a VL-CDR 1 having an amino acid sequence of SEQ ID NO: 63, a VL-CDR 2 having an amino acid sequence of SEQ ID NO: 65, and a VL-CDR 3 having an amino acid sequence of SEQ ID NO: 67;

iv. a VL-CDR 1 having an amino acid sequence of SEQ ID NO: 81, a VL-CDR 2 having an amino acid sequence of SEQ ID NO: 83, and a VL-CDR 3 having an amino acid sequence of SEQ ID NO: 85; or v. a VL-CDR 1 having an amino acid sequence of SEQ ID NO: 99, a VL-CDR 2 having an amino acid sequence of SEQ ID NO: 101, and a VL-CDR 3 having an amino acid sequence of SEQ ID NO: 103;

vi. a VL-CDR 1 having an amino acid sequence of SEQ ID NO: 117, a VL-CDR 2 having an amino acid sequence of SEQ ID NO: 119, and a VL-CDR 3 having an amino acid sequence of SEQ ID NO: 121;

vii. a VL-CDR 1 having an amino acid sequence of SEQ ID NO: 135, a VL-CDR 2 having an amino acid sequence of SEQ ID NO: 137, and a VL-CDR 3 having an amino acid sequence of SEQ ID NO: 139;

viii. a VL-CDR 1 having an amino acid sequence of SEQ ID NO: 153, a VL-CDR 2 having an amino acid sequence of SEQ ID NO: 155, and a VL-CDR 3 having an amino acid sequence of SEQ ID NO: 157;

ix. a VL-CDR 1 having an amino acid sequence of SEQ ID NO: 172, a VL-CDR 2 having an amino acid sequence of SEQ ID NO: 174, and a VL-CDR 3 having an amino acid sequence of SEQ ID NO: 176;

x. a VL-CDR 1 having an amino acid sequence of SEQ ID NO: 190, a VL-CDR 2 having an amino acid sequence of SEQ ID NO: 192, and a VL-CDR 3 having an amino acid sequence of SEQ ID NO: 194;

xi. a VL-CDR 1 having an amino acid sequence of SEQ ID NO: 207, a VL-CDR 2 having an amino acid sequence of SEQ ID NO: 209, and a VL-CDR 3 having an amino acid sequence of SEQ ID NO: 211;

xii. a VL-CDR 1 having an amino acid sequence of SEQ ID NO: 225, a VL-CDR 2 having an amino acid sequence of SEQ ID NO: 227, and a VL-CDR 3 having an amino acid sequence of SEQ ID NO: 229;

xiii. a VL-CDR 1 having an amino acid sequence of SEQ ID NO: 243, a VL-CDR 2 having an amino acid sequence of SEQ ID NO: 245, and a VL-CDR 3 having an amino acid sequence of SEQ ID NO: 247;

xiv. a VL-CDR 1 having an amino acid sequence of SEQ ID NO: 261, a VL-CDR 2 having an amino acid sequence of SEQ ID NO: 263, and a VL-CDR 3 having an amino acid sequence of SEQ ID NO: 265;

xv. a VL-CDR 1 having an amino acid sequence of SEQ ID NO: 279, a VL-CDR 2 having an amino acid sequence of SEQ ID NO: 281, and a VL-CDR 3 having an amino acid sequence of SEQ ID NO: 283;

xvi. a VL-CDR 1 having an amino acid sequence of SEQ ID NO: 297, a VL-CDR 2 having an amino acid sequence of SEQ ID NO: 299, and a VL-CDR 3 having an amino acid sequence of SEQ ID NO: 301;

xvii. a VL-CDR 1 having an amino acid sequence of SEQ ID NO: 315, a VL-CDR 2 having an amino acid sequence of SEQ ID NO: 317, and a VL-CDR 3 having an amino acid sequence of SEQ ID NO: 319;

xviii. a VL-CDR 1 having an amino acid sequence of SEQ ID NO: 333, a VL-CDR 2 having an amino acid sequence of SEQ ID NO: 335, and a VL-CDR 3 having an amino acid sequence of SEQ ID NO: 337;

xix. a VL-CDR 1 having an amino acid sequence of SEQ ID NO: 351 or SEQ ID NO: 728, a VL-CDR 2 having an amino acid sequence of SEQ ID NO: 353, and a VL-CDR 3 having an amino acid sequence of SEQ ID NO: 355;

xx. a VL-CDR 1 having an amino acid sequence of SEQ ID NO: 369, a VL-CDR 2 having an amino acid sequence of SEQ ID NO: 371, and a VL-CDR 3 having an amino acid sequence of SEQ ID NO: 373;

xxi. a VL-CDR 1 having an amino acid sequence of SEQ ID NO: 387, a VL-CDR 2 having an amino acid sequence of SEQ ID NO: 389, and a VL-CDR 3 having an amino acid sequence of SEQ ID NO: 391;

xxii. a VL-CDR 1 having an amino acid sequence of SEQ ID NO: 405, a VL-CDR 2 having an amino acid sequence of SEQ ID NO: 407, and a VL-CDR 3 having an amino acid sequence of SEQ ID NO: 409; or xxiii. a VL-CDR 1 having an amino acid sequence of SEQ ID NO: 423, a VL-CDR 2 having an amino acid sequence of SEQ ID NO: 425, and a VL-CDR 3 having an amino acid sequence of SEQ ID NO: 427;

xxiv. a VL-CDR 1 having an amino acid sequence of SEQ ID NO: 441, a VL-CDR 2 having an amino acid sequence of SEQ ID NO: 443, and a VL-CDR 3 having an amino acid sequence of SEQ ID NO: 445;

xxv. a VL-CDR 1 having an amino acid sequence of SEQ ID NO: 459, a VL-CDR 2 having an amino acid sequence of SEQ ID NO: 461, and a VL-CDR 3 having an amino acid sequence of SEQ ID NO: 463;

xxvi. a VL-CDR 1 having an amino acid sequence of SEQ ID NO: 477, a VL-CDR 2 having an amino acid sequence of SEQ ID NO: 479, and a VL-CDR 3 having an amino acid sequence of SEQ ID NO: 481;

xxvii. a VL-CDR 1 having an amino acid sequence of SEQ ID NO: 495, a VL-CDR 2 having an amino acid sequence of SEQ ID NO: 497, and a VL-CDR 3 having an amino acid sequence of SEQ ID NO: 499;

xxviii. a VL-CDR 1 having an amino acid sequence of SEQ ID NO: 513, a VL-CDR 2 having an amino acid sequence of SEQ ID NO: 515, and a VL-CDR 3 having an amino acid sequence of SEQ ID NO: 517;

xxix. a VL-CDR 1 having an amino acid sequence of SEQ ID NO: 531, a VL-CDR 2 having an amino acid sequence of SEQ ID NO: 533, and a VL-CDR 3 having an amino acid sequence of SEQ ID NO: 535;

xxx. a VL-CDR 1 having an amino acid sequence of SEQ ID NO: 549, a VL-CDR 2 having an amino acid sequence of SEQ ID NO: 551, and a VL-CDR 3 having an amino acid sequence of SEQ ID NO: 553;

xxxi. a VL-CDR 1 having an amino acid sequence of SEQ ID NO: 567, a VL-CDR 2 having an amino acid sequence of SEQ ID NO: 569, and a VL-CDR 3 having an amino acid sequence of SEQ ID NO: 571;

xxxii. a VL-CDR 1 having an amino acid sequence of SEQ ID NO: 585, a VL-CDR 2 having an amino acid sequence of SEQ ID NO: 587, and a VL-CDR 3 having an amino acid sequence of SEQ ID NO: 589;

xxxiii. a VL-CDR 1 having an amino acid sequence of SEQ ID NO: 603, a VL-CDR 2 having an amino acid sequence of SEQ ID NO: 605, and a VL-CDR 3 having an amino acid sequence of SEQ ID NO: 607;

xxxiv. a VL-CDR 1 having an amino acid sequence of SEQ ID NO: 621, a VL-CDR 2 having an amino acid sequence of SEQ ID NO: 623, and a VL-CDR 3 having an amino acid sequence of SEQ ID NO: 625;

xxxv. a VL-CDR 1 having an amino acid sequence of SEQ ID NO: 639, a VL-CDR 2 having an amino acid sequence of SEQ ID NO: 641, and a VL-CDR 3 having an amino acid sequence of SEQ ID NO: 643;

xxxvi. a VL-CDR 1 having an amino acid sequence of SEQ ID NO: 657, a VL-CDR 2 having an amino acid sequence of SEQ ID NO: 659, and a VL-CDR 3 having an amino acid sequence of SEQ ID NO: 661;

xxxvii. a VL-CDR 1 having an amino acid sequence of SEQ ID NO: 675, a VL-CDR 2 having an amino acid sequence of SEQ ID NO: 677, and a VL-CDR 3 having an amino acid sequence of SEQ ID NO: 679; or xxxviii. a VL-CDR 1 having an amino acid sequence of SEQ ID NO: 693, a VL-CDR 2 having an amino acid sequence of SEQ ID NO: 695, and a VL-CDR 3 having an amino acid sequence of SEQ ID NO: 697.

In some embodiments, the antibody or antigen-binding fragment provided herein comprises:

i. a VH-CDR 1 having an amino acid sequence of SEQ ID NO: 18, a VH-CDR 2 having an amino acid sequence of SEQ ID NO: 20, and a VH-CDR 3 having an amino acid sequence of SEQ ID NO: 22, a VL-CDR 1 having an amino acid sequence of SEQ ID NO: 27, a VL-CDR 2 having an amino acid sequence of SEQ ID NO: 29, and a VL-CDR 3 having an amino acid sequence of SEQ ID NO: 31;

ii. a VH-CDR 1 having an amino acid sequence of SEQ ID NO: 36, a VH-CDR 2 having an amino acid sequence of SEQ ID NO: 38, and a VH-CDR 3 having an amino acid sequence of SEQ ID NO: 40, a VL-CDR 1 having an amino acid sequence of SEQ ID NO: 45, a VL-CDR 2 having an amino acid sequence of SEQ ID NO: 47, and a VL-CDR 3 having an amino acid sequence of SEQ ID NO: 49;

iii. a VH-CDR 1 having an amino acid sequence of SEQ ID NO: 54, a VH-CDR 2 having an amino acid sequence of SEQ ID NO: 56, and a VH-CDR 3 having an amino acid sequence of SEQ ID NO: 58, a VL-CDR 1 having an amino acid sequence of SEQ ID NO: 63, a VL-CDR 2 having an amino acid sequence of SEQ ID NO: 65, and a VL-CDR 3 having an amino acid sequence of SEQ ID NO: 67;

iv. a VH-CDR 1 having an amino acid sequence of SEQ ID NO: 72, a VH-CDR 2 having an amino acid sequence of SEQ ID NO: 74, and a VH-CDR 3 having an amino acid sequence of GDY, a VL-CDR 1 having an amino acid sequence of SEQ ID NO: 81, a VL-CDR 2 having an amino acid sequence of SEQ ID NO: 83, and a VL-CDR 3 having an amino acid sequence of SEQ ID NO: 85;

v. a VH-CDR 1 having an amino acid sequence of SEQ ID NO: 90, a VH-CDR 2 having an amino acid sequence of SEQ ID NO: 92, and a VH-CDR 3 having an amino acid sequence of SEQ ID NO: 94, a VL-CDR 1 having an amino acid sequence of SEQ ID NO: 99, a VL-CDR 2 having an amino acid sequence of SEQ ID NO: 101, and a VL-CDR 3 having an amino acid sequence of SEQ ID NO: 103;

vi. a VH-CDR 1 having an amino acid sequence of SEQ ID NO: 108, a VH-CDR 2 having an amino acid sequence of SEQ ID NO: 110, and a VH-CDR 3 having an amino acid sequence of SEQ ID NO: 112, a VL-CDR 1 having an amino acid sequence of SEQ ID NO: 117, a VL-CDR 2 having an amino acid sequence of SEQ ID NO: 119, and a VL-CDR 3 having an amino acid sequence of SEQ ID NO: 121;

vii. a VH-CDR 1 having an amino acid sequence of SEQ ID NO: 126, a VH-CDR 2 having an amino acid sequence of SEQ ID NO: 128, and a VH-CDR 3 having an amino acid sequence of SEQ ID NO: 130, a VL-CDR 1 having an amino acid sequence of SEQ ID NO: 135, a VL-CDR 2 having an amino acid sequence of SEQ ID NO: 137, and a VL-CDR 3 having an amino acid sequence of SEQ ID NO: 139;

viii. a VH-CDR 1 having an amino acid sequence of SEQ ID NO: 144, a VH-CDR 2 having an amino acid sequence of SEQ ID NO: 146, and a VH-CDR 3 having an amino acid sequence of SEQ ID NO: 148, a VL-CDR 1 having an amino acid sequence of SEQ ID NO: 153, a VL-CDR 2 having an amino acid sequence of SEQ ID NO: 155, and a VL-CDR 3 having an amino acid sequence of SEQ ID NO: 157;

ix. a VH-CDR 1 having an amino acid sequence of SEQ ID NO: 163, a VH-CDR 2 having an amino acid sequence of SEQ ID NO: 165, and a VH-CDR 3 having an amino acid sequence of SEQ ID NO: 167, a VL-CDR 1 having an amino acid sequence of SEQ ID NO: 172, a VL-CDR 2 having an amino acid sequence of SEQ ID NO: 174, and a VL-CDR 3 having an amino acid sequence of SEQ ID NO: 176;

x. a VH-CDR 1 having an amino acid sequence of SEQ ID NO: 181, a VH-CDR 2 having an amino acid sequence of SEQ ID NO: 183, and a VH-CDR 3 having an amino acid sequence of SEQ ID NO: 185, a VL-CDR 1 having an amino acid sequence of SEQ ID NO: 190, a VL-CDR 2 having an amino acid sequence of SEQ ID NO: 192, and a VL-CDR 3 having an amino acid sequence of SEQ ID NO: 194;

xi. a VH-CDR 1 having an amino acid sequence of SEQ ID NO: 198, a VH-CDR 2 having an amino acid sequence of SEQ ID NO: 200, and a VH-CDR 3 having an amino acid sequence of SEQ ID NO: 202, a VL-CDR 1 having an amino acid sequence of SEQ ID NO: 207, a VL-CDR 2 having an amino acid sequence of SEQ ID NO: 209, and a VL-CDR 3 having an amino acid sequence of SEQ ID NO: 211;

xii. a VH-CDR 1 having an amino acid sequence of SEQ ID NO: 216, a VH-CDR 2 having an amino acid sequence of SEQ ID NO: 218, and a VH-CDR 3 having an amino acid sequence of SEQ ID NO: 220, a VL-CDR 1 having an amino acid sequence of SEQ ID NO: 225, a VL-CDR 2 having an amino acid sequence of SEQ ID NO: 227, and a VL-CDR 3 having an amino acid sequence of SEQ ID NO: 229;

xiii. a VH-CDR 1 having an amino acid sequence of SEQ ID NO: 234, a VH-CDR 2 having an amino acid sequence of SEQ ID NO: 236, and a VH-CDR 3 having an amino acid sequence of SEQ ID NO: 238, a VL-CDR 1 having an amino acid sequence of SEQ ID NO: 243, a VL-CDR 2 having an amino acid sequence of SEQ ID NO: 245, and a VL-CDR 3 having an amino acid sequence of SEQ ID NO: 247;

xiv. a VH-CDR 1 having an amino acid sequence of SEQ ID NO: 252, a VH-CDR 2 having an amino acid sequence of SEQ ID NO: 254, and a VH-CDR 3 having an amino acid sequence of SEQ ID NO: 256, a VL-CDR 1 having an amino acid sequence of SEQ ID NO: 261, a VL-CDR 2 having an amino acid sequence of SEQ ID NO: 263, and a VL-CDR 3 having an amino acid sequence of SEQ ID NO: 265;

xv. a VH-CDR 1 having an amino acid sequence of SEQ ID NO: 270, a VH-CDR 2 having an amino acid sequence of SEQ ID NO: 272, and a VH-CDR 3 having an amino acid sequence of SEQ ID NO: 274, a VL-CDR 1 having an amino acid sequence of SEQ ID NO: 279, a VL-CDR 2 having an amino acid sequence of SEQ ID NO: 281, and a VL-CDR 3 having an amino acid sequence of SEQ ID NO: 283;

xvi. a VH-CDR 1 having an amino acid sequence of SEQ ID NO: 288, a VH-CDR 2 having an amino acid sequence of SEQ ID NO: 290, and a VH-CDR 3 having an amino acid sequence of SEQ ID NO: 292, a VL-CDR 1 having an amino acid sequence of SEQ ID NO: 297, a VL-CDR 2 having an amino acid sequence of SEQ ID NO: 299, and a VL-CDR 3 having an amino acid sequence of SEQ ID NO: 301;

xvii. a VH-CDR 1 having an amino acid sequence of SEQ ID NO: 306, a VH-CDR 2 having an amino acid sequence of SEQ ID NO: 308, and a VH-CDR 3 having an amino acid sequence of SEQ ID NO: 310, a VL-CDR 1 having an amino acid sequence of SEQ ID NO: 315, a VL-CDR 2 having an amino acid sequence of SEQ ID NO: 317, and a VL-CDR 3 having an amino acid sequence of SEQ ID NO: 319;

xviii. a VH-CDR 1 having an amino acid sequence of SEQ ID NO: 324, a VH-CDR 2 having an amino acid sequence selected from the group consisting of SEQ ID NOs: 326, 726 and 727, and a VH-CDR 3 having an amino acid sequence of SEQ ID NO: 328, a VL-CDR 1 having an amino acid sequence of SEQ ID NO: 333 or 728, a VL-CDR 2 having an amino acid sequence of SEQ ID NO: 335, and a VL-CDR 3 having an amino acid sequence of SEQ ID NO: 337;

xix. a VH-CDR 1 having an amino acid sequence of SEQ ID NO: 342, a VH-CDR 2 having an amino acid sequence of SEQ ID NO: 344, and a VH-CDR 3 having an amino acid sequence of SEQ ID NO: 346, a VL-CDR 1 having an amino acid sequence of SEQ ID NO: 351, a VL-CDR 2 having an amino acid sequence of SEQ ID NO: 353, and a VL-CDR 3 having an amino acid sequence of SEQ ID NO: 355;

xx. a VH-CDR 1 having an amino acid sequence of SEQ ID NO: 360, a VH-CDR 2 having an amino acid sequence of SEQ ID NO: 362, and a VH-CDR 3 having an amino acid sequence of SEQ ID NO: 364, a VL-CDR 1 having an amino acid sequence of SEQ ID NO: 369, a VL-CDR 2 having an amino acid sequence of SEQ ID NO: 371, and a VL-CDR 3 having an amino acid sequence of SEQ ID NO: 373;

xxi. a VH-CDR 1 having an amino acid sequence of SEQ ID NO: 378, a VH-CDR 2 having an amino acid sequence of SEQ ID NO: 380, and a VH-CDR 3 having an amino acid sequence of SEQ ID NO: 382, a VL-CDR 1 having an amino acid sequence of SEQ ID NO: 387, a VL-CDR 2 having an amino acid sequence of SEQ ID NO: 389, and a VL-CDR 3 having an amino acid sequence of SEQ ID NO: 391;

xxii. a VH-CDR 1 having an amino acid sequence of SEQ ID NO: 396, a VH-CDR 2 having an amino acid sequence of SEQ ID NO: 398, and a VH-CDR 3 having an amino acid sequence of SEQ ID NO: 400, a VL-CDR 1 having an amino acid sequence of SEQ ID NO: 405, a VL-CDR 2 having an amino acid sequence of SEQ ID NO: 407, and a VL-CDR 3 having an amino acid sequence of SEQ ID NO: 409;

xxiii. a VH-CDR 1 having an amino acid sequence of SEQ ID NO: 414, a VH-CDR 2 having an amino acid sequence of SEQ ID NO: 416, and a VH-CDR 3 having an amino acid sequence of SEQ ID NO: 418, a VL-CDR 1 having an amino acid sequence of SEQ ID NO: 423, a VL-CDR 2 having an amino acid sequence of SEQ ID NO: 425, and a VL-CDR 3 having an amino acid sequence of SEQ ID NO: 427;

xxiv. a VH-CDR 1 having an amino acid sequence of SEQ ID NO: 432, a VH-CDR 2 having an amino acid sequence of SEQ ID NO: 434, and a VH-CDR 3 having an amino acid sequence of SEQ ID NO: 436, a VL-CDR 1 having an amino acid sequence of SEQ ID NO:

441, a VL-CDR 2 having an amino acid sequence of SEQ ID NO: 443, and a VL-CDR 3 having an amino acid sequence of SEQ ID NO: 445;

xxv. a VH-CDR 1 having an amino acid sequence of SEQ ID NO: 450, a VH-CDR 2 having an amino acid sequence of SEQ ID NO: 452, and a VH-CDR 3 having an amino acid sequence of SEQ ID NO: 454, a VL-CDR 1 having an amino acid sequence of SEQ ID NO: 459, a VL-CDR 2 having an amino acid sequence of SEQ ID NO: 461, and a VL-CDR 3 having an amino acid sequence of SEQ ID NO: 463;

xxvi. a VH-CDR 1 having an amino acid sequence of SEQ ID NO: 468, a VH-CDR 2 having an amino acid sequence of SEQ ID NO: 470, and a VH-CDR 3 having an amino acid sequence of SEQ ID NO: 472, a VL-CDR 1 having an amino acid sequence of SEQ ID NO: 477, a VL-CDR 2 having an amino acid sequence of SEQ ID NO: 479, and a VL-CDR 3 having an amino acid sequence of SEQ ID NO: 481;

xxvii. a VH-CDR 1 having an amino acid sequence of SEQ ID NO: 486, a VH-CDR 2 having an amino acid sequence of SEQ ID NO: 488, and a VH-CDR 3 having an amino acid sequence of SEQ ID NO: 490, a VL-CDR 1 having an amino acid sequence of SEQ ID NO: 495, a VL-CDR 2 having an amino acid sequence of SEQ ID NO: 497, and a VL-CDR 3 having an amino acid sequence of SEQ ID NO: 499;

xxviii. a VH-CDR 1 having an amino acid sequence of SEQ ID NO: 504, a VH-CDR 2 having an amino acid sequence of SEQ ID NO: 506, and a VH-CDR 3 having an amino acid sequence of SEQ ID NO: 508, a VL-CDR 1 having an amino acid sequence of SEQ ID NO: 513, a VL-CDR 2 having an amino acid sequence of SEQ ID NO: 515, and a VL-CDR 3 having an amino acid sequence of SEQ ID NO: 517;

xxix. a VH-CDR 1 having an amino acid sequence of SEQ ID NO: 522, a VH-CDR 2 having an amino acid sequence of SEQ ID NO: 524, and a VH-CDR 3 having an amino acid sequence of SEQ ID NO: 526, a VL-CDR 1 having an amino acid sequence of SEQ ID NO: 531, a VL-CDR 2 having an amino acid sequence of SEQ ID NO: 533, and a VL-CDR 3 having an amino acid sequence of SEQ ID NO: 535;

xxx. a VH-CDR 1 having an amino acid sequence of SEQ ID NO: 540, a VH-CDR 2 having an amino acid sequence of SEQ ID NO: 542, and a VH-CDR 3 having an amino acid sequence of SEQ ID NO: 544, a VL-CDR 1 having an amino acid sequence of SEQ ID NO: 549, a VL-CDR 2 having an amino acid sequence of SEQ ID NO: 551, and a VL-CDR 3 having an amino acid sequence of SEQ ID NO: 553;

xxxi. a VH-CDR 1 having an amino acid sequence of SEQ ID NO: 558, a VH-CDR 2 having an amino acid sequence of SEQ ID NO: 560, and a VH-CDR 3 having an amino acid sequence of SEQ ID NO: 562, a VL-CDR 1 having an amino acid sequence of SEQ ID NO: 567, a VL-CDR 2 having an amino acid sequence of SEQ ID NO: 569, and a VL-CDR 3 having an amino acid sequence of SEQ ID NO: 571;

xxxii. a VH-CDR 1 having an amino acid sequence of SEQ ID NO: 576, a VH-CDR 2 having an amino acid sequence of SEQ ID NO: 578, and a VH-CDR 3 having an amino acid sequence of SEQ ID NO: 580, a VL-CDR 1 having an amino acid sequence of SEQ ID NO: 585, a VL-CDR 2 having an amino acid sequence of SEQ ID NO: 587, and a VL-CDR 3 having an amino acid sequence of SEQ ID NO: 589;

xxxiii. a VH-CDR 1 having an amino acid sequence of SEQ ID NO: 594, a VH-CDR 2 having an amino acid sequence of SEQ ID NO: 596, and a VH-CDR 3 having an amino acid sequence of SEQ ID NO: 598, a VL-CDR 1 having an amino acid sequence of SEQ ID NO: 603, a VL-CDR 2 having an amino acid sequence of SEQ ID NO: 605, and a VL-CDR 3 having an amino acid sequence of SEQ ID NO: 607;

xxxiv. a VH-CDR 1 having an amino acid sequence of SEQ ID NO: 612, a VH-CDR 2 having an amino acid sequence of SEQ ID NO: 614, and a VH-CDR 3 having an amino acid sequence of SEQ ID NO: 616, a VL-CDR 1 having an amino acid sequence of SEQ ID NO: 621, a VL-CDR 2 having an amino acid sequence of SEQ ID NO: 623, and a VL-CDR 3 having an amino acid sequence of SEQ ID NO: 625;

xxxv. a VH-CDR 1 having an amino acid sequence of SEQ ID NO: 630, a VH-CDR 2 having an amino acid sequence of SEQ ID NO: 632, and a VH-CDR 3 having an amino acid sequence of SEQ ID NO: 634, a VL-CDR 1 having an amino acid sequence of SEQ ID NO: 639, a VL-CDR 2 having an amino acid sequence of SEQ ID NO: 641, and a VL-CDR 3 having an amino acid sequence of SEQ ID NO: 643;

xxxvi. a VH-CDR 1 having an amino acid sequence of SEQ ID NO: 648, a VH-CDR 2 having an amino acid sequence of SEQ ID NO: 650, and a VH-CDR 3 having an amino acid sequence of SEQ ID NO: 652, a VL-CDR 1 having an amino acid sequence of SEQ ID NO: 657, a VL-CDR 2 having an amino acid sequence of SEQ ID NO: 659, and a VL-CDR 3 having an amino acid sequence of SEQ ID NO: 661;

xxxvii. a VH-CDR 1 having an amino acid sequence of SEQ ID NO: 666, a VH-CDR 2 having an amino acid sequence of SEQ ID NO: 668, and a VH-CDR 3 having an amino acid sequence of SEQ ID NO: 670, a VL-CDR 1 having an amino acid sequence of SEQ ID NO: 675, a VL-CDR 2 having an amino acid sequence of SEQ ID NO: 677, and a VL-CDR 3 having an amino acid sequence of SEQ ID NO: 679; or xxxviii. a VH-CDR 1 having an amino acid sequence of SEQ ID NO: 684, a VH-CDR 2 having an amino acid sequence of SEQ ID NO: 686, and a VH-CDR 3 having an amino acid sequence of SEQ ID NO: 688, a VL-CDR 1 having an amino acid sequence of SEQ ID NO: 693, a VL-CDR 2 having an amino acid sequence of SEQ ID NO: 695, and a VL-CDR 3 having an amino acid sequence of SEQ ID NO: 697.

In some embodiments, the antibody or antigen-binding fragment provided herein comprises: a pair of heavy chain variable region and light chain variable region sequences selected from the group consisting of: SEQ ID NOs: 25/34, SEQ ID NOs: 43/52, SEQ ID NOs: 61/70, SEQ ID NOs: 79/88, SEQ ID NOs: 97/106, SEQ ID NOs: 115/124, SEQ ID NOs: 133/142, SEQ ID NOs: 151/160, SEQ ID NOs: 205/214, SEQ ID NOs: 223/232, SEQ ID NOs: 241/250, SEQ ID NOs: 259/268, SEQ ID NOs: 277/286, SEQ ID NOs: 295/304, SEQ ID NOs: 313/322, SEQ ID NOs: 331/340, SEQ ID NOs: 349/358, SEQ ID NOs: 367/376, SEQ ID NOs: 385/394, SEQ ID NOs: 403/412, SEQ ID NOs: 421/430, SEQ ID NOs: 439/448, SEQ ID NOs: 457/466, SEQ ID NOs: 475/484, SEQ ID NOs: 493/502, SEQ ID NOs: 511/520, SEQ ID NOs: 529/538, SEQ ID NOs: 547/556, SEQ ID NOs: 565/574, SEQ ID NOs: 583/592, SEQ ID NOs: 601/610, SEQ ID NOs: 619/628, SEQ ID NOs: 637/646, SEQ ID NOs: 655/664, SEQ ID NOs: 673/682, SEQ ID NOs: 691/161, SEQ ID NOs:

170/179, SEQ ID NOs: 188/76, or a pair of homologous sequences thereof having at least 80%, 85%, 90%, 95%, 97%, 98%, or 99% sequence identity yet retains specific binding affinity to CLDN 18.

In some embodiments, the antibody or antigen-binding fragment provided herein comprises:

a) a heavy chain variable region comprising an amino acid sequence selected from the group consisting of SEQ ID NO: 704, SEQ ID NO: 705, SEQ ID NO: 706 and SEQ ID NO: 707, and a light chain variable region comprising an amino acid sequence selected from the group consisting of SEQ ID NO: 708, SEQ ID NO: 709 and SEQ ID NO: 710; or b) a heavy chain variable region comprising an amino acid sequence selected from the group consisting of SEQ ID NO: 711, SEQ ID NO: 712, SEQ ID NO: 713 and SEQ ID NO: 714, and a light chain variable region comprising an amino acid sequence selected from the group consisting of SEQ ID NO: 715, SEQ ID NO: 716 and SEQ ID NO: 717; or c) a heavy chain variable region comprising an amino acid sequence selected from the group consisting of SEQ ID NO: 718, SEQ ID NO: 719, SEQ ID NO: 720, SEQ ID NO: 721 and SEQ ID NO: 722, and a light chain variable region comprising an amino acid sequence selected from the group consisting of SEQ ID NO: 723, SEQ ID NO: 724 and SEQ ID NO:

In some embodiments, the antibody or antigen-binding fragment provided herein further comprises one or more amino acid residue substitutions or modifications that yet retains specific binding affinity to CLDN 18. In some embodiments, at least one of the substitutions or modifications is in one or more of the CDR sequences, and/or in one or more of the non-CDR sequences of the heavy chain variable region or light chain variable region.

In some embodiments, the antibody or antigen-binding fragment provided herein further comprises one or more non-natural amino acid (NNAA) substitution.

In some embodiments, the antibody or antigen-binding fragment provided herein is a monoclonal antibody or antigen-binding fragment thereof, a polyclonal antibody or antigen-binding fragment thereof, a bispecific antibody or antigen-binding fragment thereof, a chimeric antibody or antigen-binding fragment thereof, a humanized antibody or antigen-binding fragment thereof, a recombinant antibody or antigen-binding fragment thereof, a human antibody or antigen-binding fragment thereof, a labeled antibody or antigen-binding fragment thereof, a bivalent antibody or antigen-binding fragment thereof, or an anti-idiotypic antibody or antigen-binding fragment thereof.

In some embodiments, the antibody or antigen-binding fragment provided herein is a camelized single domain antibody, a diabody, a scFv, an scFv dimer, a dsFv, a $(dsFv)_2$, a dsFv-dsFv', an Fv fragment, a Fab, a Fab', a $F(ab')_2$, a ds-diabody, a nanobody, a domain antibody, or a bivalent domain antibody.

In some embodiments, the antibody or antigen-binding fragment provided herein further comprises an immunoglobulin constant region. In some embodiments, the immunoglobulin constant region is a λ light chain, κ light chain, γ1 heavy chain, γ2 heavy chain, γ3 heavy chain, or γ4 heavy chain constant region. In some embodiments, the antibody or antigen-binding fragment provided herein is human IgG1 isotype.

In some embodiments, immunoglobulin constant region comprises an Fc region having an amino acid sequence selected from the group consisting of SEQ ID NOs. 700-703.

In some embodiments, the antibody or antigen-binding fragment provided herein specifically binds to CLDN 18.2 protein. In some embodiments, the antibody or antigen-binding fragment provided herein binds to both CLDN 18.1 protein and CLDN 18.2 protein.

In some embodiments, the binding affinity of the antibody or antigen-binding fragment provided herein to a cell expressing CLDN 18.2 is higher than or comparable with a reference antibody.

In some embodiments, the max MFI of the antibody or antigen-binding fragment provided herein to a cell expressing CLDN 18.2 is higher than the reference antibody In some embodiments, the reference antibody is IMAB362.

In some embodiments, the surface expression of CLDN 18.2 on the cell is low.

In some embodiments, the binding affinity is determined by FACS or ELISA.

In some embodiments, the antibody or antigen-binding fragment provided herein binds to the CLDN 18.2 protein with an $EC_{50}$ of less than about 10 nM, less than about 8 nM, less than about 6 nM, less than about 4 nM, or less than about 2 nM.

In some embodiments, the antibody or antigen-binding fragment provided herein is linked to one or more conjugate moieties. In some embodiments, the conjugate moiety comprises an active agent, a radioactive isotope, a detectable label, a pharmacokinetic modifying moiety, or a purifying moiety. In some embodiments, the conjugate moiety is covalently attached either directly or via a linker.

In another aspect, the present disclosure also includes the antibody or antigen-binding fragment recognizing the same antigenic determinant site as that of the antibody or antigen-binding fragment provided herein as examples.

In another aspect, the present disclosure provides a chimeric antigen receptor, comprising the antibody or antigen-binding fragment provided herein, a transmembrane region and an intracellular signal region.

In some embodiments, the intracellular signal region is selected from the group consisting of: an intracellular signal regions sequence of CD3, FcεRI, CD27, CD28, CD137, CD134, MyD88, CD40, CD278, TLRs, or a combination thereof.

In some embodiments, the transmembrane region comprises a transmembrane region of CD3, CD4, CD8 or CD28.

In another aspect, the present disclosure provides an isolated polynucleotide encoding the antibody or antigen-binding fragment or the chimeric antigen receptor provided herein.

In some embodiments, the isolated polynucleotide provided herein comprises a nucleotide sequence selected from a group consisting of: SEQ ID NOs: 24, 42, 60, 78, 96, 114, 132, 150, 204, 222, 240, 258, 276, 294, 312, 330, 348, 366, 384, 402, 420, 438, 456, 474, 492, 510, 528, 546, 564, 582, 600, 618, 636, 654, 672, 690, 169, 187, or a homologous sequence thereof having at least 80% sequence identity.

In some embodiments, the isolated polynucleotide provided herein further comprises a nucleotide sequence selected from a group consisting of: SEQ ID NOs: 33, 51, 69, 87, 105, 123, 141, 159, 213, 231, 249, 267, 285, 303, 321, 339, 357, 375, 393, 411, 429, 447, 465, 483, 501, 519, 537, 555, 573, 591, 609, 627, 645, 663, 681, 699, 178, 196, or a homologous sequence thereof having at least 80% sequence identity.

In another aspect, the present disclosure provides a vector comprising the polynucleotide provided herein.

In another aspect, the present disclosure provides a host expression system comprising the vector provided herein or having the polynucleotide provided herein integrated into genome thereof. In some embodiments, the host expression system provided herein is a microorganism, a yeast, or a mammalian cell, wherein the microorganism is selected from the group consisting of *E. coli* and *B. subtilis*, wherein the yeast is *Saccharomyces*, and wherein the mammalian cell is selected from the group consisting of COS, CHO-S, CHO-K1, HEK-293, and 3T3 cells.

In another aspect, the present disclosure provides a virus comprising the vector provided herein.

In another aspect, the present disclosure provides a method of expressing the antibody or antigen-binding fragment provided herein or the chimeric antigen receptor provided herein, comprising culturing the host expression system provided herein under conditions in which the antibody or antigen-binding fragment or the chimeric antigen receptor is expressed.

In another aspect, the present disclosure provides an antibody-drug conjugate comprising the antibody or antigen-binding fragment provided herein, linked to one or more therapeutic agents directly or via a linker.

In another aspect, the present disclosure provides a modified immune cell targeting cells expressing CLDN 18.2, comprising the antibody or antigen-binding fragment thereof provided herein or the chimeric antigen receptor provided herein, the polynucleotide provided herein, the vector provided herein or the virus provided herein.

In some embodiments, the cells expressing CLDN 18.2 are selected from the group consisting of: gastric cancer cells, pancreatic cancer cells, esophageal cancer cells, lung cancer cells, gallbladder cancer cells, colorectal cancer, and liver cancer cells.

In some embodiments, the immune cell is T lymphocyte, NK cell, monocyte, macrophage or NKT lymphocyte.

In some embodiments, the modified immune cell provided herein, further has one or more features selected from the group consisting of:

i. carrying an encoding sequence for an exogenous cytokine,
ii. expressing another chimeric antigen receptor, or a combination thereof,
iii. expressing a chemokine receptor
iv. expressing an siRNA that reduces expression of an immune checkpoint inhibitor or a protein that blocks the immune checkpoint inhibitor,
v. having endogenous immune checkpoint inhibitor knocked out
vi. expressing secretable antibody sc-fv
vii. expressing a co-stimulatory protein
viii. expressing a safety switch.

In some embodiments, the immune checkpoint inhibitor is selected from the group consisting of PD-1, CTLA-4, LAG-3, TIM-3.

In another aspect, the present disclosure provides a pharmaceutical composition comprising the antibody or antigen-binding fragment provided herein, the chimeric antigen receptor provided herein, the polynucleotide provided herein, the vector provided herein, the virus provided herein, or the modified immune cell provided herein, and one or more pharmaceutically acceptable carriers.

In some embodiments, the one or more pharmaceutical acceptable carriers are selected from the group consisting of pharmaceutically acceptable liquid, gel, solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, and non-toxic auxiliary substances.

In some embodiments, the pharmaceutical composition provided herein further comprises one or more therapeutic agents.

In some embodiments, the one or more therapeutic agents are selected from the group consisting of amrubicin, apatinib mesylate, atrasentan batabulin, calcitriol, capecitabine, cilengitide, dasatinib, decatanib, edotecarin, enzastaurin, erlotinib, everolimus, gimatecan, gossypol ipilimumab, lonafarnib, lucanthone, neuradiab, nolatrexed, oblimersen, olaparib, ofatumumab, oregovomab, panitumumab, pazopanibrubitecan, regorafenib talampanel, tegafur, temsirolimus, tesmilifene, tetrandrine, ticilimumab, trametinib, trabectedin, vandetanib, vitespan, zanolimumab, zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, epirubicin, oxaliplatin, an anti-PD1 antibody, an anti-PDL1 antibody, an anti-HER2 antibody, an anti-HER2 ADC, 5-fluorouracil and strontium 89.

In another aspect, the present disclosure provides a kit comprising: a container, and the pharmaceutical composition provided herein; or a container, and the antibody or antigen-binding fragment provided herein, the chimeric antigen receptor provided herein, the polynucleotide provided herein, the vector provided herein, the virus provided herein, or the modified immune cell provided herein.

In another aspect, the present disclosure provides a method for treating or preventing a CLDN-related condition in a subject, comprising administering a therapeutically effective amount of the antibody or antigen-binding fragment provided herein, the chimeric antigen receptor provided herein, the polynucleotide provided herein, the vector provided herein, the virus provided herein, or the modified immune cell provided herein to the subject.

In some embodiments, the CLDN-related condition is cancerous condition.

In some embodiments, the cancerous condition is selected from the group consisting of lung cancer (e.g., small cell lung cancer, non-small cell lung cancer (NSCLC), adenocarcinoma of the lung, or squamous cell carcinoma of the lung), gastric or stomach cancer (e.g., gastrointestinal cancer), pancreatic cancer, esophageal cancer, liver cancer (e.g., hepatocellular carcinoma/hepatoma), squamous cell cancer, cancer of the peritoneum, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, gallbladder cancer, idiopathic myelofibrosis, and pediatric cancers such as pediatric sarcomas (e.g., neuroblastoma, rhabdomyosarcoma, and osteosarcoma).

In some embodiments, the administration is through a parenteral route comprising subcutaneous, intraperitoneal, intravenous, intramuscular, or intradermal injection; or a non-parenteral route comprising transdermal, oral, intranasal, intraocular, sublingual, rectal, or topical.

In some embodiments, the method provided herein further includes administering to the subject in need thereof an additional therapeutic agent.

In some embodiments, the additional therapeutic agent is selected from the group consisting of: an active agent, an imaging agent, a cytotoxic agent, and angiogenesis inhibitor, a kinase inhibitor, a co-stimulation molecule agonist, a co-inhibition molecule blocker, an adhesion molecule blocker, an anti-cytokine antibody or functional fragment thereof, a detectable label or reporter, an antimicrobial, a gene editing agent, a beta agonist, an viral RNA inhibitor, a polymerase inhibitor, an interferon, and a microRNA.

In some embodiments, the additional therapeutic agent is administered to the subject in need before administration of the composition provided herein, after administration of the composition provided herein, and/or at the same time as the composition provided herein.

In another aspect, the present disclosure provides a method for diagnosing a CLDN-related condition, comprising detecting the CLDN by using the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein.

In some embodiments, the CLDN is CLDN 18.2 or CLDN 18.1.

In some embodiments, condition is selected from the group consisting of: gastric cancer, pancreatic cancer, esophageal cancer, lung cancer, gallbladder cancer, colorectal cancer and liver cancer.

In another aspect, the present disclosure provides a method for inducing the death of a cell expressing CLDN 18.2, comprising contacting the cell expressing CLDN 18.2 with the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein.

In some embodiments, the cell is contacted with the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein, in vitro or in vivo.

In some embodiments, the cell is a cancer cell. In some embodiments, the cell is a solid tumor cell.

In another aspect, the present disclosure provides use of the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein in the manufacture of a medicament for treating CLDN-related condition in a subject in need thereof.

In another aspect, the present disclosure provides use of the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein in the manufacture of a diagnostic reagent for detecting CLDN-related condition.

In another aspect, the present disclosure provides the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein for use in a method for treating CLDN-related condition in a subject in need thereof.

In another aspect, the present disclosure provides the antibody or antigen-binding fragment provided herein, the chimeric antigen receptor provided herein, the polynucleotide provided herein, the vector provided herein, the virus provided herein, the modified immune cell provided herein, the antibody-drug conjugate provided herein, the pharmaceutical composition provided herein, or the kit provided herein for use in a method for detecting CLDN-related condition.

BRIEF DESCRIPTION OF THE FIGURES

FIGS. 7A and 7B show that some of the humanized antibodies showed equal of slightly decreased affinity against GAXC031 Cells.

FIGS. 9A-9G show binding kinetics of the six humanized antibodies with VLP-Claudin 18.2.

FIGS. 10A-10F show ADC cytotoxicity activity of the humanized anti-Claudin 18.2 antibodies against CHOK1 cells or GAXC031 cells overexpressing human Claudin 18.2.

DETAILED DESCRIPTION

Figure 1A:
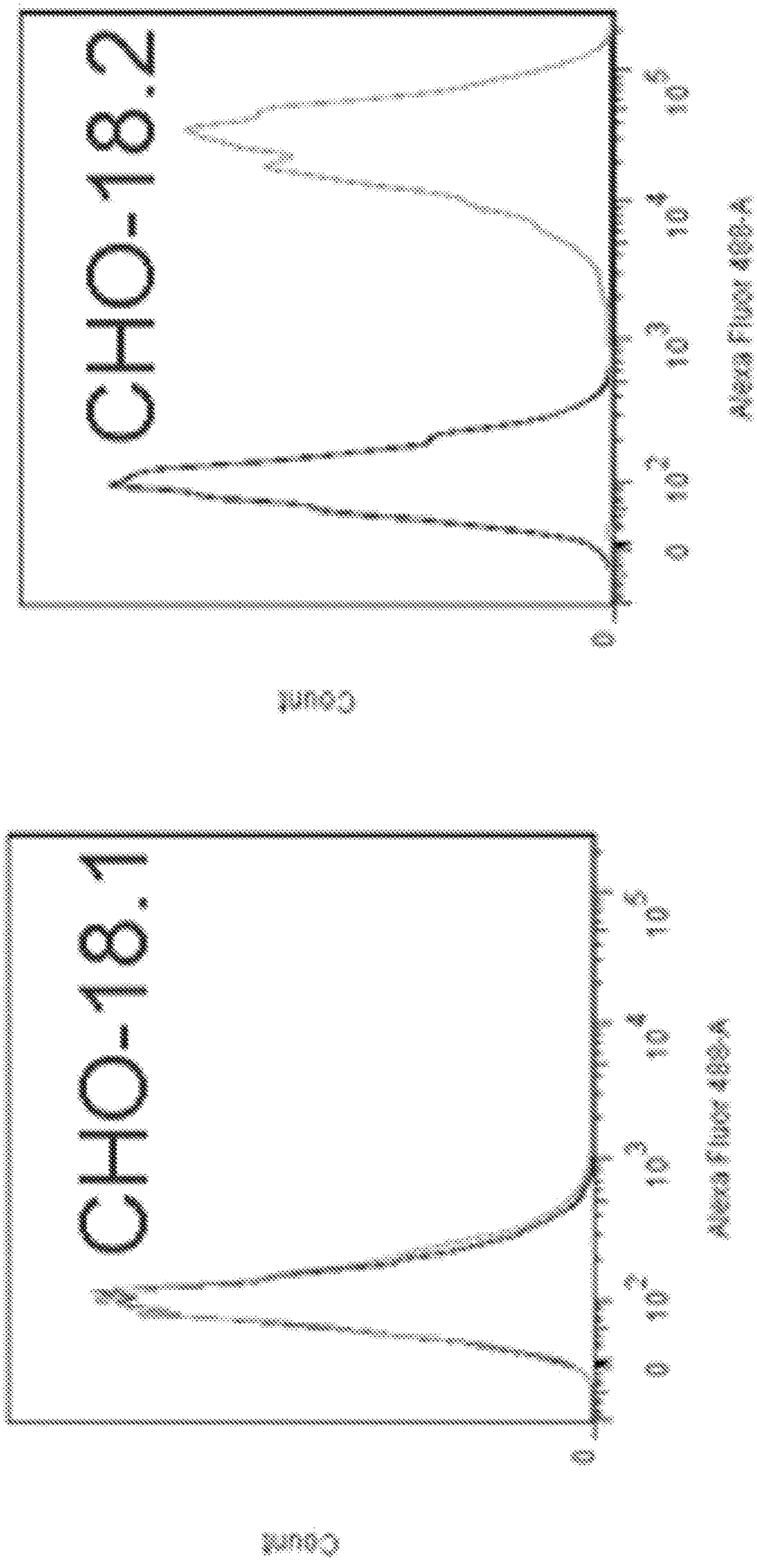
FIGS. 1A and 1B show FACs analysis suggesting that Ab10 binds with human, monkey and mouse Claudine18.2, but does not bind human Claudine18.1.
Figure 1B:
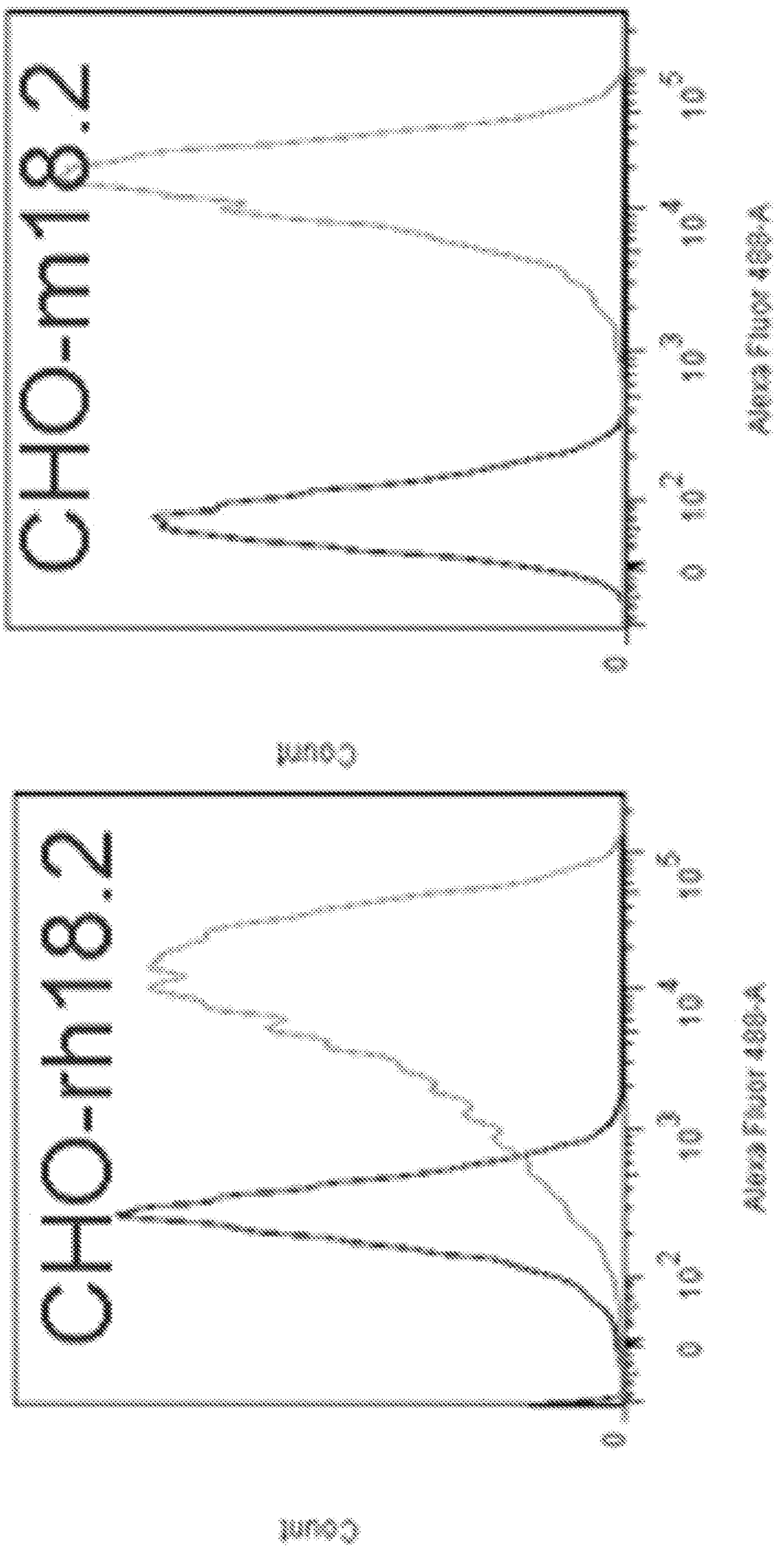

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein refers to any immunoglobulin, monoclonal antibody, polyclonal antibody, diabodies, nanobodies, linear antibodies, single chain antibodies, multivalent antibody, bivalent antibody, monovalent antibody, multispecific antibody, bispecific antibody, the antigen-binding fragment thereof that binds to a specific antigen, mutants thereof, or any other modified configuration of the immunoglobulin molecule that comprises an antigen binding site of the required specificity, including glycosylation variants of antibodies, amino acid sequence variants of antibodies, and covalently modified antibodies. A "monoclonal antibody" refers to a homogenous antibody population and a "polyclonal antibody" refers to a heterogeneous antibody population. These two terms do not limit the source of an antibody or the manner in which it is made.

A typical complete antibody comprises two heavy chains and two light chains. Each heavy chain consists of a variable region and a first, second, and third constant region, while each light chain consists of a variable region and a constant region. Mammalian heavy chains are classified as α, δ, ε, γ, or μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three hypervariable loops called the complementarity determining regions (CDRs). In particular, a light chain variable (VL) region in the light chain comprises VL-CDR1, VL-CDR2 and VL-CDR3, and a heavy chain variable (VH) region in the heavy chain comprises VH-CDR1, VH-CDR2 and VH-CDR3. The three CDRs of the light or heavy chain are interposed between flanking stretches known as framework regions (FRs), which are more highly conserved than the CDRs and form a scaffold to support the hypervariable loops. The boundaries of FRs and CDRs may be defined or identified using methodology known in the art, for example, by the Kabat definition, the Chothia definition, the AbM definition, IMGT (see, e.g., Kabat, E. A., et al. (1991) *Sequences of Proteins of Immunological Interest, Fifth Edition*, U.S. Department of Health and Human Services, NIH Publication No. 91-3242; Chothia, C. et al., J Mol Biol. December 5; 186(3):651-63 (1985); Chothia et al., (1989) Nature 342:877; Chothia, C. et al. (1987) J. Mol. Biol. 196:901-917, Al-lazikani et al (1997) J. Molec. Biol. 273: 927-948; Almagro, J. Mol. Recognit. 17:132-143 (2004); Marie-Paule Lefranc et al, Developmental and Comparative Immunology, 27: 55-77 (2003); Marie-Paule Lefranc et al, Immunome Research, 1(3), (2005); and Marie-Paule Lefranc, Molecular Biology of B cells (second edition), chapter 26, 481-514, (2015), hgmp.mrc.ac.uk and bioinf.org.uk/abs). The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "bivalent" as used herein refers to an antibody or an antigen-binding fragment having two antigen-binding sites. The two antigen binding sites may bind to the same antigen, or they may each bind to a different antigen, in which case the antibody or antigen-binding fragment is characterized as "bispecific".

The term "monovalent" refers to an antibody or an antigen-binding fragment having only one single antigen-binding site; and the term "multivalent" refers to an antibody or an antigen-binding fragment having multiple (i.e., more than two) antigen-binding sites.

The term "antigen-binding fragment" as used herein refers to an antibody fragment formed from a portion of an intact antibody comprising one or more CDRs, or any other antibody fragment that can bind to an antigen but does not comprise an intact native antibody structure. Examples of antigen-binding fragment include, without limitation, a camelized single domain antibody, a diabody, a single-chain antibody molecule (scFv), an scFv dimer (bivalent diabody), a disulfide stabilized Fv fragment (dsFv), a $(dsFv)_2$, a bispecific dsFv (dsFv-dsFv'), an Fv fragment, a Fab, a Fab', a $F(ab')_2$, a nanobody, a domain antibody, a bivalent domain antibody, a disulfide stabilized diabody (ds diabody), a bispecific ds diabody, a multispecific antibody formed from a portion of an antibody comprising one or more CDRs, or any other antibody fragment that binds to an antigen but does not comprise a complete antibody structure. An antigen-binding fragment is capable of binding to the same antigen to which the parent antibody or a parent antibody fragment (e.g., a parent scFv) binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"$F(ab')_2$" refers to a dimer of Fab'.

"Fv" with regard to an antibody refers to the smallest fragment of the antibody to bear the complete antigen binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "$(dsFv)_2$" or "(dsFv-dsFv')" comprises three peptide chains: two $V_H$ moieties linked by a peptide linker (e.g., a long flexible linker) and bound to two $V_L$ moieties, respectively, via disulfide bridges. In some embodiments, dsFv-dsFv' is bispecific in which each disulfide paired heavy and light chain has a different antigen specificity.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879 (1988)).

"Camelized single domain antibody", interchangeably used with "heavy chain antibody" or "HCAb", refers to an antibody that contains two $V_H$ domains and no light chains (Riechmann L. and Muyldermans S., J Immunol Methods. December 10; 231(1-2):25-38 (1999); Muyldermans S., J Biotechnol. June; 74(4):277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363 (6428):446-8 (1993); Nguyen V K. et al. "Heavy-chain antibodies in Camelidae; a case of evolutionary innovation," Immunogenetics. April; 54(1):39-47 (2002); Nguyen V K. et a/Immunology. May; 109(1):93-101 (2003). The variable domain of a heavy chain antibody represents the smallest known antigen-binding unit generated by adaptive immune responses (Koch-Nolte F. et al., FASEB J. November; 21(13):3490-8. Epub 2007 Jun. 15 (2007).

A "nanobody" refers to an antibody fragment that consists of one VH domain from a heavy chain antibody of a conventional IgG and two heavy chain constant domains, e.g. CH2 and CH3.

A "diabody" refers to a small antibody fragment with two antigen-binding sites, wherein the fragment comprises a $V_H$ domain connected to a $V_L$ domain in the same polypeptide chain ($V_H$-$V_L$ or $V_H$-$V_L$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "bispecific ds diabody" is a diabody targeting two different antigens (or epitopes). In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or "dsFv-dsFv" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In specific embodiments, a "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal such as mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions are derived from human.

Unless otherwise specified, the term "Claudin" or "CLDN" as used herein encompasses any or all of tight junction membrane proteins that are expressed in epithelia and endothelia and form paracellular barriers and pores that determine tight junction permeability, and is intended to encompass any form of CLDNs, for example, 1) native unprocessed CLDN molecules, "full-length" CLDN chains or naturally occurring variants of CLDNs, including, for example, allelic variants; 2) any form of CLDN that results from processing in the cell, e.g. different splicing forms, for example, splice variant 1 of Claudin 18 (CLDN18.1), splice variant 2 of Claudin 18 (CLDN18.2), and the like; or 3) a fragment (e.g., a truncated form, an extracellular/transmembrane domain) or a modified form (e.g. a mutated form, a glycosylated/PEGylated, a His-tag/immunofluorescence fused form) of CLDN subunit generated through recombinant methods. "CLDN" as used herein can be derived from any vertebrate source, including mammals such as primates (e.g. humans, monkeys) and rodents (e.g., mice and rats).

The term "Claudin 18" or "CLDN 18" refers to one family member of CLDN, with a molecular weight of approximately 27.9 KD, which comprises two splicing forms as described above, i.e., CLDN18.1 (identified by NCBI Reference Sequence: NP_057453.1, and/or accession: NM 016369.4 for *Homo sapiens* CLDN18.1) and CLDN18.2 (identified by NCBI Reference Sequence: NP_001002026.1, and/or accession: NM 001002026.3 for *Homo sapiens* CLDN18.2).

The term "anti-CLDN18 antibodies" refers to an antibody that is capable of specifically binding to CLDN18. In some embodiments, the anti-CLDN18 antibodies provided herein are capable of binding to both CLDN18.2 and CLDN18.1. In some embodiments, the anti-CLDN18 antibodies provided herein are capable of specifically binding to CLDN18.2, but does not bind to CLDN18.1 or bind less well to CLDN18.1 (e.g., the binding affinity to CLDN18.1 is at least 10-fold lower than that to CLDN18.2, or at least 50-fold lower, or at least 100-fold lower, or at least 200-fold lower). In some embodiments, the anti-CLDN18 antibodies provided herein do not have detectable binding affinity to CLDN18.1. In some embodiments, the binding affinity is determined by FACs. In some embodiments, the binding affinity is determined by MFI detected by FACs.

The term "specific binding" or "specifically binds" as used herein refers to a non-random binding reaction between two molecules, such as for example between an antibody and an antigen. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (CLDN18.2) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method). Alternatively, or in addition, the anti-CLDN18 antibodies described herein may specifically binds human, mouse, or Rhesus monkey CLDN18.2 or a fragment thereof as relative to human CLDN18.1 (e.g., having a binding affinity at least 10-fold higher to one antigen than the other as determined in the same assay under the same assay conditions).

As used herein, a "conservative amino acid substitution" refers to an amino acid substitution that does not alter the relative charge or size characteristics of the protein in which the amino acid substitution is made. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated polynucleotide sequence" refers to the sequence of an isolated polynucleotide molecule. In certain embodiments, an "isolated antibody" refers to the antibody having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% as determined by electrophoretic methods (such as SDS-PAGE, isoelectric focusing, capillary electrophoresis), or chromatographic methods (such as ion exchange chromatography or reverse phase HPLC).

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and complement component 1q (C1q) on the C1 complex; antibody-dependent cell-mediated cytotoxicity (ADCC) induced by binding of Fc region of an antibody to Fc receptor on an effector cell; and phagocytosis.

"Antibody-dependent cell-mediated cytotoxicity" and "ADCC" refer to a cell-mediated reaction in which effector cells that express Fc receptors (FcRs) recognize bound antibody or antigen-binding fragment on a target cell and subsequently cause lysis of the target cell. "ADCC activity" or "ADCC effect" refers to the ability of the antibody or antigen-binding fragment which is bound on the target cell to elicit an ADCC reaction as described above.

"Target cells" are cells to which antibodies comprising an Fc region specifically bind, generally via the protein part that is C-terminal to the Fc region. "Effector cells" are leukocytes which express one or more Fc receptors and perform effector functions. Examples of human leukocytes which mediate ADCC include peripheral blood mononuclear cells (PBMCs), natural killer (NK) cells, monocytes, cytotoxic T cells and neutrophils; with PBMCs and NK cells being preferred. The effector cells may be isolated from a native source thereof, e.g., from blood or PBMCs as is known in the art.

As used herein a "vector" refers to a polynucleotide molecule which enables replicating/cloning of a desired nucleic acid fragment contained therein, or enables expressing of a protein encoded by such desired nucleic acid fragment as introduced into an appropriate cell host. Vectors include both cloning vectors and expression vectors. The term "expression vector" as used herein refers to a vehicle into which a polynucleotide encoding a protein may be operably inserted so as to bring about the expression of that protein. An expression vector may contain a variety of elements for controlling expression, including promoter sequences, transcription initiation sequences, enhancer sequences, selectable elements, and reporter genes. In addition, the vector may contain an origin of replication.

The phrase "host cell" as used herein refers to a cell into which an exogenous polynucleotide and/or a vector has been introduced.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

A "CLDN-related" condition as used herein refers to any disease or condition that is susceptible to treatment with a CLDN modulator, or is associated with expression or overexpression of CLDN. In some embodiments, the CLDN-related condition is a CLDN18.2-relating condition. In certain embodiments, the CLDN18.2-relating condition is cancerous condition. In certain embodiments, the cancerous condition is positive for CLDN18.2 expression or elevated expression.

"Cancerous condition" as used herein refers to any medical condition characterized by malignant cell growth or neoplasm, abnormal proliferation, infiltration or metastasis, and includes both solid tumors and non-solid cancers. As used herein "solid tumor" refers to a solid mass of neoplastic and/or malignant cells. "Non-solid cancer" refers to hematologic malignancies such as leukemia, lymphoma, myeloma and other hematologic malignancies. Examples of cancer or tumor include hematological malignancies (for example, lymphoma, Hodgkin's lymphoma, non-Hodgkin's lymphoma and B-cell lymphoma), oral carcinomas (for example of the lip, tongue or pharynx), tumors in digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from the group consisting of lung cancer (e.g., small cell lung cancer, non-small cell lung cancer (NSCLC), adenocarcinoma of the lung, or squamous cell carcinoma of the lung), gastric or stomach cancer (e.g., gastrointestinal cancer), pancreatic cancer, esophageal cancer, liver cancer (e.g., hepatocellular carcinoma/hepatoma), squamous cell cancer, cancer of the peritoneum, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, gallbladder cancer, idiopathic myelofibrosis, and pediatric cancers such as pediatric sarcomas (e.g., neuroblastoma, rhabdomyosarcoma, and osteosarcoma).

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

As used herein, "an effective amount" refers to the amount of each active agent required to confer therapeutic effect on the subject, either alone or in combination with one or more other active agents. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation.

Anti-CLDN18 Antibodies

The present disclosure provides anti-CLDN18 antibodies, each comprising one or more (e.g. 1, 2, 3, 4, 5, or 6) CDR sequences of each of the exemplary antibodies Ab01-Ab38 as shown in Table 1. The term "Ab01-Ab38" as used herein refers to 38 mouse monoclonal antibodies having a pair of heavy chain variable region and light chain variable region sequences as shown in Table 1. In a particular aspect, the present disclosure provides anti-CLDN18 antibodies that specifically bind to both CLDN18.2 protein and CLDN18.1 protein, such as antibodies, each comprising one or more (e.g. 1, 2, 3, 4, 5, or 6) CDR sequences of each of the exemplary antibodies Ab01, Ab04 and Ab36-Ab38 as shown in Table 1. In another particular aspect, the present disclosure provides anti-CLDN18 antibodies that showing higher binding affinity to CLDN18.2 protein than CLDN18.1 protein, such as antibodies, each comprising one or more (e.g. 1, 2, 3, 4, 5, or 6) CDR sequences of each of the exemplary antibodies Ab02, Ab03 and Ab05-Ab35 as shown in Table 1.

TABLE 1

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| Ab01 | VH | SEQ ID NO: 25 DVQLQESGPGLVKPSQSLSLTCSVTGYSITSGYYWNWIRQFPGNKLEWMGYITYDGSNNYNPSLKNRISITRDTSKNQFFLKLNSVTTEDAATYFCARDPNYYGTTLPAWFVYWGQGTLVTVSA | SEQ ID NO: 18 SGYYWN | SEQ ID NO: 20 YITYDGSNNYNPSLKN | SEQ ID NO: 22 DPNYYGTTLPAWFVY |
| | VL | SEQ ID NO: 34 DIVVTQSHKFMSTSVGDRVSITCKASQDVGTAVAWYQQKPGQSPKLLIYWASTRHTGVPDRFTGSGSGTDFTLTISNVQSEDLTDYFCQQYSSYVTFGAGTKLELK | SEQ ID NO: 27 KASQDVGTAVA | SEQ ID NO: 29 WASTRHT | SEQ ID NO: 31 QQYSSYVT |
| Ab02 | VH | SEQ ID NO: 43 QVQLKESGPGLVAPSQSLSITCTVSGFSLTSYAINWVRQPPGKGLEWLGVIWTGGGTNYNSALKSRLSINKDNSKSQVFLKMNSLQTDDTARYYCARFYDGYYSWFAYWGQGTLVTVSA | SEQ ID NO: 36 SYAIN | SEQ ID NO: 38 VIWTGGGTNYNSALKS | SEQ ID NO: 40 FYDGYYSWFAY |
| | VL | SEQ ID NO: 52 DIVMTQSHKFMSTSVGDRVSITCKASQDVGTAVTWYQQKPGQSPKLLIYWASTRHTGVPDRFTGSGSGTDFTLTISNVQSEDLADYFCQQYSSYPFTFGSGTKLEIK | SEQ ID NO: 45 KASQDVGTAVT | SEQ ID NO: 47 WASTRHT | SEQ ID NO: 49 QQYSSYPFT |
| Ab03 | VH | SEQ ID NO: 61 EVQLQQSGPELVKPGASVKIACKASGYTFTDYNMDWVKQSHGKSLEWIGNINSYYGGTIYNQKFKGKATLTVDKSSSTAYMVLRSLTSEDNAVYYCARPHLGNALDYWGQGTSITVSS | SEQ ID NO: 54 DYNMD | SEQ ID NO: 56 NINSYYGGTIYNQKFKG | SEQ ID NO: 58 PHLGNALDY |
| | VL | SEQ ID NO: 70 DIVVTQSPSSLTVTPGEKVTMSCKSSQSLFNSGNQKNYLSWYQQNPGQPPKLLIYWASTRQSGVPDRFTGSGSGTDFTLTISSVQAEDLAGYYCQNDYIFPLTFGAGTKLELK | SEQ ID NO: 63 KSSQSLFNSGNQKNYLS | SEQ ID NO: 65 WASTRQS | SEQ ID NO: 67 QNDYIFPLT |
| Ab04 | VH | SEQ ID NO: 79 EVQLQQSGPELVKPGASVKMSCMASGYTFTDYNIHWVKRSHGSRLEWIGYISPISGGAGYNQKFMDKATLTVDKSSNTAYMELRSLTSEDSAVYYCTRGDYWGQGTT | SEQ ID NO: 72 DYNIH | SEQ ID NO: 74 YISPISGGAGYNQKFMD | GDY |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | | LTVSS | | | |
| | VL | SEQ ID NO: 88 DIVMTQSPSSLAVTVGEKVTMSCKSSQSLLNSGNQKNYLTWYQQKPGQPPKLLIYWASTRKSGVPDRFTGSGSGTDFTLTISSVQAEDLGIYYCLNDYGFPLTFGAGSKLELK | SEQ ID NO: 81 KSSQSLLNSGNQKNYLT | SEQ ID NO: 83 WASTRKS | SEQ ID NO: 85 LNDYGFPLT |
| Ab05 | VH | SEQ ID NO: 97 DVKLVESGEDLVKPGGSLKLSCAASGFTFSNYAMSWVRQTPEKRLEWVAYVSSGGDYIYYADTVKGRFIISRDNARNTLYLQMNSLRSEDTAMYYCARVYFGNSLDYWGQGTTLTVSS | SEQ ID NO: 90 NYAMS | SEQ ID NO: 92 YVSSGGDYIYYADTVKG | SEQ ID NO: 94 VYFGNSLDY |
| | VL | SEQ ID NO: 106 DIVMTQSPSSLTVTAGEKVTLSCKSSQSLLNGGNQKNYLTWYQQRPGQPPKLLIYWASTRESGVPDRFTGSGSGTDFTLIISSVQAEDLAVYYCQNDYYYPWTFGGGTKLEIK | SEQ ID NO: 99 KSSQSLLNGGNQKNYLT | SEQ ID NO: 101 WASTRES | SEQ ID NO: 103 QNDYYYPWT |
| Ab06 | VH | SEQ ID NO: 115 EVQLVASGGGLVKPGGSLKLSCAASGITFRSYAMSWVRQTPEKRLEWVATITDGGSYIFYPDNVKGRFTISGDHAKNNLYLQMSHLKSEDTALYFCVRLYYGNSFAYWGQGTLVTVSA | SEQ ID NO: 108 SYAMS | SEQ ID NO: 110 TITDGGSYIFYPDNVKG | SEQ ID NO: 112 LYYGNSFAY |
| | VL | SEQ ID NO: 124 DIVMTQSPSSLTVTAGEKVTLNCKSSQSLFNSGNQKNYLTWYQQKPGQPPKLLIYWASTRESGVPDRFTGSGSGTDFTLTFSSVQAEDLAVYYCQNAYIYPFTFGSGTKLEIK | SEQ ID NO: 117 KSSQSLFNSGNQKNYLT | SEQ ID NO: 119 WASTRES | SEQ ID NO: 121 QNAYIYPFT |
| Ab07 | VH | SEQ ID NO: 133 EVQLQQSGPELVKPGASVKISCKASGYSFTDYFMNWVKQSHGKGLEWIGRINPYNGDTFYNQKFKGKATLTVDKSSSTAHMELLSLTSEDFAVYYCALYDGYWGAFVYWGQGTLVTVSA | SEQ ID NO: 126 DYFMN | SEQ ID NO: 128 RINPYNGDTFYNQKFKG | SEQ ID NO: 130 LYDGYWGAFVY |
| | VL | SEQ ID NO: 142 DIQMTQSPASLSVFVGETVTITCRASENIYSNLAWYQQKQGKSPQLLVYAATNLADGVPSRFSGSGSGTQYSLKINSLQSEDFGSYYCQHFWGTPLTFGAGTKLELK | SEQ ID NO: 135 RASENIYSNLA | SEQ ID NO: 137 AATNLAD | SEQ ID NO: 139 QHFWGTPLT |
| Ab08 | VH | SEQ ID NO: 151 QVQLQQPGAELVKPGASVKLSCKASGYTFTSYLLHWVKQRPGQGLEWIGMIHPNGGSTNYNEKFKTKATLTVDKSSSTAYMQLSSLTSEDSAVYYCAPVYFGNSFAYWGQGTLVTVSA | SEQ ID NO: 144 SYLLH | SEQ ID NO: 146 MIHPNGGSTNYNEKFKT | SEQ ID NO: 148 VYFGNSFAY |
| | VL | SEQ ID NO: 160 DIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYYYPFTFGSGTKLEKK | SEQ ID NO: 153 KSSQSLLNSGNQKNYLT | SEQ ID NO: 155 WASTRES | SEQ ID NO: 157 QNDYYYPFT |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| Ab09 | VH | SEQ ID NO: 205 EVQLQQSGPELVKPGTSVKMSCKASGYTFTDYNMHWVKLSHGKSLEWIGYINPNNGGTIYNQRFKGKATLTVNKSSRTAYMDLRSLTSEDSAVYYCARQGYYGNSMDYWGQGNSVTVSS | SEQ ID NO: 198 DYNMH | SEQ ID NO: 200 YINPNNGGTIYNQRFKG | SEQ ID NO: 202 QGYYGNSMDY |
| | VL | SEQ ID NO: 214 DIVMTQSPSSLTVTPGERVTMSCKSSQSLLNGGNQRNYLTWYQQKPGQPPKLLIYWASTRESGVPDRFAGSGSGTDFTLTISRVQAEDLSFYYCQNSYFYPFTFGSGTKLDLR | SEQ ID NO: 207 KSSQSLLNGGNQRNYLT | SEQ ID NO: 209 WASTRES | SEQ ID NO: 211 QNSYFYPFT |
| Ab10 | VH | SEQ ID NO: 223 EVMLVESGGGLVKPGGSLKLSCAASGFTFSSYTMSWVRQTPEKRLEWVATISVIGGNTYYVDSVKGRFTISRDKAKNTLYLQMSSLRSEDTALYYCARLGQTQRNAMDYWGQGTSVTVSS | SEQ ID NO: 216 SYTMS | SEQ ID NO: 218 TISVIGGNTYYVDSVKG | SEQ ID NO: 220 LGQTQRNAMDY |
| | VL | SEQ ID NO: 232 DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYSYPLTFGAGTKLELK | SEQ ID NO: 225 KSSQSLLNSGNQKNYLA | SEQ ID NO: 227 GASTRES | SEQ ID NO: 229 QNDYSYPLT |
| Ab11 | VH | SEQ ID NO: 241 EVMLVESGGDLVKPGGSLKLSCAASGFTFSRYTMSWVRQTPEKRLEWVATVSVGSGNTYYLDSVKGRFTISRDNAKNTLFLQMNSLRSEDTALYYCTRLGQTQRNAVDYWGQGTSVTVSS | SEQ ID NO: 234 RYTMS | SEQ ID NO: 236 TVSVGSGNTYYLDSVKG | SEQ ID NO: 238 LGQTQRNAVDY |
| | VL | SEQ ID NO: 250 DIVMTQSPSFLSVSAGEKVTMSCKSSQSLFNGGNQKNYLAWYQQKPGQPPKLLIYGASTRDSGVPDRFTGSGSGTDFTLTISNVQAEDLAIYFCQNDHSFPLTFGAGTKLELK | SEQ ID NO: 243 KSSQSLFNGGNQKNYLA | SEQ ID NO: 245 GASTRDS | SEQ ID NO: 247 QNDHSFPLT |
| Ab12 | VH | SEQ ID NO: 259 EVMLVESGGGLVKPGGSLKLSCAASGFTFSSYTMSWVRQTPEKRLEWVATIIGGYGNTYYADSVKGRFTISRDSAKNTLYLQMLSLRSEDTALYYCTRLGQTQRNAMDYWGQGTSVTVSS | SEQ ID NO: 252 SYTMS | SEQ ID NO: 254 TIIGGYGNTYYADSVKG | SEQ ID NO: 256 LGQTQRNAMDY |
| | VL | SEQ ID NO: 268 DILMTQSPSSLSVSAGEKVTMSCKSSQSLLNSGNQRNYLAWYQQKPGQPPKLLIYGASTRESGVPDRFTGSGSGTDFTLTISSVQAEDLAVYYCQNDYYYPLTFGAGTKLELK | SEQ ID NO: 261 KSSQSLLNSGNQRNYLA | SEQ ID NO: 263 GASTRES | SEQ ID NO: 265 QNDYYYPLT |
| Ab13 | VH | SEQ ID NO: 277 EVRLVESGGGLVKPGGSLKLSCAGSGFTFSSYTMSWVRQTPEKRLEWVATITIGVNIYYLDSVKGRFTISRDNAKNTLYLQMNSLRSEDTALYYCTRLGQTQRNAMDYWGQGTSVTVSS | SEQ ID NO: 270 SYTMS | SEQ ID NO: 272 TITIGVNIYYLDSVKG | SEQ ID NO: 274 LGQTQRNAMDY |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | VL | SEQ ID NO: 286 DIVMTQSPTSLSVSAGEKVTMTCKSSQSLLNSGNQKNYLAWYQEKPGQPPKLLIYGASTRESGVPDRFTGSGSGTDFTLTISSVQAEDLAVYYCQNNHFYPLTFGAGTKLELK | SEQ ID NO: 279 KSSQSLLNSGNQKNYLA | SEQ ID NO: 281 GASTRES | SEQ ID NO: 283 QNNHFYPLT |
| Ab14 | VH | SEQ ID NO: 295 QVQLQQPGAELVKPGASVKLSCKASGYTFTSYLLHWVKQRPGQGLEWIGMIHPNGGSTNYNEKFKTKATLTVDKSSSTAYMQLSSLTSEDSAVYYCAPVYFGNSFAYWGQGTLVTVSA | SEQ ID NO: 288 SYLLH | SEQ ID NO: 290 MIHPNGGSTNYNEKFKT | SEQ ID NO: 292 VYFGNSFAY |
| | VL | SEQ ID NO: 304 DIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYYYPFTFGSGTKLEKK | SEQ ID NO: 297 KSSQSLLNSGNQKNYLT | SEQ ID NO: 299 WASTRES | SEQ ID NO: 301 QNDYYYPFT |
| Ab15 | VH | SEQ ID NO: 313 EVMLVESGGDLVKPGGSLKLSCAASGFTFSTYTMSWVRQTPEKRLEWVATIVGGGGYTYYLDSVKGRFTISRDNAKNTLYLQMISLRSEDTALYYCARMGLTQRNALDYWGQGTSITVSS | SEQ ID NO: 306 TYTMS | SEQ ID NO: 308 TIVGGGGYTYYLDSVKG | SEQ ID NO: 310 MGLTQRNALDY |
| | VL | SEQ ID NO: 322 DIVMTQSPSSLSVSEGEKVTLNCKSSQSLFNSGNQKNYLAWYQQKPGQPPKLLIYGASTRESGVPDRFTGSGFGTDFTLTISSVQAEDLAVYYCQNDHTYPLTFGAGAKLELK | SEQ ID NO: 315 KSSQSLFNSGNQKNYLA | SEQ ID NO: 317 GASTRES | SEQ ID NO: 319 QNDHTYPLT |
| Ab16 | VH | SEQ ID NO: 331 EVMLVESGGGLVKPGGSLKLSCAASGFTFNSYTMSWVRQTPEKRLEWVATITVIGGNTYYLDSVKGRFTISIDNGKNTLYLQMSSLRSEDTALYYCARMGQTQRNAMDYWGQGTSVTVSS | SEQ ID NO: 324 SYTMS | SEQ ID NO: 326 TITVIGGNTYYLDSVKG | SEQ ID NO: 328 MGQTQRNAMDY |
| | VL | SEQ ID NO: 340 DIVMTQSPSSLSVSAGQKVTMRCKSSQSLLNSGNQKNYLAWYQQKLGQPPKLLIYGASTRESGVPDRFSGSGSGTDFTLTITSVQAEDLAVYYCQNDYSFPLTFGAGTKLELK | SEQ ID NO: 333 KSSQSLLNSGNQKNYLA | SEQ ID NO: 335 GASTRES | SEQ ID NO: 337 QNDYSFPLT |
| Ab17 | VH | SEQ ID NO: 349 QVQLKESGPGLVAPSQSLSITCTVSGFSLTSYAISWVRQPPGKGLEWLGEIWTGGGTNYNSALKSRLSISKDNSKSQVFLKMNSLQTDDTARYYCGRLSYGNSLDYWGQGTTLTVSS | SEQ ID NO: 342 SYAIS | SEQ ID NO: 344 EIWTGGGTNYNSALKS | SEQ ID NO: 346 LSYGNSLDY |
| | VL | SEQ ID NO: 358 DIVMTQSPSSLTVTAGEKVTMSCKSSQSLLNSGNQKNYLTWYQQKPGQPPKLLIYWASTRESGVPDRFTGSGSGTDFTLTVSSVQAEDLAVYYCQNNFIYPLTFGPGTKLELK | SEQ ID NO: 351 KSSQSLLNSGNQKNYLT | SEQ ID NO: 353 WASTRES | SEQ ID NO: 355 QNNFIYPLT |
| Ab18 | VH | SEQ ID NO: 367 QVQLKESGPG | SEQ ID NO: 360 TYGIN | SEQ ID NO: 362 VIWGDGS | SEQ ID NO: 364 SSYYGNAM |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | | LVAPSQSLSITCTVSGFSLTTYGINWVRQPPGKGLEWLGVIWGDGSTNYHSALISRLSISKDNSKSQVFLKLNSLQTDDTATYYCVKSSYYGNAMDYWGQGTSVTVSS | | TNYHSALIS | DY |
| | VL | SEQ ID NO: 376 DIVMTQSPSSLTVTAGETVTMSCKSSQSLLNSGNQKNYLTWYQQKPGQPPKLLIYWASTRESGVPDRFTGSGSGTDFTLTISSVQAEDLAVYYCQNVYSYPFTFGSGTKLEI | SEQ ID NO: 369 KSSQSLLNSGNQKNYLT | SEQ ID NO: 371 WASTRES | SEQ ID NO: 373 QNVYSYPFT |
| Ab19 | VH | SEQ ID NO: 385 EVMLVESGGDLVKPGGSLKLSCAASGFSFSRYTMSWVRQTPEKRLEWVATVSVGSGNTYYLDSVKGRFTISRDNAKNTLFLQMSSLRSEDTALYYCARMGQTQRNAVDYWGQGTSVTVSS | SEQ ID NO: 378 RYTMS | SEQ ID NO: 380 TVSVGSGNTYYLDSVKG | SEQ ID NO: 382 MGQTQRNAVDY |
| | VL | SEQ ID NO: 394 DIVMTQSPSSLSVSAGEKVTMSCKSSQSLFNSGNQKNYLAWYQQKPGQPPKLLIYGASTRESGVPDRFTGSGSGTDFTLTISNVQAEDLAVYLCQNDHSFPLTFGAGTKLEL | SEQ ID NO: 387 KSSQSLFNSGNQKNYLA | SEQ ID NO: 389 GASTRES | SEQ ID NO: 391 QNDHSFPLT |
| Ab20 | VH | SEQ ID NO: 403 EVMLVESGGGLVKPGGSLKLSCVASGFTFSSYTMSWVRQTPEKRLEWVATIIGGYGNTYYSDSVKGRITISRDSAKNTLYLQMISLRSEDTALYYCTRLGQTQRNAM | SEQ ID NO: 396 SYTMS | SEQ ID NO: 398 TIIGGYGNTYYSDSVKG | SEQ ID NO: 400 LGQTQRNAMDY |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | | DYWGQGTSVTVSS | | | |
| | VL | SEQ ID NO: 412 DILMTQSPSSLSVSAGEKVTMNCKSSQSLLNSGNQKNYLAWYQQKPGQPPKLLIYGASTRESGVPDRFTGSGSGTDFTLTISSVQAEDLAVYYCQNDYYYPFTFGAGTKLEL | SEQ ID NO: 405 KSSQSLLNSGNQKNYLA | SEQ ID NO: 407 GASTRES | SEQ ID NO: 409 QNDYYYPFT |
| Ab21 | VH | SEQ ID NO: 421 EVMLVESGGGLVKPGGSLKLSCAASGFTFSSYTMSWVRQTPEKRLEWVATIIGGYGNTYYVDSVKGRFTISRDSAKNTLYLQMISLRSEDTALYYCTRLGQTQRNAMDYWGQGTSVTVSS | SEQ ID NO: 414 SYTMS | SEQ ID NO: 416 TIIGGYGNTYYVDSVKG | SEQ ID NO: 418 LGQTQRNAMDY |
| | VL | SEQ ID NO: 430 DILMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYYYPFTFGAGTKLEL | SEQ ID NO: 423 KSSQSLLNSGNQKNYLA | SEQ ID NO: 425 GASTRES | SEQ ID NO: 427 QNDYYYPFT |
| Ab22 | VH | SEQ ID NO: 439 EVMLVESGGGLVKPGGSLKLSCAASGFTFSSYTMSWVRQTPEKRLEWVATIIGGYGNTYYADSVKGRFTISRDSAKNTLYLQMISLRSEDTALYYCTRLGQTQRNAMDYWGQGTSVTVSS | SEQ ID NO: 432 SYTMS | SEQ ID NO: 434 TIIGGYGNTYYADSVKG | SEQ ID NO: 436 LGQTQRNAMDY |
| | VL | SEQ ID NO: 448 DILMTQSPSSLSVSAGEKVTMSCKSSQSLLNSGNQKNYL | SEQ ID NO: 441 KSSQSLLNSGNQKNYLA | SEQ ID NO: 443 GASTRES | SEQ ID NO: 445 QNDYYYPFT |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | | AWYQQKPGQPPKLLIYGASTRESGVPDTFTGSGSGTDFTLTISSVQAEDLAVYYCQNDYYYPFTFGAGTKLEL | | | |
| Ab23 | VH | SEQ ID NO: 457 EVMLVESGGGLVKPGGSLKLSCVASGFTFSSYTMSWVRQTPEKRLEWVATLSVVGGNTYYVDSVKGRFTISRDKAKNTLYLQMSSLRSEDTALYYCARLGQTQRNAMDYWGQGTSVTVSS | SEQ ID NO: 450 SYTMS | SEQ ID NO: 452 TLSVVGGNTYYVDSVKG | SEQ ID NO: 454 LGQTQRNAMDY |
| | VL | SEQ ID NO: 466 DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYSYPLTFGAGTKLEL | SEQ ID NO: 459 KSSQSLLNSGNQKNYLA | SEQ ID NO: 461 GASTRES | SEQ ID NO: 463 QNDYSYPLT |
| Ab24 | VH | SEQ ID NO: 475 EVKLVESGGGLVKPGGSLKLSCAGSGFTFSSYTMSWVRQTPEKRLEWVATITIGVNIYYLDSVKGRFTISRDNAKNTLYLQMNSLRSEDTALYYCTRLGQTQRNAMDYWGQGTSVTVSS | SEQ ID NO: 468 SYTMS | SEQ ID NO: 470 TITIGVNIYYLDSVKG | SEQ ID NO: 472 LGQTQRNAMDY |
| | VL | SEQ ID NO: 484 DIVMTQSPTSLSVSAGEKVTMTCKSSQSLFNSGNQKNYLAWYQEKPGQPPKLLIYGASTRESGVPDRFTGSGSGTDFTLTISSVQAEDLAVYYCQNVHFYPFTFGAGTKLEL | SEQ ID NO: 477 KSSQSLFNSGNQKNYLA | SEQ ID NO: 479 GASTRES | SEQ ID NO: 481 QNVHFYPFT |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| Ab25 | VH | SEQ ID NO: 493 EAQLQQSGPELVKPGASVKIFCKASGYTFTDYYINWVKQSHGKSLEWIGDINPNNGGTTYNQKFKGKATLTVDKSSSTASMELRRLTSEDSSVYYCARRDAMDYWGQGTSVTVSS | SEQ ID NO: 486 DYYIN | SEQ ID NO: 488 DINPNNGGTTYNQKFKG | SEQ ID NO: 490 RDAMDY |
| | VL | SEQ ID NO: 502 DIVMTQSQKFMSTTVGDRVSITCTASQNVGPAVAWYQQKPGQSPKLLIYSASRRFTGVPDRFTGSGSGTVFTLTINNVQSEDLADYFCQQYISYPLTFGAGTKLELK | SEQ ID NO: 495 TASQNVGPAVA | SEQ ID NO: 497 SASRRFT | SEQ ID NO: 499 QQYISYPLT |
| Ab26 | VH | SEQ ID NO: 511 EVMLVESGGGLVKPGGSLKLSCTASGFTFRSYTMSWVRQTPEKRLEWVATITGGGGNTYFLDSVKGRFTFSRDNAKNALYLQMNSLRSEDTALYYCARLGQTQRNAMDYWGQGTSVTVSS | SEQ ID NO: 504 SYTMS | SEQ ID NO: 506 TITGGGGNTYFLDSVKG | SEQ ID NO: 508 LGQTQRNAMDY |
| | VL | SEQ ID NO: 520 DIVMTQSPSSLSVSAGEKVTMSCKSSQSLLNSGNQMNYLAWYQQKPGQPPKLLIYGASTRESGVPDRFTGSGSGTDFTLTISSVQAEDLAIYYCQNDHTYPLTFGAGTKLEL | SEQ ID NO: 513 KSSQSLLNSGNQMNYLA | SEQ ID NO: 515 GASTRES | SEQ ID NO: 517 QNDHTYPLT |
| Ab27 | VH | SEQ ID NO: 529 QVQLQQSGAELVRPGSSVKISCKASGYAFSNYWMNWVKQRPGQGLEWIGQIYPGNGDTNYNGKFKGKATLTADKSSTTAYIQLSSLTS | SEQ ID NO: 522 NYWMN | SEQ ID NO: 524 QIYPGNGDTNYNGKFKG | SEQ ID NO: 526 IYYGNSFAY |

TABLE 1-continued

Amino acid sequences of variable regions of the exemplary antibodies of the present disclosure

| Anti-body ID No. | Vari-able Chain | Amino Acid Sequence of Each Variable Chain | Amino Acid Se-quence of CDR1 | Amino Acid Se-quence of CDR2 | Amino Acid Sequence of CDR3 |
|---|---|---|---|---|---|
| | | EDSAVYFCTRIYYGNSFAYWGQGTLVTVS | | | |
| | VL | SEQ ID NO: 538 DIVMTQSPSSLTVTAGERVTMSCKSSQSLLNSGNQKNYLTWYQQKPGQPPKLLIYWASTRESGVPDRFTGSGSGTDFTLTISRVQAQDLAVYYCQNDYYYPLTFGAGTKLELK | SEQ ID NO: 531 KSSQSLLNSGNQKNYLT | SEQ ID NO: 533 WASTRES | SEQ ID NO: 535 QNDYYYPLT |
| Ab28 | VH | SEQ ID NO: 547 QVQLKESGPGLVAPSQSLSITCTVSGFSLTSHGVHWVRQPPGKGLEWLGVIWAGGSINFNSALMSRLSISKDNSKNQVFLKMNSLQSDDTAMYYCARDYYYGIGLDYWGQGTTLTVS | SEQ ID NO: 540 SHGVH | SEQ ID NO: 542 VIWAGGSINFNSALMS | SEQ ID NO: 544 DYYYGIGLDY |
| | VL | SEQ ID NO: 556 DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYYYPFTFGSGTKLEIK | SEQ ID NO: 549 KSSQSLLNSGNQKNYLA | SEQ ID NO: 551 GASTRES | SEQ ID NO: 553 QNDYYYPFT |
| Ab29 | VH | SEQ ID NO: 565 EVLLQQSGPELVKPGASVKIPCKASGYTLTDHSMDWVKQSHGKSLEWIGNILPNNGGNIYNQKFRGKATLTVDKSSSTAYMELRSLTSEDTAVYNCARGHYGNSFAYWGQGTLVIVS | SEQ ID NO: 558 DHSMD | SEQ ID NO: 560 NILPNNGGNIYNQKFRG | SEQ ID NO: 562 GHYGNSFAY |
| | VL | SEQ ID NO: 574 DIVMTQSPSSLTVRAGEKVTIYCKSSQSLFNSGNQKNYLTWYQQKPGQPPKLLIYWASTRESGVPHRFTGSGSGTDFTLTISSMQADDLATYYCQNGYFFPYTFGGGTKLEIK | SEQ ID NO: 567 KSSQSLFNSGNQKNYLT | SEQ ID NO: 569 WASTRES | SEQ ID NO: 571 QNGYFFPYT |
| Ab30 | VH | SEQ ID NO: 583 QVQLKESGPGLVAPSQSLSITCTVSGFSLTKFGVNWVRQPPGKGLEWLGAIWGDGSTNYHSALISRLSINKDNSKSQVFLKLSSLQNVDTATYYCAKSGYGNAMDYWGHGTSVTVSS | SEQ ID NO: 576 KFGVN | SEQ ID NO: 578 AIWGDGSTNYHSALIS | SEQ ID NO: 580 SGYGNAMDY |
| | VL | SEQ ID NO: 592 DIVMTQSPSSLTVTTGEKVTLNCKSSQSLLNSGNLKNYLTWYQQRPGQPPKLLIYWASTRESGVPYRFTGSGSGTDFTLTISNVQAEDLAIYYCQNDYFFPFTFGSGTKLEIK | SEQ ID NO: 585 KSSQSLLNSGNLKNYLT | SEQ ID NO: 587 WASTRES | SEQ ID NO: 589 QNDYFFPFT |
| Ab31 | VH | SEQ ID NO: 601 QIQLAQSGPELKKPGETVKISCKASGYSFTNYGMNWVKQAPGKGLKWMGWINTYSGETKYADDFKGRFDFSLETSARTAYLQIKNLKIEDTATYFCARRDAMDYWGQGTSVTVSS | SEQ ID NO: 594 NYGMN | SEQ ID NO: 596 WINTYSGETKYADDFKG | SEQ ID NO: 598 RDAMDY |
| | VL | SEQ ID NO: 610 DIVMTQAAPSVPVTPGESVSISCRSSKSLLNSNGNTYLYWFLQRPGQSPQLLIYRMSNLASGVPDRFSGSGSGTAFTLRISRVEAEDVGVYYCMQHLEFPFTFGSGTKLEIK | SEQ ID NO: 603 RSSKSLLNSNGNTYLY | SEQ ID NO: 605 RMSNLAS | SEQ ID NO: 607 MQHLEFPFT |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| Ab32 | VH | SEQ ID NO: 619 QVQLKESGPGLVAPSQSLSITCTVSGFSLTSHGVHWVRQPPGKGLEWLGVIWAGGSINFNSALMSRLSISKDNSKNQVFLKMNSLQSDDTAMYYCARDYYYGIGLDYWGQGTTLTVS | SEQ ID NO: 612 SHGVH | SEQ ID NO: 614 VIWAGGSINFNSALMS | SEQ ID NO: 616 DYYYGIGLDY |
| | VL | SEQ ID NO: 628 DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYYYPFTFGSGTKLEIK | SEQ ID NO: 621 KSSQSLLNSGNQKNYLA | SEQ ID NO: 623 GASTRES | SEQ ID NO: 625 QNDYYYPFT |
| Ab33 | VH | SEQ ID NO: 637 DVNLVESGGGLVKPGGSLKLSCAASGFTFSSYTMSWVRQTPEKRLEWVATITYGRIYTYYLDSVKGRFTISRDNAKNTLYLQMSSLRSEDTAMYYCTRMITGNAMDSWGLGTSVTVSS | SEQ ID NO: 630 SYTMS | SEQ ID NO: 632 TITYGRIYTYYLDSVKG | SEQ ID NO: 634 MITGNAMDS |
| | VL | SEQ ID NO: 646 DIVMTQSPSSLTVTAGEKVTMSCKSSQSLLNSGNQKNYLTWYQQKPGQPPKLLIYWASTRESGVPDRFTGSGSGTDFTLTISGVQGEDLAVYYCQNDYSYPLTFGGGTKLELK | SEQ ID NO: 639 KSSQSLLNSGNQKNYLT | SEQ ID NO: 641 WASTRES | SEQ ID NO: 643 QNDYSYPLT |
| Ab34 | VH | SEQ ID NO: 655 EVLLQQSGPELVKPGASVKIPCKASGYTFSDYNMDWVKQSHGKSLEWIGHINPNNDNTIYNQKFKGKATLTVDKSSNTAYMDLRSLSSEDTAVYYCARGAYYGNSMDYWGQGTSVTVSS | SEQ ID NO: 648 SDYNMD | SEQ ID NO: 650 HINPNNDNTIYNQKFKG | SEQ ID NO: 652 GAYYGNSMDY |
| | VL | SEQ ID NO: 664 DIVMTQSPSSLTVTAGERVTMSCKSSQSLLNGGNQRNYLTWYQQKPGQSPKLLIYWASTWESGVPDRFTGSGSGTDFTLTISSVQAEDLAVYYCQNAYFYPYTFGGGTKLEIK | SEQ ID NO: 657 KSSQSLLNGGNQRNYLT | SEQ ID NO: 659 WASTWES | SEQ ID NO: 661 QNAYFYPYT |
| Ab35 | VH | SEQ ID NO: 673 DVFLQESGPGLVKPSQSLSLTCTVTGYSITSDYAWNWIRQFPGNKLEWVTYIGYSGTTSYNPSLKSRISITRDTSKNQFFLQLNSVSTEDTATYYCVRRGSYYGSYWFFDVWGAGTTVTVSS | SEQ ID NO: 666 SDYAWN | SEQ ID NO: 668 YIGYSGTTSYNPSLKS | SEQ ID NO: 670 RGSYYGSYWFFDV |
| | VL | SEQ ID NO: 682 QVVLSQSPAILSASPGEKVTMTCRASSSVSYMHWYQQKPGSSPKPWIYATSNLASGVPPHFSGSGSGTSYSLTISRVEAEDAATYYCQQWTSNPPTFGGGTKLEIK | SEQ ID NO: 675 RASSSVSYMH | SEQ ID NO: 677 ATSNLAS | SEQ ID NO: 679 QQWTSNPPT |
| Ab36 | VH | SEQ ID NO: 691 EVKLEESGGGLVQPGGSMKLSCVASGFTFSNYWMNWVRQSPEKGLEWVAQIRLKSDNYATHYAESVKGMFTISRDDSKSSVYLQMNNLRAEDTGIYYCTAGGDYWGQGTTLTVSS | SEQ ID NO: 684 NYWMN | SEQ ID NO: 686 QIRLKSDNYATHYAESVKG | SEQ ID NO: 688 GGDY |
| | VL | SEQ ID NO: 161 DIVMTQSQKFMSTTVGDRVS | SEQ ID NO: 693 KASQNVGTAVA | SEQ ID NO: 695 SASNRYT | SEQ ID NO: 697 QQYINYLLT |

TABLE 1-continued

Amino acid sequences of variable regions of the exemplary antibodies of the present disclosure

| Antibody ID No. | Variable Chain | Amino Acid Sequence of Each Variable Chain | Amino Acid Sequence of CDR1 | Amino Acid Sequence of CDR2 | Amino Acid Sequence of CDR3 |
|---|---|---|---|---|---|
| | | ITCKASQNVGTAVAWYHQKPGQSPKLLIYSASNRYTGVPDRFIGSGSGTDFTLTISNVQSEDLGNYFCQQYINYLLTFGSGTKLEIK | | | |
| Ab37 | VH | SEQ ID NO: 170 EVKLEESGGGLVQPGGSMKLSCVASGFTFSNYWMNWVRQYPEQGLEWVAQIRLNSDNYATHYAESVKGRFTISRDDSRSTVYLQMNNLRAEDTGIYYCTGGGEYWGQGTTLTVSS | SEQ ID NO: 163 NYWMN | SEQ ID NO: 165 QIRLNSDNYATHYAESVKG | SEQ ID NO: 167 GGEY |
| | VL | SEQ ID NO: 179 DIVMTQSQKFMSTTIGDRVSITCKASQNVDTAVAWYQQKPGQSPKLLIYSASTRYTGVPDRFTGSGSGTDFTLTISNMQSEDLADYFCQQYISYQLTFGAGTKLELK | SEQ ID NO: 172 KASQNVDTAVA | SEQ ID NO: 174 SASTRYT | SEQ ID NO: 176 QQYISYQLT |
| Ab38 | VH | SEQ ID NO: 188 QIQLVQSGPELKKPGETVKISCKASGYTFTNYGMSWVKQAPGKGLKWMGWINTYSGVPTYADDFKGRFVFSLEASASTAYLQINNLKNEDAATYFCSRWSGPDPLEDHWGQGTTLTVSS | SEQ ID NO: 181 NYGMS | SEQ ID NO: 183 WINTYSGVPTYADDFKG | SEQ ID NO: 185 WSGPDPLEDH |
| | VL | SEQ ID NO: 76 QIVLTQSPAIMSASPGEKVTMTCTASLSLNYIHWYRQRSGTSPKRWIYDTSKLASGVPSRFSGSGSGTSYSLTISSMEAEDAATYYCQQWSSNPWTFGGGTKLEIK | SEQ ID NO: 190 TASLSLNYIH | SEQ ID NO: 192 DTSKLAS | SEQ ID NO: 194 QQWSSNPWT |

Also within the scope of the present disclosure are functional variants of any of the exemplary anti-CLDN18 antibodies as disclosed herein, for example, in Table 1. Such functional variants are substantially similar to the exemplary antibody, both structurally and functionally. A functional variant comprises substantially the same VH- and VL-CDRs as the exemplary antibody. For example, it may comprise only up to 3 (e.g., 2 or 1) amino acid residue variations in the total CDR regions of the antibody and binds the same epitope of CLDN18.2 with substantially similar affinity (e.g., having a mean fluorescence intensity (MFI) value in the same order). Alternatively or in addition, the amino acid residue variations are conservative amino acid residue substitutions.

Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

CDRs are known to be responsible for antigen binding, however, it has been found that not all of the 6 CDRs are indispensable or unchangeable. In other words, it is possible to replace or change or modify one or more CDRs in Ab01-Ab38, yet substantially retain the specific binding affinity to CLDN, in particular, to CLDN18.2

In certain embodiments, the anti-CLDN18 antibodies provided herein comprise a VH-CDR 1 having an amino acid sequence selected from the group consisting of GDY, SEQ ID NOs: 18, 36, 54, 72, 90, 108, 126, 144, 163, 181, 198, 216, 234, 252, 270, 288, 206, 324, 342, 360, 378, 396, 414, 432, 450, 468, 486, 504, 522, 540, 558, 576, 594, 612, 630, 648, 666 and 684, a VH-CDR2 having an amino acid sequence selected from the group consisting of SEQ ID NOs: 20, 38, 56, 74, 92, 110, 128, 146, 165, 183, 200, 218, 236, 254, 272, 290, 308, 326, 344, 362, 380, 398, 416, 434, 452, 470, 488, 506, 524, 542, 560, 578, 596, 614, 632, 650, 668 and 686, a VH-CDR3 having an amino acid sequence selected from the group consisting of GDY and SEQ ID NOs: 22, 40, 58, 94, 112, 130, 148, 167, 185, 202, 220, 238, 256, 274, 292, 310, 328, 346, 364, 382, 400, 418, 436, 454, 472, 490, 508, 526, 544, 562, 580, 598, 616, 634, 652, 670 and 688; and optionally a VL-CDR 1 having an amino acid sequence selected from the group consisting of SEQ ID NOs: 27, 45, 63, 81, 99, 117, 135, 153, 172, 190, 207, 225, 243, 261, 279, 297, 315, 333, 351, 369, 387, 405, 423, 441, 459, 477, 495, 513, 531, 549, 567, 585, 603, 621, 639, 657, 675 and 693, a VL-CDR2 having an amino acid sequence selected from the group consisting of SEQ ID NOs: 29, 47, 65, 83, 101, 119, 137, 155, 174, 192, 209, 227, 245, 263, 281, 299, 317, 335, 353, 371, 389, 407, 425, 443, 461, 479, 497, 515, 533, 551, 569, 587, 605, 623, 641, 659, 677 and 695, a VL-CDR3 having an amino acid sequence selected from the group consisting of SEQ ID NOs: 31, 49, 67, 85, 103, 121, 139, 157, 176, 194, 211, 229, 247, 265, 283, 301, 319, 337, 355, 373, 391, 409, 427, 445, 463, 481, 499, 517, 535, 553, 571, 589, 607, 625, 643, 661, 679 and 697, as shown in Table 1.

In certain embodiments, the anti-CLDN18 antibodies provided herein further comprise suitable framework region (FR) sequences, as long as the antibodies can specifically bind to CLDN18.2. The CDR sequences provided in Table 1 are obtained from a mouse antibody, but they can be grafted to any suitable FR sequences of any suitable species such as mouse, human, rat, rabbit, among others, using suitable methods known in the art such as recombinant techniques.

In certain embodiments, the anti-CLDN18 antibodies provided herein further comprise one light chain constant domain and/or one or more heavy chain constant domains. When needed, the anti-CLDN18 antibodies as described herein may comprise a modified constant region. For example, it may comprise a modified constant region that can enhance antibody-dependent cell mediated cytotoxicity (ADCC). ADCC activity can be assessed using methods disclosed in U.S. Pat. No. 5,500,362. In certain embodiments, the modified constant region comprises an amino acid sequence of SEQ ID NOs: 701-702 as shown in Table 2, wherein S122D, A213L and I215E were bolded and underlined.

TABLE 2

Amino acid sequences of Fc regions.

| SEQ ID NO | Name | Amino acid sequence |
|---|---|---|
| 700 | Human IgG1 Heavy Chain Fc-wt | ASTKGPSVFPLAPSSKSTSGGT<br>AALGCLVKDYFPEPVTVSWNSG<br>ALTSGVHTFPAVLQSSGLYSLS<br>SWTVPSSSLGTQTYICNVNHKP<br>SNTKVDKKVEPKSCDKTHTCPP<br>CPAPELLGGPSVFLFPPKPKDT<br>LMISRTPEVTCVVVDVSHEDPE<br>VKFNWYVDGVEVHNAKTKPREE<br>QYNSTYRVVSVLTVLHQDWLNG<br>KEYKCKVSNKALPAPIEKTISK<br>AKGQPREPQVYTLPPSRDELTK<br>NQVSLTCLVKGFYPSDIAVEWE<br>SNGQPENNYKTTPPVLDSDGSF<br>FLYSKLTVDKSRWQQGNVFSCS<br>VMHEALHNHYTQKSLSLSPGK |
| 701 | Human IgG1 Heavy Chain Fc-DE Mutation | ASTKGPSVFPLAPSSKSTSGGT<br>AALGCLVKDYFPEPVTVSWNSG<br>ALTSGVHTFPAVLQSSGLYSLS<br>SWTVPSSSLGTQTYICNVNHKP<br>SNTKVDKKVEPKSCDKTHTCPP<br>CPAPELLGGP**D**VFLFPPKPKDT<br>LMISRTPEVTCVVVDVSHEDPE<br>VKFNWYVDGVEVHNAKTKPREE<br>QYNSTYRVVSVLTVLHQDWLNG<br>KEYKCKVSNKALPAP**E**EKTISK<br>AKGQPREPQVYTLPPSRDELTK<br>NQVSLTCLVKGFYPSDIAVEWE<br>SNGQPENNYKTTPPVLDSDGSF<br>FLYSKLTVDKSRWQQGNVFSCS<br>VMHEALHNHYTQKSLSLSPGK |
| 702 | Human IgG1 Heavy Chain Fc-DLE Mutation | ASTKGPSVFPLAPSSKSTSGGT<br>AALGCLVKDYFPEPVTVSWNSG<br>ALTSGVHTFPAVLQSSGLYSLS<br>SWTVPSSSLGTQTYICNVNHKP<br>SNTKVDKKVEPKSCDKTHTCPP<br>CPAPELLGGP**D**VFLFPPKPKDT<br>LMISRTPEVTCVVVDVSHEDPE<br>VKFNWYVDGVEVHNAKTKPREE<br>QYNSTYRVVSVLTVLHQDWLNG<br>KEYKCKVSNKALP**L**P**E**EKTISK<br>AKGQPREPQVYTLPPSRDELTK<br>NQVSLTCLVKGFYPSDIAVEWE<br>SNGQPENNYKTTPPVLDSDGSF<br>FLYSKLTVDKSRWQQGNVFSCS<br>VMHEALHNHYTQKSLSLSPGK |

TABLE 2-continued

Amino acid sequences of Fc regions.

| SEQ ID NO | Name | Amino acid sequence |
|---|---|---|
| 703 | Mouse IgG2a Heavy Chain Fc | AKTTAPSVYPLAPVCGDTTGSS<br>VTLGCLVKGYFPEPVTLTWNSG<br>SLSSGVHTFPAVLQSDLYTLSS<br>SVTVTSSTWPSQSITCNVAHPA<br>SSTKVDKKIEPRGPTIKPCPPC<br>KCPAPNLLGGPSVFIFPPKIKD<br>LVMISLSPIVTCVVVDVSEDDP<br>VDQISWFVNNVEVHTAQTQTHR<br>EDYNSTLRVVSALPIQHQDWMS<br>GKEFKCKVNNKDLPAPIERTIS<br>KPKGSVRAPQVYVLPPPEEEMT<br>KKQVTLTCMVTDFMPEDIYVEW<br>TNNGKTELNYKNTEPVLDSDGS<br>YFMYSKLRVEKKNWVERNSYSC<br>SVVHEGLHNHHTTKSFSRTPGK |

Antibody heavy and light chain constant regions are well known in the art, e.g., those provided in the IMGT database (www.imgt.org) or at www.vbase2.org/vbstat.php., both of which are incorporated by reference herein.

In one example, the antibodies described herein are a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Methods for constructing humanized antibodies are also well known in the art (see, e.g., Queen et al., Proc. Natl. Acad. Sci. USA, 86:10029-10033 (1989)). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

In another example, the antibody described herein is a chimeric antibody, which can include a heavy constant region or a part thereof and/or a light constant region or a part thereof from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

"chAb01-chAb38" as used herein refers to chimeric antibodies based on Ab01-Ab38, each of which comprises a mouse heavy chain variable region as shown in Table 1, and a mouse light chain variable region as shown in Table 1, fused respectively to human heavy chain constant region and human light chain constant region. In certain embodiments, the human heavy chain constant region and human light chain constant region are from human IgG1. In certain embodiments, the human heavy chain constant region and human light chain constant region are from wild-type human IgG1 having an amino acid sequence of SEQ ID NO: 700 as shown in Table 2.

In certain embodiments, the anti-CLDN18 antibodies provided herein may contain one or more modifications or substitutions in one or more variable region sequences provided herein, yet retaining specific binding affinity to CLDN18. In certain embodiments, at least one (or all) of the substitution(s) in the CDR sequences, FR sequences, or variable region sequences is a conservative substitution(s).

Various methods known in the art can be used to achieve this purpose. For example, a library of antibody variants (such as Fab or scFv variants) can be generated and expressed with phage display technology, and then screened for the binding affinity to human CLDN18. For another example, computer software can be used to virtually simulate the binding of the antibodies to CLDN18, and identify the amino acid residues on the antibodies which form the binding interface. Such residues may be either avoided in the substitution so as to prevent reduction in binding affinity, or targeted for substitution to provide for a stronger binding.

In some embodiments, the anti-CLDN18 antibodies may comprise heavy chain CDRs that are at least 80% (e.g., 85%, 90%, 95%, or 98%) sequence identity, individually or collectively, as compared with the VH-CDRs of the exemplary antibodies described herein and as shown in Table 1. Alternatively or in addition, the anti-CLDN18 antibodies may comprise light chain CDRs that are at least 80% (e.g., 85%, 90%, 95%, or 98%) sequence identity, individually or collectively, as compared with the VL-CDRs of the exemplary antibodies described herein and as shown in Table 1.

In certain embodiments, the anti-CLDN18 antibodies provided herein comprise a constant region capable of inducing effector function such as ADCC or CDC. Effector functions such as ADCC and CDC can lead to cytotoxicity to cells expressing CLDN18, and can be evaluated using various assays such as Fc receptor binding assay, C1q binding assay, and cell lysis assay. In certain embodiments, the constant region is of IgG1 isotype, which is known to induce ADCC.

In certain embodiments, the anti-CLDN18 antibodies comprise one or more modifications in the constant region that renders enhanced ADCC. As used herein, the term "enhanced ADCC" is defined as either an increase in the number of target cells that are lysed in a given time, at a given concentration of antibody in the medium surrounding the target cells, by the mechanism of ADCC defined above, and/or a reduction in the concentration of antibody, in the medium surrounding the target cells, required to achieve the lysis of a given number of target cells in a given time, by the mechanism of ADCC.

Characterization of Anti-CLDN18 Antibodies

Binding Affinity

In certain embodiments, the anti-CLDN18 antibodies provided herein specifically bind to human CLDN18, mouse CLDN18, and Ehesus monkey CLDN18. In certain embodiments, the anti-CLDN18 antibodies provided herein more specifically bind to human CLDN18.2, mouse CLDN18.2, and Ehesus monkey CLDN18.2 than corresponding CLDN18.1.

In certain embodiments, specific binding of the antibodies provided herein to human CLDN18.2 is represented by "half maximal effective concentration" ($EC_{50}$) value, which refers to the concentration of an antibody where 50% of its maximal effect (e.g., binding) is observed. The $EC_{50}$ value can be measured by methods known in the art, for example, sandwich assay such as ELISA, Western Blot, flow cytometry assay, and other binding assay. In certain embodiments, the antibodies provided herein specifically bind to human CLDN18.2 at an $EC_{50}$ (i.e. 50% binding concentration) of no more than 6 nM, no more than 5 nM, no more than 4 nM, no more than 3 nM, no more than 2 nM, no more than 1.5 nM, no more than 1 nM, no more than 0.9 nM, no more than 0.8 nM, no more than 0.7 nM, no more than 0.6 nM, no more than 0.5 nM, no more than 0.4 nM, no more than 0.3 nM, no more than 0.2 nM or no more than 0.1 nM measured by FACs.

In certain embodiments, specific binding of the antibodies to human CLDN18.2 is represented by median fluorescence intensity (MFI) or maximum MFI (MAX MFI) as measured by FACs. Higher MAX MFI indicates higher binding affinity when the measurement conditions remain the same among different samples. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

In certain embodiments, the antibodies provided herein have a specific binding affinity to human CLDN18.2 which is sufficient to provide for diagnostic and/or therapeutic use. In certain embodiments, the antibodies provided herein have a specific binding affinity to human CLDN18.2, the expression of which is too low to be specifically bound by existing anti-CLDN18.2 antibodies, such as IMAB362. In certain embodiments, the antibodies provided herein specifically bind to CLDN18.2 low-expressing cells with less than 10000 anti-CLDN18.2 antibody binding sites per cell, less than 9000 anti-CLDN18.2 antibody binding sites per cell, less than 8000 anti-CLDN18.2 antibody binding sites per cell, less than 7000 anti-CLDN18.2 antibody binding sites per cell, less than 6000 anti-CLDN18.2 antibody binding sites per cell, or less than 5000 anti-CLDN18.2 antibody binding sites per cell, or less than 4000 anti-CLDN18.2 antibody binding sites per cell.

ADCC

To assess ADCC activity of a molecule of interest, an in vitro ADCC assay, such as that described in U.S. Pat. No. 5,500,362; Hellstrom et al. Proc Natl Acad Sci USA 83, 7059-7063 (1986) and Hellstrom et al, Proc Natl Acad Sci USA 82, 1499-1502 (1985); U.S. Pat. No. 5,821,337; or Bruggemann et al, J Exp Med 166, 1351-1361 (1987) may be performed. Alternatively, non-radioactive assays methods may be employed (see, for example, ACTI™ non-radioactive cytotoxicity assay for flow cytometry (Cell Technology Inc., Mountain View, CA); and CytoTox 96® non-radioactive cytotoxicity assay (Promega, Madison, WI)). Additionally, ADCC activity of the molecule of interest may be assessed in vivo, e.g., in an animal model such as that disclosed in Clynes et al., PNAS (USA) 95:652-656 (1998).

ADCC activity of an antibody can be enhanced by engineering the glycosylation forms of the antibody. A number of glycosylation forms have been reported to enhance ADCC activity of an antibody through enhancing its binding to the Fc receptor of the effector cells. The different glycosylation form includes any of several forms of glycans attached to the antibody, with different saccharides (e.g., lacks one type of saccharide such as fucose, or has a high level of one type of saccharide such as mannose), or having a different structure (e.g., various branched structure, such as biantennary (two branches), triantennary (three branches) or tetraantennary (four branches) structures).

In certain embodiments, the anti-CLDN18 antibodies provided herein are glyco-engineered. A "glyco-engineered" antibody or antigen-binding fragment may have an increased or decreased glycosylation level, a change in the glycosylation form, or both, as compared to its non-glyco-engineered counterpart. In certain embodiments, the glyco-engineered antibodies exhibit enhanced ADCC activity than its non-engineered counterpart. In some embodiments, the enhanced ADCC activity is characterized in at least 10%, 15%, 20%, 25%, 30%, 35%, 40%, 45%, 50%, 60%, 65%, 70%, or 75% higher lysis of CLDN18.2 expressing cell.

The antibodies can be glyco-engineered by methods known in the art, including any manipulation to the peptide backbone (e.g., modifications to the amino acid sequence, and/or to the side chain group of individual amino acids), and/or, manipulation to the post-translational modifications through a host cell line (e.g., modifications to glycosylation pattern). Methods of altering ADCC activity by engineering of glycosylation of an antibody have also been described in the art, see for example, Weikert et al. (1999) Nature Biotech., 17:116-121; Shields R. L. et al. (2002), J. Biol. Chem., 277: 26733-26740; Shinkawa et al. (2003), J Biol Chem., 278, 3466-3473; Ferrara et al. (2006), Biotech. Bioeng., 93, 851-861; Yamane-Ohnuki et al. (2004), Biotech Bioeng., 87, 614-622; Niwa et al. (2006), J Immunol Methods 306, 151-160; Shinkawa T. et al, J. Biol. Chem, (2003), 278: 3466-3473.

In some embodiments, the glyco-engineered antibodies provided herein are afucosylated (i.e. contain no fucose). Several studies have shown that afucosylated (i.e., fucose deficient, or non-fucosylated) antibody exhibited an increased binding to CLDN18.2 and thus provoked a higher ADCC activity (Shields et al. (2002) J. Biol. Chem., 277: 26733-26740; Shinkawa et al. (2003) J. Biol. Chem., 278: 3466-3473; and European Patent Appln. Pub. No. 1176195). In some embodiments, the afucosylated antibody provided herein lacks fucose at asparagine 297 (Asn297) of the heavy chain (based on Kabat numbering). Asn297 is a conserved N-linked glycosylation site found in each CH2 domain of the Fc region of IgG1 isotype of antibodies (Arnold et al., Glycobiology and Medicine, 564:27-43, 2005).

In some embodiments, the glyco-engineered antibodies provided herein are characterized in a high mannose glycosylation form (e.g., mannose e5, mannose 7, 8, 9 glycan). High mannose glycosylation form has been proved to enhance ADCC activity (Yu et al. (2012), Landes Bioscience, mAbs 4:4, 475-487).

In some embodiments, the antibody provided herein further comprises within its constant region one or more modifications which: a) introduces or removes a glycosylation site, b) introduces a free cysteine residue, c) enhances binding to an activating Fc receptor, and/or d) enhances ADCC.

Antigen-Binding Fragments

The present disclosure also provides antigen-binding fragments that can specifically bind to CLDN18. Various types of antigen-binding fragments are known in the art and can be developed based on the anti-CLDN18 antibodies provided herein, including for example, the exemplary antibodies whose CDR and variable sequences are shown in Table 1, and their different variants containing modification or substitution.

In certain embodiments, an anti-CLDN18 antigen-binding fragment provided herein is a camelized single domain antibody, a diabody, a single chain Fv fragment (scFv), an scFv dimer, a dsFv, a $(dsFv)_2$, a dsFv-dsFv', an Fv fragment, a Fab, a Fab', a $F(ab')_2$, a ds-diabody, a nanobody, a domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as *E. coli* (e.g. for Fab, Fv and ScFv antibody fragments), screening from a phase display library as discussed above (e.g. for ScFv), and chemical coupling of two Fab'-SH fragments to form $F(ab')_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

Conjugates

In some embodiments, the anti-CLDN18 antibodies further comprise a conjugate moiety. The conjugate moiety can be linked to an antibody provided herein. A conjugate moiety is a non-proteinaceous or peptic moiety that can be attached to the antibody. It is contemplated that a variety of conjugate moieties may be linked to the antibodies provided herein (see, for example, "Conjugate Vaccines", Contributions to Microbiology and Immunology, J. M. Cruse and R. E. Lewis, Jr. (eds.), Carger Press, New York, (1989)). The conjugate moiety may be linked to the antibody by covalent binding, affinity binding, intercalation, coordinate binding, complexation, association, blending, or addition, among other methods.

In certain embodiments, the anti-CLDN18 antibodies is linked to one or more conjugates via a linker. In certain embodiments, the linker is a hydrazine linker, a disulfide linker, a bifunctional linker, dipeptide linker, glucuronide linker, or a thioether linker. In certain embodiments, the linker is a lysosomally cleavable dipeptide, e.g. valine-citrulline (vc).

The conjugate moiety can be a therapeutic agent (e.g., a cytotoxic agent), a radioactive isotope, a detectable label (e.g., a lanthanide, a luminescent label, a fluorescent label, or an enzyme-substrate label), a pharmacokinetic modifying moiety, or a purifying moiety (such as a magnetic bead or nanoparticle).

Examples of detectable label may include a fluorescent label (e.g. fluorescein, rhodamine, dansyl, phycoerythrin, or Texas Red), enzyme-substrate label (e.g. horseradish peroxidase, alkaline phosphatase, luceriferases, glucoamylase, lysozyme, saccharide oxidases or β-D-galactosidase), radioisotope, luminescent label, chromophoric moiety, digoxigenin, biotin/avidin, a DNA molecule or gold for detection.

Examples of radioisotopes may include $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$ and other lanthanides. Radioisotope labelled antibodies are useful in receptor targeted imaging experiments.

In certain embodiments, the pharmacokinetic modifying moiety can be a clearance-modifying agent which helps increase half-life of the antibody. Illustrative examples include water-soluble polymers, such as PEG, carboxymethylcellulose, dextran, polyvinyl alcohol, polyvinyl pyrrolidone, copolymers of ethylene glycol/propylene glycol, and the like. The polymers may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead or a nanoparticle.

Antibody-Drug Conjugates

In certain embodiments, the conjugates provided herein are antibody-drug conjugates (ADC) comprising any of the above anti-CLDN18 antibodies conjugated to a cytotoxic agent. In other words, the conjugate moiety comprises a cytotoxic agent.

ADCs can be useful for local delivery of a cytotoxic agent, for example, in the treatment of cancer. This allows for targeted delivery of cytotoxic agents to tumors and intracellular accumulation therein, which is particularly useful where systemic administration of these unconjugated cytotoxic agents may result in unacceptable levels of toxicity to normal cells as well as the tumor cells sought to be eliminated (Baldwin et al., (1986), Lancet, 603-05; Thorpe, (1985), Monoclonal Antibodies, 84; Pinchera et al. (ed.s), Biological And Clinical Applications, 475-506; Syrigos and Epenetos (1999), Anticancer Research 19:605-614; Niculescu-Duvaz and Springer (1997) Adv. Drg Del. Rev. 26:151-172; and U.S. Pat. No. 4,975,278).

A "cytotoxic agent" can be any agent that is detrimental to cancer cells or that can damage or kill cancer cells. In certain embodiments, the cytotoxic agent is optionally a chemotherapeutic agent (such as a growth inhibitory agent, a DNA-alkylators, a topoisomerase inhibitor, a tubulin-binders, or other anticancer drugs), a toxin, or a highly reactive radioactive isotope.

Examples of cytotoxic agent include large molecular bacterial toxins and plant toxins, such as for example, diphtheria toxin, exotoxin A chain (from *Pseudomonas aeruginosa*), ricin, abrin, modeccin, alpha-sarcin, *Aleurites fordii*, proteins, dianthin proteins, *Phytolaca americana* proteins (PART, PAPII, and PAP-S), *Momordica charantia* inhibitor, curcin, crotin, *Sapaonaria officinalis* inhibitor, gelonin, restrictocin, phenomycin, enomycin, and the tricothecenes (see, e.g., WO 93/21232). Such a large molecule toxin can be conjugated to the antibodies provided herein using methods known in the art, for example, as described in Vitetta et al (1987) Science, 238:1098.

The cytotoxic agent can also be small molecule toxins and chemotherapeutic drugs, such as geldanamycin (Mandler et al (2000) Jour. of the Nat. Cancer Inst. 92(19):1573-1581; Mandler et al (2002) Bioconjugate Chem. 13:786-791), maytansinoids (EP 1391213; Liu et al., (1996) Proc. Natl. Acad. Sci. USA 93:8618-8623), calicheamicin (Lode et al (1998) Cancer Res. 58:2928; Hinman et al (1993) Cancer Res. 53:3336-3342), taxol, cytochalasin B, gramicidin D, ethidium bromide, emetine, mitomycin, etoposide, tenoposide, vincristine, vinblastine, vindesine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), calicheamicin, maytansinoids, dolastatins, auristatins (such as monomethyl auristatin E (MMAE) and Monomethyl auristatin F (MMAF)), a trichothecene, and CC1065, and the derivatives thereof having cytotoxic activity. Such toxin can be conjugated to the antibodies provided herein using methods known in the art, for example, as described in U.S. Pat. No. 7,964,566; Kline, T. et al, Pharmaceutical Research, 32(11): 3480-3493.

The cytotoxic agent can also be a highly radioactive isotope. Examples include $At^{211}$, $I^{131}$, $I^{125}$, $Y^{90}$, $Re^{186}$, $Sm^{153}$, $Bi^{212}$, $P^{32}$, $Pb^{212}$ and radioactive isotopes of Lu. Methods of conjugation of a radioisotope to an antibody is known in the art, for example, via a suitable ligand reagent (see, e.g., WO94/11026; Current Protocols in Immunology, Volumes 1 and 2, Coligen et al, Ed. Wiley-Interscience, New York, N.Y., Pubs. (1991)). A ligand reagent has a chelating ligand that can bind, chelate or otherwise complex a radioisotope metal, and also has a functional group that is reactive with a thiol of cysteine of an antibody or antigen-binding fragment. Exemplary chelating ligands include DOTA, DOTP, DOTMA, DTPA and TETA (Macrocyclics, Dallas, Tex.).

In certain embodiments, the antibodies are attached to the conjugate moiety via a linker, for example, a hydrazine linker, a disulfide linker, a bifunctional linker, dipeptide linker, glucuronide linker, or a thioether linker.

Exemplary bifunctional linkers include, such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluom-2,4-dinitrobenzene).

In certain embodiments, the linker is cleavable under a particular physiological environment, thereby facilitating release of the cytotoxic agent in the cell. For example, the linker can be an acid-labile linker, peptidase-sensitive linker, photolabile linker, dimethyl linker or disulfide-containing linker (Chari et al., Cancer Research 52:127-131 (1992); U.S. Pat. No. 5,208,020). In some embodiments, the linker may comprise amino acid residues, such as a dipeptide, a tripeptide, a tetrapeptide or a pentapeptide. The amino acid residues in the linker may be natural or non-naturally occurring amino acid residues. Examples of such linkers include: valine-citrulline (ye or val-cit), alanine-phenylalanine (af or ala-phe), glycine-valine-citrulline (gly-yal-cit), glycine-glycine-glycine (gly-gly-gly), an valine-citrullin-p-aminobenzyloxycaronyl ("vc-PAB"). Amino acid linker components can be designed and optimized in their selectivity for enzymatic cleavage by a particular enzyme, for example, a tumor-associated protease, cathepsin B, C and D, or a plasmin protease.

The ADC provided herein may be prepared by any suitable methods known in the art. In certain embodiments, a nucleophilic group of the antibody is first reacted with a bifunctional linker reagent and then linked to the cytotoxic agent, or the other way around, i.e., first reacting a nucleophilic of the cytotoxic agent with a bifunctional linker and then linking to the antibody.

In certain embodiments, the cytotoxic agent may contain (or modified to contain) a thiol reactive functional group which may react with a cysteine thiol of a free cysteine of the antibodies provided herein. Exemplary thiol-reactive functional group include, for example, a maleimide, an iodoacetamide, a pyridyl disulfide, haloacetyl, succinimidyl ester (e.g., NHS, N-hydroxysuccinimide), isothiocyanate, sulfonyl chloride, 2,6-dichlorotriazinyl, pentafluorophenyl ester, or phosphoramidite (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

The cytotoxic agent or the antibody may react with a linking reagent before being conjugated to form the ADC. For example, N-hydroxysuccinimidyl ester (NHS) of a cytotoxic agent may be performed, isolated, purified, and/or characterized, or it may be formed in situ and reacted with a nucleophilic group of an antibody.

In some embodiments, the cytotoxic agent and the antibody may be linked by in situ activation and reaction to form the ADC in one step. In another example, the antibody may be conjugated to biotin, then indirectly conjugated to a second conjugate that is conjugated to avidin.

In certain embodiments, the conjugate moiety is randomly attached to a specific type of surface-exposed amino acid residue in the antibody, for example a cysteine residue or a lysine residue.

In certain embodiments, the conjugate moiety is attached to a specifically defined site to provide ADC populations with high homogeneity and batch-to-batch consistency with respect to drug-to-antibody ratio (DAR) and attachment site. In certain embodiments, the conjugate moiety is attached to specifically defined sites in antibody molecules via natural amino acids, unnatural amino acid, short peptide tags, or Asn297 glycans. For example, the conjugation may be at a specific site outside the epitope binding portion.

Site-specific attachment can be achieved by substituting a native amino acid at a specific site of the antibody with, or introducing before/after a specific site of the antibody, an amino acid such as cysteine to which a drug moiety can be conjugated (see Stimmel et al. (2000), JBC, 275(39):30445-30450; Junutula et al. (2008), Nature Biotechnology, 26(8): 925-932; and WO2006/065533). Alternatively, site-specific conjugation can be achieved by engineering antibodies to contain unnatural amino acids (e.g., p-acetylphenylalanine (pAcF), N6-((2-azidoethoxy)carbonyl)-L-lysine, p-azidomethyl-L-phenylalanine (pAMF), and selenocysteine (Sec)) at specific sites in their heavy and/or light chains as described by Axup et al. ((2012), Proc Natl Acad Sci USA. 109(40): 16101-16116), wherein the unnatural amino acids provide the additional advantage that orthogonal chemistry can be designed to attach the linker reagent and drug. Exemplary specific sites (e.g., light chain V205, heavy chain A114, S239, H274, Q295, S396, etc.) useful in the two above-described site-specific conjugation method are described in many prior arts, for example, Strop et al. (2013), Chemistry & Biology, 20, 161-167; Qun Zhou (2017), Biomedicines, 5, 64; Dimasi et al. (2017), Mol. Pharm., 14, 1501-1516; WO2013/093809 and WO2011/005481. Another site-specific ADC conjugation method is glycan-mediated conjugation, in which a drug-linker can be conjugated to Asn297 glycans (such as fucose, galactose, N-acetylgalactosamine, N-acetylglucosamine, sialic acid) located in CH2 domain instead of coupling the relatively hydrophobic cytotoxic agent into amino acid backbone of the antibody. Efforts have also been made to introduce unique short peptide tags (such as LLQG, LPETG, LCxPxR) into antibodies via specific sites (e.g., sites in N terminal or C terminal regions), which then allow specific amino acids in the peptide tags to be functionalized and coupled to the drug-linkers (Strop et al. (2013), Chemistry & Biology, 20, 161-167; Beerli et al. (2015), PLoS ONE, 10, e0131177; Wu et al. (2009), Proc. Natl. Acad. Sci. 106, 3000-3005; Rabuka (2012), Nat. Protoc. 7, 1052-1067).

Polynucleotides and Recombinant Methods

The present disclosure provides isolated polynucleotides that encode the anti-CLDN18 antibodies provided herein.

The term "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

In certain embodiments, the isolated polynucleotides comprise one or more nucleotide sequences as shown in Table 3, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions, and encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

TABLE 3

| Polynucleotides of variable regions of the exemplary antibodies | | |
|---|---|---|
| Anti-body ID No. | Vari-able Chain | Polynucleotide of Each Variable Chain |
| Ab01 | VH | SEQ ID NO: 24<br>GATGTACAGCTTCAGGAGTCAGGACCTGGC<br>CTCGTGAAACCTTCTCAGTCTCTGTCTCTC<br>ACCTGCTCTGTCACTGGCTACTCCATCACC<br>AGTGGTTATTACTGGAACTGGATCCGGCAG<br>TTTCCAGGAAACAAATTGGAATGGATGGGC<br>TACATAACCTACGATGGTAGCAATAACTAC<br>AACCCATCTCTCAAAAATCGAATCTCCATC<br>ACTCGTGACACATCTAAGAACCAGTTTTTC<br>CTGAAGTTGAATTCTGTGACTACTGAGGAC<br>GCAGCCACATATTTCTGTGCAAGAGATCCA<br>AATTACTACGGTACTACCCTACCGGCCTGG<br>TTTGTTTACTGGGGCCAAGGGACTCTGGTC<br>ACTGTCTCTGCA |
| | VL | SEQ ID NO: 33<br>GACATTGTGGTGACCCAGTCTCACAAATTC<br>ATGTCCACATCAGTAGGAGACAGGGTCAGC<br>ATCACCTGCAAGGCCAGTCAGGATGTGGGT<br>ACTGCTGTAGCCTGGTATCAACAGAAACCA<br>GGGCAATCTCCTAAATTACTGATTTACTGG<br>GCATCCACCCGGCACACTGGAGTCCCTGAT<br>CGCTTCACAGGCAGTGGATCTGGGACAGAT<br>TTCACTCTCACCATTAGCAATGTGCAGTCT<br>GAAGACTTGACAGATTATTTCTGTCAGCAA<br>TATAGCAGCTATGTCACGTTCGGTGCTGGG<br>ACCAAGCTGGAGCTGAAA |
| Ab02 | VH | SEQ ID NO: 42<br>CAGGTGCAGCTGAAGGAGTCAGGACCTGGC<br>CTGGTGGCGCCCTCACAGAGCCTGTCCATC<br>ACATGCACTGTCTCTGGGTTCTCATTAACC<br>AGCTATGCTATAAACTGGGTTCGCCAGCCA<br>CCAGGAAAGGGTCTGGAGTGGCTTGGAGTA<br>ATTTGGACTGGTGGAGGCACAAATTATAAT<br>TCAGCTCTCAAATCCAGACTGAGCATCAAC<br>CAAAGAAACTCCAAGAGTCAAGTTTTCTTA<br>AAAATGAACAGTCTGCAAACTGATGACACA<br>GCCAGGTACTACTGTGCCCGATTCTATGAT<br>GGTTACTACTCCTGGTTTGCTTACTGGGGC<br>CAAGGGACTCTGGTCACTGTCTCTGCA |
| | VL | SEQ ID NO: 51<br>GACATTGTGATGACCCAGTCTCACAAATTC<br>ATGTCCACATCAGTAGGAGACAGGGTCAGC<br>ATCACCTGCAAGGCCAGTCAGGATGTGGGT<br>ACTGCTGTAACCTGGTATCAACAGAAACCA<br>GGGCAATCTCCTAAACTACTGATTTACTGG<br>GCATCCACCCGGCACACTGGAGTCCCTGAT<br>CGCTTCACAGGCAGTGGATCTGGGACAGAT<br>TTCACTCTCACCATTAGCAATGTGCAGTCT<br>GAAGACTTGGCAGATTATTTCTGTCAACAA<br>TATAGTAGCTATCCATTCACGTTCGGCTCG<br>GGGACAAAGTTGGAAATAAAA |
| Ab03 | VH | SEQ ID NO: 60<br>GAGGTCCAGCTGCAACAGTCTGGACCTGAG<br>CTGGTGAAGCCTGGGGCTTCAGTGAAGATA<br>GCCTGCAAGGCTTCTGGATACACATTCACT<br>GACTACAACATGGACTGGGTGAAGCAGAGC<br>CATGGAAAGAGCCTTGAGTGGATTGGAAAT<br>ATTAATTCTTATTATGGTGGTACTATCTAT<br>AATCAGAAATTCAAAGGCAAGGCCACATTG<br>ACTGTAGACAAGTCTTCCAGCACAGCCTAC<br>ATGGTCCTCCGCAGCCTGACATCTGAGGAC<br>AATGCAGTCTATTACTGTGCAAGACCCCAC<br>TTGGGGAATGCTCTGGACTACTGGGGTCAA<br>GGAACCTCAATCACCGTCTCCTCA |
| | VL | SEQ ID NO: 69<br>GACATTGTGGTGACACAGTCTCCATCCTCC<br>CTGACTGTGACACCAGGAGAAAAGGTCACT |

TABLE 3-continued

| Polynucleotides of variable regions of the exemplary antibodies | | |
|---|---|---|
| Anti-body ID No. | Vari-able Chain | Polynucleotide of Each Variable Chain |
| | | ATGAGCTGCAAGTCCAGTCAGAGTCTGTTT<br>AACAGTGGAAATCAAAAGAACTACTTGTCC<br>TGGTACCAGCAGAAACCCAGGGCAGCCTCCT<br>AAACTGTTGATCTACTGGGCATCCACTAGG<br>CAATCTGGGGTCCCTGATCGCTTCACTGGC<br>AGTGGATCTGGAACAGATTTCACTCTCACC<br>ATCAGCAGTGTGCAGGCTGAAGACCTGGCA<br>GGTTATTACTGTCAGAATGATTATATTTTT<br>CCGCTCACGTTCGGTGCTGGGACCAAGCTG<br>GAGCTGAAA |
| Ab04 | VH | SEQ ID NO: 78<br>GAGGTCCAGCTGCAACAGTCTGGACCTGAG<br>CTGGTGAAGCCTGGGGCTTCAGTGAAGATG<br>TCCTGCATGGCTTCTGGATACACATTCACT<br>GACTACAACATACACTGGGTGAAGCGGAGC<br>CATGGATCCCGTCTTGAGTGGATTGGATAT<br>ATTAGTCCTATCAGTGGTGGTGCTGGCTAC<br>AACCAGAAGTTCATGGACAAGGCCACATTG<br>ACTGTAGACAAGTCCTCCAACACAGCCTAC<br>ATGGAGCTCCGCAGCCTGACATCGGAAGAT<br>TCTGCAGTCTATTACTGTACAAGAGGGGAC<br>TACTGGGGCCAGGGCACCACTCTCACAGTC<br>TCCTCA |
| | VL | SEQ ID NO: 87<br>GACATTGTGATGACACAGTCTCCATCCTCC<br>CTGGCTGTGACAGTAGGAGAGAAGGTCACT<br>ATGAGCTGCAAGTCCAGTCAGAGTCTGTTA<br>AACAGTGGAAATCAAAAGAACTACTTGACC<br>TGGTATCAGCAGAAACCAGGGCAGCCTCCT<br>AAATTGTTGATCTACTGGGCATCCACTAGG<br>AAATCTGGGGTCCCTGATCGCTTCACAGGC<br>AGTGGATCTGGAACAGATTTCACTCTCACC<br>ATCAGCAGTGTGCAGGCTGAAGACCTGGGA<br>ATTTATTACTGTCTGAATGATTATGGTTTT<br>CCGCTCACGTTCGGTGCTGGGTCCAAGCTG<br>GAGCTGAAA |
| Ab05 | VH | SEQ ID NO: 96<br>GACGTGAAGTTGGTGGAGTCTGGGGAAGAC<br>TTAGTGAAGCCTGGAGGGTCCCTGAAACTC<br>TCCTGTGCTGCCTCTGGGTTCACTTTCAGT<br>GAACTATCCATGTCTTGGGTTCGCCAGACT<br>CCAGAGAAGAGGCTGGAGTGGGTCGCATAT<br>GTTAGTAGTGGTGGTGATTACATCTACTAT<br>GCAGACACTGTGAAGGGCCGATTCATCATC<br>TCCAGAGACAATGCCAGGAACACCCTGTAC<br>CTGCAAATGAACAGTCTGAGGTCTGAGGAC<br>ACAGCCATGTATTACTGTGCAAGAGTCTAC<br>TTTGGTAACTCCCTTGACTACTGGGGCCAA<br>GGCACCACTCTCACAGTCTCCTCA |
| | VL | SEQ ID NO: 105<br>GACATTGTGATGACACAGTCTCCATCCTCC<br>CTGACTGTGACAGCAGGAGAGAAGGTCACT<br>CTGAGCTGCAAGTCCAGTCAGAGTCTCTTA<br>AATGGTGGAAATCAAAAGAACTACTTGACC<br>TGGTACCAGCAGAGACCAGGACAGCCTCCT<br>AAACTGTTGATCTACTGGGCATCCACTAGG<br>GAATCTGGGGTCCCTGATCGCTTCACAGGC<br>AGTGGATCTGGAACAGATTTCACTCTCATC<br>ATCAGCAGTGTGCAGGCTGAAGACCTGGCA<br>GTTTATTACTGTCAGAATGATTATTATTAT<br>CCGTGGACGTTCGGTGGAGGCACCAAGCTG<br>GAAATCAAA |
| Ab06 | VH | SEQ ID NO: 114<br>GAAGTGCAGCTGGTGGCGTCTGGGGGAGGC<br>TTAGTGAAGCCTGGAGGGTCCCTGAAACTC<br>TCCTGTGCAGCCTCTGGAATCACTTTCAGA<br>AGTTATGCCATGTCTTGGGTTCGCCAGACT |

TABLE 3-continued

Polynucleotides of variable regions of the exemplary antibodies

| Antibody ID No. | Variable Chain | Polynucleotide of Each Variable Chain |
|---|---|---|
| | | CCGGAAAAGAGGCTGGAGTGGGTCGCAACC<br>ATTACTGATGGTGGTAGTTACATCTTCTAT<br>CCAGACAATGTAAAGGGCCGATTCACCATC<br>TCCGGAGACCATGCCAAGAACAACCTGTAC<br>CTGCAAATGAGCCATCTGAAGTCTGAGGAC<br>ACAGCCTTGTATTTCTGTGTAAGACTCTAC<br>TATGGAAACTCGTTTGCTTACTGGGGCCAA<br>GGGACTCTGGTCACTGTCTCTGCA |
| | | SEQ ID NO: 123 |
| | VL | GACATTGTGATGACACAGTCTCCATCCTCC<br>CTGACTGTGACAGCAGGAGAGAAGGTCACT<br>TTGAACTGCAAGTCCAGTCAGAGTCTGTTC<br>AACAGTGGAAATCAAAAGAACTACTTGACC<br>TGGTACCAGCAGAAACCAGGGCAGCCTCCT<br>AAACTGTTGATCTACTGGGCATCCACTAGG<br>GAATCTGGGGTCCCTGATCGCTTCACAGGC<br>AGTGGATCTGGAACAGATTTCACTCTCACC<br>TTCAGCAGTGTGCAGGCTGAAGACCTGGCA<br>GTTTATTACTGTCAGAATGCTTATATTTAT<br>CCATTCACGTTCGGCTCGGGGACAAAATTG<br>GAAATAAAA |
| | | SEQ ID NO: 132 |
| Ab07 | VH | GAGGTTCAGCTGCAGCAGTCTGGACCTGAG<br>CTGGTGAAGCCTGGGGCTTCAGTGAAGATA<br>TCCTGCAAGGCTTCTGGTTACTCATTTACT<br>GACTACTTTATGAACTGGGTGAAGCAGAGC<br>CATGGAAAGGGCCTTGAGTGGATTGGACGT<br>ATTAATCCTTACAATGGTGATACTTTCTAC<br>AACCAGAAGTTCAAGGGCAAGGCCACATTG<br>ACTGTAGACAAATCCTCTAGCACAGCCCAC<br>ATGGAGCTCCTGAGCCTGACATCTGAGGAC<br>TTTGCAGTCTATTATTGTGCCCTCTATGAT<br>GGTTACTGGGGGGCTTTTGTTTACTGGGGC<br>CAAGGGACTCTGGTCACTGTCTCTGCA |
| | | SEQ ID NO: 141 |
| | VL | GACATCCAGATGACTCAGTCTCCAGCCTCC<br>CTCTCTGTATTTGTGGGAGAAACTGTCACC<br>ATCACATGTCGAGCAAGTGAGAATATTTAC<br>AGTAATTTAGCATGGTATCAGCAGAAACAG<br>GGAAAATCTCCTCAGCTCCTGGTCTATGCT<br>GCAACAAACTTAGCAGATGGTGTGCCATCA<br>AGGTTCAGTGGCAGTGGATCAGGCACACAG<br>CTATTCCTCAAGATCAACAGCCTGCAGTCT<br>GAAGATTTTGGGAGTTATTACTGTCAACAT<br>TTTTGGGGTACTCCGCTCACGTTCGGTGCT<br>GGGACCAAGCTGGAGCTGAAA |
| | | SEQ ID NO: 150 |
| Ab08 | VH | CAGGTCCAACTGCAGCAGCCTGGGGCTGAG<br>TTGGTAAAGCCTGGGGCTTCAGTGAAGTTG<br>TCCTGCAAGGCTTCTGGCTACACTTTCACC<br>AGCTACTTACTACACTGGGTGAAACAGAGG<br>CCTGGACAAGGCCTTGAGTGGATTGGAATG<br>ATTCATCCTAATGGTGGTAGTACTAACTAC<br>AATGAGAAGTTCAAGACCAAGGCCACACTG<br>ACTGTAGACAAATCCTCCAGCACAGCCTAC<br>ATGCAACTCAGCAGCCTGACATCTGAGGAC<br>TCTGCGGTCTATTACTGTGCCCCTGTCTAC<br>TTTGGTAACTCGTTTGCTTACTGGGGCCAA<br>GGGACTCTGGTCACTGTCTCTGCA |
| | | SEQ ID NO: 159 |
| | VL | GACATTGTGATGACACAGTCTCCATCCTCC<br>CTGACTGTGACAGCAGGAGAGAAGGTCACT<br>ATGAGCTGCAAGTCCAGTCAGAGTCTGTTA<br>AACAGTGGAAATCAAAAGAACTACTTGACC<br>TGGTACCAGCAAAAACCAGGGCAGCCTCCT<br>AAACTGTTGATCTACTGGGCATCCACTAGG<br>GAATCTGGGGTCCCTGATCGCTTCACAGGC |

TABLE 3-continued

Polynucleotides of variable regions of the exemplary antibodies

| Antibody ID No. | Variable Chain | Polynucleotide of Each Variable Chain |
|---|---|---|
| | | AGTGGATCTGGAACAGATTTCACTCTCACC<br>ATCAGCAGTGTGCAGGCTGAAGACCTGGCA<br>GTTTATTACTGTCAGAATGATTATTATTAT<br>CCATTCACGTTCGGTTCGGGGACAAAGTTG<br>GAAAAAAAA |
| | | SEQ ID NO: 204 |
| Ab09 | VH | GAGGTCCAACTGCAACAGTCTGGACCTGAG<br>GCTGGTAAGCCTGGGACTTCAGTGAAGATG<br>TCCTGCAAGGCTTCTGGATACACATTCACT<br>GACTACAACATGCACTGGGTGAAACTGAGC<br>CATGGAAAGAGCCTTGAGTGGATTGGATAT<br>ATTAACCCTAATAATGGGGGTACTATCTAC<br>AACCAGCGATTCAAGGGCAAGGCCACATTG<br>AACTGTAACAAGTCCTCCAGAACAGCCTAC<br>ATGGACCTCCGCAGCCTGACATCGGAGGAT<br>TCTGCAGTCTATTACTGTGCGCGACAGGGT<br>TACTACGGTAACTCTATGGACTACTGGGGT<br>CAAGGAAATTCAGTCACCGTCTCCTCA |
| | | SEQ ID NO: 213 |
| | VL | GACATTGTGATGACACAGTCTCCATCCTCC<br>CTGACTGTGACACCAGGAGAGAGGGTCACT<br>ATGAGCTGCAAGTCCAGTCAGAGTCTGTTA<br>AACGGTGGAAATCAAAGGAACTACTTGACC<br>TGGTACCAGCAAAAACCAGGGCAGCCTCCT<br>AAACTGTTGATCTACTGGGCATCCACTAGG<br>GAATCTGGGGTCCCTGATCGCTTCGCAGGC<br>AGTGGATCTGGAACAGATTTCACTCTCACC<br>ATCAGCAGAGTGCAGGCTGAAGACCTGTCA<br>TTTTATTACTGTCAGAATTCTTATTTTTAT<br>CCGTTCACGTTCGGCTCGGGGACAAAGTTG<br>GACCTAAGA |
| | | SEQ ID NO: 222 |
| Ab10 | VH | GAAGTGATGCTGGTGGAGTCTGGGGGAGGC<br>TTAGTGAAGCCTGGAGGGTCCCTGAAACTC<br>TCCTGTGCAGCCTCTGGATTCACTTTCAGT<br>AGCTATACCATGTCTTGGGTTCGCCAGACT<br>CCGGAGAAGAGGCTGGAGTGGGTCGCAACC<br>ATTAGTGTTATTGGTGGTAACACCTACTAT<br>GTAGACAGTGTGAAGGGTCGATTCACCATC<br>TCCAGAGACAAAGCCAAGAACACCCTGTAC<br>CTGCAAATGAGCAGTCTGAGGTCTGAGGAC<br>ACGGCCTTATATTACTGTGCAAGACTGGGA<br>CAGACACAGAGAAATGCTATGGACTACTGG<br>GGTCAAGGAACCTCAGTCACCGTCTCCTCA |
| | | SEQ ID NO: 231 |
| | VL | GACATTGTGATGACACAGTCTCCATCCTCT<br>CTGAGTGTGTCAGCAGGAGAGAAGGTCACA<br>ATGAGCTGCAAGTCCAGTCAGAGTCTGTTA<br>AACAGTGGAAATCAAAAGAACTACTTGGCC<br>TGGTACCAGCAGAAACCAGGGCAGCCTCCT<br>AAACTGTTGATCTACGGGGCATCTACTAGG<br>GAATCTGGGGTCCCTGATCGCTTCACAGGC<br>AGTGGATCTGGAACCGATTTCACTCTTACC<br>ATCAGCAGTGTGCAGGCTGAAGACCTGGCA<br>GTTTATTACTGTCAGAATGATTATAGTTAT<br>CCGCTCACGTTCGGTGCTGGGACCAAGCTG<br>GAGCTGAAA |
| | | SEQ ID NO: 240 |
| Ab11 | VH | GAAGTGATGTTGGTGGAATCTGGGGGAGAC<br>TTAGTGAAGCCTGGAGGGTCCCTGAAACTC<br>TCCTGTGCAGCCTCTGGATTCACTTTCAGT<br>CGTTATACCATGTCTTGGGTTCGCCAGACT<br>CCGGAGAAGAGGCTGGAGTGGGTCGCAACC<br>GTTAGTGTTGGTTCTGGTAACACCTACTAT<br>TTAGACAGTGTGAAGGGTCGATTCACCATC<br>TCCAGAGACAATGCCAAGAACACCCTGTTC<br>CTGCAAATGAACAGTCTGAGGTCTGAGGAC |

TABLE 3-continued

| Polynucleotides of variable regions of the exemplary antibodies | | |
|---|---|---|
| Antibody ID No. | Variable Chain | Polynucleotide of Each Variable Chain |
| | | ACGGCCTTATATTACTGTACAAGACTGGGACAGACACAGAGAAATGCTGTGGACTACTGGGGTCAAGGCACCTCAGTCACCGTCTCCTCA |
| | VL | SEQ ID NO: 249 GACATTGTGATGACACAGTCTCCATCCTTCCTGAGTGTGTCAGCGGGAGAGAAGGTCACTATGAGCTGCAAGTCCAGTCAGAGTCTGTTCAACGGTGGAAATCAAAAGAACTACTTGGCCTGGTACCAGCAGAAACCAGGGCAGCCTCCTAAACTGTTGATCTACGGGGCATCCACTAGGGACTCTGGGGTCCCTGATCGCTTCACAGGCAGTGGATCTGGAACCGATTTCACTCTTACCATCAGCAATGTGCAGGCTGAAGACCTGGCAATTTATTTCTGTCAGAATGATCATA |
| Ab12 | VH | SEQ ID NO: 258 GAAGTGATGCTGGTGGAGTCTGGGGGAGGCTTAGTGAAGCCTGGAGGGTCCCTGAAACTCTCCTGTGCAGCCTCTGGATTCACTTTCAGTAGCTATACCATGTCTTGGGTTCGCCAGACTCCGGAGAAGAGGCTGGAGTGGGTCGCAACCATTATTGGTGGTTATGGTAACACCTACTATGCAGACAGTGTGAAGGGTCGATTCACCATCTCCAGAGACAGTGCCAAGAACACCCTGTACCTACAAATGCTCAGTCTGAGGTCTGAGGACACGGCCTTGTATTACTGTACAAGACTGGGACAGACACAGAGAAATGCTATGGACTACTGGGGTCAAGGAACCTCAGTCACCGTCTCCTCA |
| | VL | SEQ ID NO: 267 GACATTTTGATGACACAGTCTCCATCCTCCCTGAGTGTGTCAGCAGGAGAGAAGGTCACTATGAGCTGCAAGTCCAGTCAGAGTCTGTTAAACAGTGGAAATCAAAGGAACTATTTGGCCTGGTACCAACAGAAACCAGGGCAGCCTCCTAAATTGTTGATCTATGGGGCATCCACTAGGGAATCTGGGGTCCCTGATCGCTTCACAGGCAGTGGATCTGGAACCGATTTCACTCTTACCATCAGCAGTGTGCAGGCTGAAGACCTGGCAGTTTATTATTGTCAGAATGATTATTATTATCCACTCACGTTCGGTGCTGGGACCAAGCTGGAGCTGAAA |
| Ab13 | VH | SEQ ID NO: 276 GAAGTGAGGCTGGTGGAGTCTGGGGGAGGCTTAGTGAAGCCTGGAGGGTCCCTGAAACTCTCCTGTGCAGGCTCTGGATTCACTTTCAGTAGCTATACCATGTCTTGGGTTCGCCAGACTCCGGAGAAGAGGCTGGAGTGGGTCGCAACCATTACTATTGGTGTTAACATCTACTATCTAGACAGTGTGAAGGGTCGATTCACCATCTCCAGAGACAATGCCAAGAACACCCTGTACCTGCAAATGAACAGTCTGAGGTCTGAGGACACGGCCTTGTATTATTGTACAAGACTGGGACAGACACAGCGAAATGCTATGGACTACTGGGGTCAAGGAACCTCAGTCACCGTCTCCTCA |
| | VL | SEQ ID NO: 285 GACATTGTGATGACACAGTCTCCAACCTCCCTGAGTGTGTCAGCAGGAGAGAAGGTCACTATGACCTGCAAGTCCAGTCAGAGTCTATTAAACAGTGGAAATCAAAAGAACTACTTGGCCTGGTACCAGGAGAAACCAGGGCAGCCTCCTAAACTGTTGATCTACGGGGCATCCACTAGGGAATCTGGGGTCCCTGATCGCTTCACAGGCAGTGGATCTGGAACCGATTTCACTCTTACCATCAGCAGTGTGCAGGCTGAAGACCTGGCAGTTTATTACTGTCAGAATAATCATTTTTATCCGCTCACTTTCGGTGCTGGGACCAAGCTGGAACTGAAA |

TABLE 3-continued

| Polynucleotides of variable regions of the exemplary antibodies | | |
|---|---|---|
| Antibody ID No. | Variable Chain | Polynucleotide of Each Variable Chain |
| Ab14 | VH | SEQ ID NO: 294 CAGGTCCAACTGCAGCAGCCTGGGGCTGAGTTGGTAAAGCCTGGGGCTTCAGTGAAGTTGTCCTGCAAGGCTTCTGGCTACACTTTCACCAGCTACTTACTACACTGGGTGAAACAGAGGCCTGGACAAGGCCTTGAGTGGATTGGAATGATTCATCCTAATGGTGGTAGTACTAACTACAATGAGAAGTTCAAGACCAAGGCCACACTGACTGTAGACAAATCCTCCAGCACAGCCTACATGCAACTCAGCAGCCTGACATCTGAGGACTCTGCGGTCTATTACTGTGCCCCTGTCTACTTTGGTAACTCGTTTGCTTACTGGGGCCAAGGGACTCTGGTCACTGTCTCTGCA |
| | VL | SEQ ID NO: 303 GACATTGTGATGACACAGTCTCCATCCTCCCTGACTGTGACAGCAGGAGAGAAGGTCACTATGAGCTGCAAGTCCAGTCAGAGTCTGTTAAACAGTGGAAATCAAAAGAACTACTTGACCTGGTACCAGCAAAAACCAGGGCAGCCTCCTAAACTGTTGATCTACTGGGCATCCACTAGGGAATCTGGGGTCCCTGATCGCTTCACAGGCAGTGGATCTGGAACAGATTTCACTCTCACCATCAGCAGTGTGCAGGCTGAAGACCTGGCAGTTTATTACTGTCAGAATGATTATTATTATCCATTCACGTTCGGTTCGGGGACAAAGTTGGAAAAAAAA |
| Ab15 | VH | SEQ ID NO: 312 GAAGTGATGCTGGTGGAGTCTGGGGGAGACTTAGTGAAGCCTGGAGGGTCCCTGAAACTCTCCTGTGCAGCCTCTGGATTCACTTTCAGTACCTATACCATGTCTTGGGTTCGCCAGACTCCGGAGAAGAGGCTGGAGTGGGTCGCAACCATTGTTGGTGGTGGTGGTTACACCTACTATCTAGACAGTGTGAAGGGTCGATTCACCATCTCCAGAGACAATGCCAAGAACACCCTGTACCTGCAAATGATCAGTCTGAGGTCTGAGGACACGGCCTTATATTACTGTGCAAGAATGGGACTGACACAGAGAAATGCTCTGGACTACTGGGGTCAAGGAACCTCAATCACCGTCTCCTCA |
| | VL | SEQ ID NO: 321 GACATTGTGATGACACAGTCTCCATCCTCCCTGAGTGTGTCAGAAGGAGAGAAGGTCACTCTGAACTGCAAGTCCAGTCAGAGTCTGTTCAACAGTGGAAATCAAAAGAACTACTTGGCCTGGTACCAGCAGAAACCAGGGCAGCCTCCTAAACTGTTAATCTACGGGGCATCCACTAGAGAATCTGGGGTCCCTGATCGTTTCACAGGCAGTGGATTTGGCACCGATTTCACTCTTACCATCAGCAGTGTGCAGGCTGAAGACCTGGCAGTTTATTACTGTCAGAATGATCATACTTATCCGCTCACGTTCGGTGCTGGGGCCAAGCTGGAGCTGAAA |
| Ab16 | VH | SEQ ID NO: 330 GAAGTGATGCTGGTGGAGTCTGGGGGAGGCTTAGTGAAGCCTGGAGGGTCCCTGAAACTCTCCTGTGCAGCCTCTGGATTCACTTTCAATAGTTATACCATGTCTTGGGTTCGCCAGACTCCGGAGAAGAGGCTGGAGTGGGTCGCAACCATTACTGTTATTGGTGGTAACACCTACTATTTAGACAGTGTGAAGGGTCGATTCACCATTTCCATAGACAATGGCAAGAACACCCTGTACCTGCAAATGAGCAGTCTGAGGTCTGAGGACACGGCCTTGTATTACTGTGCAAGAATGGGACAGACACAGAGAAATGCTATGGACTACTGGGGTCAAGGAACCTCAGTCACCGTCTCCTCA |
| | VL | SEQ ID NO: 339 GACATTGTGATGACACAGTCTCCATCCTCC |

TABLE 3-continued

Polynucleotides of variable regions of the exemplary antibodies

| Antibody ID No. | Variable Chain | Polynucleotide of Each Variable Chain |
|---|---|---|
| | | CTGAGTGTGTCAGCAGGACAGAAGGTCACT<br>ATGAGGTGCAAGTCCAGTCAGAGTCTGTTA<br>AACAGTGGAAATCAAAAGAACTACTTGGCC<br>TGGTATCAGCAGAAACTAGGGCAGCCTCCT<br>AAACTACTGATCTACGGGGCATCCACTAGG<br>GAATCTGGGGTCCCTGATCGCTTCTCAGGC<br>AGTGGATCTGGAACCGATTTCACTCTTACC<br>ATCACCAGTGTGCAGGCTGAAGACCTGGCA<br>GTTTATTACTGTCAGAATGATTATAGTTTT<br>CCGCTCACGTTCGGTGCTGGGACCAAGCTG<br>GAGCTGAAA |
| | | SEQ ID NO: 348 |
| Ab17 | VH | CAGGTGCAGCTGAAGGAGTCAGGACCTGGC<br>CTGGTGGCGCCCTCACAGAGCCTGTCCATC<br>ACATGCACTGTCTCTGGGTTCTCATTAACC<br>AGCTATGCTATAAGCTGGGTTCGCCAGCCA<br>CCAGGAAAGGGTCTGGAGTGGCTTGGAGAA<br>ATATGGACTGGTGGAGGCACAAATTATAAT<br>TCAGCTCTCAAATCCAGACTGAGCATCAGC<br>AAAGACAACTCCAAGAGTCAAGTTTTCTTA<br>AAAATGAACAGTCTGCAAACTGATGACACA<br>GCCAGGTACTACTGTGGCAGACTTTCCTAT<br>GGTAATTCCCTTGACTACTGGGGCCAAGGC<br>ACCACTCTCACAGTCTCCTCA |
| | | SEQ ID NO: 357 |
| | VL | GACATTGTGATGACACAGTCTCCATCCTCC<br>CTGACTGTGACAGCAGGAGAGAAGGTCACT<br>ATGAGTTGCAAGTCCAGTCAGAGTCTGTTA<br>AACAGTGGAAATCAAAAGAACTACTTGACC<br>TGGTACCAGCAGAAACCAGGGCAGCCTCCT<br>AAACTGTTGATCTACTGGGCATCCACTAGG<br>GAATCTGGGGTCCCTGATCGCTTCACTGGC<br>AGTGGATCTGGAACAGATTTCACTCTCACC<br>GTCAGCAGTGTGCAGGCTGAAGACCTGGCA<br>GTTTATTACTGTCAGAATAATTTTATTTAT<br>CCTCTCACGTTCGGTCCTGGGACCAAGCTG<br>GAGTTGAAA |
| | | SEQ ID NO: 366 |
| Ab18 | VH | CAGGTGCAGCTGAAGGAGTCAGGACCTGGC<br>CTGGTGGCGCCCTCACAGAGCCTGTCCATC<br>ACATGCACTGTCTCAGGGTTCTCATTAACC<br>ACCTATGGTATAAACTGGGTTCGCCAGCCT<br>CCAGGAAAGGGTCTGGAGTGGCTGGGAGTC<br>ATATGGGGTGACGGGAGCACAAATTATCAT<br>TCAGCTCTCATATCCAGACTGAGCATCAGC<br>AAGGATAACTCCAAGAGCCAAGTTTTCTTA<br>AAACTGAACAGTCTGCAAACTGATGACACA<br>GCCACGTACTACTGTGTCAAATCCTCTTAC<br>TACGGTAATGCTATGGACTACTGGGGTCAA<br>GGAACCTCAGTCACCGTCTCCTCA |
| | | SEQ ID NO: 375 |
| | VL | GACATTGTGATGACTCAGTCTCCATCCTCC<br>CTGACTGTGACAGCAGGAGAGACGGTCACT<br>ATGAGCTGCAAGTCCAGTCAGAGTCTGTTA<br>AACAGTGGAAATCAAAAGAACTACTTGACC<br>TGGTACCAGCAGAAACCAGGGCAGCCTCCT<br>AAACTGTTGATCTACTGGGCATCCACTAGG<br>GAATCTGGGGTCCCTGATCGCTTCACAGGC<br>AGTGGATCTGGAACAGATTTCACTCTCACC<br>ATCAGCAGTGTGCAGGCTGAAGACCTGGCA<br>GTTTATTACTGTCAGAATGTTTATAGTTAT<br>CCATTCACGTTCGGCTCGGGGACAAAGTTG<br>GAAATAAAA |
| | | SEQ ID NO: 384 |
| Ab19 | VH | GAAGTGATGCTGGTGGAGTCTGGGGGAGAC<br>TTAGTGAAGCCTGGAGGGTCCCTGAAACTC<br>TCCTGTGCAGCCTCTGGATTCAGTTTCAGT |

TABLE 3-continued

Polynucleotides of variable regions of the exemplary antibodies

| Antibody ID No. | Variable Chain | Polynucleotide of Each Variable Chain |
|---|---|---|
| | | CGCTATACCATGTCTTGGGTTCGCCAGACT<br>CCGGAGAAGAGGCTGGAGTGGGTCGCAACC<br>GTTAGTGTTGGTTCTGGTAACACCTACTAT<br>TTAGACAGTGTGAAGGGTCGATTCACCATC<br>TCCAGAGACAATGCCAAGAACACCCTGTTC<br>CTGCAAATGAGTAGTCTGAGGTCTGAGGAC<br>ACGGCCTTATATTACTGTGCAAGAATGGGA<br>CAGACACAGAGAAATGCTGTGGACTACTGG<br>GGTCAAGGCACCTCAGTCACCGTCTCCTCA |
| | | SEQ ID NO: 393 |
| | VL | GACATTGTGATGACACAGTCTCCATCCTCC<br>TTGAGTGTGTCAGCAGGAGAGAAGGTCACT<br>ATGAGCTGCAAGTCCAGTCAGAGTCTGTTC<br>AACAGTGGAAATCAAAAGAACTACTTGGCC<br>TGGTACCAGCAGAAACCAGGGCAGCCTCCT<br>AAGCTGTTGATCTACGGGGCATCCACTAGG<br>GAATCTGGGGTCCCTGATCGCTTCACAGGC<br>AGTGGATCTGGAACCGATTTCACTCTTACC<br>ATCAGCAATGTGCAGGCTGAAGACCTGGCA<br>GTTTATCTCTGTCAGAATGATCATAGTTTT<br>CCGCTGACGTTCGGTGCTGGGACCAAGCTG<br>GAGCTGAGA |
| | | SEQ ID NO: 402 |
| Ab20 | VH | GAAGTGATGCTGGTGGAGTCTGGGGGAGGC<br>TTAGTGAAGCCTGGAGGGTCCCTGAAACTC<br>TCCTGTGTAGCCTCTGGATTCACTTTCAGT<br>AGTTATACCATGTCTTGGGTTCGCCAGACT<br>CCGGAGAAGAGGCTGGAGTGGGTCGCAACC<br>ATTATTGGTGGTTATGGTAACACCTACTAT<br>TCAGACAGTGTGAAGGGTCGAATCACCATC<br>TCCAGAGACAGCGCCAAGAACACCCTGTAC<br>CTGCAAATGATCAGTCTGAGGTCTGAGGAC<br>ACGGCCTTGTATTACTGTACAAGACTGGGA<br>CAGACACAGAGAAATGCTATGGACTACTGG<br>GGTCAAGGAACCTCAGTCACCGTCTCCTCA |
| | | SEQ ID NO: 411 |
| | VL | GACATTTTGATGACACAGTCTCCATCCTCC<br>CTGAGTGTGTCAGCAGGAGAGAAGGTCACT<br>ATGAACTGCAAGTCCAGTCAGAGTCTGTTA<br>AACAGTGGAAATCAAAAGAACTATTTGGCC<br>TGGTACCAGCAGAAACCAGGGCAGCCTCCT<br>AAATTGTTGATCTATGGGGCATCCACTAGG<br>GAATCTGGGGTCCCTGATCGCTTCACAGGC<br>AGTGGATCTGGAACCGATTTCACTCTTACC<br>ATCAGCAGTGTGCAGGCTGAAGACCTGGCA<br>GTTTATTACTGTCAGAATGATTATTATTAT<br>CCATTCACGTTCGGTGCTGGGACCAAGCTG<br>GAGCTGAAA |
| | | SEQ ID NO: 420 |
| Ab21 | VH | GAAGTGATGCTGGTGGAATCTGGGGGAGGC<br>TTAGTGAAGCCTGGAGGGTCCCTGAAACTC<br>TCCTGTGCAGCCTCTGGATTCACTTTCAGT<br>AGCTATACCATGTCTTGGGTTCGCCAGACT<br>CCGGAGAAGAGACTGGAGTGGGTCGCAACC<br>ATTATTGGTGGTTATGGTAACACCTACTAT<br>GTAGACAGTGTGAAGGGTCGATTCACCATC<br>TCCAGAGACAGTGCCAAGAACACCCTCTAC<br>CTACAAATGATCAGTCTGAGGTCTGAGGAC<br>ACGGCCTTGTATTACTGTACAAGACTGGGA<br>CAGACACAGAGAAATGCTATGGACTACTGG<br>GGTCAAGGAACCTCAGTCACCGTCTCCTCA |
| | | SEQ ID NO: 429 |
| | VL | GACATTTTGATGACACAGTCTCCATCCTCC<br>CTGAGTGTGTCAGCAGGAGAGAAGGTCACT<br>ATGAGCTGCAAGTCCAGTCAGAGTCTGTTA<br>AACAGTGGAAATCAAAAGAACTATTTGGCC<br>TGGTACCAGCAGAAACCAGGGCAGCCTCCT |

TABLE 3-continued

| Polynucleotides of variable regions of the exemplary antibodies | | |
|---|---|---|
| Anti-body ID No. | Vari-able Chain | Polynucleotide of Each Variable Chain |
| | | AAATTATTGATCTATGGGGCATCTACTAGG<br>GAATCTGGGGTCCCTGATCGCTTCACAGGC<br>AGTGGATCTGGAACCGATTTCACTCTTACC<br>ATCAGCAGTGTGCAGGCTGAAGACCTGGCA<br>GTTTATTATTGTCAGAATGATTATTATTAT<br>CCGTTCACGTTCGGTGCTGGGACCAAGCTG<br>GAGCTGAAA |
| Ab22 | VH | SEQ ID NO: 438<br>GAAGTGATGCTGGTGGAGTCTGGGGGAGGC<br>TTAGTGAAGCCTGGAGGGTCCCTGAAACTC<br>TCCTGTGCAGCCTCTGGATTCACTTTCAGT<br>AGCTATACCATGTCTTGGGTTCGCCAGACT<br>CCGGAGAAGAGGCTGGAGTGGGTCGCAACC<br>ATTATTGGTGGTTATGGTAACACCTACTAT<br>GCAGACAGTGTGAAGGGTCGATTCACCATC<br>TCCAGAGACAGTGCCAAGAACACCCTGTAC<br>CTGCAAATGATCAGTCTGAGGTCTGAGGAC<br>ACGGCCTTGTATTACTGTACAAGACTGGGA<br>CAGACACAGAGAAATGCTATGGACTACTGG<br>GGTCAAGGAACCTCAGTCACCGTCTCCTCA |
| | VL | SEQ ID NO: 447<br>GACATTTTGATGACACAGTCTCCATCCTCC<br>CTGAGTGTGTCAGCAGGAGAGAAGGTCACT<br>ATGAGCTGCAAGTCCAGTCAGAGTCTGTTA<br>AACAGTGGAAATCAAAAGAACTATTTGGCC<br>TGGTACCAGCAGAAACCAGGGCAGCCTCCT<br>AAATTGTTGATCTATGGGGCATCCACTAGG<br>GAATCTGGGGTCCCTGATACCTTCACAGGC<br>AGTGGATCTGGAACCGATTTCACTCTTACC<br>ATCAGCAGTGTGCAGGCTGAAGACCTGGCA<br>GTTTATTACTGTCAGAATGATTATTATTAT<br>CCGTTCACGTTCGGTGCTGGGACCAAGCTG<br>GAGCTGAAG |
| Ab23 | VH | SEQ ID NO: 456<br>GAAGTGATGCTGGTGGAGTCTGGGGGAGGC<br>TTAGTGAAGCCTGGAGGGTCCCTGAAACTC<br>TCCTGTGTAGCCTCTGGATTCACTTTCAGT<br>AGCTATACCATGTCTTGGGTTCGCCAGACT<br>CCGGAGAAGAGGCTGGAGTGGGTCGCAACC<br>CTTAGTGTTGTTGGTGGTAACACCTACTAT<br>GTAGACAGTGTGAAGGGTCGATTCACCATC<br>TCCAGAGACAAAGCCAAGAACACCCTGTAC<br>CTGCAAATGAGCAGTCTGAGGTCTGAGGAC<br>ACGGCCTTATATTACTGTGCAAGACTGGGA<br>CAGACACAGAGAAATGCTATGGACTACTGG<br>GGTCAAGGAACCTCAGTCACCGTCTCCTCA |
| | VL | SEQ ID NO: 465<br>GACATTGTGATGACACAGTCTCCATCCTCT<br>CTGAGTGTGTCAGCAGGAGAGAAGGTCACA<br>ATGAGTTGCAAGTCCAGTCAGAGTCTGTTA<br>AACAGTGGAAATCAAAAGAACTACTTGGCC<br>TGGTACCAGCAGAAACCAGGGCAGCCTCCT<br>AAACTGTTGATCTACGGGGCATCTACTAGG<br>GAATCTGGGGTCCCTGATCGCTTCACAGGC<br>AGTGGATCTGGAACCGATTTCACTCTTACC<br>ATCAGTAGTGTGCAGGCTGAAGACCTGGCA<br>GTTTATTACTGTCAGAATGATTATAGTTAT<br>CCGCTCACGTTCGGTGCTGGGACCAAGCTG<br>GAGCTGAAA |
| Ab24 | VH | SEQ ID NO: 474<br>GAAGTGAAGCTGGTGGAGTCTGGGGGAGGC<br>TTAGTGAAGCCTGGAGGGTCCCTGAAACTC<br>TCCTGTGCAGGCTCTGGATTCACTTTCAGT<br>AGCTATACCATGTCTTGGGTTCGCCAGACT<br>CCGGAGAAGAGGCTGGAGTGGGTCGCAACC<br>ATTACTATTGGTGTTAACATCTACTATCTA<br>GACAGTGTGAAGGGTCGATTCACCATCTCC |

TABLE 3-continued

| Polynucleotides of variable regions of the exemplary antibodies | | |
|---|---|---|
| Anti-body ID No. | Vari-able Chain | Polynucleotide of Each Variable Chain |
| | | AGAGACAATGCCAAGAACACCTTGTACCTG<br>CAAATGAACAGTCTGAGGTCTGAGGACACG<br>GCCTTGTATTATTGTACAAGACTGGGACAG<br>ACACAGCGAAATGCTATGGACTACTGGGGT<br>CAAGGAACCTCAGTCACCGTCTCCTCA |
| | VL | SEQ ID NO: 483<br>GACATTGTGATGACACAGTCTCCAACCTCC<br>CTGAGTGTGTCAGCAGGAGAGAAGGTCACT<br>ATGACCTGCAAGTCCAGTCAGAGTCTGTTC<br>AACAGTGGAAATCAAAAGAACTACTTGGCC<br>TGGTATCAGGAGAAACCAGGACAGCCTCCT<br>AAACTGTTGATCTACGGGGCATCCACTAGG<br>GAGTCTGGGGTCCCTGATCGCTTCACAGGC<br>AGTGGATCTGGAACCGATTTCACTCTTACC<br>ATCAGCAGTGTGCAGGCTGAAGACCTGGCC<br>GTTTATTACTGTCAGAATGTTCATTTTTAT<br>CCGTTCACGTTCGGTGCTGGGACCAAGCTG<br>GAGCTGAAA |
| Ab25 | VH | SEQ ID NO: 492<br>GAGGCCCAGCTGCAACAATCTGGACCTGAG<br>CTGGTGAAGCCTGGGGCGTCAGTGAAGATA<br>TTCTGTAAGGCTTCTGGATACACGTTCACT<br>GACTACTACATCAACTGGGTGAAACAGAGC<br>CATGGAAAGAGCCTTGAGTGGATTGGAGAT<br>ATTAATCCTAACAATGGTGGTACTACCTAC<br>AACCAGAAGTTCAAGGGCAAGGCCACATTG<br>ACTGTAGACAAGTCCTCCAGCACAGCCTCC<br>ATGGAGCTCCGCAGACTGACATCTGAAGAC<br>TCTTCAGTCTATTACTGTGCAAGACGCGAT<br>GCTATGGACTACTGGGGTCAAGGAACCTCA<br>GTCACCGTCTCCTCA |
| | VL | SEQ ID NO: 501<br>GACATTGTGATGACCCAGTCTCAAAAATTC<br>ATGTCCACAACAGTAGGAGACAGGGTCAGC<br>ATCACCTGCACGGCCAGTCAGAATGTGGGT<br>CCTGCTGTTGCCTGGTATCAACAGAAACCA<br>GGACAATCTCCTAAACTACTGATTTACTCA<br>GCATCCCGTCGGTTCACTGGAGTCCCTGAT<br>CGCTTCACAGGCAGTGGATCTGGGACAGTT<br>TTCACTCTCACCATTAACAATGTGCAGTCT<br>GAAGACCTGGCAGATTATTTCTGTCAGCAA<br>TATATCAGCTATCCTCTCACGTTCGGTGCT<br>GGGACCAAGCTGGAGCTGAAA |
| Ab26 | VH | SEQ ID NO: 510<br>GAAGTGATGCTGGTGGAGTCTGGGGGAGGC<br>TTAGTGAAGCCTGGAGGGTCCCTGAAACTC<br>TCCTGTACAGCCTCTGGATTCACTTTCAGA<br>AGCTATACCATGTCTTGGGTTCGCCAGACT<br>CCGGAGAAGAGGCTGGAGTGGGTCGCAACT<br>ATTACTGGTGGTGGTGGAAATACCTACTTT<br>CTAGACAGTGTGAAGGGTCGATTCACCTTC<br>TCCAGAGACAATGCCAAGAACGCCCTGTAC<br>CTGCAAATGAACAGTCTGAGGTCTGAGGAC<br>ACGGCCTTGTATTACTGTGCAAGACTGGGA<br>CAGACACAGAGAAATGCTATGGACTACTGG<br>GGTCAAGGAACCTCAGTCACCGTCTCCTCA |
| | VL | SEQ ID NO: 519<br>GACATTGTGATGACACAGTCTCCATCCTCC<br>CTGAGTGTGTCAGCCGGAGAGAAGGTCACT<br>ATGAGCTGCAAGTCCAGTCAGAGTCTATTA<br>AACAGTGGAAATCAAATGAACTACTTGGCC<br>TGGTACCAGCAGAAACCAGGACAGCCTCCT<br>AAATTGTTGATCTATGGGGCATCCACTAGG<br>GAATCTGGGGTCCCTGATCGCTTCACAGGC<br>AGTGGATCTGGAACCGATTTCACTCTTACC<br>ATCAGCAGTGTGCAGGCTGAAGACCTGGCA<br>ATTTATTACTGTCAGAATGATCATACTTAT |

TABLE 3-continued

Polynucleotides of variable regions of the exemplary antibodies

| Anti-body ID No. | Vari-able Chain | Polynucleotide of Each Variable Chain |
| --- | --- | --- |
| | | CCGCTCACGTTCGGTGCTGGGACCAAACTG<br>GAGCTGAAA |
| Ab27 | VH | SEQ ID NO: 528<br>CAGGTTCAGCTGCAGCAGTCTGGGGCTGAA<br>CTGGTGAGGCCTGGGTCCTCAGTGAAGATT<br>TCCTGCAAGGCTTCTGGCTATGCATTCAGT<br>AACTACTGGATGAACTGGGTGAAGCAGAGG<br>CCTGGACAGGGTCTTGAGTGGATTGGACAG<br>ATTTATCCTGGAAATGGTGATACTAACTAC<br>AATGGAAAGTTCAAGGGTAAAGCCACACTG<br>ACTGCAGACAAATCCTCCACCACAGCCTAC<br>ATTCAGCTCAGCAGCCTAACTTCTGAGGAC<br>TCTGCGGTCTATTTCTGTACAAGGATCTAC<br>TATGGTAACTCTTTTGCTTACTGGGGCCAA<br>GGCACTCTGGTCACTGTCTCTGCA |
| | VL | SEQ ID NO: 537<br>GACATTGTGATGACACAGTCTCCATCCTCC<br>CTGACTGTGACAGCAGGAGAGAGGGTCACT<br>ATGAGCTGCAAGTCCAGTCAGAGTCTGTTA<br>AACAGTGGAAATCAAAAGAACTACTTGACC<br>TGGTACCAGCAGAAACCAGGGCAGCCTCCT<br>AAACTGTTGATCTACTGGGCATCCACTAGG<br>GAATCTGGGGTCCCTGATCGCTTCACAGGC<br>AGTGGATCTGGAACAGATTTCACCCTCACC<br>ATCAGCAGGGTGCAGGCTCAAGACCTGGCA<br>GTTTATTACTGTCAGAATGATTATTATTAT<br>CCACTCACGTTCGGTGCTGGGACCAAGCTG<br>GAGCTGAAA |
| Ab28 | VH | SEQ ID NO: 546<br>CAGGTGCAGTTGAAGGAGTCAGGACCAGGC<br>CTGGTGGCGCCCTCACAGAGCCTGTCCATC<br>ACTTGCACTGTCTCCGGGTTTTCATTAACC<br>AGCCATGGTGTACACTGGGTTCGCCAGCCT<br>CCAGGAAAGGGTCTGGAGTGGCTGGGAGTA<br>ATATGGGCTGGAGGAAGCATAAACTTTAAT<br>TCGGCTCTCATGTCCAGACTGAGCATCAGC<br>AAAGACAACTCCAAAAACCAGGTTTTCTTA<br>AAAATGAACAGTCTGCAAAGTGATGACACA<br>GCCATGTACTACTGTGCCAGAGACTATTAC<br>TACGGTATTGGTCTTGACTATTGGGGCCAA<br>GGCACCACTCTCACAGTCTCCTCA |
| | VL | SEQ ID NO: 555<br>GACATTGTGATGACACAGTCTCCATCCTCC<br>CTGAGTGTGTCAGCAGGAGAGAAGGTCACT<br>ATGAGCTGCAAGTCCAGTCAGAGTCTGTTA<br>AACAGTGGAAATCAAAAGAACTACTTGGCC<br>TGGTACCAGCAGAAACCAGGACAGCCTCCT<br>AAACTGTTGATCTACGGGGCATCCACTAGG<br>GAATCTGGGGTCCCTGATCGCTTCACAGGC<br>AGTGGGTCTGGAACCGATTTCACTCTTACC<br>ATCAGCAGTGTGCAGGCTGAAGACCTGGCA<br>GTTTATTACTGTCAGAATGATTATTATTAT<br>CCATTCACGTTCGGCTCGGGGACAAAGTTG<br>GAAATAAAA |
| Ab29 | VH | SEQ ID NO: 564<br>GAGGTCCTGCTGCAACAGTCTGGACCTGAA<br>CTGGTGAAGCCTGGGGCTTCAGTGAAGATA<br>CCCTGCAAGGCTTCTGGATACACTTTGACT<br>GACCACAGCATGGACTGGGTGAAGCAGAGC<br>CATGGAAAGAGCCTTGAGTGGATTGGAAAT<br>ATTCTTCCTAATAATGGTGGTAATATATAC<br>AACCAGAAGTTCAGGGGCAAGGCCACACTG<br>ACTGTCGACAAGTCCTCCAGCACAGCCTAC<br>ATGGAGCTCCGCAGCCTGACATCTGAAGAC<br>ACTGCAGTCTATAACTGTGCAAGGGGCCAC<br>TATGGTAACTCATTTGCTTACTGGGGCCAA<br>GGGACTCTGGTCATAGTCTCTGCA |
| | VL | SEQ ID NO: 573<br>GACATTGTGATGACACAGTCTCCATCCTCC<br>CTGACTGTGAGAGCAGGAGAGAAGGTCACT<br>ATATACTGCAAGTCCAGTCAGAGTCTGTTT<br>AACAGTGGAAATCAAAAAAACTACTTGACC<br>TGGTACCAGCAGAAACCGGGCCAGCCTCCT<br>AAATTGTTGATCTACTGGGCATCCACTAGG<br>GAATCTGGGGTCCCTCATCGCTTCACAGGC<br>AGTGGATCTGGGACAGATTTCACTCTCACC<br>ATCAGCAGTATGCAGGCTGATGACCTGGCA<br>ACTTATTACTGTCAGAATGGTTATTTTTTT<br>CCGTACACGTTCGGAGGGGGGACCAAGCTG<br>GAGATAAAA |
| Ab30 | VH | SEQ ID NO: 582<br>CAGGTACAACTGAAGGAGTCAGGACCTGGC<br>CTGGTGGCGCCCTCACAGAGCCTGTCCATC<br>ACATGCACTGTCTCAGGGTTCTCATTAACC<br>AAGTTTGGTGTAAACTGGGTTCGCCAGCCT<br>CCAGGAAAGGGTCTGGAGTGGCTGGGAGCA<br>ATATGGGGTGACGGGAGCACAAATTATCAT<br>TCAGCTCTCATATCCAGACTGAGCATCAAC<br>AAGGATAACTCCAAGAGCCAAGTTTTCTTA<br>AAACTGAGCAGTCTGCAAAATGTTGACACA<br>GCCACTTACTACTGTGCCAAAAGTGGGTAC<br>GGTAATGCTATGGACTACTGGGGTCACGGA<br>ACCTCAGTCACCGTCTCCTCA |
| | VL | SEQ ID NO: 591<br>GACATTGTGATGACACAGTCTCCATCCTCC<br>CTGACTGTGACAACAGGAGAGAAGGTCACT<br>CTGAACTGCAAGTCCAGTCAGAGTCTGTTA<br>AACAGTGGAAATCTAAAGAACTACTTGACC<br>TGGTACCAGCAGAGACCGGGGCAGCCTCCT<br>AAACTGTTGATCTACTGGGCATCCACTAGG<br>GAATCTGGGGTCCCTTATCGCTTCACAGGC<br>AGTGGATCTGGAACAGATTTCACTCTCACC<br>ATCAGCAATGTGCAGGCTGAAGACCTGGCA<br>ATTTATTACTGTCAGAATGATTATTTTTTT<br>CCATTCACGTTCGGCTCGGGGACAAAGTTG<br>GAAATTAAA |
| Ab31 | VH | SEQ ID NO: 600<br>CAGATCCAGTTGGCGCAGTCTGGACCTGAG<br>CTGAAGAAGCCTGGAGAGACAGTCAAGATC<br>TCCTGCAAGGCTTCTGGGTATAGTTTCACA<br>AACTATGGAATGAACTGGGTGAAGCAGGCT<br>CCAGGAAAGGGCTTAAAGTGGATGGGCTGG<br>ATAAACACCTACAGTGGAGAGACAAAATAT<br>GCTGATGACTTCAAGGGACGGTTCGACTTT<br>TCATTGGAAACCTCTGCCAGGACAGCCTAT<br>TTGCAGATCAAAAACCTCAAAATTGAGGAC<br>ACGGCTACATATTTCTGTGCAAGACGGGAT<br>GCTATGGACTACTGGGGTCAAGGAACCTCA<br>GTCACCGTCTCCTCA |
| | VL | SEQ ID NO: 609<br>GATATTGTGATGACTCAGGCTGCACCCTCT<br>GTACCTGTCACTCCTGGAGAGTCAGTGTCC<br>ATTTCTTGCAGGTCTAGTAAGAGTCTCCTG<br>AATAGTAATGGTAACACTTATTTGTATTGG<br>TTCCTACAGAGGCCAGGCCAGTCTCCTCAG<br>CTCCTGATATATCGGATGTCTAACCTTGCC<br>TCAGGAGTCCCAGACAGGTTCAGTGGCAGT<br>GGGTCAGGGACTGCTTTCACACTGAGAATC<br>AGTAGAGTGGAGGCTGAGGATGTGGGTGTT<br>TATTATTGTATGCAACATCTAGAATTTCCA<br>TTCACGTTCGGCTCGGGGACAAAGTTGGAA<br>ATAAAA |

TABLE 3-continued

Polynucleotides of variable regions of the exemplary antibodies

| Antibody ID No. | Variable Chain | Polynucleotide of Each Variable Chain |
|---|---|---|
| Ab32 | VH | SEQ ID NO: 618<br>CAGGTGCAGTTGAAGGAGTCAGGACCAGGCCTGGTGGCGCCCTCACAGAGCCTGTCCATCACTTGCACTGTCTCCGGGTTTTCATTAACCAGCCATGGTGTACACTGGGTTCGCCAGCCTCCAGGAAAGGGTCTGGAGTGGCTGGGAGTAATATGGGCTGGAGGAAGCATAAACTTTAATTCGGCTCTCATGTCCAGACTGAGCATCAGCAAAGACAACTCCAAAAACCAGGTTTTCTTAAAAATGAACAGTCTGCAAAGTGATGACACAGCCATGTACTACTGTGCCAGAGACTATTACTACGGTATTGGTCTTGACTATTGGGGCCAAGGCACCACTCTCACAGTCTCCTCA |
| | VL | SEQ ID NO: 627<br>GACATTGTGATGACACAGTCTCCATCCTCCCTGAGTGTGTCAGCAGGAGAGAAGGTCACTATGAGCTGCAAGTCCAGTCAGAGTCTGTTAAACAGTGGAAATCAAAAGAACTACTTGGCCTGGTACCAGCAGAAACCAGGACAGCCTCCTAAACTGTTGATCTACGGGGCATCCACTAGGGAATCTGGGGTCCCTGATCGCTTCACAGGCAGTGGGTCTGGAACCGATTTCACTCTTACCATCAGCAGTGTGCAGGCTGAAGACCTGGCAGTTTATTACTGTCAGAATGATTATTATTATCCATTCACGTTCGGCTCGGGGACAAAGTTGGAAATAAAA |
| Ab33 | VH | SEQ ID NO: 636<br>GACGTGAACCTGGTGGAGTCTGGGGGAGGCTTAGTGAAGCCTGGAGGGTCCCTGAAACTCTCCTGTGCAGCCTCTGGATTCACTTTCAGTAGCTATACCATGTCTTGGGTTCGCCAGACTCCGGAGAAGAGGCTGGAGTGGGTCGCAACCATTACTTATGGTCGTATTTACACCTACTATCTAGACAGTGTAAAGGGCCGATTCACCATCTCCAGAGACAATGCCAAAAACACCCTGTACCTGCAGATGAGCAGTCTGAGGTCTGAGGACACAGCCATGTATTACTGTACAAGGATGATTACGGGGAATGCTATGGACTCCTGGGGTCTAGGAACCTCAGTCACCGTCTCCTCA |
| | VL | SEQ ID NO: 645<br>GACATTGTGATGACACAGTCTCCATCCTCCCTGACTGTGACAGCAGGAGAGAAGGTCACTATGAGCTGCAAGTCCAGTCAGAGTCTGTTAAACAGTGGAAATCAAAAAAACTACTTGACCTGGTACCAGCAGAAACCAGGGCAGCCTCCTAAACTGTTGATCTACTGGGCATCCACTAGGGAATCTGGGGTCCCTGATCGCTTCACAGGCAGTGGATCTGGAACAGATTTCACTCTCACCATCAGCGGTGTGCAGGGTGAAGACCTGGCAGTTTATTACTGTCAGAATGATTATAGTTATCCGCTCACGTTCGGTGGTGGGACCAAGCTGGAGCTGAAA |
| Ab34 | VH | SEQ ID NO: 654<br>GAGGTCCTGCTGCAACAGTCTGGACCTGAGTTGGTGAAGCCTGGGGCTTCAGTGAAAATACCCTGCAAGGCTTCTGGATACACATTCTCTGACTACAACATGGACTGGGTGAAGCAGAGCCATGGAAAGAGCCTTGAGTGGATTGGACATATTAATCCTAACAATGATAATACTATCTACAACCAGAAGTTCAAGGGCAAGGCCACATTGACTGTAGACAAGTCCTCCAATACAGCCTACATGGACCTCCGCAGCCTGTCATCTGAGGACACTGCAGTCTATTACTGTGCAAGAGGGGCCTACTATGGTAACTCTATGGACTACTGGGGTCAAGGAACCTCAGTCACCGTCTCCTCA |
| | VL | SEQ ID NO: 663<br>GACATTGTGATGACACAGTCTCCATCCTCCCTGACTGTGACAGCAGGAGAGAGGGTCACTATGAGCTGCAAGTCCAGTCAGAGTCTGTTAAACGGTGGAAATCAAAGGAACTACTTGACCTGGTACCAGCAGAAACCAGGGCAGTCTCCTAAACTGTTGATCTACTGGGCATCCACTTGGGAATCTGGGGTCCCTGATCGCTTCACAGGCAGTGGGTCTGGAACAGATTTCACTCTCACCATCAGCAGTGTGCAGGCTGAGGACCTGGCAGTTTATTACTGTCAAAATGCTTATTTTTATCCGTACACGTTCGGAGGGGGGACCAAGCTGGAAATAAAA |
| Ab35 | VH | SEQ ID NO: 672<br>GATGTGTTTCTTCAGGAGTCGGGACCTGGCCTGGTGAAACCTTCTCAGTCTCTGTCCCTCACCTGCACCGTCACTGGCTACTCAATCACCAGTGATTATGCCTGGAACTGGATCCGGCAGTTTCCAGGAAACAAACTGGAGTGGGTGACCTACATAGGCTACAGTGGTACCACTAGCTACAACCCATCTCTCAAAAGTCGAATCTCTATCACTCGAGACACATCCAAGAACCAGTTCTTCCTGCAGTTGAATTCTGTGTCTACTGAGGACACAGCCACATATTACTGTGTAAGAAGGGGGAGTTACTATGGGAGTTACTGGTTCTTCGATGTCTGGGGCGCAGGGACCACGGTCACCGTCTCCTCA |
| | VL | SEQ ID NO: 681<br>CAAGTTGTTCTCTCCCAGTCTCCAGCAATCCTGTCTGCATCTCCAGGGGAGAAGGTCACAATGACTTGCAGGGCCAGTTCAAGTGTAAGTTACATGCACTGGTATCAGCAGAAGCCAGGATCCTCCCCCAAACCCTGGATTTATGCCACATCCAACCTGGCTTCTGGAGTCCCTCCTCACTTCAGTGGCAGTGGGTCTGGGACCTCGTACTCTCTCACAATCAGCAGAGTGGAGGCTGAAGATGCTGCCACTTATTACTGCCAGCAGTGGACTAGTAACCCACCCACGTTCGGAGGGGGGACCAAGTTGGAAATAAAA |
| Ab36 | VH | SEQ ID NO: 690<br>GAAGTGAAGCTTGAGGAGTCTGGAGGAGGCTTGGTGCAGCCTGGAGGATCCATGAAACTCTCCTGTGTTGCCTCTGGATTCACTTTCAGTAACTACTGGATGAACTGGGTCCGCCAGTCTCCAGAGAAGGGGCTTGAGTGGGTTGCTCAAATTAGATTGAAATCTGATAATTATGCAACACATTATGCGGAGTCTGTGAAAGGGATGTTCACCATCTCAAGAGATGATTCCAAAAGTAGTGTCTACCTGCAAATGAACAACTTAAGGGCTGAAGACACTGGAATTTATTACTGCACAGCAGGCGGGGACTACTGGGGCCAAGGCACCACTCTCACAGTCTCCTCA |
| | VL | SEQ ID NO: 699<br>GACATTGTGATGACCCAGTCTCAAAAATTCATGTCCACAACAGTAGGAGACAGGGTCAGCATCACCTGCAAGGCCAGTCAGAATGTGGGTACTGCTGTAGCCTGGTATCACCAGAAACCAGGACAATCTCCTAAACTCCTGATTTACTCAGCATCCAATCGGTACACTGGAGTCCCTGATCGCTTCATAGGCAGTGGATCTGGGACAGATTTCACTCTCACCATTAGCAATGTGCAGTCTGAAGACCTGGGAAATTATTTCTGTCAGCAATATATCAACTATCTTCTCACGTTCGGCTCGGGGACAAAGTTGGAAATAAAA |
| Ab37 | VH | SEQ ID NO: 169<br>GAAGTGAAGCTTGAGGAGTCTGGAGGAGGC |

TABLE 3-continued

Polynucleotides of variable regions of the exemplary antibodies

| Antibody ID No. | Variable Chain | Polynucleotide of Each Variable Chain |
|---|---|---|
| | | TTGGTGCAACCTGGAGGATCCATGAAACTC<br>TCCTGTGTTGCCTCTGGATTCACTTTCAGT<br>AACTACTGGATGAACTGGGTCCGCCAGTAT<br>CCAGAGCAGGGGCTTGAGTGGGTTGCTCAA<br>ATTAGATTGAATTCTGATAATTATGCAACG<br>CATTATGCGGAGTCTGTGAAAGGGAGGTTC<br>ACCATCTCAAGAGATGATTCCAGAAGTACT<br>GTCTACCTACAAATGAACAACTTAAGGGCT<br>GAAGACACTGGAATTTATTACTGCACAGGC<br>GGGGGGGAGTACTGGGGCCAAGGCACCACT<br>CTCACAGTCTCCTCA |
| | | SEQ ID NO: 178 |
| | VL | GACATTGTGATGACCCAGTCTCAAAAATTC<br>ATGTCCACAACAATAGGAGACAGGGTCAGC<br>ATCACCTGCAAGGCCAGTCAGAATGTGGAT<br>ACTGCTGTAGCCTGGTATCAACAGAAACCA<br>GGACAATCTCCTAAACTACTGATTTACTCA<br>GCATCCACTCGGTACACTGGAGTCCCTGAT<br>CGCTTCACAGGCAGTGGATCTGGGACAGAT<br>TTCACTCTCACCATTAGTAATATGCAGTCT<br>GAAGACCTGGCAGATTATTTCTGTCAGCAA<br>TATATCAGTTATCAGCTCACGTTCGGTGCT<br>GGGACCAAGCTGGAGCTGAAA |
| | | SEQ ID NO: 187 |
| Ab38 | VH | CAGATCCAGTTGGTACAGTCTGGACCTGAG<br>CTGAAGAAGCCTGGAGAGACAGTCAAGATC<br>TCCTGCAAGGCTTCTGGATATACCTTCACA<br>AACTATGGAATGAGTTGGGTGAAACAGGCT<br>CCAGGAAAGGGATTAAAGTGGATGGGCTGG<br>ATAAACACCTATTCTGGAGTGCCAACATAT<br>GCTGATGACTTCAAGGGACGGTTTGTCTTC<br>TCTTTGGAAGCCTCTGCCAGCACTGCCTAT<br>TTGCAGATCAACAACCTCAAAAATGAGGAC<br>GCGGCTACATATTTCTGTTCAAGGTGGTCT<br>GGGCCCGATCCGCTTGAGGACCACTGGGGC<br>CAAGGCACCACTCTCACAGTCTCCTCA |
| | | SEQ ID NO: 196 |
| | VL | CAAATTGTTCTCACCCAGTCTCCAGCAATC<br>ATGTCTGCATCTCCAGGGGAGAAGGTCACC<br>ATGACCTGCACTGCCAGTTTAAGTCTAAAT<br>TACATTCACTGGTACCGACAGAGGTCAGGC<br>ACCTCCCCCAAACGATGGATTTATGACACA<br>TCCAAGCTGGCTTCTGGAGTCCCTTCTCGT<br>TTCAGTGGCAGTGGATCTGGGACCTCTTAC<br>TCTCTCACAATCAGCAGCATGGAGGCTGAA<br>GATGCTGCCACTTATTACTGCCAGCAGTGG<br>AGTAGTAACCCCTGGACGTTCGGTGGAGGC<br>ACCAAGCTGGAAATCAAA |

The isolated polynucleotide that encodes the anti-CLDN18 antibodies (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence. A vector may also include materials to aid in its entry into the cell, including but not limited to a viral particle, a liposome, or a protein coating.

The present disclosure provides vectors (e.g., cloning vectors or expression vectors) containing the nucleic acid sequence provided herein encoding the antibodies, at least one promoter (e.g., SV40, CMV, EF-1α) operably linked to the nucleic acid sequence, and at least one selection marker. Examples of vectors include, but are not limited to, plasmids, phagemids, cosmids, and artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as expression vectors include retrovirus (including lentivirus), adenovirus, adeno-associated virus, herpesvirus (e.g., herpes simplex virus), poxvirus, baculovirus, papillomavirus, and papovavirus (e.g., SV40). Exemplary plasmids include, pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, and pEF-Bos etc.

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces.*

In addition to prokaryotes, eukaryotic microbes such as filamentous fungi or yeast are suitable cloning or expression hosts for anti-CLDN18 antibodies-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; Yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of antibodies or antigen-fragment provided here are derived from multicellular organisms. Examples of invertebrate cells include plant and insect cells. Numerous baculoviral strains and variants and corresponding permissive insect host cells from hosts such as *Spodoptera frupperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture)

has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse myeloma cell line (NS0, Galfrè and Milstein (1981), Methods in Enzymology, 73:3-46; Sp2/0-Ag14, ATCC CRL-1581); Chinese hamster ovary cells/-DHFR (CHO, Urlaub et al., *Proc. Natl. Acad. Sci. USA* 77:4216 (1980)); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is mammalian cultured cells, such as CHO cells, BHK cells, or NS0 cells.

In some embodiments, the host cell is capable of producing a glyco-engineered antibody. For example, a host cell line can provide for the required glycosylation machinery during post-translation modification. Examples of such host cell lines includes but are not limited to those with altered (increased or decreased) activity of glycosylation related enzymes, such as, glucosaminyltransferase (e.g., β(1,4)-N-acetylglucosaminyltransferase III (GnTIII)), glycosyltransferase (e.g., β(1,4)-galactosyltransferase (GT)), sialyltransferase (e.g., α(2,3)-sialyltransferase (ST)), mannosidase (e.g., α-mannosidase II (ManII), fucosyltransferase (e.g., alpha-1,6-fucosyltransferase gene (FUT8), (1,3) fucosyltransferase), prokaryotic GDP deoxy-D-lyxo-4-hexulose reductase (RMD), GDP-fucose transporter (GFT), natively or through genetic engineering.

In some embodiments, the host cell is characterized in lack of functional FUT8, overexpression of a heterologous GnTIII, expression of a prokaryotic GDP-6-deoxy-D-lyxo-4-hexulose reductase (RMD), or lack of functional GFT. A FUT8 knock out host cell line is fucosylation-deficient and produces afucosylated antibodies. Overexpression of GnTIII in a host cell line (see for example, the Glycart technology by Roche) results in the formation of bisected, non-fucosylated glycosylation form of an antibody. Expression of RMD (e.g. as in GlymaxX® system from ProBioGen AG) inhibits fucose de-novo biosynthesis, and as a consequence, antibodies generated by such host cell lines also exhibit reduced fucosylation. GFT knockout in CHO cell line (see for example, technology by Beijing Mabworks Biotech) block both fucose de-novo and fucose salvage biosynthesis pathways and results in reduced fucosylation.

Host cells are transformed with the above-described expression or cloning vectors for anti-CLDN18 antibodies production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-CLDN18 antibodies prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

Pharmaceutical Composition

The present disclosure further provides pharmaceutical compositions comprising an anti-CLDN18 antibodies or antigen-binding fragment thereof, the chimeric antigen receptor, the polynucleotides, the vector, or the modified immune cells provided herein and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof. Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-CLDN18 antibodies or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined. The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

In some examples, the pharmaceutical composition described herein comprises liposomes containing the antibodies (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

In certain embodiments, the pharmaceutical composition of the present disclosure further comprises one or more therapeutic agents. In certain embodiments, the one or more therapeutic agents are selected from the group consisting of amrubicin, apatinib mesylate, atrasentan batabulin, calcitriol, capecitabine, cilengitide, dasatinib, decatanib, edotecarin, enzastaurin, erlotinib, everolimus, gimatecan, gossypol ipilimumab, lonafarnib, lucanthone, neuradiab, nolatrexed, oblimersen, olaparib, ofatumumab, oregovomab, panitumumab, pazopanibrubitecan, regorafenib talampanel, tegafur, temsirolimus, tesmilifene, tetrandrine, ticilimumab, trametinib, trabectedin, vandetanib, vitespan, zanolimumab, zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, epirubicin, oxaliplatin, an anti-PD1 antibody, an anti-PDL1 antibody, an anti-HER2 antibody, an anti-HER2 ADC and 5-fluorouracil and strontium 89.

Therapeutical Application

The present disclosure also provides therapeutic methods comprising: administering a therapeutically effective amount of the antibody or antigen-binding fragment thereof, the chimeric antigen receptor, the polynucleotides, the vector, or the modified immune cells as provided herein to a subject in need thereof, thereby treating or preventing a CLDN18.2-related condition or disorder. In some embodiments, the CLDN18.2-related condition or disorder is cancer, optionally the cancer is characterized in expressing or over-expressing CLDN18.2. Expression or over-expression may be determined in a diagnostic or prognostic assay by evaluating increased levels of CLDN18.2 in a biological sample (such as a sample derived from cancer cell or tissue, or tumor infiltrating immune cells) from a subject. Various methods can be used. For example, diagnostic or prognostic assay can be used to evaluate expression levels of CLDN18.2 present on the surface of a cell (e.g. via an immunohistochemistry assay; IHC). Alternatively, or additionally, one may measure levels of CLDN-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. In some embodiments, the CLDN18.2-related condition or disorder is cancer, wherein the cancer is characterized in expressing CLDN18.2 at a level of less than 10000 antibody binding sites per cell, less than 9000 antibody binding sites per cell, less than 8000 antibody binding sites per cell, less than 7000 antibody binding sites per cell, less than 6000 antibody binding sites per cell, less than 5000 antibody binding sites per cell, or less than 4000 antibody binding sites per cell.

In some embodiments, the CLDN18.2-related condition or disorder is cancer, wherein the cancer is selected from the group consisting of lung cancer (e.g., small cell lung cancer, non-small cell lung cancer (NSCLC), adenocarcinoma of the lung, or squamous cell carcinoma of the lung), gastric or stomach cancer (e.g., gastrointestinal cancer), pancreatic cancer, esophageal cancer, liver cancer (e.g., hepatocellular carcinoma/hepatoma), squamous cell cancer, cancer of the peritoneum, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, gallbladder cancer, idiopathic myelfibrosis, and pediatric cancers such as pediatric sarcomas (e.g., neuroblastoma, rhabdomyosarcoma, and osteosarcoma). In certain embodiments, the cancer is selected from the group consisting of gastric cancer, pancreatic cancer, esophageal cancer, lung cancer, gallbladder cancer, colorectal cancer and liver cancer.

The therapeutically effective amount of an antibody or antigen-binding fragment thereof, the chimeric antigen receptor, the polynucleotides, the vector, or the modified immune cells as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

The antibodies disclosed herein may be administered by any route known in the art, such as for example parenteral (e.g., subcutaneous, intraperitoneal, intravenous, including intravenous infusion, intramuscular, or intradermal injection) or non-parenteral (e.g., oral, transdermal, intranasal, intraocular, sublingual, rectal, or topical) routes.

The present disclosure further provides methods of using the anti-CLDN18 antibodies.

In some embodiments, the present disclosure provides methods of detecting presence or amount of CLDN18.2 in a sample, comprising contacting the sample with the antibody, and determining the presence or the amount of CLDN18.2 in the sample.

In some embodiments, the present disclosure provides methods of diagnosing a CLDN18.2-related disease or condition in a subject, comprising: a) contacting a sample obtained from the subject with the antibody provided herein; b) determining presence or amount of CLDN18.2 in the sample; c) correlating the presence or the amount of CLDN18.2 to existence or status of the CLDN18.2-related disease or condition in the subject.

In some embodiments, the present disclosure provides kits comprising the antibody provided herein, optionally conjugated with a detectable moiety. The kits may be useful in detection of CLDN18.2 or diagnosis of CLDN18.2 related disease.

In some embodiments, the present disclosure also provides use of the antibody provided herein in the manufacture of a medicament for treating a disease or condition that would benefit from modulation of CLDN18.2 expression in a subject, in the manufacture of a diagnostic/prognostic reagent for diagnosing/prognosing a CLDN18.2-related disease or condition. To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a cancer or an immune disorder such as an autoimmune disease.

A subject having a target cancer can be identified by routine medical examination, e.g., laboratory tests, organ functional tests, CT scans, or ultrasounds. In some embodiments, the subject to be treated by the method described herein may be a human cancer patient who has undergone or is subjecting to an anti-cancer therapy, for example, chemotherapy, radiotherapy, immunotherapy, or surgery.

Treatment efficacy for a target disease/disorder can be assessed by methods well-known in the art.

Combined Therapy

The anti-CLDN18 antibodies described herein may be utilized in conjunction with other types of therapy for the target disease such as cancer. The anti-CLDN18 antibodies described herein can be combined with an anti-cancer therapy, for example, those known in the art. Additional anti-cancer therapy includes chemotherapy, surgery, radiation, immunotherapy, gene therapy, and so forth.

Alternatively, the treatment of the present disclosure can be combined with a chemotherapeutic agent, for example, pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors. In certain embodiments, the treatment of the present disclosure can be combined with one or more therapeutic agents are selected from the group consisting of amrubicin, apatinib mesylate, atrasentan batabulin, calcitriol, capecitabine, cilengitide, dasatinib, decatanib, edotecarin, enzastaurin, erlotinib, everolimus, gimatecan, gossypol ipilimumab, lonafarnib, lucanthone, neuradiab, nolatrexed, oblimersen, olaparib, ofatumumab, oregovomab, panitumumab, pazopanibrubitecan, regorafenib talampanel, tegafur, temsirolimus, tesmilifene, tetrandrine, ticilimumab, trametinib, trabectedin, vandetanib, vitespan, zanolimumab, zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, epirubicin, oxaliplatin, an anti-PD1 antibody, an anti-PDL1 antibody, an anti-HER2 antibody, an anti-HER2 ADC and 5-fluorouracil and strontium 89.

When a second therapeutic agent is used, such an agent can be administered simultaneously or sequentially (in any order) with the therapeutic agent described herein. When co-administered with an additional therapeutic agent, suitable therapeutically effective dosages for each agent may be lowered due to the additive action or synergy.

Kits for Therapeutical Uses

The present disclosure also provides kits for use in treating or alleviating a target diseases, such as cancer and immune disorders as described herein. Such kits can include one or more containers comprising an anti-CLDN18 antibodies, e.g., any of those described herein, and optionally a second therapeutic agent to be co-used with the anti-CLDN18 antibodies, which is also described herein.

In some embodiments, the kit can comprise instructions for use in accordance with any of the methods described herein. The included instructions can comprise a description of administration of the anti-CLDN18 antibodies, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-CLDN18 antibodies generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease, such as cancer or immune disorders (e.g., an autoimmune disease). Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CLDN18 antibodies as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Hybridoma Development

1. Methods 1.1. Immunization and Serum Titer Determination

The immunogen and immunization strategies applied in the present disclosure include cell immunization (human Claudin18.2 (CLDN18.2) overexpressing cells, e.g. HEK293F-hCLDN18.2), genetic immunization (full length human CLDN18.2 expression construct), and protein immunization (recombinant human CLDN18.2 protein).

Balb/c or SJL mice were divided into 5 groups, with 5 mice in each group. Each group of mice were immunized with human Claudin18.2 (CLDN18.2) overexpressing cells (Claudin18.2 cells, e.g. HEK293F-hCLDN18.2), full length human CLDN18.2 expression construct (Claudin18.2 expression construct), or recombinant human CLDN18.2 protein (Recombinant Claudin18.2 protein). The outline of the immunization strategies were summarized in Table 4. The primary immunization were followed by several boosts until animals developed satisfactory antiserum titers suitable for hybridoma development. All the immunization strategies were carried out in parallel in order to compare the performance and immune response in serum level.

TABLE 4

The outline of the immunization strategies

| Group | Immunogen | Route | Animal/ Strain | Group size | Dosage |
|---|---|---|---|---|---|
| 1 | Claudin18.2 cells | I.P. | SJL | 5 | 0.5-1 × $10^7$ cells |
| 2 | Claudin18.2 cells | I.P. | Balb/c | 5 | 0.5-1 × $10^7$ cells |
| 3 | Claudin18.2 expression construct | Gene gun | SJL | 5 | 4 μg |
| 4 | Claudin18.2 expression construct | Gene gun | Balb/c | 5 | 4 μg |
| 5 | Recombinant Claudin18.2 protein | I.P. | SJL | 5 | 25-50 μg |

1.1.2. Immunization Schedules

The detailed immunization schedule for cell immunization was shown in Table 5 below.

TABLE 5

| Immunization schedule (Cell immunization) | |
|---|---|
| Day 0 | Pre-bleed (15-30 μL serum/mouse) Primary: 0.5-1 × $10^6$/mouse, IP |
| 14 | Boost 1: 0.5-1 × $10^7$ cell per mouse, IP |
| 21 | Test Bleed (15-30 μL serum/mouse) (TB1) |
| 22 | Test bleed FACS |
| 35 | Boost 2: 0.5-1 × $10^7$ cell per mouse, IP |
| 42 | Test Bleed (15-30 μL serum/mouse) (TB2) |
| 43 | Test bleed FACS |
| 44 | Data analysis and phase conclusion |
| 56 | Pre-fusion (final) Boost: 0.5-1 × $10^7$ cell per mouse, IP |

Animals not selected for cell fusion will be maintained in cage and may be given additional boost immunizations.

The detailed immunization schedule for genetic immunization was shown in Table 6 below.

TABLE 6

| Immunization schedule (Genetic immunization) | |
|---|---|
| Day 0 | Pre-bleed (15-30 μL serum/mouse) Primary: 1 μg/shot, 4 shots/animal |
| 14 | Boost 1: 1 μg/shot, 4 shots/animal |
| 21 | Test Bleed (15-30 μL serum/mouse) |
| 22 | Test bleed FACS |
| 28 | Boost 2: 1 μg/shot, 4 shots/animal |
| 35 | Test Bleed (15-30 μL serum/mouse) |
| 36 | Test bleed FACS |
| 42 | Boost 3: 1 μg/shot, 4 shots/animal |
| 49 | Test Bleed (15-30 μL serum/mouse) |
| 50 | Test bleed FACS |
| 51 | Data analysis and phase conclusion |
| 63 | Pre-fusion (final) Boost: 0.5-1 × $10^6$ per mouse |
| 67 | Fusion |

Animals not selected for cell fusion will be maintained in cage and may be given additional boost immunizations.

The detailed immunization schedule for protein immunization was shown in Table 7 below.

TABLE 7

| Immunization schedule (Protein immunization) | |
|---|---|
| Day 0 | Pre-bleed (15-30 μL serum/mouse) Primary: 50 μg/mouse, IP, CFA |
| 14 | Boost 1: 25 μg/mouse, IP, IFA |
| 21 | Test Bleed (15-30 μL serum/mouse) (TB1) |
| 22 | Test bleed FACS |
| 35 | Boost 2: 25 μg/mouse, IP, IFA |
| 42 | Test Bleed (15-30 μL serum/mouse) (TB2) |
| 43 | Test bleed FACS |
| 44 | Data analysis and phase conclusion |
| 56 | Pre-fusion (final) Boost, 25 μg/mouse, IP |

Animals not selected for cell fusion will be maintained in cage and may be given additional boost immunizations.

1.1.3. Test Bleed Antiserum Analysis

Test bleeds were performed and evaluated by testing using FACS on CHO-K1 cell line stably over-expressing human Claudine18.2 (i.e., CHOK1-18.2).

1.2. Hybridoma Generation and Screening 1.2.1. Cell Fusion and Screening

Fusion: Splenocyte fusions were performed on the mice which show the best response to the immunizations as determined by test bleed FACS. The lymphocytes from spleens and lymph nodes were fused to a Sp2/0-Ag14 cell line using an optimized electrofusion protocol. Multiple fusions were performed to ensure success of the project.

Screening and Expansion: The fusion was plated ($10^4$ to $10^5$ per well) into a stack of 96-well plates. Plates were monitored for growth and fed weekly. Wells with cell growth were screened by primary screening assays in 10-14 days with Acumen (HCI488NM) and/or other feasible assays. Multiple fusions for each targeting antigen were performed and screened by Acumen. The positive parental clones which showed positive binding with CHOK1-18.2 from primary screening were expanded into 24-well plates for secondary screening.

Additional Antibody Screening: Following primary screening, positive parental clones expanded into 24-well plates were screened again by the assay described in the hybridoma screening funnel below in section 1.2.2.

Hybridomas of interest were chosen to proceed to subcloning.

1.2.2. Hybridoma Subcloning, Screening and Cryopreservation

Subcloning: The parental hybridomas with desired reactivity and isotypes from the screening funnel above were then subcloned by multiple rounds of limiting dilution or single cell sorting until monoclones were obtained.

Screening & Expansion: The subcloning plates were screened by Acumen assay and the subclones with good binding ability were expanded to 24-wells for confirmation tests. The specificity and cross-reactivity of these subclones were confirmed with FACs analysis. Briefly, parental CHO-K1 cells, CHOK1-18.2, CHO-K1 cell line stably over-expressing human Claudine18.1 (CHOK1-18.1), CHO-K1 cell line stably over-expressing Rhesus monkey Claudine18.2 (CHOK1-rh18.2), and CHO-K1 cell line stably over-expressing mouse Claudine18.2 (CHOK1-m18.2) were incubated with antibodies produced by each subclone respectively. Fluorescent dye-conjugated secondary antibody was used to detect the binding of the primary antibody with the cells. Median fluorescence intensity (MFI) was measured by FACs analysis.

Cryopreservation: The desired subclonal cell lines were sequenced and further expanded into culture flasks for cryopreservation. 4-6 vials per cell line at 0.5-1.0×$10^7$ cells/vial were initially cryopreserved. Master cell bank and working cell bank can be established for the selected most valuable cell lines if desired.

2. Results

We discovered 38 antibodies with unique sequences showing positive binding with CHO-K1 cell stably over-expressing human Claudine18.2 protein (CHOK1-18.2). Among which, 33 antibodies did not bind with CHO-K1 cell line stably over-expressing human Claudine18.1 protein (CHOK1-18.1), which suggested that these antibodies specifically recognize Claudine 18.2. Five antibodies had positive binding with both CHOK1-18.2 and CHOK1-18.1, but did not bind to parental CHOK1 cells, suggesting these antibodies are Pan-Claudine 18 recognizing antibody. All 38 antibodies could bind with monkey and mouse Claudin18.2 protein. The MFI of the antibodies staining CHOK1-18.2, CHOK1-18.1, CHOK1-rh18.2, CHOK1-m18.2, detected by FACs were summarized in Table 8 below. Anti-Pan-Claudine18 antibodies were underlined.

TABLE 8

MFI of antibodies binding to different cell lines

| Clone | SEQ ID NOs of VH-CDR 1, VH-CDR 2, VH-CDR 3 (upper) and VL-CDR 1, VL-CDR 2, VL-CDR 3 (lower) | FACS MFI (CHOK1-18.1) | FACS MFI (CHOK1-18.2) | FACS MFI (CHOK1-rh18.2) | FACS MFI (CHOK1-m18.2) |
|---|---|---|---|---|---|
| Ab01 | SEQ ID NOs: 18, 20, 22<br>SEQ ID NOs: 27, 29, 31 | 7247.1 | 12315.7 | 8383.4 | 12698.6 |
| Ab02 | SEQ ID NOs: 36, 38, 40<br>SEQ ID NOs: 45, 47, 49 | 101.4 | 1378.9 | 1402.4 | 2036 |
| Ab03 | SEQ ID NOs: 54, 56, 58<br>SEQ ID NOs: 63, 65, 67 | 95.6 | 1957.3 | 1434.7 | 2973.8 |
| Ab04 | SEQ ID NOs: 72 and 74, GDY<br>SEQ ID NOs: 81, 83, 85 | 6920 | 17564.3 | 2133 | 8444 |
| Ab05 | SEQ ID NOs: 90, 92, 94<br>SEQ ID NOs: 99, 101, 103 | 97 | 16003.9 | 9851.9 | 12520.7 |
| Ab06 | SEQ ID NOs: 108, 110, 112<br>SEQ ID NOs: 117, 119, 121 | 789.4 | 46072.7 | 13988.5 | 13203.5 |
| Ab07 | SEQ ID NOs: 126, 128, 130<br>SEQ ID NOs: 135, 137, 139 | 764.4 | 13716.6 | 9042 | 15007.2 |
| Ab08 | SEQ ID NOs: 144, 146, 148<br>SEQ ID NOs: 153, 155, 157 | 97 | 19354 | 8351.8 | 13100.6 |
| Ab09 | SEQ ID NOs: 198, 200, 202<br>SEQ ID NOs: 207, 209, 211 | 95.6 | 17055.7 | 8104.1 | 12561.9 |
| Ab10 | SEQ ID NOs: 216, 218, 220<br>SEQ ID NOs: 225, 227, 229 | 80.8 | 8401.8 | 7071.4 | 17133.6 |
| Ab11 | SEQ ID NOs: 234, 236, 238<br>SEQ ID NOs: 243, 245, 247 | 80.8 | 9799 | 7803.5 | 11248.4 |
| Ab12 | SEQ ID NOs: 252, 254, 256<br>SEQ ID NOs: 261, 263, 265 | 83.8 | 8816.3 | 7613.1 | 13134.5 |
| Ab13 | SEQ ID NOs: 270, 272, 274<br>SEQ ID NOs: 279, 281, 283 | 82.3 | 7463.2 | 5627.9 | 12543.5 |
| Ab14 | SEQ ID NOs: 288, 290, 292<br>SEQ ID NOs: 297, 299, 301 | 97 | 21360.6 | 6845.1 | 13628.4 |
| Ab15 | SEQ ID NOs: 306, 308, 310<br>SEQ ID NOs: 315, 317, 319 | 80.8 | 7386.8 | 6319.5 | 12165.7 |
| Ab16 | SEQ ID NOs: 324, 326, 328<br>SEQ ID NOs: 333, 335, 337 | 80.8 | 8170.3 | 6662 | 14313.4 |
| Ab17 | SEQ ID NOs: 342, 344, 346<br>SEQ ID NOs: 351, 353, 355 | 82.3 | 11454.2 | 6681.1 | 13289.5 |
| Ab18 | SEQ ID NOs: 360, 362, 364<br>SEQ ID NOs: 369, 371, 373 | 79.4 | 9910.7 | 7885.1 | 13519.6 |
| Ab19 | SEQ ID NOs: 378, 380, 382<br>SEQ ID NOs: 387, 389, 391 | 80.8 | 7343.4 | 6293.1 | 13391.7 |
| Ab20 | SEQ ID NOs: 396, 398, 400<br>SEQ ID NOs: 405, 407, 409 | 82.3 | 7580.8 | 7047.2 | 13845.9 |
| Ab21 | SEQ ID NOs: 414, 416, 418<br>SEQ ID NOs: 423, 425, 427 | 79.4 | 10079.8 | 8239.4 | 15216.7 |
| Ab22 | SEQ ID NOs: 432, 434, 436<br>SEQ ID NOs: 441, 443, 445 | 82.3 | 9024.3 | 7329.4 | 15518.1 |

TABLE 8-continued

MFI of antibodies binding to different cell lines

| Clone | SEQ ID NOs of VH-CDR 1, VH-CDR 2, VH-CDR 3 (upper) and VL-CDR 1, VL-CDR 2, VL-CDR 3 (lower) | FACS MFI (CHOK1-18.1) | FACS MFI (CHOK1-18.2) | FACS MFI (CHOK1-rh18.2) | FACS MFI (CHOK1-m18.2) |
|---|---|---|---|---|---|
| Ab23 | SEQ ID NOs: 450, 452, 454<br>SEQ ID NOs: 459, 461, 463 | 82.3 | 8597.3 | 7242.7 | 16527.2 |
| Ab24 | SEQ ID NOs: 468, 470, 472<br>SEQ ID NOs: 477, 479, 481 | 80.8 | 10085.7 | 7519.1 | 12839.7 |
| Ab25 | SEQ ID NOs: 486, 488, 490<br>SEQ ID NOs: 495, 497, 499 | 82.3 | 12559.7 | 11970.9 | 23445 |
| Ab26 | SEQ ID NOs: 504, 506, 508<br>SEQ ID NOs: 513, 515, 517 | 80.8 | 9731.4 | 8292.3 | 15676.1 |
| Ab27 | SEQ ID NOs: 522, 524, 526<br>SEQ ID NOs: 531, 533, 535 | 97 | 7147.1 | 9241.9 | 8236.4 |
| Ab28 | SEQ ID NOs: 540, 542, 544<br>SEQ ID NOs: 549, 551, 553 | 205.8 | 8878.8 | 11085.3 | 9531.5 |
| Ab29 | SEQ ID NOs: 558, 560, 562<br>SEQ ID NOs: 567, 569, 571 | 97 | 19077.7 | 25720.6 | 21851.6 |
| Ab30 | SEQ ID NOs: 576, 578, 580<br>SEQ ID NOs: 585, 587, 589 | 98.5 | 7563.2 | 10476.7 | 9613.8 |
| Ab31 | SEQ ID NOs: 594, 596, 598<br>SEQ ID NOs: 603, 605, 607 | 97 | 5524.3 | 8010 | 7789.5 |
| Ab32 | SEQ ID NOs: 612, 614, 616<br>SEQ ID NOs: 621, 623, 625 | 172 | 8731.1 | 11070.6 | 9237.5 |
| Ab33 | SEQ ID NOs: 630, 632, 634<br>SEQ ID NOs: 639, 641, 643 | 97 | 8195.3 | 9659.4 | 9753.5 |
| Ab34 | SEQ ID NOs: 648, 650, 652<br>SEQ ID NOs: 657, 659, 661 | 91.1 | 9072.8 | 6719.4 | 10670.7 |
| Ab35 | SEQ ID NOs: 666, 668, 670<br>SEQ ID NOs: 675, 677, 679 | 92.6 | 11264.6 | 8339.3 | 9613.8 |
| Ab36 | SEQ ID NOs: 684, 686, 688<br>SEQ ID NOs: 693, 695, 697 | 4304.2 | 18040.7 | 17420.4 | 21601.1 |
| Ab37 | SEQ ID NOs: 163, 165, 167<br>SEQ ID NOs: 172, 174, 176 | 4589.9 | 15168.3 | 16699.4 | 18634.8 |
| Ab38 | SEQ ID NOs: 181, 183, 185<br>SEQ ID NOs: 190, 192, 194 | 4472.6 | 15683.7 | 15612.6 | 20379.2 |

Example 2: Antibody Characterization: Affinity

1. Methods

Sequences of 15 mouse antibodies from Table 8 were selected to generate and produce human IgG1 chimeric antibodies. The binding affinity of these antibodies and the bench mark antibody (i.e., IMAB362 (Zolbetuximab)) with CHOK1-18.2 cells and human patient derived gastric cancer cell line (i.e., GAXC031) was determined by FACs analysis. The protocol for FACs analysis was described as follows:

a. Digested cells using TrypLE™ Express Enzyme (1×), and then centrifuged the harvested cells at 400 g for 5 min and discarded the supernatant.
b. Washed the cells twice with cold FACS buffer by centrifuging at 400 g for 5 min and discarded the supernatant.
c. Resuspended the cells, and seeded $2*10^5$ cell/well into the assay plate in 50 µl FACS buffer, then added 50 µl primary antibody (primary antibody final concentration: 50.00, 16.67, 5.56, 1.85, 0.62, 0.21, 0.07, 0.02, 0.01, 0.00 µg/ml) and incubated at 40° C. for 1 hour.
d. Washed the cells twice by using the condition in step b, and then resuspended the cells with 100 µl/well diluted secondary antibody (i.e. AlexaFluor488-anti-human IgG), and incubated at 4° C. for 1 hour in the dark.
e. Washed the cells twice by using the condition in step b, and then resuspended the cells with 100 µl/well cold FACS buffer. Kept the cells in dark for FACS analysis.

2. Results

Figure 3A:
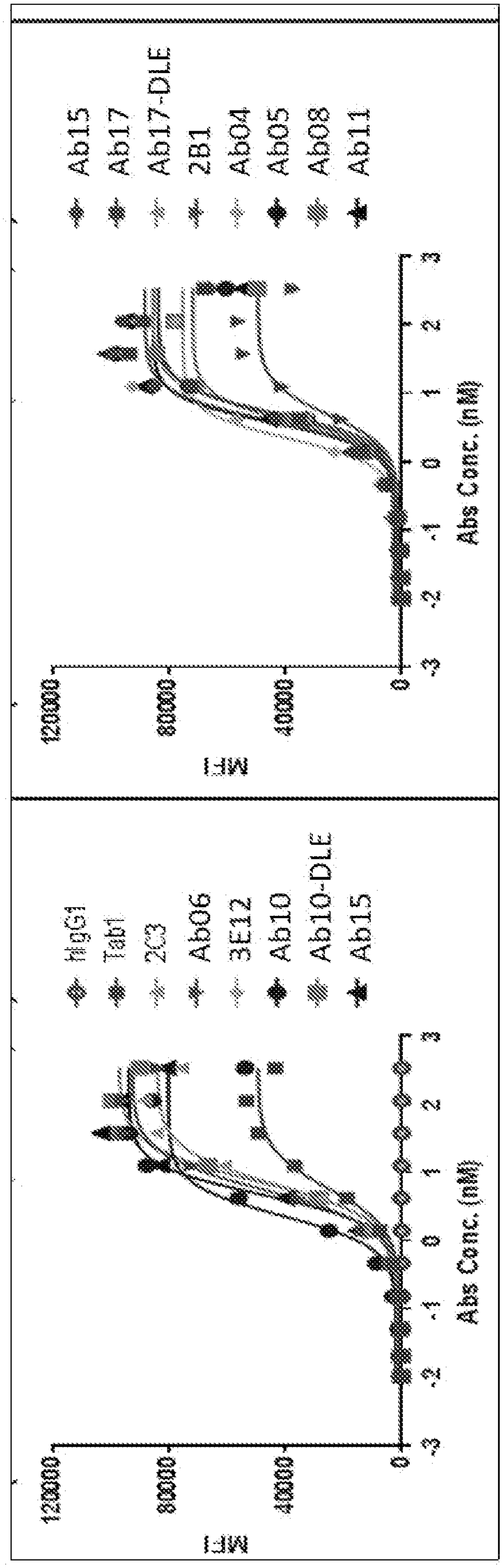
FIG. 3 shows FACs analysis suggesting that the binding affinity of the selected antibodies on CHOK1-18.2 and GAXC031 are higher or comparable with bench mark antibody IMAB362 (Tab1), with higher max MFI. DLE refers to enhanced human IgG1 Fc comprising an amino acid sequence of SEQ ID NO: 702, which is a human IgG1 heavy chain Fc with mutations of S122D, A213L and I215E. 2B1 is the antibody 2B1 included in the patent application No PCT/CN2017/092381; 2C3 is the antibody 2-C3 included in the patent application No PCT/US2019/020872; 3E12 is the antibody 3E12 included in the patent application No PCT/CN2017/092381.

The binding affinity of the selected antibodies on CHOK1-18.2 were higher than or comparable with the bench mark antibody IMAB362 (see Table 9 and FIG. 3).

Compared with IMAB362, the max MFI (primary antibody concentration at 50 μg/ml) of the selected antibodies on Claudin18.2-low expressing cells GAXC031 and CHOK1-18.2 were much higher (see Table 9).

Figure 2:
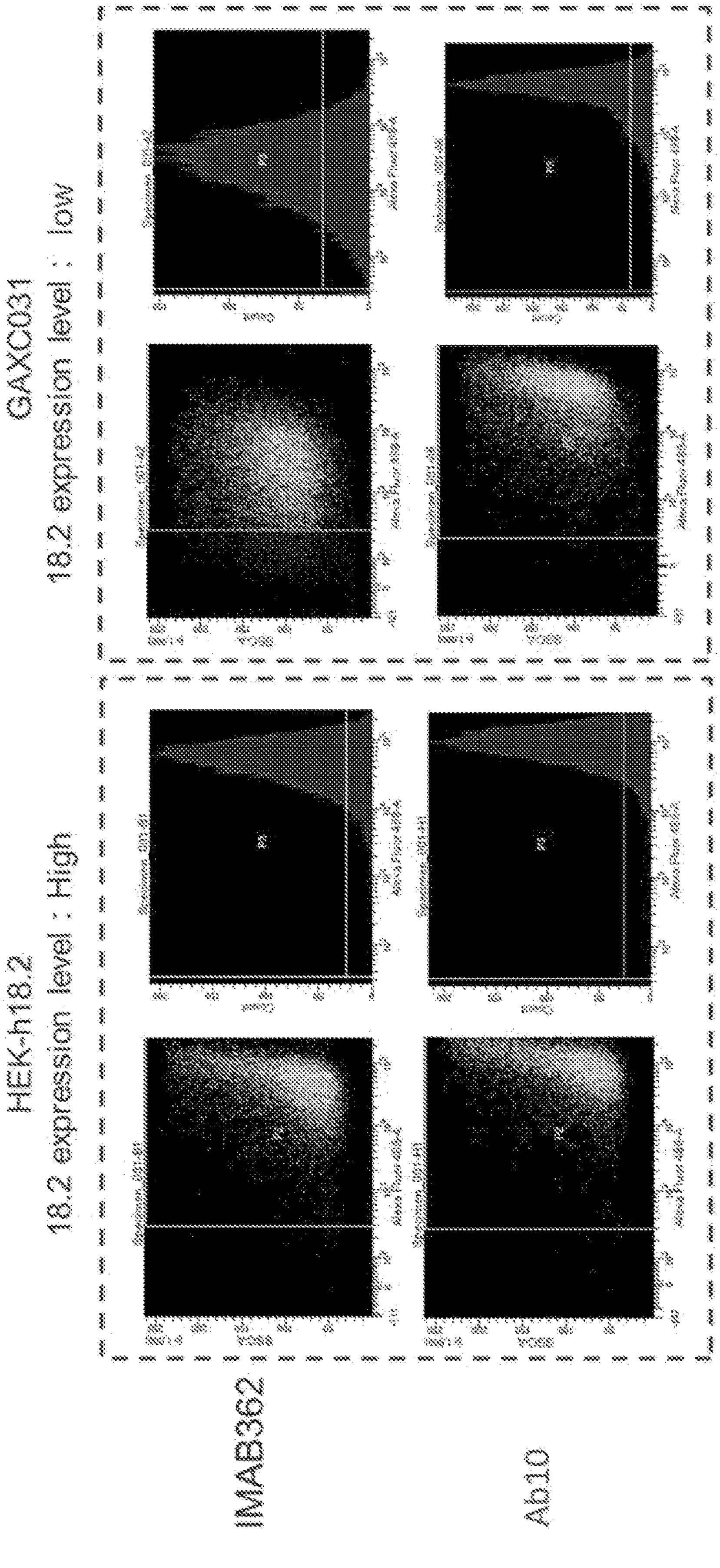
FIG. 2 shows that chAb10 is more sensitive on Claudine18.2-low expressing cell (i.e., GAXC031 cells) compared with IMAB362. Some of the GAXC031 cells were negatively stained with IMAB362, while chAb10 stains all GAXC031 cells.

The selected antibodies were more sensitive on Claudin18.2-low expressing cells GAXC031 compared with IMAB362 (see FIG. 2), with higher max MFI and higher or comparable $EC_{50}$ (see Table 9 and FIG. 3).

TABLE 9

Binding affinity of the antibodies on GAXC031 and CHOK1-18.2 ("ch" refers to chimeric)

| Clones | SEQ ID NOs of VH-CDR 1, VH-CDR 2, VH-CDR 3 (upper) and VL-CDR 1, VL-CDR 2, VL-CDR 3 (lower) | GAXC031 MAX MFI | GAXC031 $EC_{50}$ (nM) | CHOK1-18.2 MAX MFI | CHOK1-18.2 $EC_{50}$ (nM) |
|---|---|---|---|---|---|
| IMAB362 | SEQ ID NOs: 2, 4, 6<br>SEQ ID NOs: 10, 12, 14 | 742 | 36.11 | 49613 | 5.686 |
| chAb06 | SEQ ID NOs: 108, 110, 112<br>SEQ ID NOs: 117, 119, 121 | 5462 | / | 92848 | 5.425 |
| chAb10 | SEQ ID NOs: 216,218, 220<br>SEQ ID NOs: 225, 227, 229 | 6937 | 29.24 | 80356 | 2.274 |
| chAb15 | SEQ ID NOs: 306, 308, 310<br>SEQ ID NOs: 315, 317, 319 | 6112 | 31.86 | 94002 | 4.645 |
| chAb17 | SEQ ID NOs: 342, 344, 346<br>SEQ ID NOs: 351, 353, 355 | 4231 | 94.18 | 83797 | 4.736 |
| chAb04 | SEQ ID NOs: 72 and 74, GDY<br>SEQ ID NOs: 81, 83, 85 | 3864 | / | 75326 | 2.14 |
| chAb05 | SEQ ID NOs: 90, 92, 94<br>SEQ ID NOs: 99, 101, 103 | 4599 | 73.81 | 83869 | 5.001 |
| chAb08 | SEQ ID NOs: 144, 146, 148<br>SEQ ID NOs: 153, 155, 157 | 5834 | / | 71852 | 3.6 |
| chAb11 | SEQ ID NOs: 234, 236, 238<br>SEQ ID NOs: 243, 245, 247 | 6425 | / | 85566 | 3.635 |
| chAb18 | SEQ ID NOs: 360, 362, 364<br>SEQ ID NOs: 369, 371, 373 | 3686 | / | 60243 | 7.715 |
| chAb24 | SEQ ID NOs: 468, 470, 472<br>SEQ ID NOs: 477, 479, 481 | 5859 | / | 64484 | 4.989 |
| chAb25 | SEQ ID NOs: 486, 488, 490<br>SEQ ID NOs: 495, 497, 499 | 3015 | / | 56138 | 8.266 |
| chAb20 | SEQ ID NOs: 396, 398, 400<br>SEQ ID NOs: 405, 407, 409 | 6265 | 42.94 | 65685 | 3.882 |
| chAb30 | SEQ ID NOs: 576, 578, 580<br>SEQ ID NOs: 585, 587, 589 | 4462 | / | 65007 | 9.761 |
| chAb29 | SEQ ID NOs: 558, 560, 562<br>SEQ ID NOs: 567, 569, 571 | 5635 | / | 63401 | 6.629 |
| chAb31 | SEQ ID NOs: 594, 596, 598<br>SEQ ID NOs: 603, 605, 607 | 3773 | / | 59932 | 5.165 |

Example 3: Antibody Characterization: ADCC

1. Methods

GAXC031 cells were labeled with fluorescence enhancing ligand (DELFIA BATDA Reagent, Perkin Elmer, AD0116) according to operational manuscript (i.e., 1*10^6/ml cells were labeled with 2 μl/ml fluorescence enhancing ligand (DELFIA BATDA Reagent) and incubate for 20 min at 37° C. in a cell incubator) and 10,000 cells/well in 100 μL were seeded to 96 wells V-bottom sterile plate (Corning, cat: 3894). After that, added 50 μL serial diluted antibodies listed in Table 9 (at a concentration gradient of 100 nM, 20 nM, 4 nM, 0.8 nM, 0.16 nM, 0.032 nM, 0.0064 nM, 0.00128 nM, 0.000256 nM, and 0 nM) to each well and incubated the plate at 37° C., 5% $CO_2$ for 5-10 min, meanwhile, harvested NK-92 CD16a 176V cells and resuspended them in no pheno red RPMI1640 medium (Gibco, Cat No. #11835-030)+10% FBS to 1*10^6/ml. 50 μL NK92/CD16a cells as mentioned were supply into each well of the assay plate. After 2 hours incubated in 37° C., 5% $CO_2$, transferred 25 μL of the supernatant to a new flat-bottom detection plate (PERKIN ELMER, Cat No. #AAAND-0001). Added 200 μL of Europium Solution (Perkin Elmer, Envision 2105, AD0116-B, Lot #2610848) and shaked the plate at 250 rpm for 15 min at room temperature and detected the values by Envision (Perkin Elmer, Envision 2105).

2. Results

Figure 4:
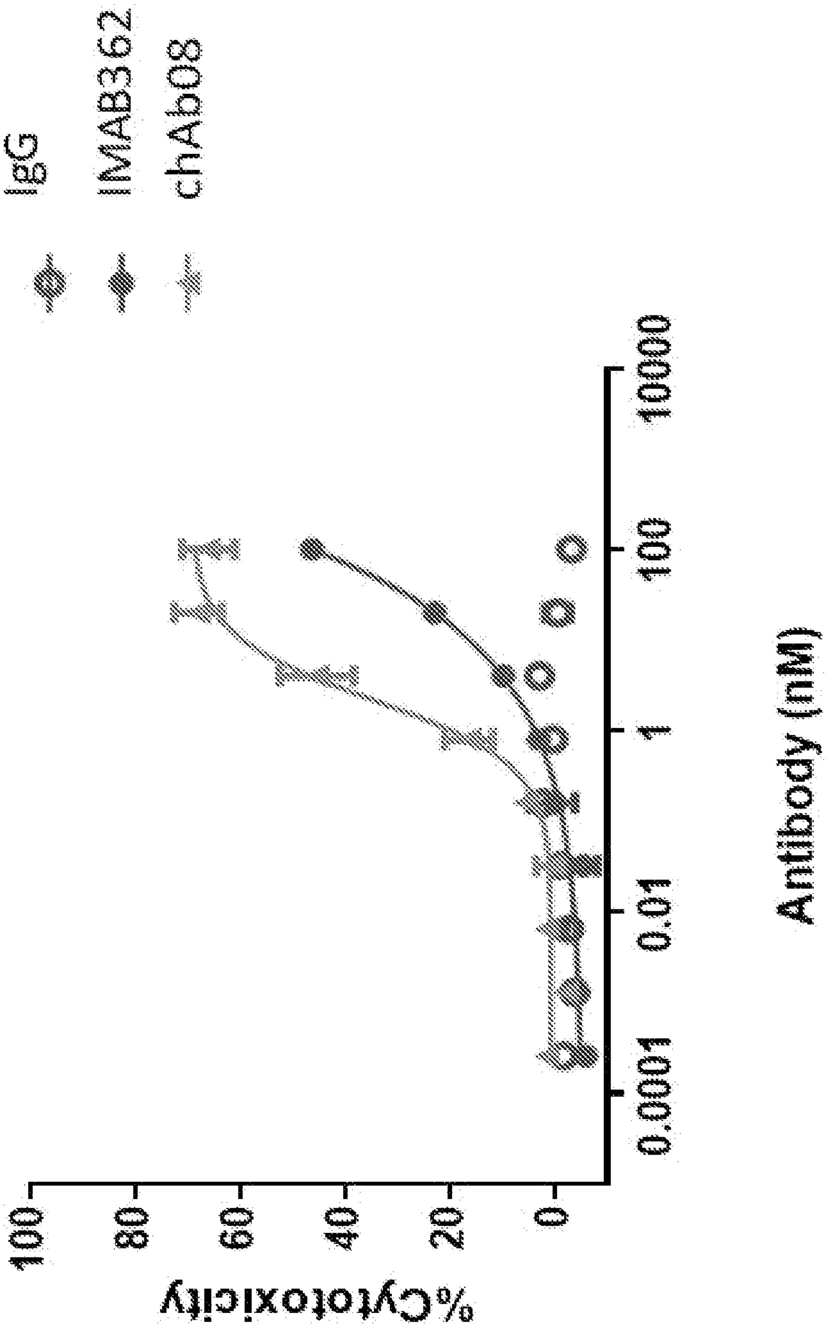
FIG. 4 shows that chAb08 showed more potent ADCC effect compared with IMAB362 on GAXC031 cells.
Figure 5A:
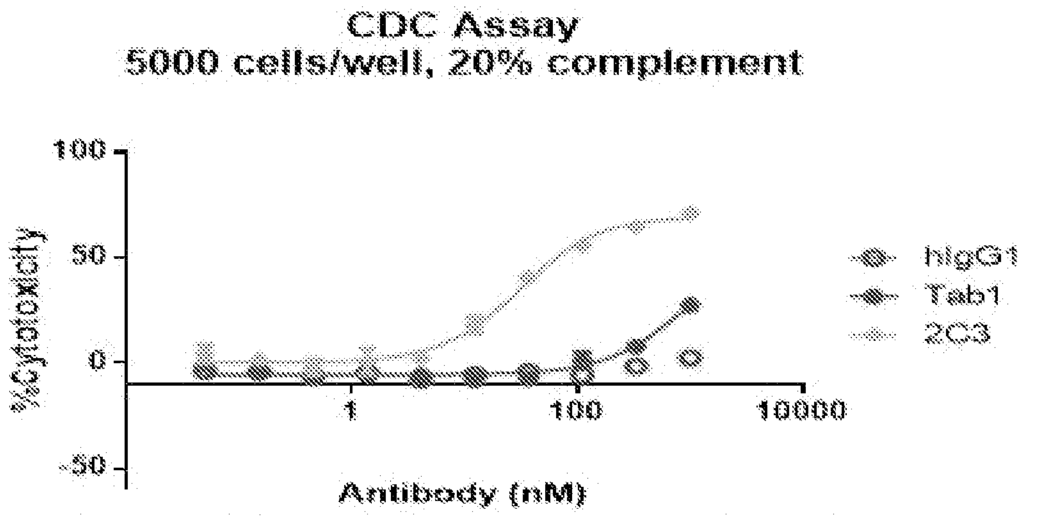
FIG. 5 shows that our antibodies showed more potent ADCC effect compared with IMAB362 (Tab1) on GAXC031 cells.
Figure 5B:
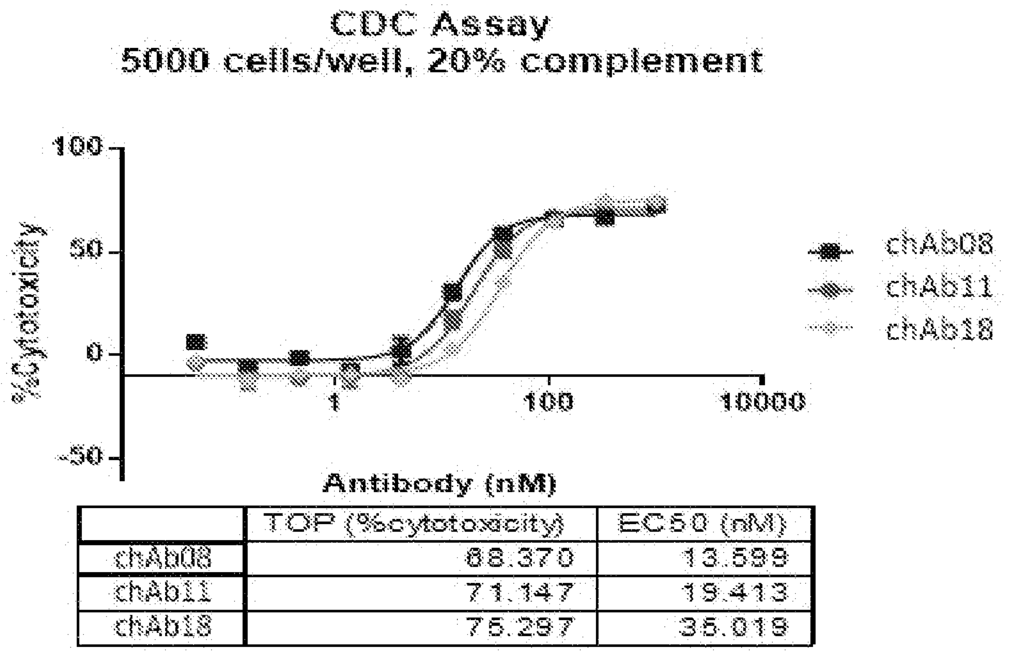
Figure 5C:
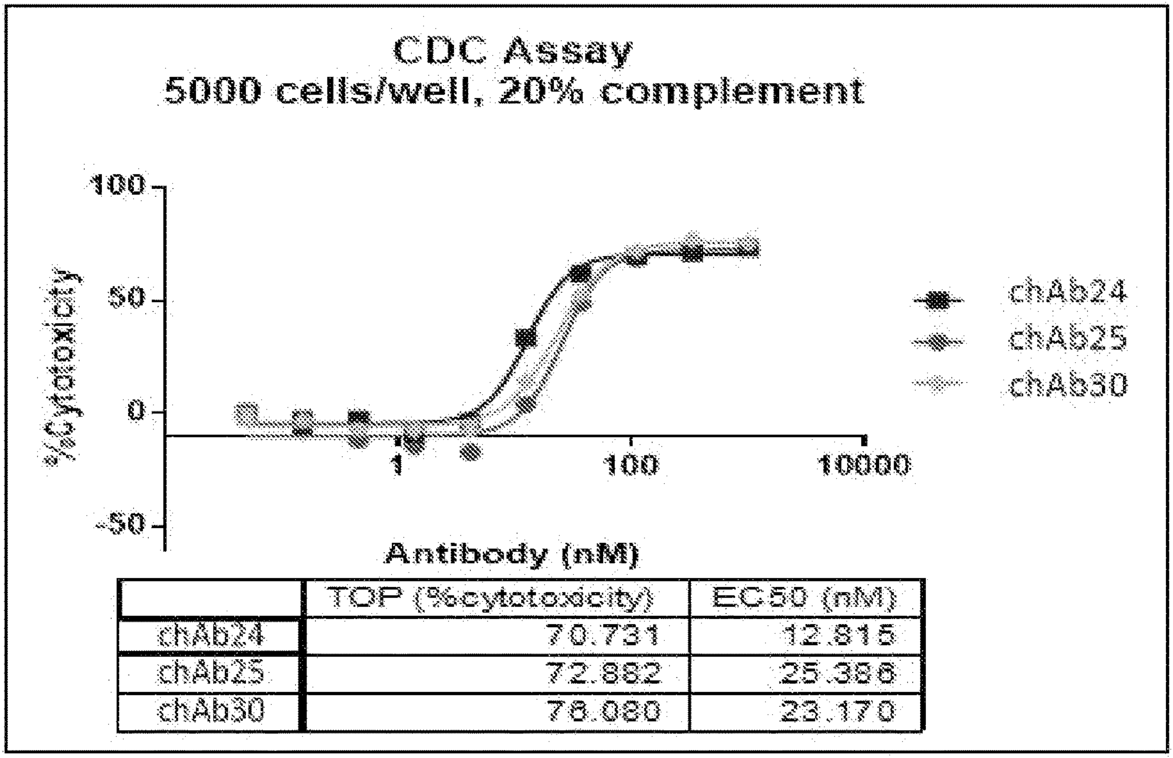

All our antibodies showed potent ADCC effect on GAXC031 cells. Our antibodies showed higher max ADCC induced cell killing on GAXC031 cells, and lower $EC_{50}$ compared with bench mark antibody (i.e., IMAB362) (see Table 10 and FIG. 4).

TABLE 10

Max GAXC031 killing percentage and $EC_{50}$ of antibody induced ADCC effect

| Samples ID. | SEQ ID NOs of VH-CDR 1, VH-CDR 2, VH-CDR 3 (upper) and VL-CDR 1, VL-CDR 2, VL-CDR 3 (lower) | Max tumor cell killing (% of control) | $EC_{50}$ (nM) |
|---|---|---|---|
| IMAB362 | SEQ ID NOs: 2, 4, 6<br>SEQ ID NOs: 10, 12, 14 | 30.68 | 36.08 |
| chAb06 | SEQ ID NOs: 108, 110, 112<br>SEQ ID NOs: 117, 119, 121 | 40.56 | 3.008 |
| chAb10 | SEQ ID NOs: 216, 218, 220<br>SEQ ID NOs: 225, 227, 229 | 55.17 | 1.68 |
| chAb15 | SEQ ID NOs: 306, 308, 310<br>SEQ ID NOs: 315, 317, 319 | 36.52 | 2.652 |
| chAb17 | SEQ ID NOs: 342, 344, 346<br>SEQ ID NOs: 351, 353, 355 | 60.62 | 2.456 |
| chAb04 | SEQ ID NOs: 72 and 74, GDY<br>SEQ ID NOs: 81, 83, 85 | / | / |
| chAb05 | SEQ ID NOs: 90, 92, 94<br>SEQ ID NOs: 99, 101, 103 | 57.91 | 5.925 |
| chAb08 | SEQ ID NOs: 144, 146, 148<br>SEQ ID NOs: 153, 155, 157 | 69.35 | 2.216 |
| chAb11 | SEQ ID NOs: 234, 236, 238<br>SEQ ID NOs: 243, 245, 247 | 54.68 | 3.702 |
| chAb18 | SEQ ID NOs: 360, 362. 364<br>SEQ ID NOs: 369, 371, 373 | 61.5 | 5.07 |
| chAb24 | SEQ ID NOs: 468, 470, 472<br>SEQ ID NOs: 477, 479, 481 | 66.59 | 4.457 |
| chAb25 | SEQ ID NOs: 486, 488, 490<br>SEQ ID NOs: 495, 497, 499 | 76.85 | 8.38 |
| chAb20 | SEQ ID NOs: 396, 398, 400<br>SEQ ID NOs: 405, 407, 409 | 62.86 | 4.141 |
| chAb30 | SEQ ID NOs: 576. 578. 580<br>SEQ ID NOs: 585, 587, 589 | 80.2 | 7.441 |
| chAb29 | SEQ ID NOs: 558, 560, 562<br>SEQ ID NOs: 567, 569, 571 | 60.94 | 5.267 |
| chAb31 | SEQ ID NOs: 594, 596, 598<br>SEQ ID NOs: 603, 605, 607 | 78.84 | 8.159 |

Example 4: Antibody Characterization: CDC

1. Methods

GAXC031 cells were adjusted to 1e5/ml in L-15 medium (GE HYCLONE, Cat No #SH30525.01), then seeded 50 μL cells into 96-flat well plate (Corning, Cat No. #3903), 25 μl serial diluted antibody (at a concentration gradient of 1000 nM, 333.33 nM, 111.11 nM, 37.04 nM, 12.35 nM, 4.12 nM, 1.37 nM, 0.46 nM, 0.15 nM, and 0 nM) were add to each well. After incubating the plate at 37° C., 5% $CO_2$ for 30 min, 25 μL normal human serum complement (Quidel corporation, Cat A113) (final concentration is 20%) were supplied into each well and incubate overnight. On day 2, added 50 μL Cell Titer-Glo Luminescent Buffer (Promega, Cat No. #G7572) to the wells and shake the plate for 2 minutes and put the plate at room temperature for 10 minutes. Signals were measured by Spectra Max M5.

2. Results

All our antibodies showed potent CDC effect on GAXC031 cells. Our antibody showed higher max CDC induced cell killing on GAXC031 cells, and lower $EC_{50}$ compared with bench mark antibody (i.e., IMAB362) (see Table 11 and FIG. 3).

TABLE 11

Max GAXC031 killing percentage and $EC_{50}$ of antibody induced CDC effect

| Samples ID. | SEQ ID NOs of VH-CDR 1, VH-CDR 2, VH-CDR 3 (upper) and VL-CDR 1, VL-CDR 2, VL-CDR 3 (lower) | Max CDC induced tumor cell killing (% of control) | $EC_{50}$ (nM) |
|---|---|---|---|
| IMAB362 | SEQ ID NOs: 2, 4, 6<br>SEQ ID NOs: 10, 12, 14 | 52.52 | 809.4 |
| chAb06 | SEQ ID NOs: 108, 110, 112<br>SEQ ID NOs: 117, 119, 121 | 75.38 | 9.722 |
| chAb10 | SEQ ID NOs: 216, 218, 220<br>SEQ ID NOs: 225, 227, 229 | 82.745 | 2.695 |
| chAb15 | SEQ ID NOs: 306, 308, 310<br>SEQ ID NOs: 315, 317, 319 | 77.44 | 8.155 |
| chAb17 | SEQ ID NOs: 342, 344, 346<br>SEQ ID NOs: 351, 353, 355 | 70.81 | 9.925 |
| chAb05 | SEQ ID NOs: 90, 92, 94<br>SEQ ID NOs: 99, 101, 103 | 78.86 | 17.75 |
| chAb08 | SEQ ID NOs: 144, 146, 148<br>SEQ ID NOs: 153, 155, 157 | 68.37 | 13.6 |
| chAb11 | SEQ ID NOs: 234, 236, 238<br>SEQ ID NOs: 243, 245, 247 | 71.15 | 19.41 |
| chAb18 | SEQ ID NOs: 360, 362, 364<br>SEQ ID NOs: 369, 371, 373 | 75.3 | 35.02 |
| chAb24 | SEQ ID NOs: 468, 470, 472<br>SEQ ID NOs: 477, 479, 481 | 70.73 | 12.81 |
| chAb25 | SEQ ID NOs: 486, 488, 490<br>SEQ ID NOs: 495, 497, 499 | 72.88 | 25.39 |
| chAb20 | SEQ ID NOs: 396, 398, 400<br>SEQ ID NOs: 405, 407, 409 | 72.96 | 8.82 |
| chAb30 | SEQ ID NOs: 576, 578, 580<br>SEQ ID NOs: 585, 587, 589 | 76.08 | 23.17 |
| chAb29 | SEQ ID NOs: 558, 560, 562<br>SEQ ID NOs: 567, 569, 571 | 67.83 | 12.72 |
| chAb31 | SEQ ID NOs: 594, 596, 598<br>SEQ ID NOs: 603, 605, 607 | 60.74 | 37.86 |

Example 5: Antibody Characterization: Indirect ADC Cytotoxicity

1. Methods

GAXC031 cells were incubated with selected chimeric antibodies (primary antibody) and vc-MMAF-conjugated anti-human IgG (secondary antibody), to evaluate the antibody-drug conjugation induced cytotoxicity efficacy of the antibodies. The method is described as follows:

a. GAXC031 cells were seeded at 2000 cells/well in 65 μl assay medium;

b. Treated the cell with primary antibody with a series dilutions in 25 μl assay medium follow the design layout the next day (final starting working concentration 100 nM, 1:5 serial dilution), then added 10 μl of secondary antibody (final working concentration: 2 μg/ml);

c. Continued to culture for 120 hours; and d. Measured the cell viability at 120-hour time point according to the celltiter Glo manual.

2. Results

Figure 6:
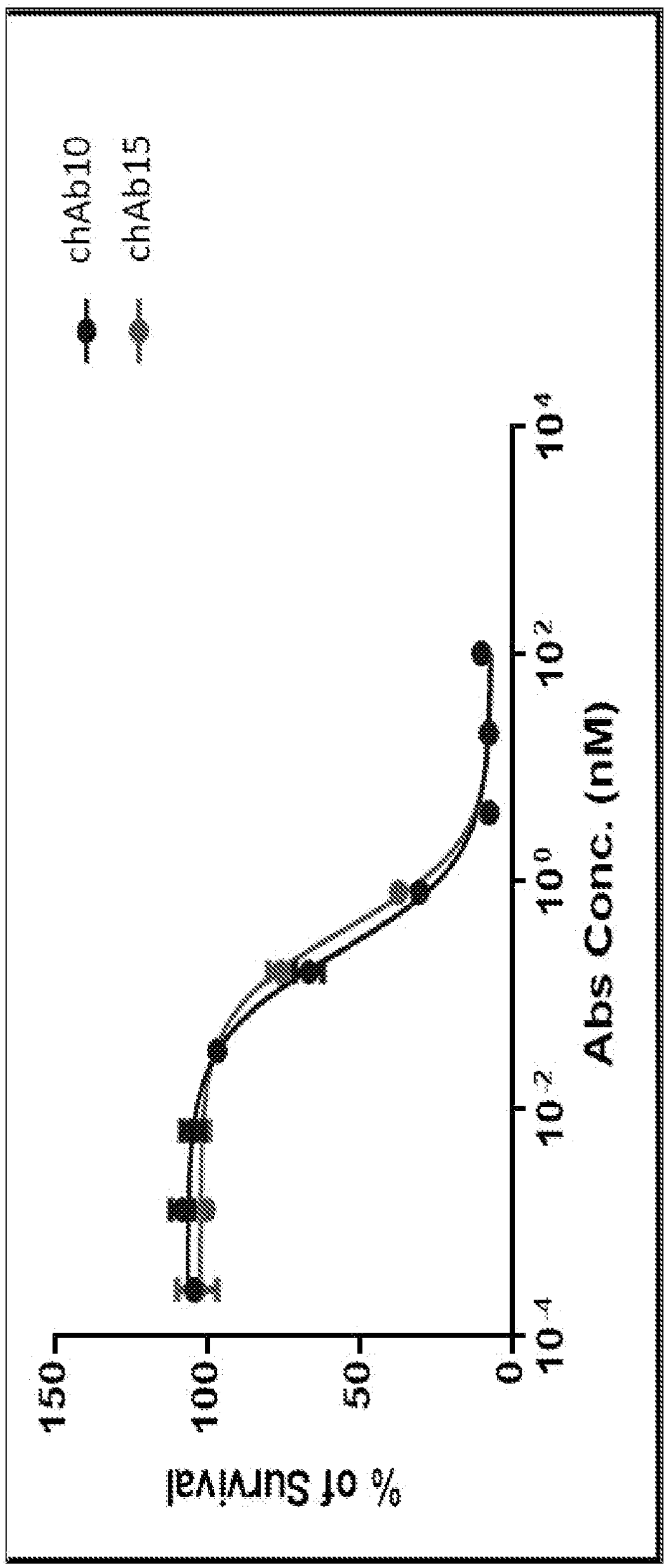
FIG. 6 shows that chAb10 and chAb15 showed potent indirect ADC cytotoxicity on GAXC031 cells.

All our antibodies showed potent indirect ADC effect on GAXC031 cells, with higher max cell killing (max growth inhibition), and lower $IC_{50}$ compared with bench mark antibody (i.e., IMAB362) (see Table 12 and FIG. 6).

TABLE 12

Max GAXC031 growth inhibiton % and $IC_{50}$ of indirect ADC cytotoxicity

| Samples ID. | SEQ ID NOs of VH-CDR1 VH-CDR 2 VH-CDR 3 (upper) and VL-CDR1, VL-CDR 2, VL-CDR 3 | IC50 (nM) | Max inhibition % |
|---|---|---|---|
| IMAB362 | SEQ ID NOs: 2, 4, 6<br>SEQ ID NOs: 10, 12, 14 | 4.75 | 81.80 |
| chAb06 | SEQ ID NOs: 108, 110, 112<br>SEQ ID NOs: 117, 119, 121 | 0.61 | 91.78 |
| chAb10 | SEQ ID NOs: 216, 218, 220<br>SEQ ID NOs: 225, 227, 229 | 0.24 | 92.83 |
| chAb15 | SEQ ID NOs: 306, 308, 310<br>SEQ ID NOs: 315, 317, 319 | 0.38 | 92.43 |
| chAb17 | SEQ ID NOs: 342, 344, 346<br>SEQ ID NOs: 351, 353, 355 | 0.88 | 92.40 |
| chAb05 | SEQ ID NOs: 90, 92, 94<br>SEQ ID NOs: 99, 101, 103 | 0.99 | 92.28 |
| chAb08 | SEQ ID NOs: 144, 146, 148<br>SEQ ID NOs: 153, 155, 157 | 0.45 | 92.52 |
| chAb11 | SEQ ID NOs: 234, 236, 238<br>SEQ ID NOs: 243, 245, 247 | 0.87 | 93.49 |
| chAb18 | SEQ ID NOs: 360, 362, 364<br>SEQ ID NOs: 369, 371, 373 | 1.58 | 90.72 |
| chAb24 | SEQ ID NOs: 468, 470, 472<br>SEQ ID NOs: 477, 479, 481 | 0.85 | 92.72 |
| chAb25 | SEQ ID NOs: 486, 488, 490<br>SEQ ID NOs: 495, 497, 499 | 0.86 | 92.91 |
| chAb20 | SEQ ID NOs: 396, 398, 400<br>SEQ ID NOs: 405, 407, 409 | 0.47 | 92.83 |
| chAb30 | SEQ ID NOs: 576, 578. 580<br>SEQ ID NOs: 585, 587, 589 | 1.58 | 92.38 |
| chAb29 | SEQ ID NOs: 558, 560, 562<br>SEQ ID NOs: 567, 569, 571 | 0.91 | 93.53 |
| chAb31 | SEQ ID NOs: 594, 596, 598<br>SEQ ID NOs: 603, 605, 607 | 2.35 | 91.69 |

Example 6: Antibody Humanization

Lead candidates Ab15, Ab10 and Ab 17 were selected for antibody humanization. Briefly, mouse antibody sequences were analyzed and then 1) Modelling of the mouse antibody VH and VL domains;
2) Alignment with a range of preferred human germline sequences;
3) Assessment of conflicts between non-human CDRs and human FRs and design of back mutations to prevent a loss of affinity in the final products;
4) CDR grafting onto preferred germline backbones;
5) ~5 different humanized sequences generated, cloning and small-scale production of all humanized variants and chimeric in mammalian expression system;

The finally obtained heavy chains and light chains of the humanized sequences were listed below (the amino acids in red refer to the amino acids of CDRs):

>Ab15 HM-VH1
(SEQ ID NO: 704)
EVMLVESGGGLVQPGGSLRLSCAASGFTFSTYTMSWVRQTPEKRLEWVAT
IVGGGGYTYYLDSVKGRFTISRDNAKNTLYLQMNSLRAEDTALYYCARMG
LTQRNALDYWGQGTLITVSS

>Ab15 HM-VH2
(SEQ ID NO: 705)
EVQLVESGGGLVKPGGSLRLSCAASGFTFSTYTMSWVRQTPEKRLEWVAT
IVGGGGYTYYLDSVKGRFTISRDNAKNTLYLQMNSLRAEDTALYYCARMG
LTQRNALDYWGQGTLITVSS

>Ab15 HM-VH3
(SEQ ID NO: 706)
EVMLVESGGGVVQPGGSLRLSCAASGFTFSTYTMSWVRQTPEKRLEWVAT
IVGGGGYTYYLDSVKGRFTISRDNAKNTLYLQMNSLRTEDTALYYCARMG
LTQRNALDYWGQGTLITVSS

>Ab15-HM-VH-N1
(SEQ ID NO: 707)
EVMLVESGGGLVQPGGSLRLSCAASGFTFSTYTMSWVRQTPGKRLEWVAT
IVGGGGYTYYLDSVKGRFTISRDNSKNTLYLQMNSLRAEDTAVYYCARMG
LTQRNALDYWGQGTSITVSS

>Ab15 HM-VL1
(SEQ ID NO: 708)
DIVMTQSPDSLAVSLGERATINCKSSQSLFNSGNQKNYLAWYQQKPGQPP
KLLIYGASTRESGVPDRFTGSGFGTDFTLTISSLQAEDVAVYYCQNDHTY
PLTFGAGTKLEIK

>Ab15 HM-VL2
(SEQ ID NO: 709)
DIVMTQSPLSLPVTPGEPASISCKSSQSLFNSGNQKNYLAWYLQKPGQPP
KLLIYGASTRESGVPDRFTGSGFGTDFTLKISRVEAEDVGVYYCQNDHTY
PLTFGAGTKLEIK

>Ab15-HM-VL-N1
(SEQ ID NO: 710)
DIVMTQSPDSLAVSLGERATINCKSSQSLFNSGNQKNYLAWYQQKPGQPP
KLLIYGASTRESGVPDRFSGSGSGTDFTLTISSLQAEDVAVYYCQNDHTY
PLTFGAGTKLEIK

>Ab10-HM-VH2

-continued (SEQ ID NO: 711)
EVMLVESGGGLVKPGGSLRLSCAASGFTFSSYTMSWVRQAPEKRLEWVAT
ISVIGGNTYYVDSVKGRFTISRDKAKNTLYLQMNSLRAEDTALYYCARLG
QTQRNAMDYWGQGTLVTVSS >Ab10-HM-VH3
(SEQ ID NO: 712)
EVQLVESGGGLVQPGGSLRLSCAASGFTFSSYTMSWVRQAPEKRLEWVAT
ISVIGGNTYYVDSVKGRFTISRDKAKNTLYLQMNSLRAEDTALYYCARLG
QTQRNAMDYWGQGTLVTVSS >Ab10-HM-VH4
(SEQ ID NO: 713)
EVMLVESGGGLVQPGGSLRLSCAASGFTFSSYTMSWVRQTPEKRLEWVAT
ISVIGGNTYYVDSVKGRFTISRDKAKNTLYLQMNSLRAEDTALYYCARLG
QTQRNAMDYWGQGTLVTVSS >Ab10-HM-VH-N1
(SEQ ID NO: 714)
EVMLVESGGGLVQPGGSLRLSCAASGFTFSSYTMSWVRQTPGKRLEWVAT
ISVIGGNTYYVDSVKGRFTISRDKSKNTLYLQMNSLRAEDTAVYYCARLG
QTQRNAMDYWGQGTLVTVSS >Ab10 HM-VL1
(SEQ ID NO: 715)
DIVMTQSPDSLAVSLGERATINCKSSQSLLNSGNQKNYLAWYQQKPGQPP
KLLIYGASTRESGVPDRFTGSGSGTDFTLTISSLQAEDVAVYYCQNDYSY
PLTFGAGTKLEIK >Ab10 HM-VL2
(SEQ ID NO: 716)
EIVMTQSPATLSLSPGERATLSCKSSQSLLNSGNQKNYLAWYQQKPGQPP
RKLIYGASTRESGIPARFTGSGSGTDFTLTISSLQPEDFAVYYCQNDYSY
PLTFGAGTKLEIK >Ab10-HM-VL-N1
(SEQ ID NO: 717)
DIVMTQSPDSLAVSAGERATMNCKSSQSLLNSGNQKNYLAWYQQKPGQPP
KLLIYGASTRESGVPDRFSGSGSGTDFTLTISSLQAEDVAVYYCQNDYSY
PLTFGAGTKLEIK >Ab17 HM-VH1
(SEQ ID NO: 718)
QVQLKESGPGLVKPSETLSLTCTVSGFSLTSYAISWVRQPPGKGLEWLGE
IWTGGGTNYNSALKSRVSISKDNSKSQVFLKLSSVQAADTARYYCGRLSY
GNSLDYWGQGTLVTVSS >Ab17 HM-VH2
(SEQ ID NO: 719)
QVQLQESGPGLVKPSQTLSLTCTVSGFSLTSYAISWVRQPAGKGLEWLGE
IWTGGGTNYNSALKSRVSISKDNSKSQVFLKLSSVQAADTARYYCGRLSY
GNSLDYWGQGTLVTVSS >Ab17 HM-VH3
(SEQ ID NO: 720)
QVQLQESGPGLVKPSQTLSLTCTVSGFSLTSYAISWVRQPPGKGLEWLGE
IWTGGGTNYP ALKSRVSISKDNSKSQVFLKLSSVTAADTARYYCGRLSY
GNSLDYWGQGTLVTVSS >Ab17 HM-VH3-CDR2

-continued (SEQ ID NO: 726)
EIWTGGGTNYB ALKS

>Ab17 HM-VH5

(SEQ ID NO: 721)
QVQLQESGPGLVKPSQTLSLTCTVSGFSLTSYAISWVRQPAGKGLEWLGE

IWTGGGTNYNSALKSRVSISKDNSKSQVFLKLSSVTAADTARYYCGRLSY

GNSLDYWGQGTLVTVSS

>Ab17 HM-VH1-N1

(SEQ ID NO: 722)
QVQLQESGPGLVKPSETLSLTCTVSGFSLTSYAISWVRQPPGKGLEWIGE

IWTGGGTNYNS LKSRVTISKDNSKSQVSLKLSSVQAADTARYYCGRLSY

GNSLDYWGQGTLVTVSS

>Ab17 HM-VH1-N1-CDR2

(SEQ ID NO: 727)
EIWTGGGTNYNS LKS

>Ab17 HM-VL1

(SEQ ID NO: 723)
DIVMTQSPDSLTVSLGERATINCKSSQSLLNSGNQKNYLTWYQQKPGQPP

KLLIYWASTRESGVPDRFTGSGSGTDFTLTISSLQAEDVAVYYCQNNFIY

PLTFGPGTKLEIK

>Ab17 HM-VL2

(SEQ ID NO: 724)
DIVMTQSPLSLPVTLGEPASISCKSSQSLLNSGNQKNYLTWYLQKPGQPP

KLLIYWASTRESGVPDRFTGSGSGTDFTLKISRVEAEDVGVYYCQNNFIY

PLTFGPGTKLEIK

>Ab17 HM-VL1-N (SEQ ID NO: 725)
DIVMTQSPDSTTVLLGERATINCKSSQSLLNSGNQKNYA WYQQKPGQPP

KLLIYWASTRESGVPDRFSGSGSGTDFTLTISSLQAEDVAVYYCQNNFIY

PLTFGPGTKLEIK

>Ab17 HM-VL1-N-CDR1

(SEQ ID NO: 728)
KSSQSLLNSGNQKNYA

1. Cell Based Binding Affinity (GAXC031)

Figure 7A:
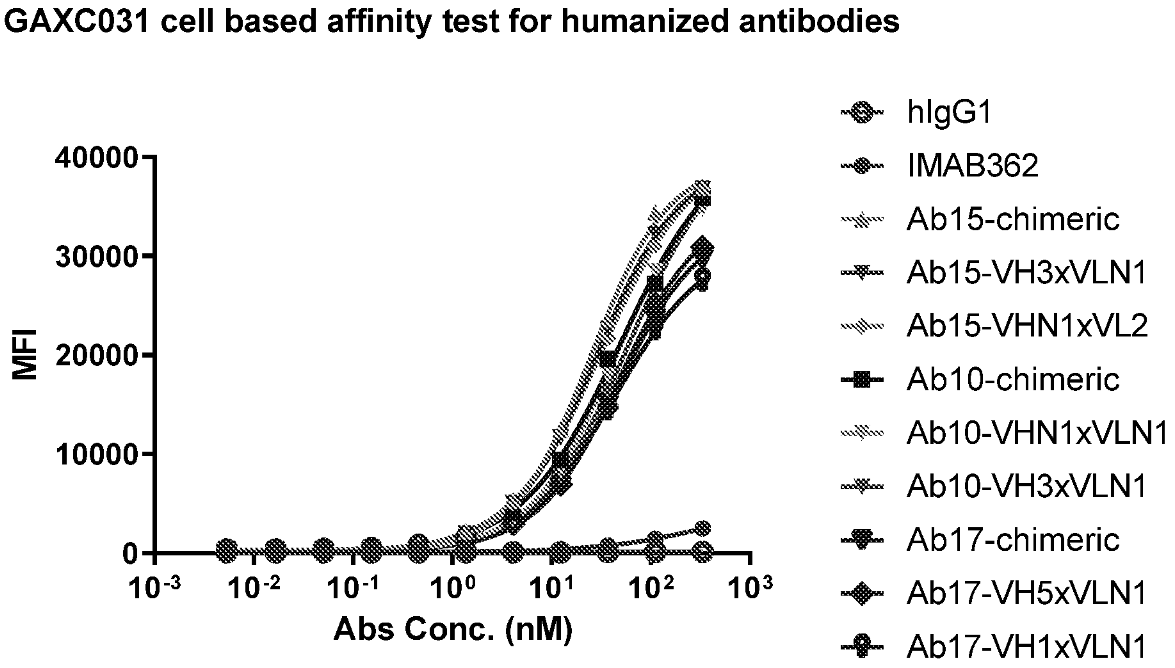

Humanized antibodies with different combination of light and heavy chains were expressed. Cell based affinity was tested using GAXC031 cells. Some of the humanized antibody showed equal or slightly decreased affinity against GAXC031 cells as shown in FIG. 7.

2. Cell Based Binding Affinity (KatoIII and SNU620)

KatoIII and SNU620 cells that express very low level Claudin 18.2 were tested for the binding affinity with Ab15, Ab10 and Ab17. Briefly, these gastric cancer cells were collected and washed twice with 1×PBS buffer and then incubated with mAbs of this disclosure at a series of concentrations for 1 hour. Samples were washed twice and incubated with FITC-labeled secondary antibody for the following flow cytometry analysis.

Figure 8A:
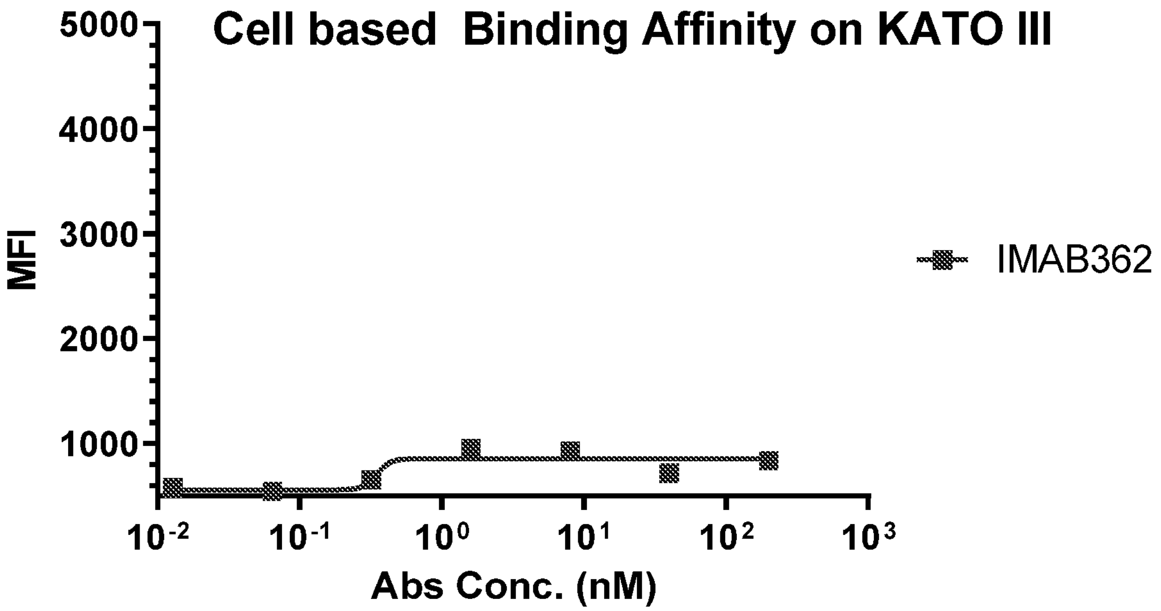
FIGS. 8A-8C show that the antibodies, especially mAb Ab15, displayed detectable binding affinity onto KatoIII and SNU620 cells expressing very low level of Claudin 18.2, which are hardly detected by benchmark antibody IMAB362.
Figure 8B:
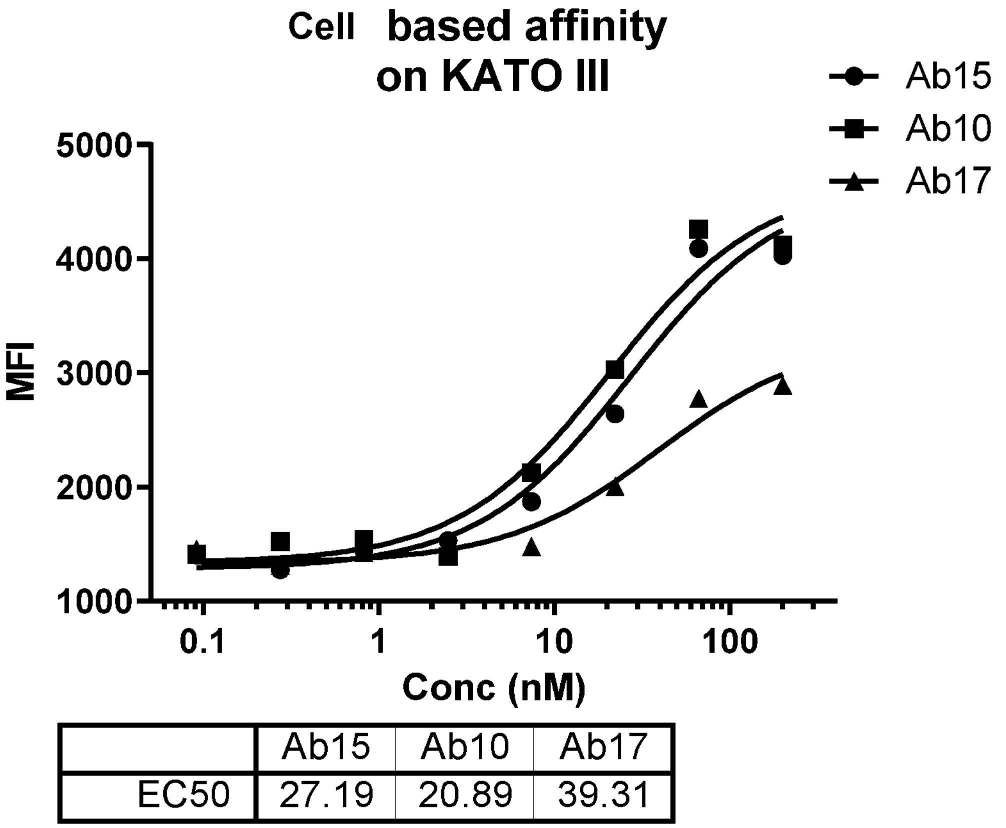
Figure 8C:
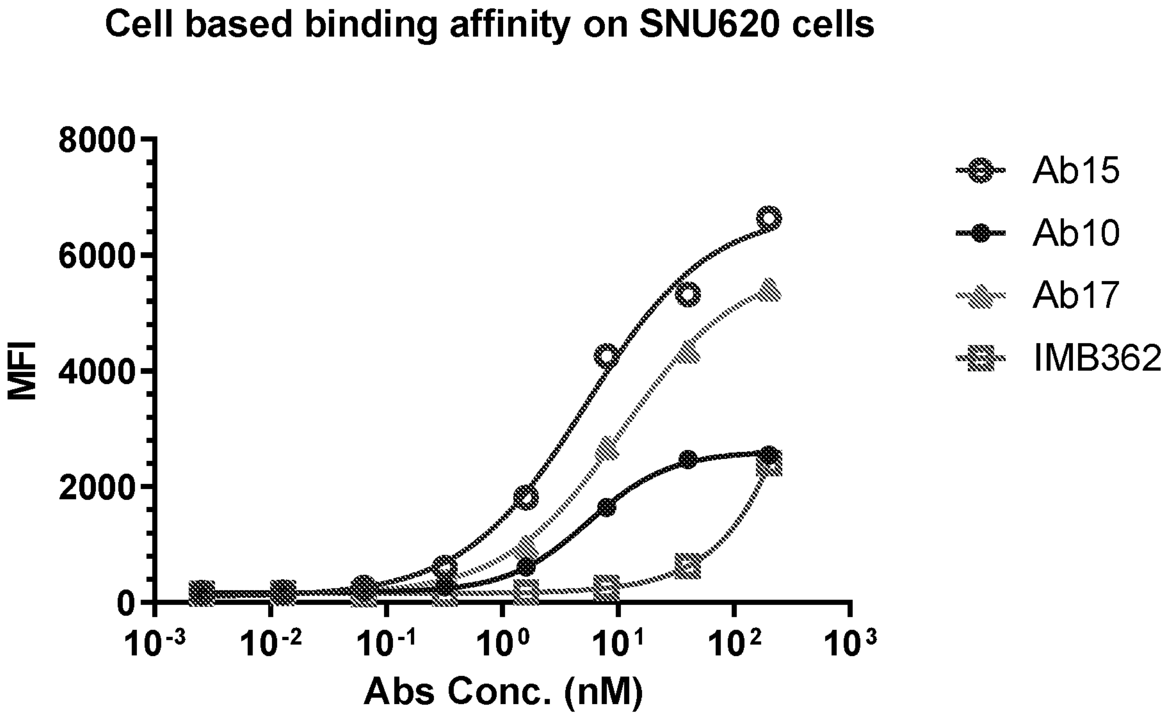
Figure 9A:
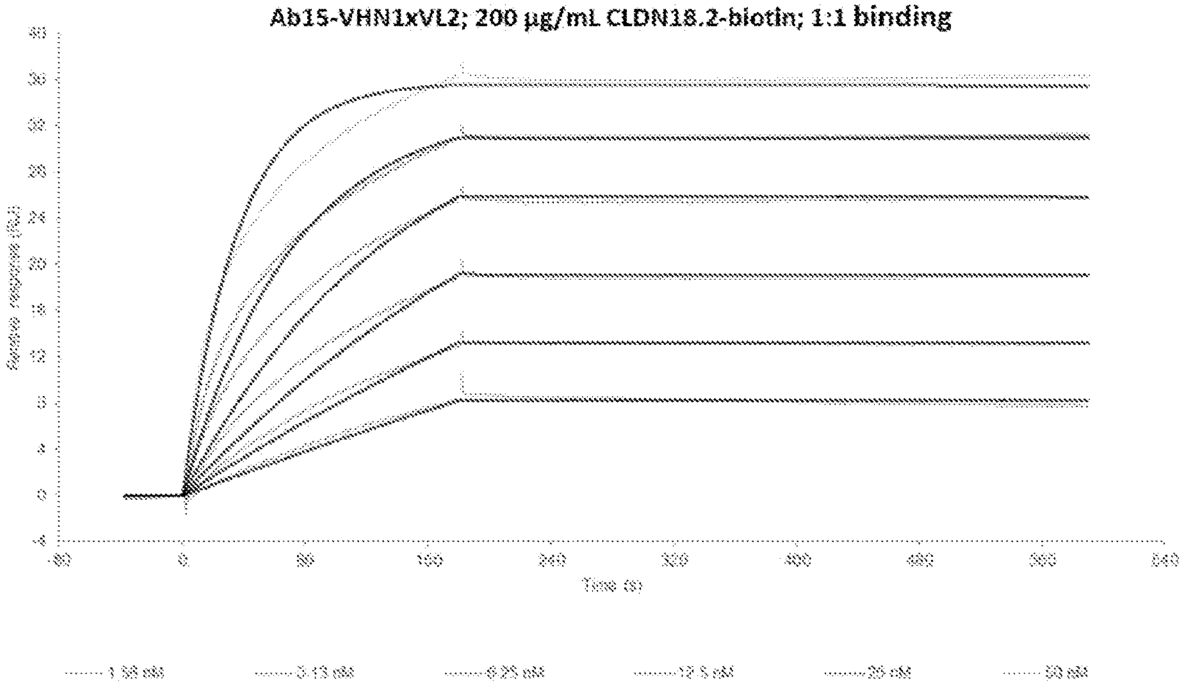
Figure 9B:
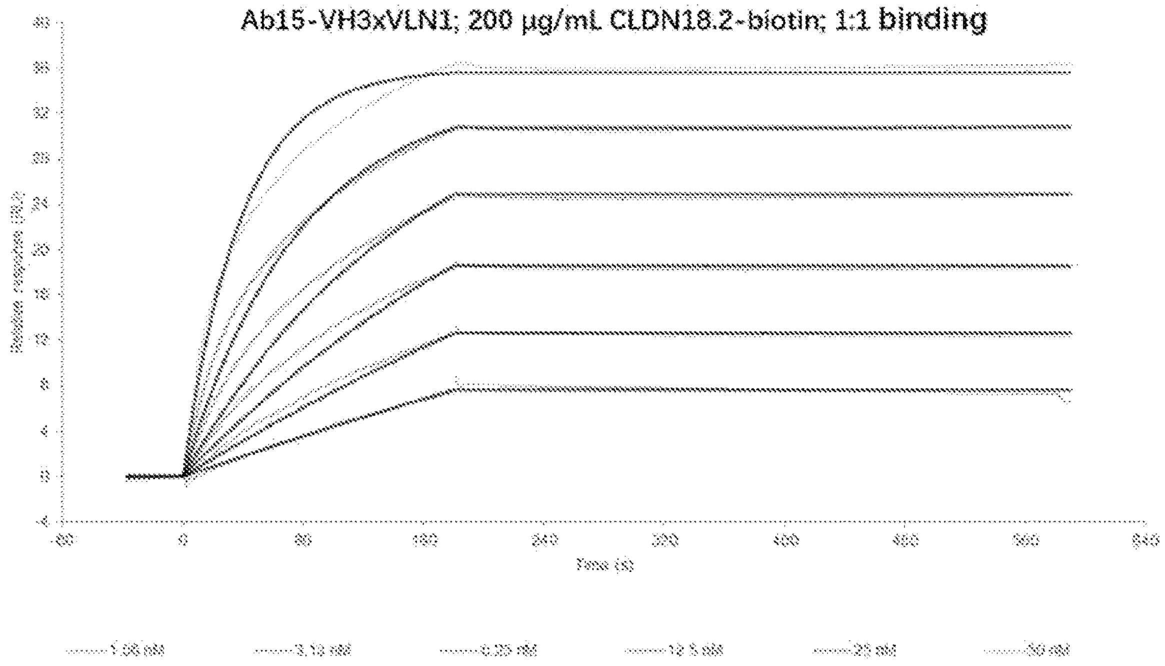
Figure 9C:
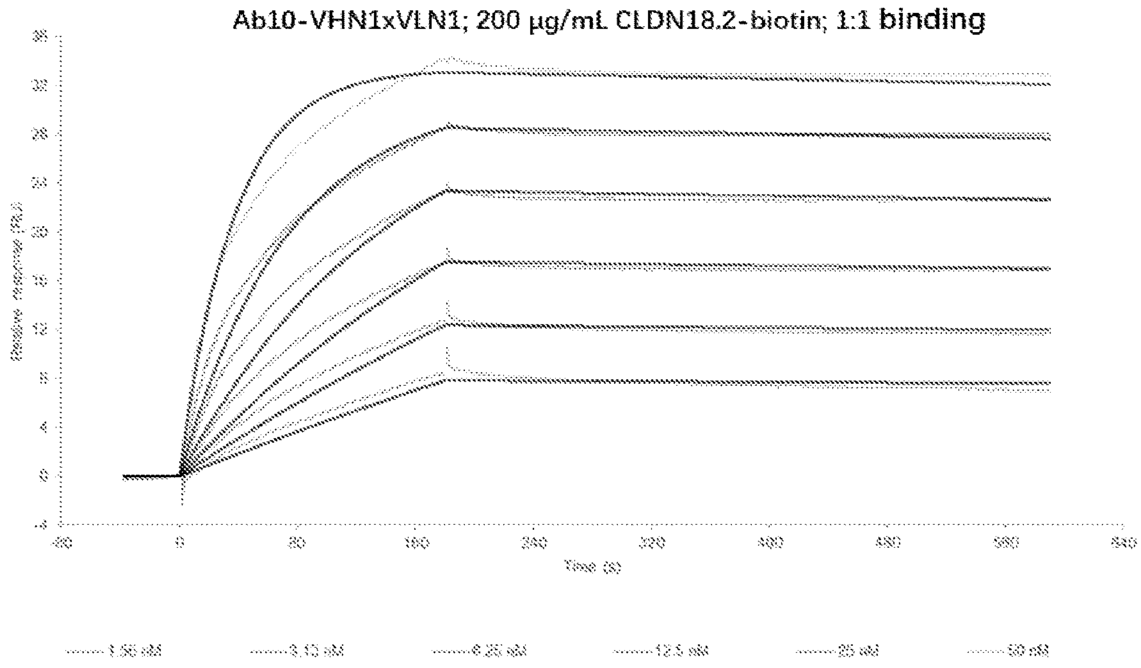
Figure 9D:
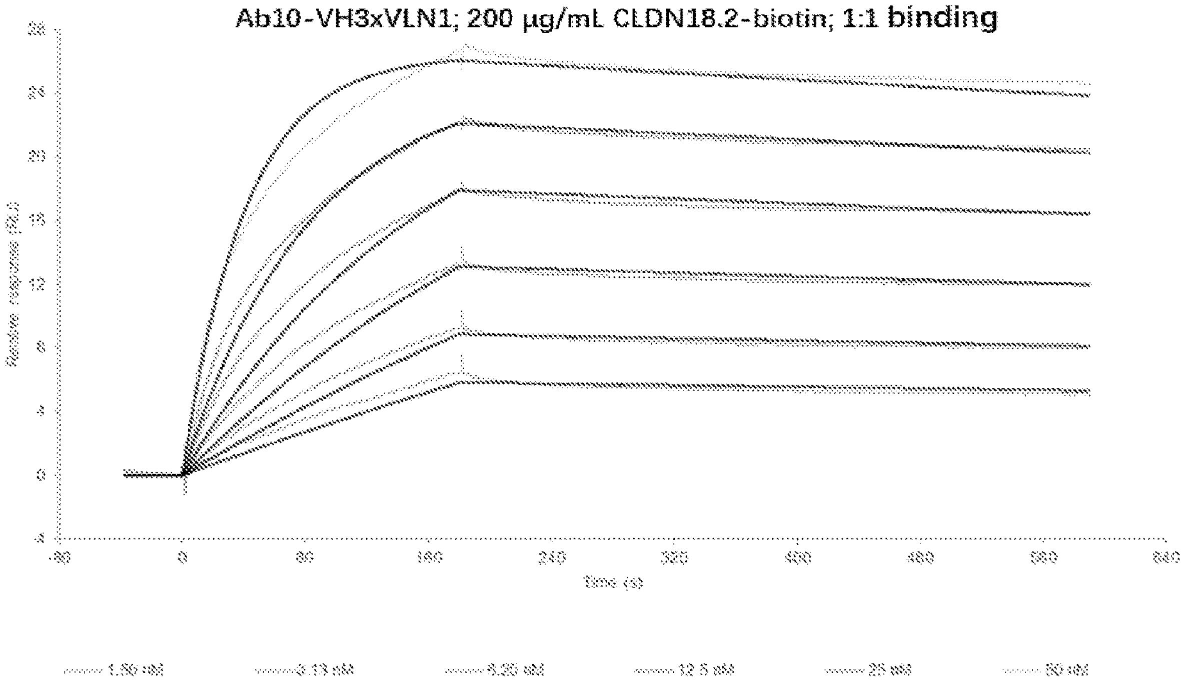
Figure 9E:
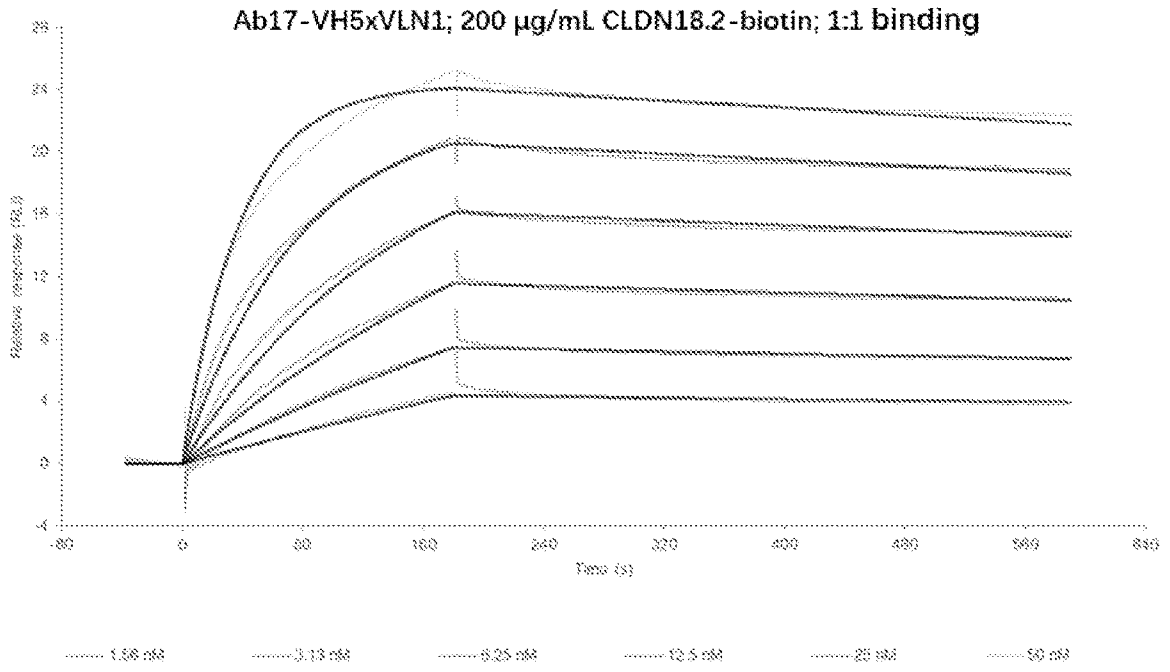
Figure 9F:
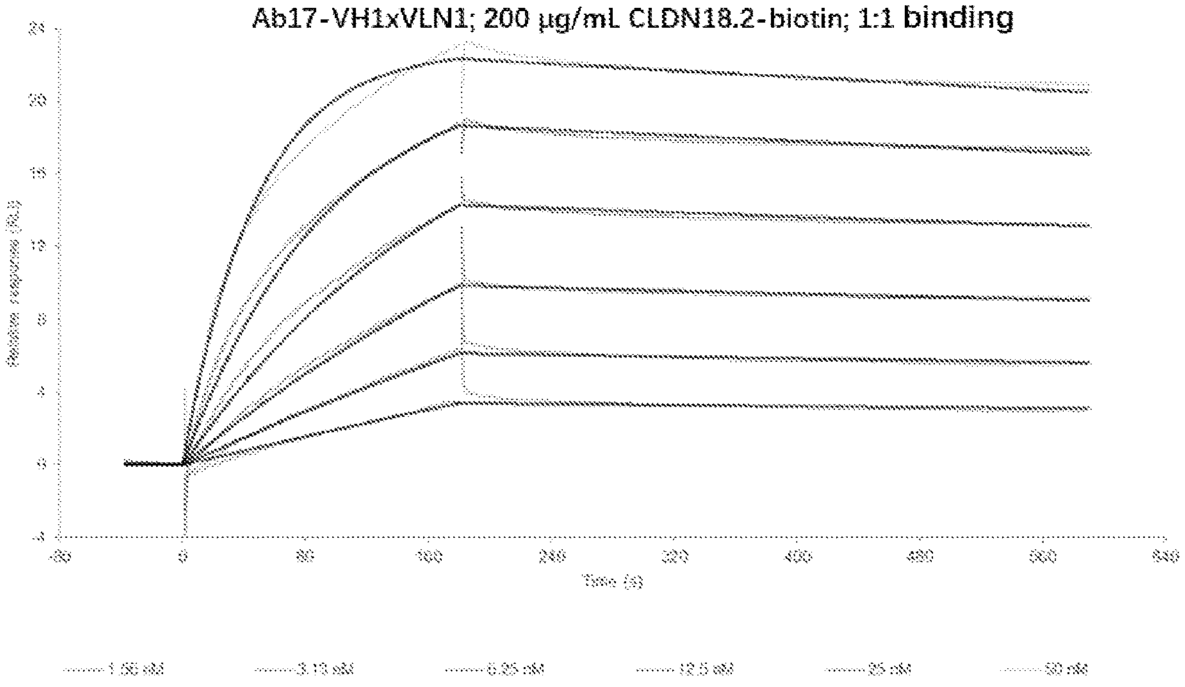
Figure 10A:
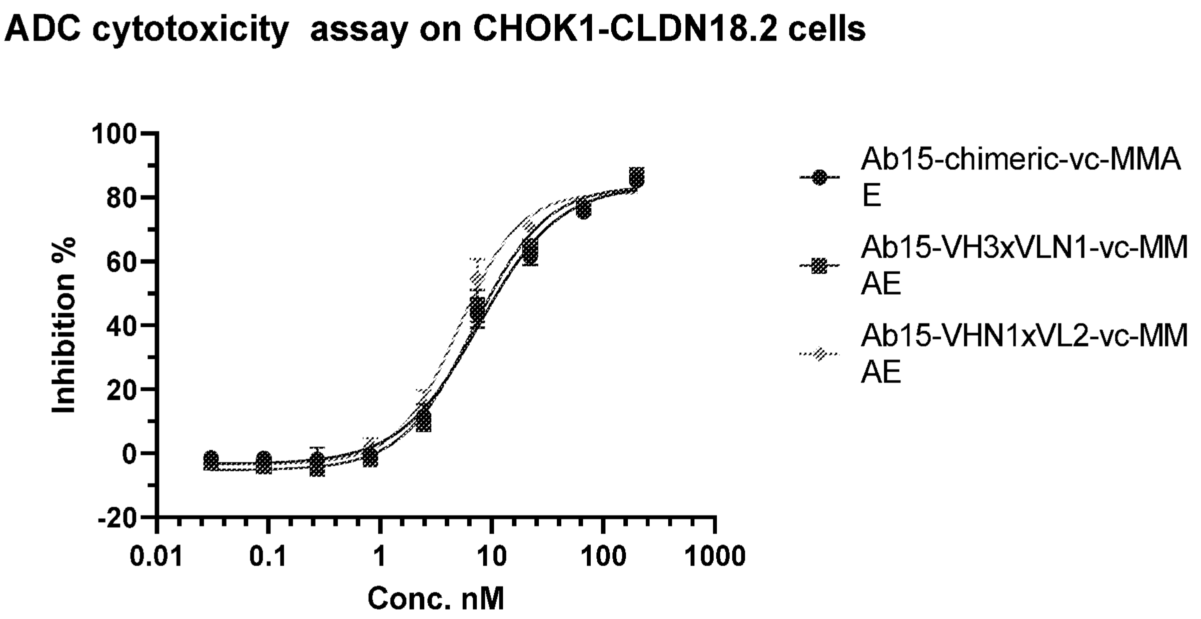
Figure 10B:
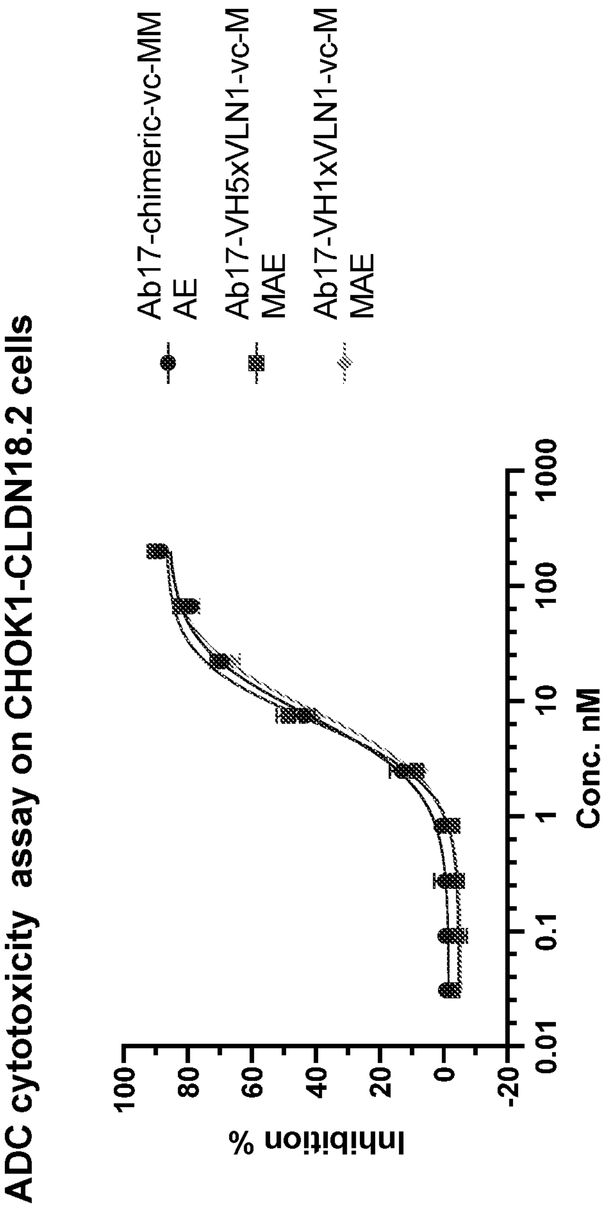
Figure 10C:
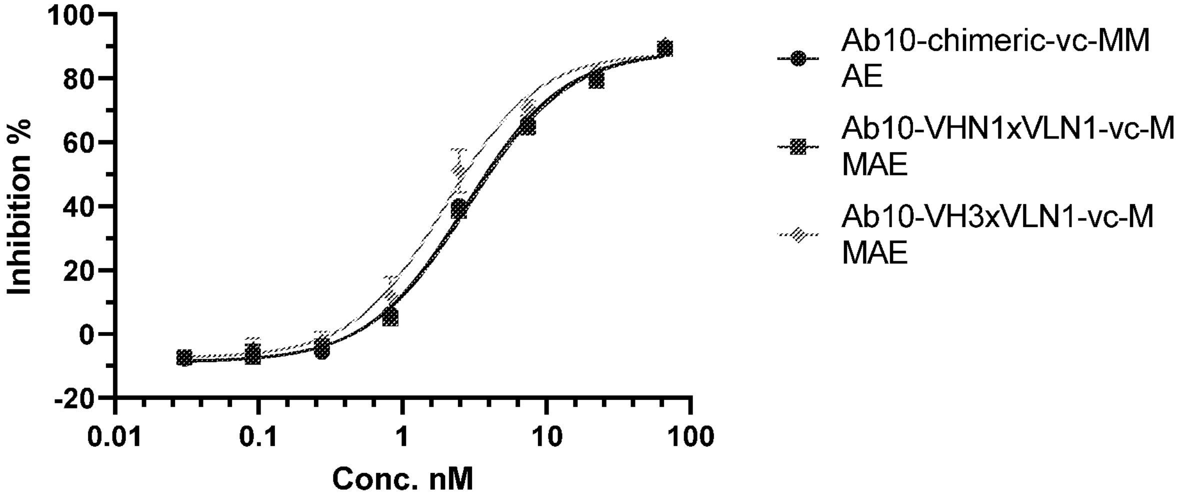
Figure 10D:
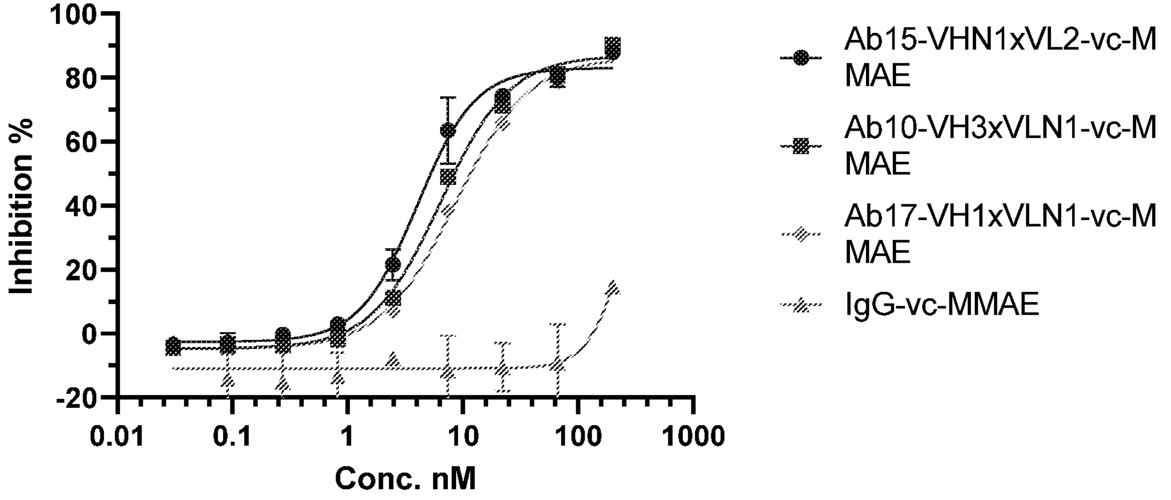
Figure 10E:
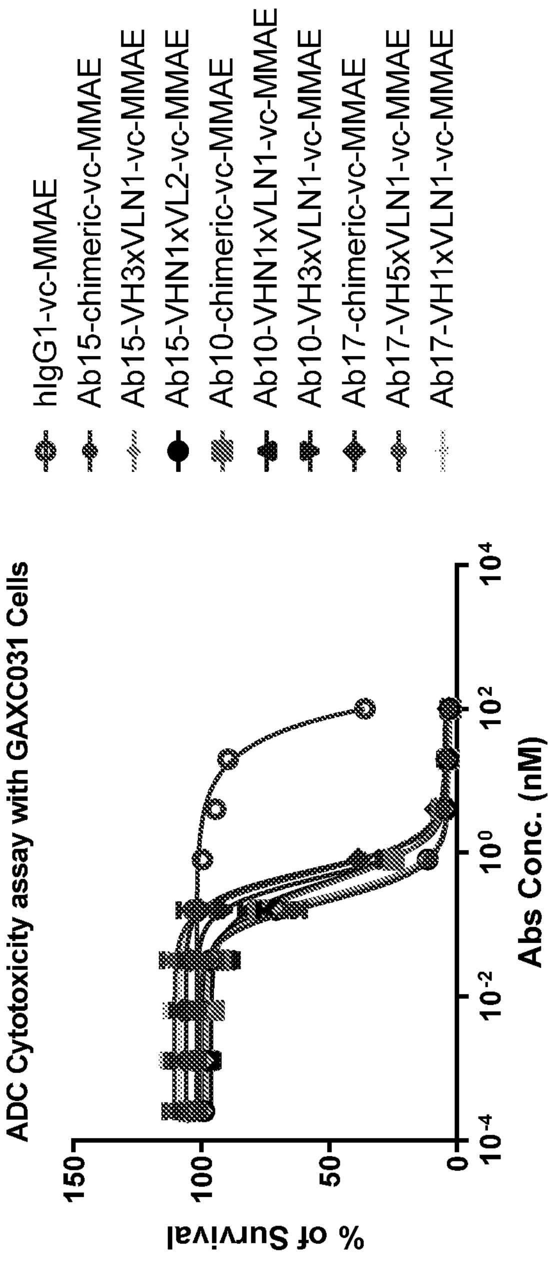

These two gastric cancer cell lines actually expressed relatively low levels of Claudin 18.2, which was detected by antibodies of this disclosure while the reference antibody IMAB362 could hardly detect the signal (see FIG. 8). Again, mAb Ab 15 displayed the highest affinity.

3. SPR Analysis for Lead Candidates

The affinity of antibodies with VLP-Claudin 18.2-biotin was determined by BIAcore 8K (GE Healthcare). 200 μg/ml VLP-Claudin 18.2-biotin was immobilized to Series S Sensor Chip SA at a flow rate of 10 μl/min for 120 s to reach the immobilization level around 1200RU. Antibodies were injected at a flow rate of 30 μl/min at room temperature with the concentration gradient (1.56~50 nM). The contact time was set to 180 s and dissociation time was 400 s. At the end of each cycle, 10 mM Glycine pH=1.5 was injected to remove the tested antibody from the surface. At last, binding kinetics was calculated using BIAcore Insight Evaluation Software and a 1:1 binding model was used for curve fitting.

As shown in FIG. 9, the humanized Ab15 (VH3×VLN1), humanized Ab15 (VHN1×VL2), humanized Ab10 (VHN1×VLN1), humanized Ab10 (VH3×VLN1), humanized Ab17 (VH5×VLN1) and humanized Ab17 (VH1×VLN1) have a KD of $7.07\times10^{-13}$, $9.40\times10^{-12}$, $1.39\times10^{-10}$, $4.41\times10^{-10}$, $4.60\times10^{-10}$ and $4.95\times10^{-10}$, respectively.

Example 7: Efficacy Assay of Antibody Drug Conjugates

1. In Vitro Efficacy Assay (ADC Efficacy Included)

Target tumor cells were seeded at 2000 cells/well in 75 μL assay medium and were then treated with an antibody drug conjugate (ADC) in the form of antibody-vc-A/MAE with a series dilution in 25 μl assay medium following the design layout the next day (final starting working concentration 100 nM, 1:5 serial dilution). The Cells were continued to be cultured for 120 hours and the cell viability was measured at 120 hours time point according to the celltiter Glo manual.

CHOK1 cells over-expressing hClaudin18.2 (HOK1-hClaudin18.2) and GAXC031 cells were treated with ADC derived from Ab15, Ab10 and Ab 17 chimeric antibodies (or with their humanized sequences) and human IgG1-vc-MMAE. Survival percentage was measured after 120 hours incubation.

Cytotoxicity could be detected when target cells were incubated with ADCs derived from antibody of the present disclosure conjugating vc-MMAE. Sub-nanomolar or nanomolar efficacy could be observed for the in vitro cytotoxicity assay (see FIG. 10).

2. In Vivo Efficacy Evaluation:

1) In Vivo Study for mAbs

Briefly, MC38-hClaudin18.2 cells were inoculated into C57BL/6 mice. The mice were randomly divided into 10 groups when the tumor volume was ~100 $mm^3$. Antibodies (Ab15, Ab10, Ab17, 6E8A2, 25G1F4, 51E3H5 and reference antibody IMAB362) with a mIgG2a Fc were administrated into mice at a dosage of 5 mg/kg.

Figure 11A:
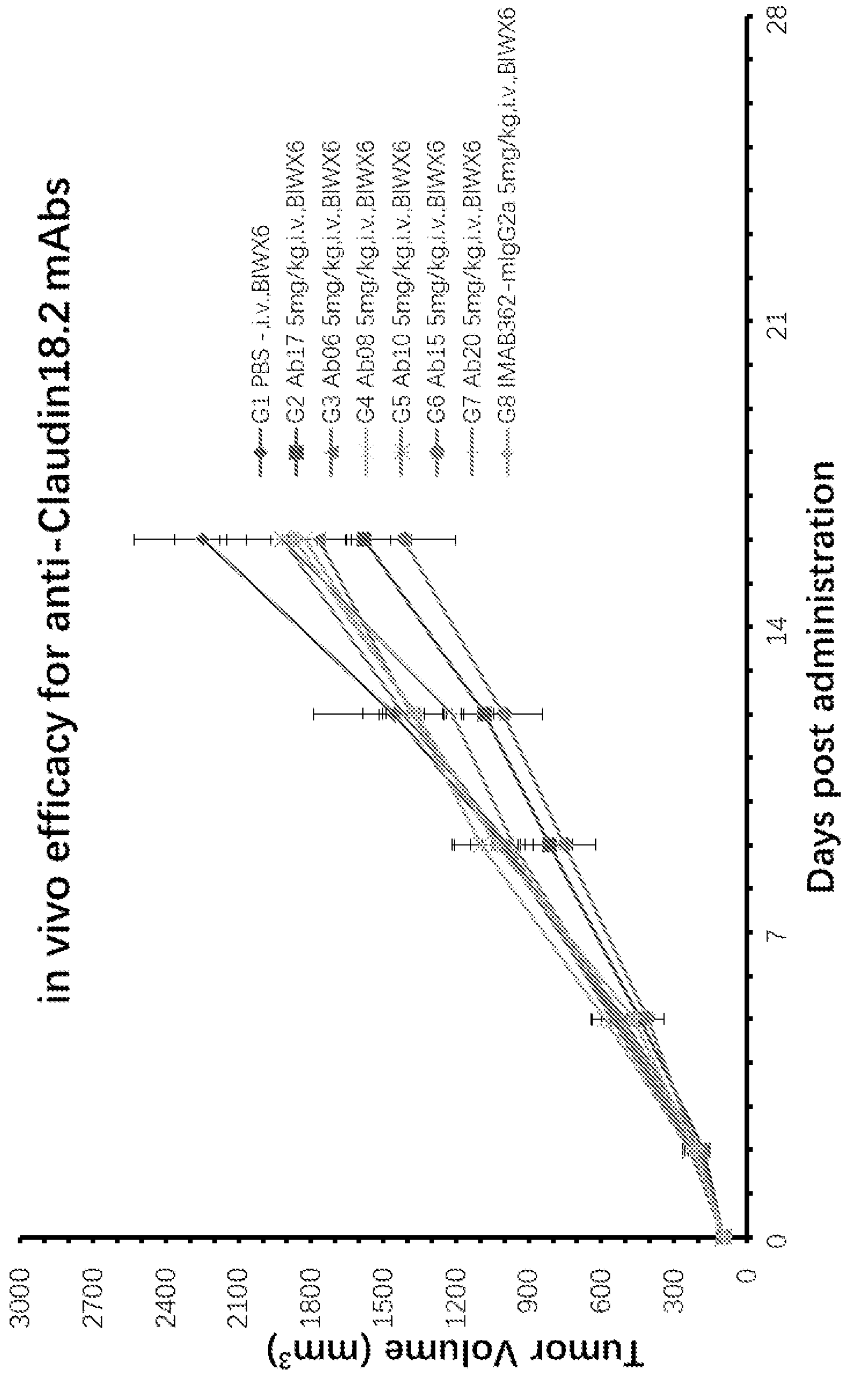
FIGS. 11A and 11B show in vivo efficacy and toxicity of mAb Ab15, Ab10, Ab17, Ab06, Ab08 and Ab20.
Figure 11B:
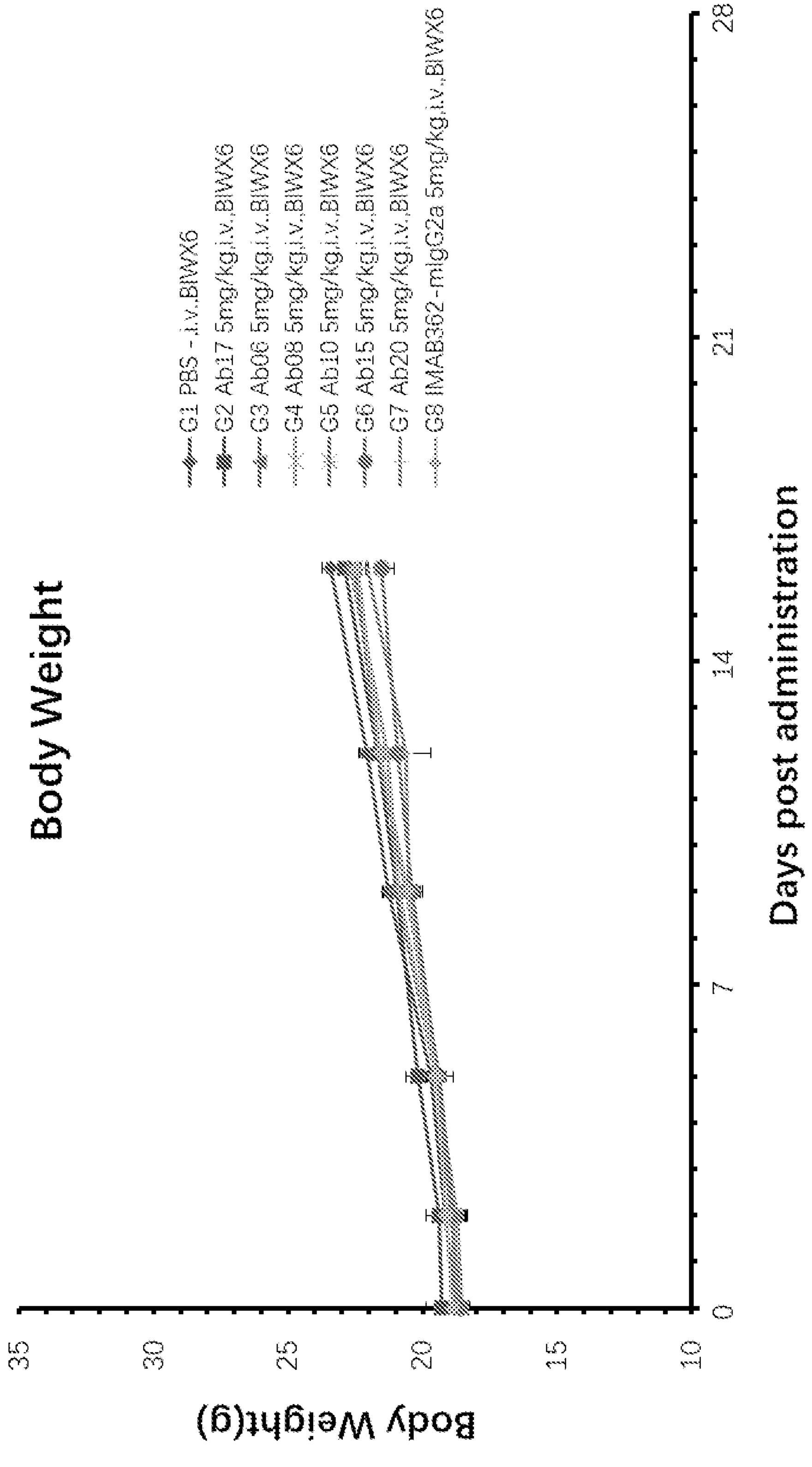

Compared with PBS control group, most of the antibodies administrated showed inhibition of tumor growth. Tumor growth inhibition (TGI) ranged from 15.3% to 38.6%, among which, Ab15 showed best monotherapy efficacy (see FIG. 11A). All the antibodies administrated did not show toxicity to mice as the body weight didn't decline (see FIG. 11B).

2) In Vivo Efficacy Study for ADC

Firstly, Ab10-vc-MMAF was tested for in vivo efficacy study. Briefly, GAXC031 cells were inoculated to BABL/c nude mice (female, 6-8 weeks). When the mean tumor volume reached ~120 $mm^3$, ADC drugs (Ab10-vc-MMAF and IMAB362-vc-MMAF) as well as the controls (PBS vehicle and hIgG-vc-MMAF) were administrated via intravenous injection at a Quality to be delivered every 2 weeks (Q2W) frequency for twice. Tumor volume was measured twice a week for 3 weeks.

TGI and body weight as well as survival proportions were detected.

Figure 12A:
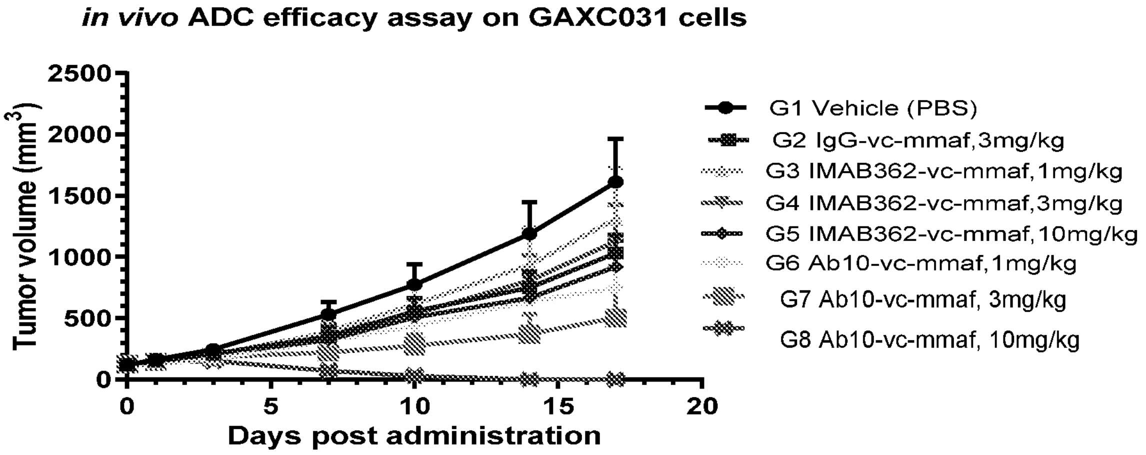
FIGS. 12A-12J show the in vivo ADC efficacy and toxicity of Ab10-vc-MMAF on GAXC03 cells.
Figure 12B:
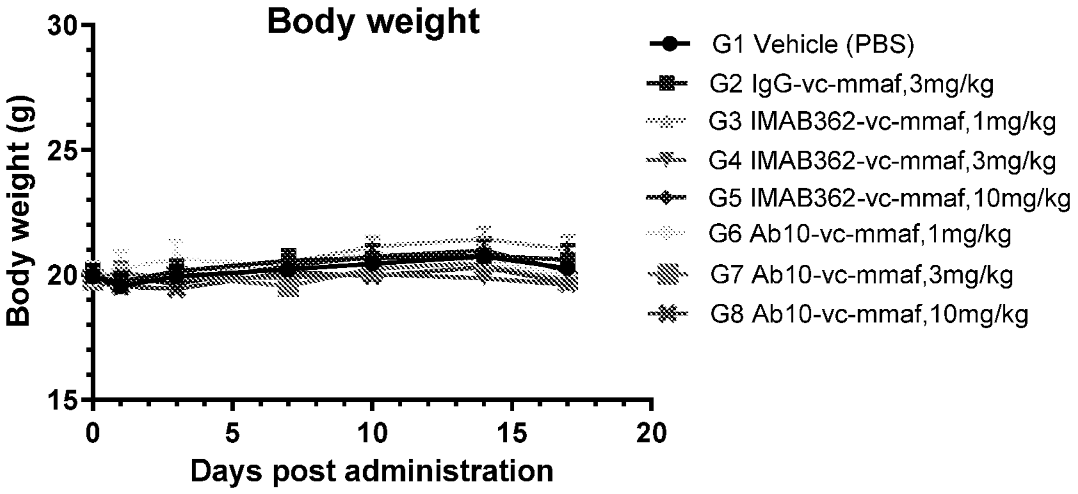
Figure 12C:
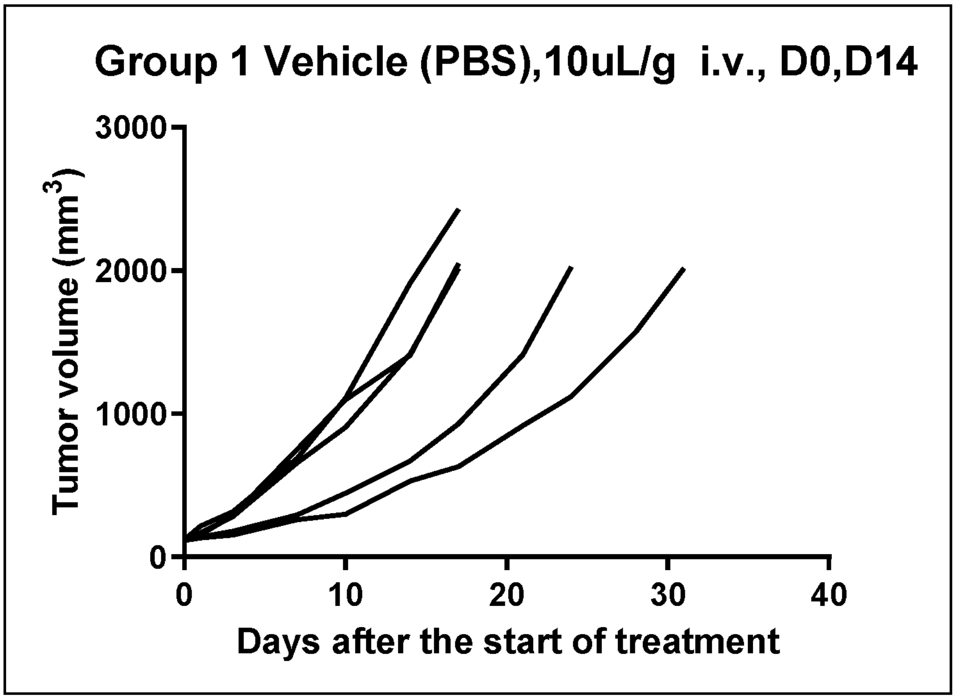
Figure 12D:
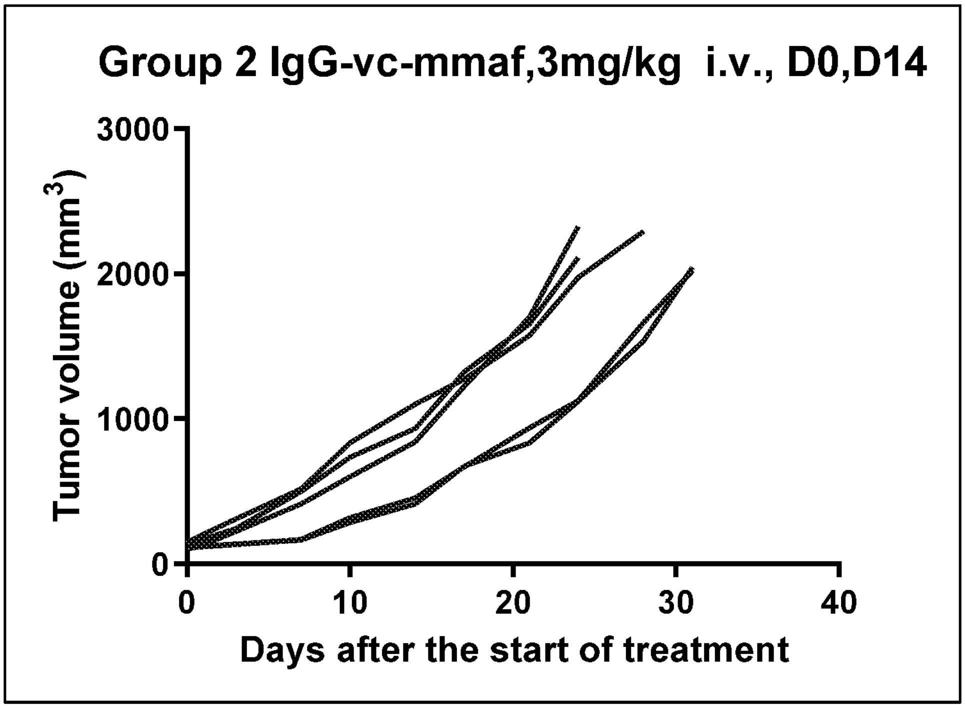
Figure 12E:
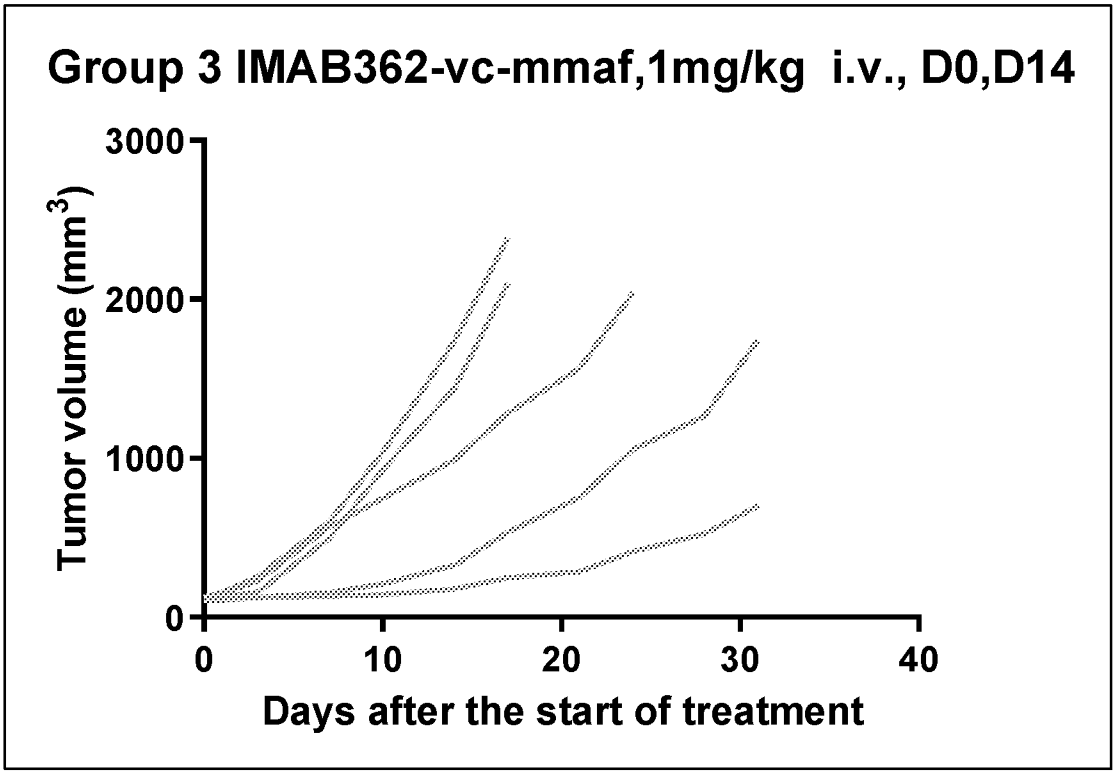
Figure 12F:
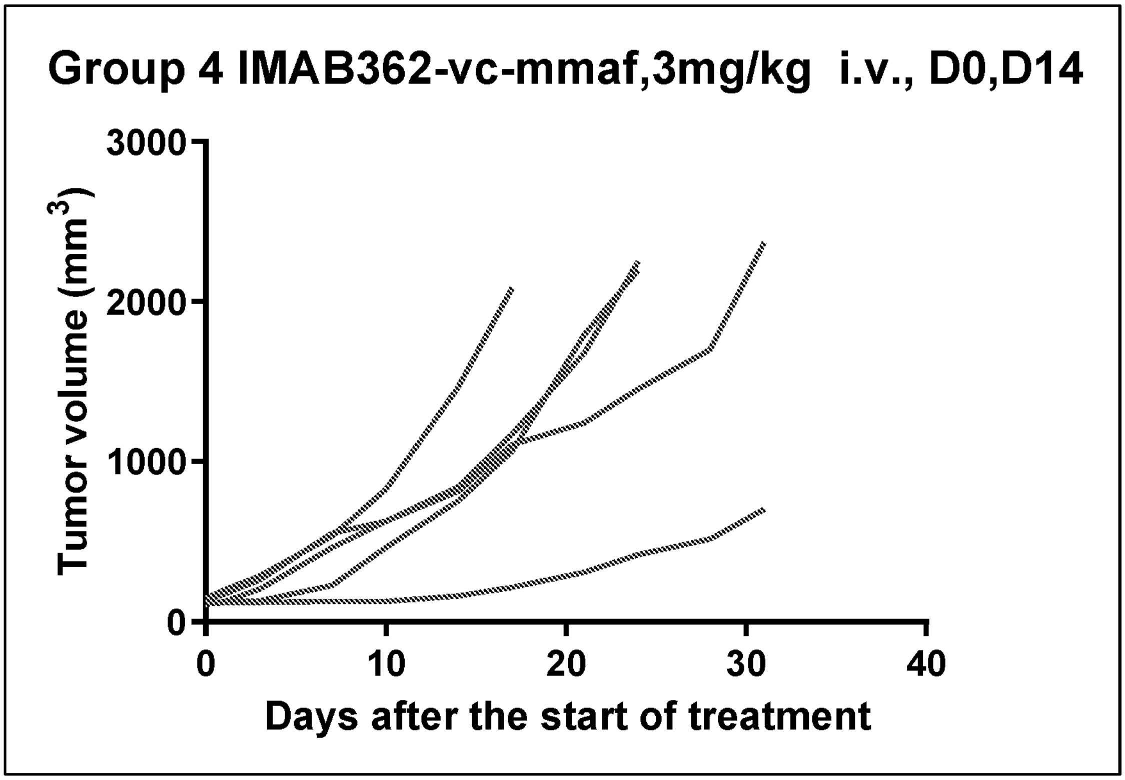
Figure 12G:
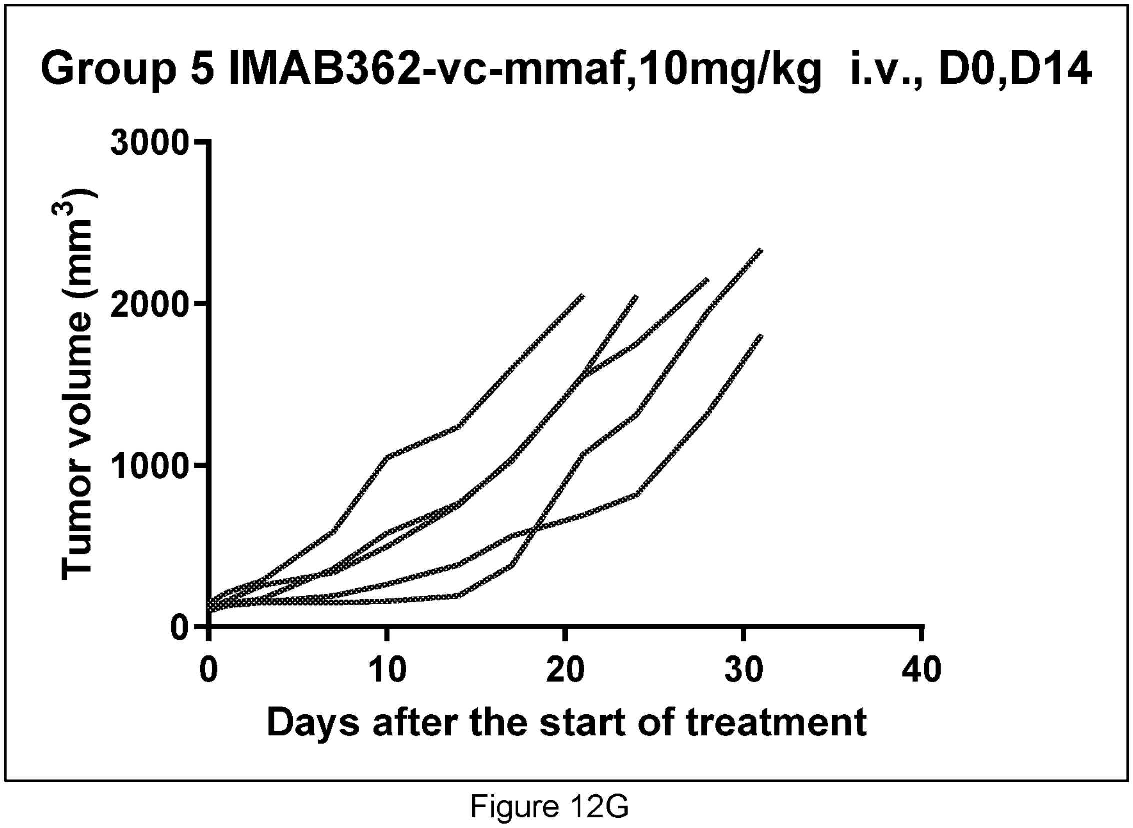
Figure 12H:
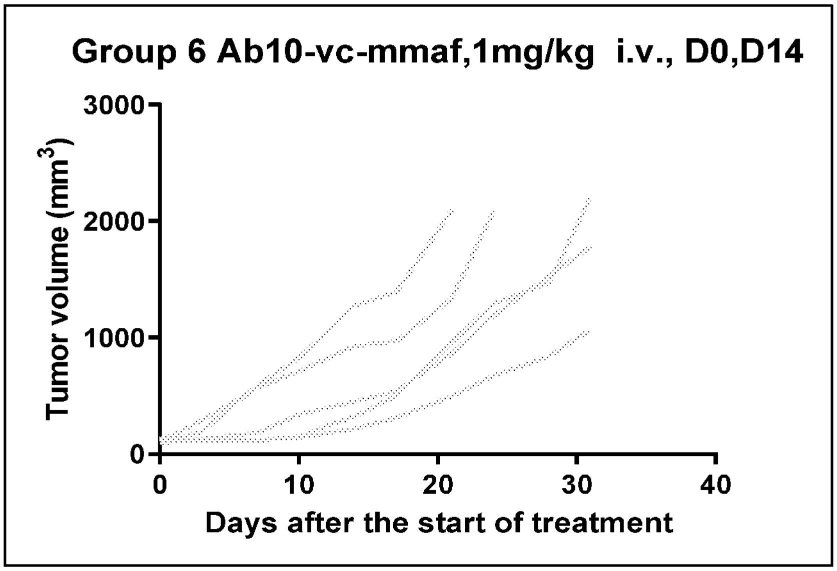
Figure 12I:
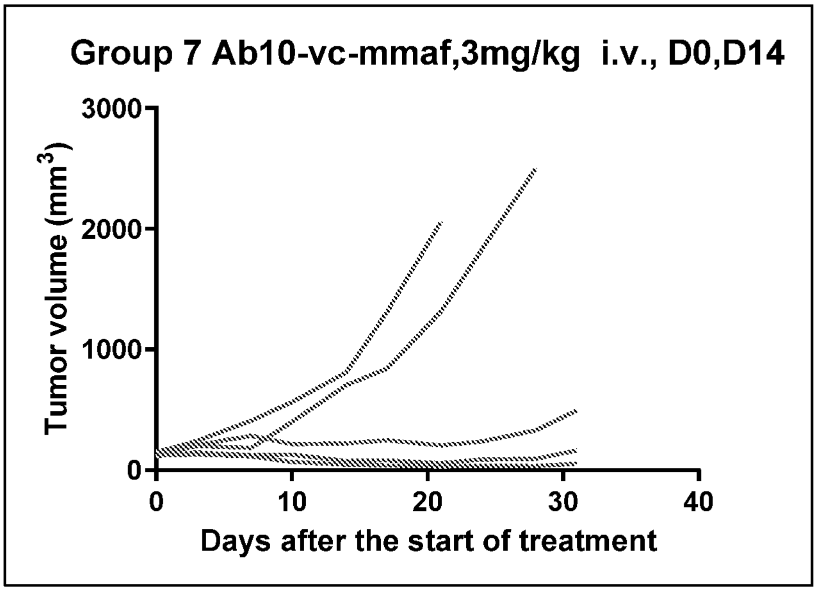
Figure 12J:
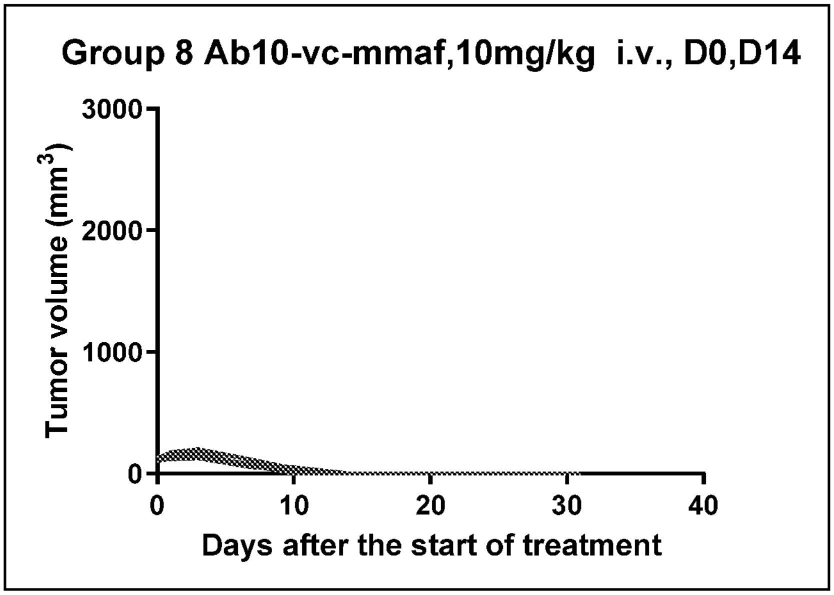
Figure 12K:
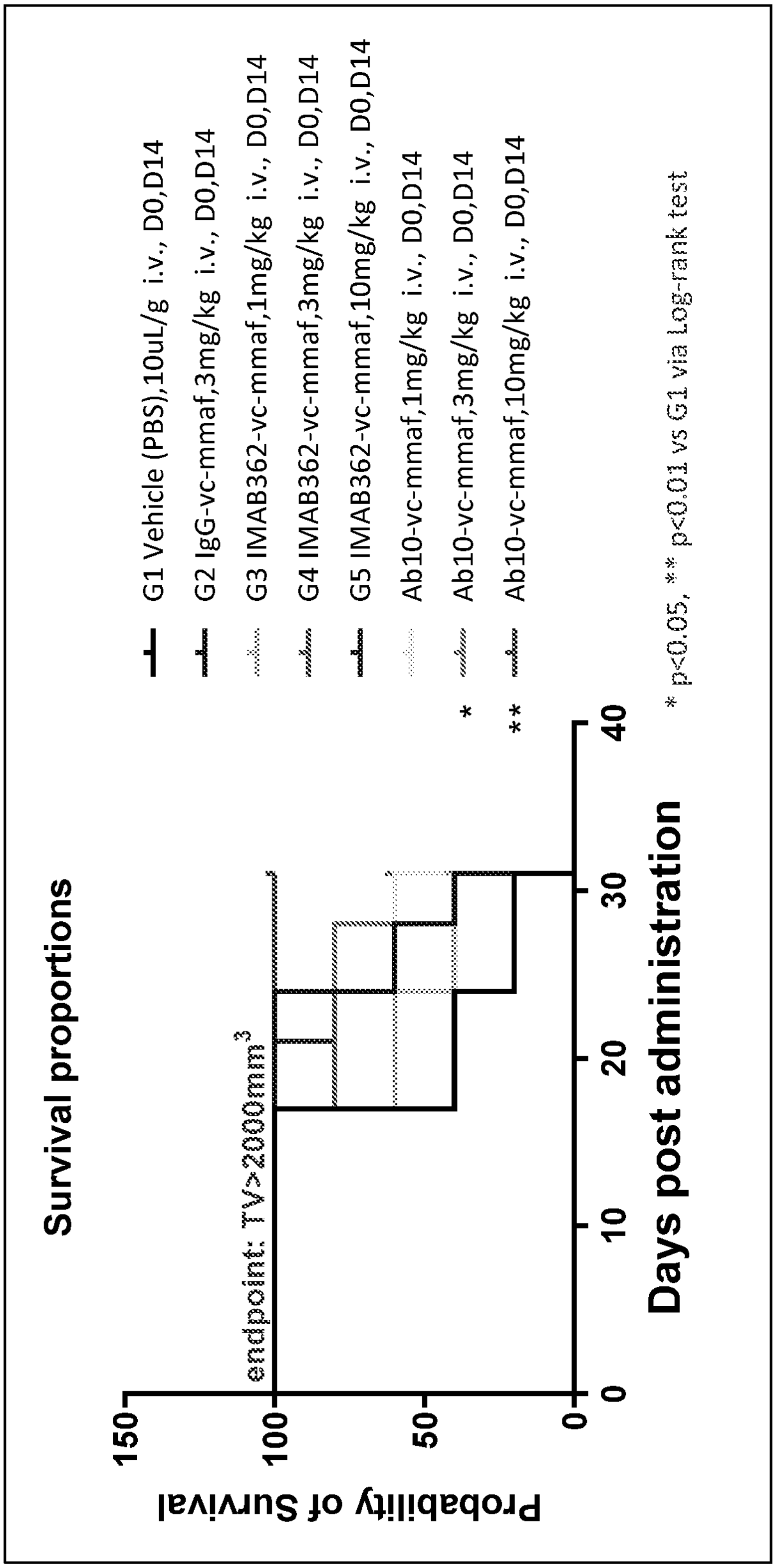
FIG. 12K shows survival curves of mice treated with Ab10-vc-MMAF.
Figure 13A:
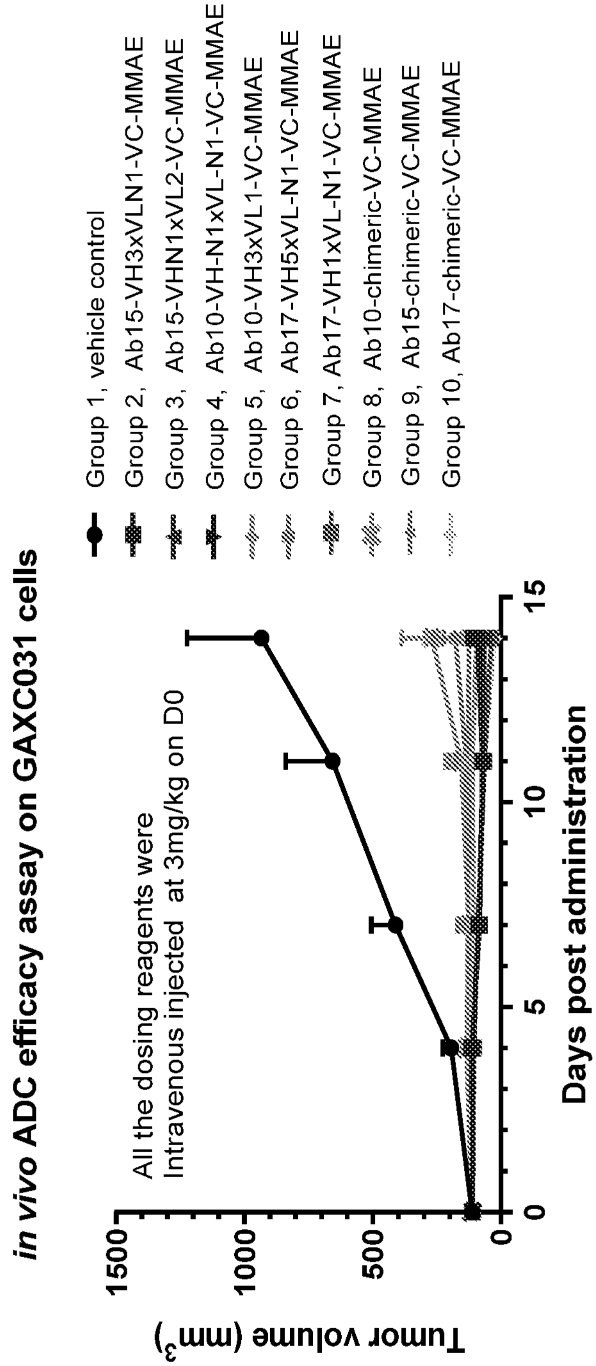
FIGS. 13A-13L show the in vivo ADC efficacy and toxicity of humanized or chimeric antibodies on GAXC03 cells and FIG. 13M shows survival curves of mice treated with ADC of humanized or chimeric antibodies.
Figure 13B:
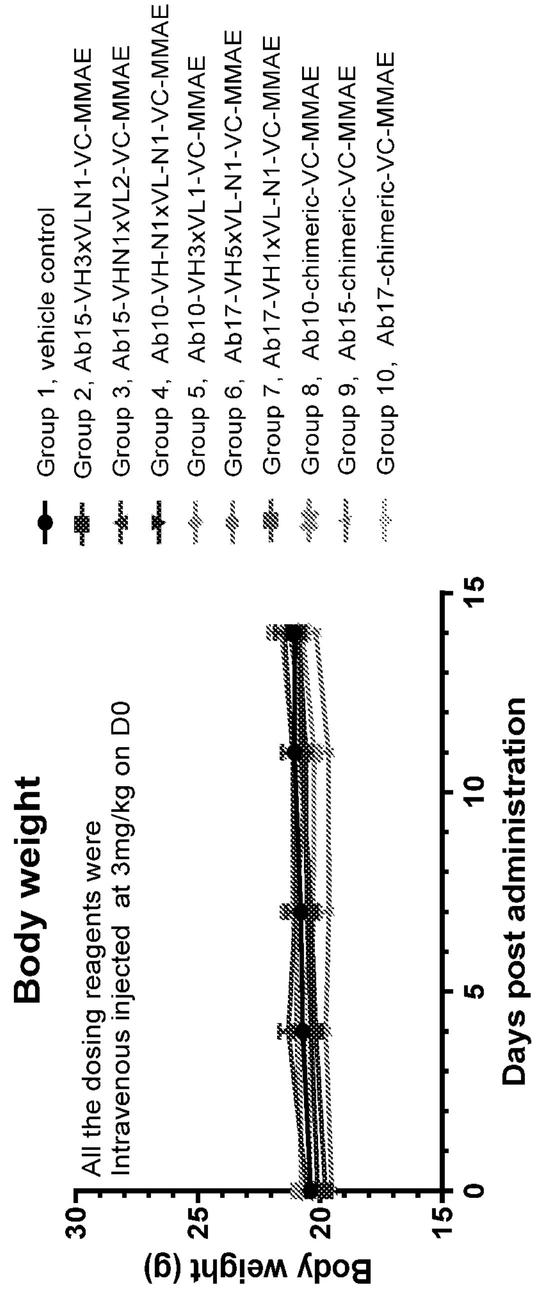
Figure 13C:
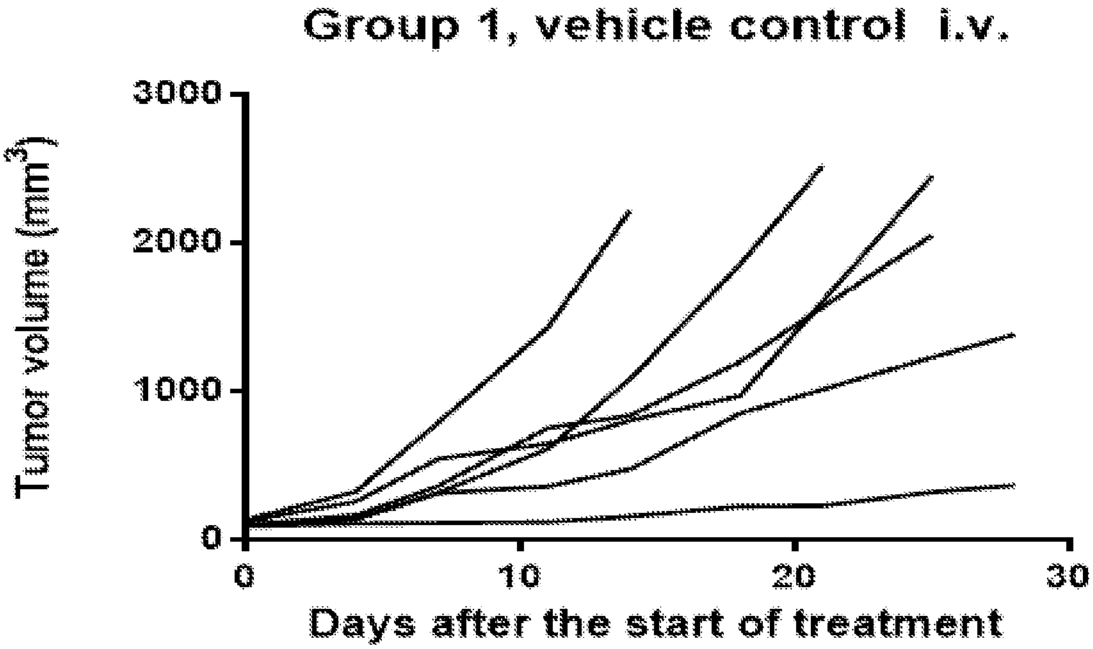
Figure 13D:
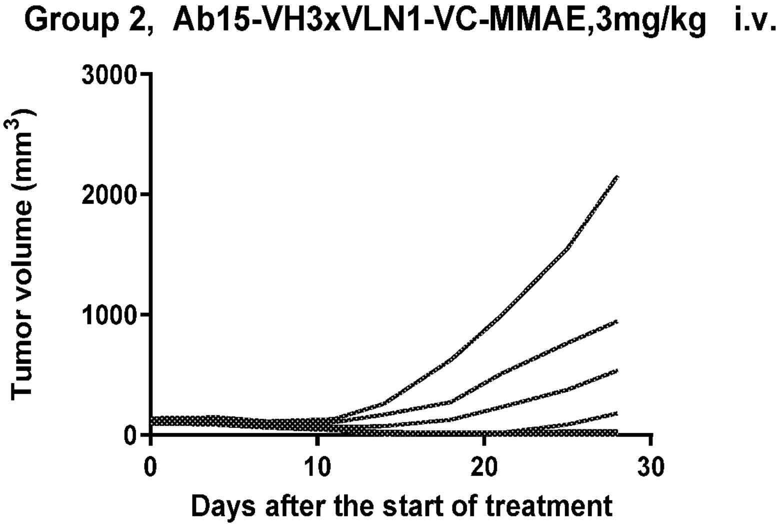
Figure 13E:
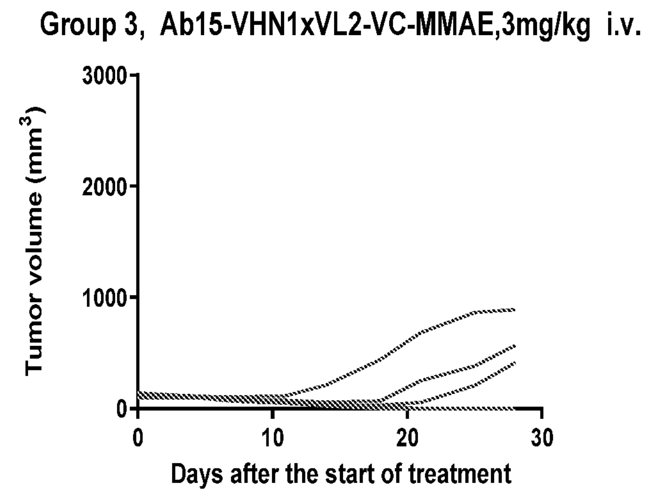
Figure 13F:
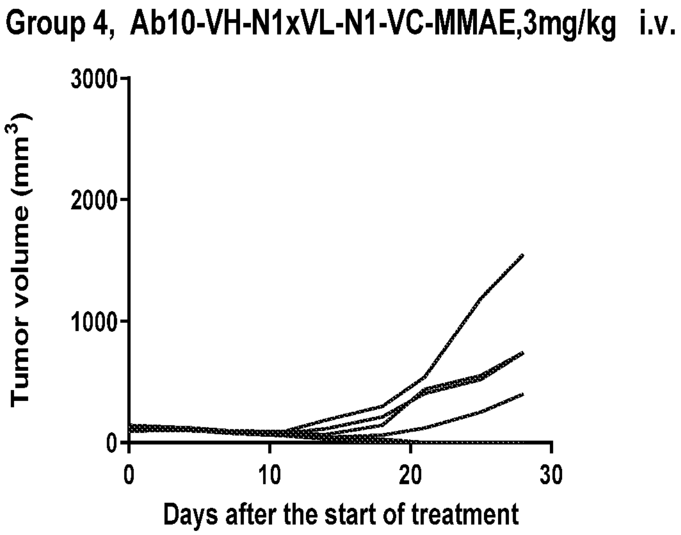
Figure 13G:
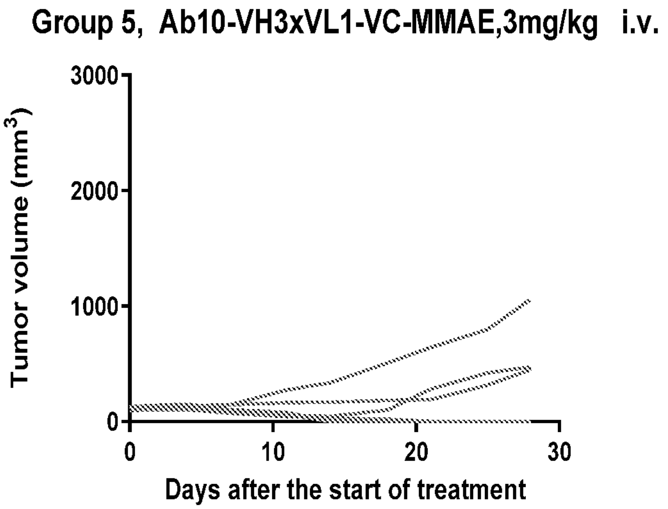
Figure 13H:
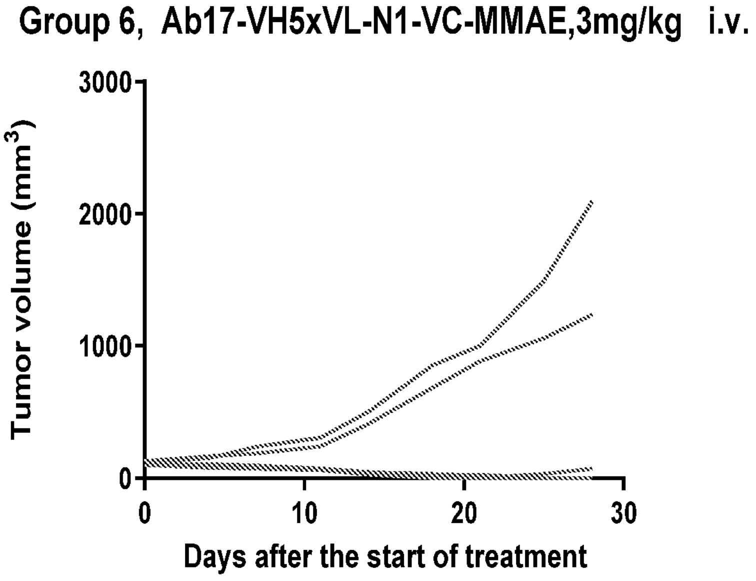
Figure 13I:
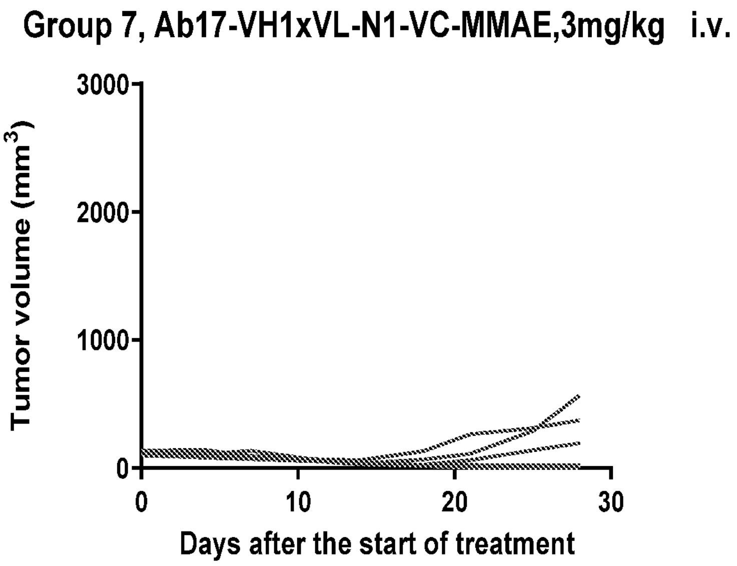
Figure 13J:
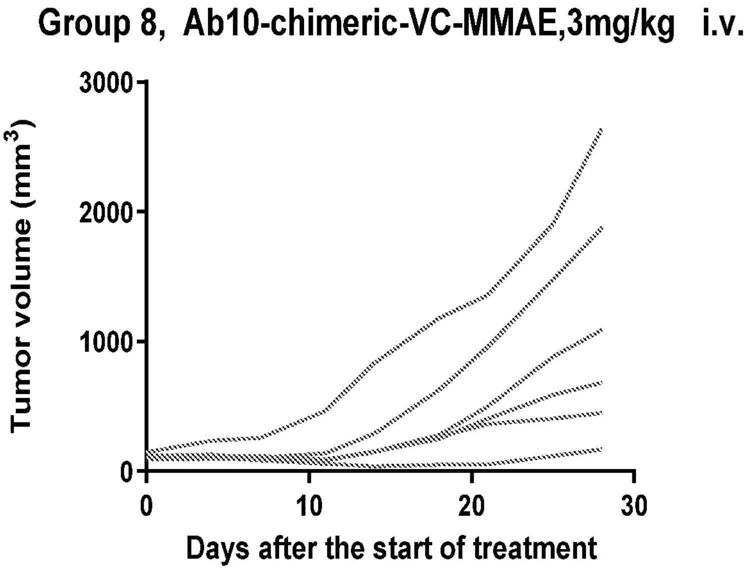
Figure 13K:
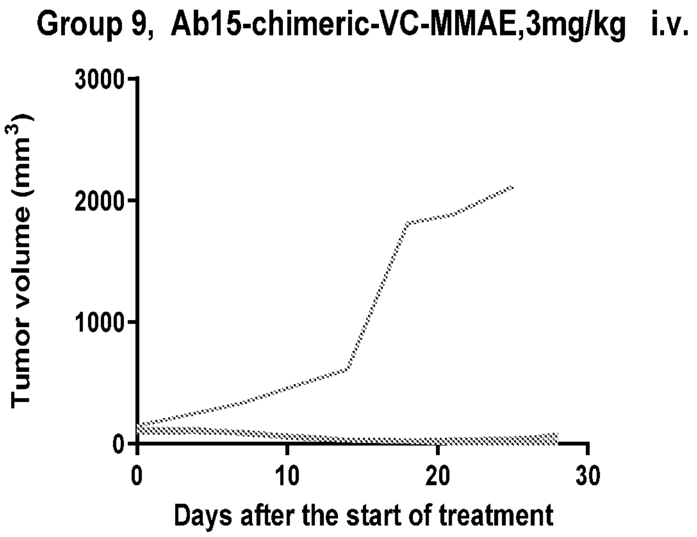
Figure 13L:
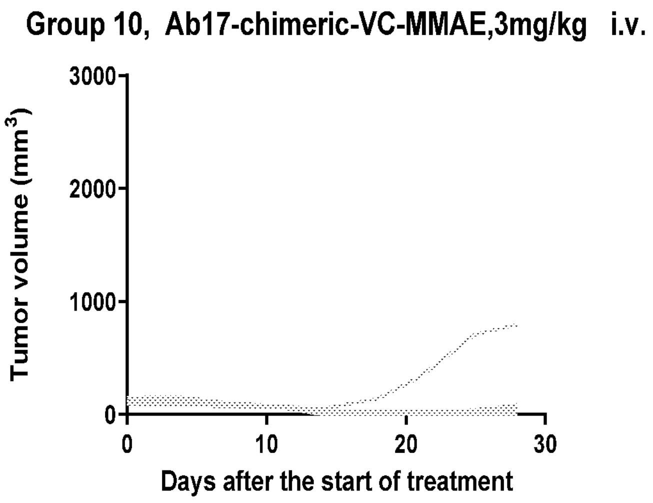
Figure 13M:
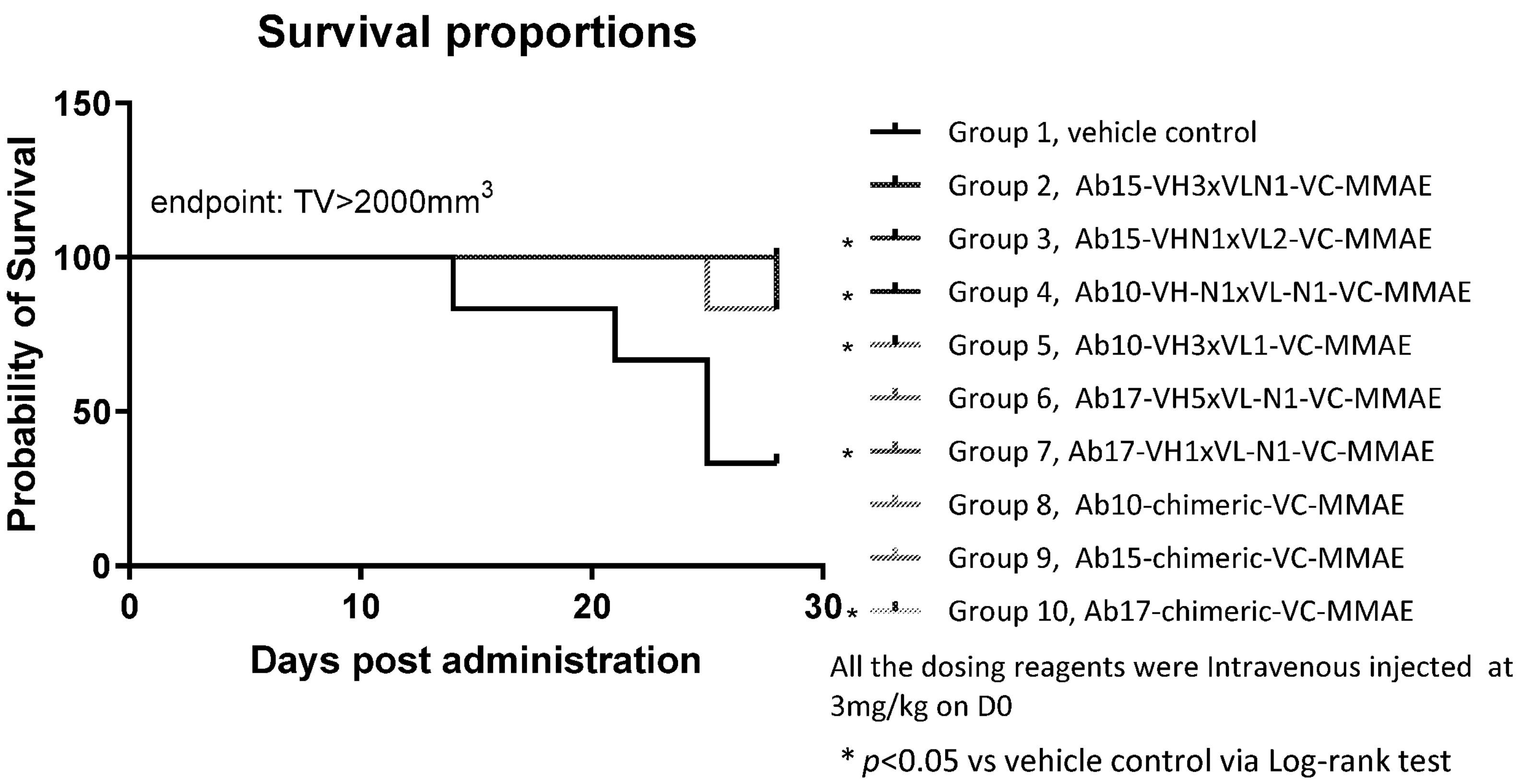

Compared with control and reference antibody ADC, Ab10-vc-MMAF showed much better efficacy and high dose group (10 mg/kg) showed total tumor regression (see FIGS. 12A and 12C-12J). Survival curve showed that ADC dosed groups mice lived for longer time (see FIG. 12K). Again, the ADC drugs did not show any toxicity since the body weight did not decrease (see FIG. 12B).

3) In Vivo Efficacy Study for Humanized Antibody ADC (Vc-MMAE as Linker-Payload).

GAXC031 cells were inoculated to BABL/c nude mice (female, 6-8w). When the mean tumor volume reached ~120 $mm^3$, ADC drugs (vc-MMAE conjugated Ab15, Ab10, Ab 17 and their humanized antibodies) as well as PBS vehicle control were administrated via intravenous injection only once at the dosage of 3 mg/kg. Tumor volume was measured twice a week for 3 weeks. TGI and body weight as well as survival proportions were detected.

All the ADCs were quite potent against the GAXC031 model. Tumor regression could be observed in most of the ADC treatment groups (see FIG. 13).

What is claimed is:

1. An antibody or antigen-binding fragment thereof which specifically binds to Claudin-18 (CLDN 18), wherein the antibody or antigen-binding fragment thereof comprises: a VH-CDR 1 having an amino acid sequence of SEQ ID NO: 306, a VH-CDR 2 having an amino acid sequence of SEQ ID NO: 308, a VH-CDR 3 having an amino acid sequence of SEQ ID NO: 310, a VL-CDR 1 having an amino acid sequence of SEQ ID NO: 315, a VL-CDR 2 having an amino acid sequence of SEQ ID NO: 317, and a VL-CDR 3 having an amino acid sequence of SEQ ID NO: 319.

2. The antibody or antigen-binding fragment thereof of claim 1, comprising a pair of heavy chain variable region and light chain variable region sequences of SEQ ID NOs: 313/322, or a pair of homologous sequences thereof having at least 80%, 85%, 90%, 95%, 97%, 98%, or 99% sequence identity yet retains specific binding affinity to CLDN 18.

3. The antibody or antigen-binding fragment thereof of claim 1, comprising: a heavy chain variable region comprising an amino acid sequence selected from the group consisting of SEQ ID NO: 704, SEQ ID NO: 705, SEQ ID NO: 706 and SEQ ID NO: 707, and a light chain variable region comprising an amino acid sequence selected from the group consisting of SEQ ID NO: 708, SEQ ID NO: 709 and SEQ ID NO: 710.

4. The antibody or antigen-binding fragment thereof of claim 1, the antibody is a monoclonal antibody, a polyclonal antibody, a bispecific antibody, a chimeric antibody, a humanized antibody, a recombinant antibody, a human antibody, a labeled antibody, a bivalent antibody, or an anti-idiotypic antibody.

5. The antibody or antigen-binding fragment thereof of claim 1, wherein the antibody or antigen-binding fragment is human IgG1 isotype.

6. The antibody or antigen-binding fragment thereof of claim 1, being linked to one or more conjugate moieties.

7. A chimeric antigen receptor, comprising the antibody or antigen-binding fragment of claim 1, a transmembrane region and an intracellular signal region.

8. An isolated polynucleotide encoding the antibody or antigen-binding fragment of claim 1.

9. A vector comprising the polynucleotide of claim 8.

10. A virus comprising the vector of claim 9.

11. A method of expressing the antibody or antigen-binding fragment of claim 1, comprising culturing a host expression system comprising the polynucleotide encoding the antibody or antigen-binding fragment of claim 1 under conditions in which the antibody or antigen-binding fragment of claim 1 is expressed.

12. An antibody-drug conjugate comprising the antibody or antigen-binding fragment thereof of claim 1, linked to one or more therapeutic agents directly or via a linker.

13. A modified immune cell targeting cells expressing CLDN 18, comprising the antibody or antigen-binding fragment thereof of claim 1.

14. A pharmaceutical composition comprising the antibody or antigen-binding fragment thereof of claim 1, and one or more pharmaceutically acceptable carriers.

15. A kit comprising:

a container, and the pharmaceutical composition of claim 14.

16. A method for alleviating a CLDN 18-related condition in a subject, comprising administering a therapeutically effective amount of the antibody or antigen-binding fragment thereof of claim 1 to the subject, wherein the CLDN 18-related condition is cancerous condition, wherein the cancerous condition is selected from the group consisting of gastric or stomach cancer, colon cancer, colorectal cancer, and rectal cancer.

17. A method for diagnosing a CLDN 18-related condition, comprising detecting the CLDN 18 by using the antibody or antigen-binding fragment thereof of claim 1.

18. A method for inducing the death of a cell expressing CLDN 18, comprising contacting the cell expressing CLDN 18 with the antibody or antigen-binding fragment thereof of claim 1.

19. The method of claim 16, wherein the gastric or stomach cancer is gastrointestinal cancer.

* * * * *